US012729312B2

(12) United States Patent
Seo et al.

(10) Patent No.: US 12,729,312 B2
(45) Date of Patent: Sep. 8, 2026

(54) COMPOUND, COATING COMPOSITION COMPRISING SAME, ORGANIC LIGHT-EMITTING DEVICE USING SAME, AND MANUFACTURING METHOD THEREFOR

(71) Applicant: LG Chem, Ltd., Seoul (KR)

(72) Inventors: Minseob Seo, Daejeon (KR); Youngju Park, Daejeon (KR); Songrim Jang, Daejeon (KR); Jiyeon Shin, Daejeon (KR); Kwanghyun Kim, Daejeon (KR); Jaesoon Bae, Daejeon (KR); Jaechol Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 821 days.

(21) Appl. No.: 18/022,416

(22) PCT Filed: Oct. 6, 2021

(86) PCT No.: PCT/KR2021/013685
§ 371 (c)(1),
(2) Date: Feb. 21, 2023

(87) PCT Pub. No.: WO2022/075735
PCT Pub. Date: Apr. 14, 2022

(65) Prior Publication Data

US 2023/0329095 A1 Oct. 12, 2023

(30) Foreign Application Priority Data

Oct. 8, 2020 (KR) ........................ 10-2020-0130338

(51) Int. Cl.
*C09D 7/41* (2018.01)
*C07C 211/61* (2006.01)
(Continued)

(52) U.S. Cl.
CPC .............. *C09D 7/41* (2018.01); *C07C 211/61* (2013.01); *C07C 217/94* (2013.01);
(Continued)

(58) Field of Classification Search
CPC ...... C09D 7/41; C07D 311/82; C07D 307/91; C07D 311/96; H10K 85/636; H10K 85/633; C07C 211/61; C07C 217/94; C09K 11/06
(Continued)

(56) References Cited

U.S. PATENT DOCUMENTS 6,452,711 B1 9/2002 Heuer et al.
11,691,983 B2 * 7/2023 Nishimae ............ H10K 85/654 428/690
(Continued)

FOREIGN PATENT DOCUMENTS

CN 105733562 A 7/2016
CN 108623481 A 10/2018
(Continued)

OTHER PUBLICATIONS

Search Report dated Oct. 11, 2023 from the Office Action for Chinese Application No. 202180056003.5 issued Oct. 12, 2023, pp. 1-3.

(Continued)

*Primary Examiner* — James D Sells
(74) *Attorney, Agent, or Firm* — Lerner David LLP

(57) ABSTRACT

The present disclosure relates to a compound represented by Chemical Formula 1, a coating composition including the compound represented by Chemical Formula 1, an organic light emitting device using the same, and a method for manufacturing the same, (Continued)

[Chemical Formula 1]

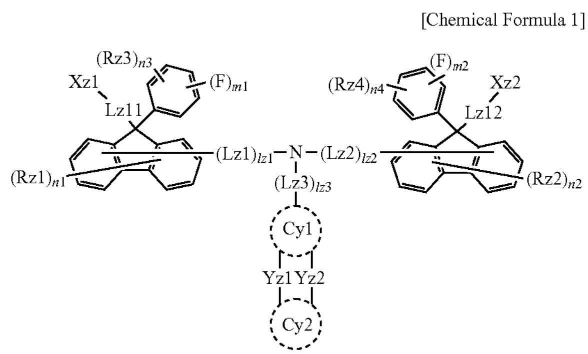

all the variables are described herein.

13 Claims, 1 Drawing Sheet

(51) Int. Cl.

| | |
|---|---|
| ***C07C 217/94*** | (2006.01) |
| ***C07D 307/91*** | (2006.01) |
| ***C07D 311/82*** | (2006.01) |
| ***C07D 311/96*** | (2006.01) |
| ***C09K 11/06*** | (2006.01) |
| ***H10K 85/60*** | (2023.01) |
| *H10K 50/17* | (2023.01) |

(52) U.S. Cl.

CPC .......... *C07D 307/91* (2013.01); *C07D 311/82* (2013.01); *C07D 311/96* (2013.01); *C09K 11/06* (2013.01); *H10K 85/633* (2023.02); *H10K 85/636* (2023.02); *C07C 2603/18* (2017.05); *C09K 2211/1007* (2013.01); *C09K 2211/1011* (2013.01); *C09K 2211/1014* (2013.01); *C09K 2211/1018* (2013.01); *H10K 50/17* (2023.02); *H10K 85/626* (2023.02); *H10K 85/6574* (2023.02)

(58) Field of Classification Search

USPC .......................................................... 428/690

See application file for complete search history.

(56) References Cited

U.S. PATENT DOCUMENTS

| | | | |
|---|---|---|---|
| 2016/0176801 | A1 | 6/2016 | Kato et al. |
| 2016/0181525 | A1 | 6/2016 | Kato et al. |
| 2017/0222152 | A1 | 8/2017 | Haketa et al. |
| 2017/0229661 | A1 | 8/2017 | Haketa et al. |
| 2018/0145265 | A1 | 5/2018 | Haketa et al. |
| 2018/0190904 | A1 | 7/2018 | Kato et al. |
| 2019/0237669 | A1 | 8/2019 | Kang et al. |
| 2019/0338140 | A1 | 11/2019 | Shin et al. |
| 2020/0055803 | A1 | 2/2020 | Yu et al. |
| 2020/0277502 | A1 | 9/2020 | Kang et al. |
| 2020/0343450 | A1 | 10/2020 | Ha et al. |
| 2021/0147358 | A1 | 5/2021 | Kim et al. |
| 2023/0354697 | A1 | 11/2023 | Lim et al. |

FOREIGN PATENT DOCUMENTS

| | | | |
|---|---|---|---|
| CN | 109843850 | A | 6/2019 |
| CN | 109863135 | A | 6/2019 |
| CN | 110121493 | A | 8/2019 |
| CN | 111094465 | A | 5/2020 |
| JP | H11144875 | A | 5/1999 |
| JP | 3838766 | B2 | 10/2006 |
| KR | 20080111968 | A | 12/2008 |
| KR | 20120112277 | A | 10/2012 |
| KR | 20170027691 | A | 3/2017 |
| KR | 20170030449 | A | 3/2017 |
| KR | 20180137263 | A | 12/2018 |
| KR | 20190035514 | A | 4/2019 |
| KR | 20190081263 | A | 7/2019 |
| KR | 20190085659 | A | 7/2019 |
| KR | 20190133626 | A | 12/2019 |
| KR | 20190136999 | A | 12/2019 |
| WO | 2018230848 | A1 | 12/2018 |
| WO | 2021154041 | A1 | 8/2021 |

OTHER PUBLICATIONS

International Search Report for Application No. PCT/KR2021/013685 mailed Jan. 25, 2022, pp. 1-3.

* cited by examiner

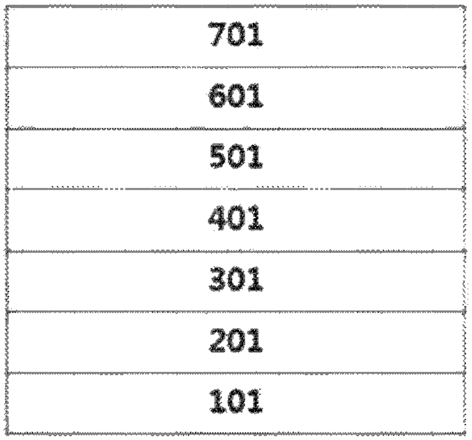
701
601
501
401
301
201
101

COMPOUND, COATING COMPOSITION COMPRISING SAME, ORGANIC LIGHT-EMITTING DEVICE USING SAME, AND MANUFACTURING METHOD THEREFOR

CROSS-REFERENCE TO RELATED APPLICATIONS

The present application is a national stage entry under 35 U.S.C. § 371 of International Application No. PCT/KR2021/013685 filed on Oct. 6, 2021, which claims priority from Korean Patent Application No. 10-2020-0130338 filed on Oct. 8, 2020, all the disclosures of which are incorporated herein by reference.

TECHNICAL FIELD

The present disclosure relates to a novel compound, a coating composition including the compound, an organic light emitting device formed using the coating composition, and a method for manufacturing the same.

BACKGROUND ART

An organic light emission phenomenon is one of examples converting a current to visible light by an internal process of specific organic molecules. A principle of an organic light emission phenomenon is as follows. When an organic material layer is placed between an anode and a cathode and a current is applied between the two electrodes, electrons and holes are injected to the organic material layer from the cathode and the anode, respectively. The holes and the electrons injected to the organic material layer recombine to form excitons, and light emits when these excitons fall back to the ground state. An organic electroluminescent device using such a principle may be generally formed with a cathode, an anode, and an organic material layer placed therebetween, for example, a hole injection layer, a hole transfer layer, a light emitting layer, an electron injection layer and an electron transfer layer.

A deposition process has been mainly used in the art to manufacture an organic light emitting device. However, manufacturing an organic light emitting device using a deposition process has problems in that it causes much material loss and manufacturing a large area device is difficult, and a device using a solution process has been developed in order to resolve these problems.

Accordingly, development of materials for a solution process has been required.

DISCLOSURE

Technical Problem

The present disclosure is directed to providing a novel compound and/or an organic light emitting device including the same.

Technical Solution

One embodiment of the present disclosure provides a compound represented by the following Chemical Formula 1.

[Chemical Formula 1]

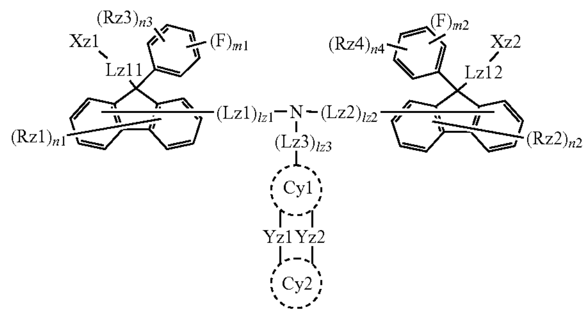

In Chemical Formula 1,

Yz1 and Yz2 are the same as or different from each other, and each independently a direct bond, O, S, CRaRb or SiRcRd, and when any one of Yz1 or Yz2 is a direct bond, the other one is O, S, CRaRb or SiRcRd, Ra, Rb, Rc and Rd are the same as or different from each other, and each independently hydrogen; deuterium; a substituted or unsubstituted alkyl group; a substituted or unsubstituted aryl group; a substituted or unsubstituted heteroaryl group, or bond to adjacent groups to form a substituted or unsubstituted ring, Cy1 and Cy2 are the same as or different from each other, and each independently a substituted or unsubstituted benzene ring; or a substituted or unsubstituted naphthalene ring, Lz1 to Lz3 are the same as or different from each other, and each independently a direct bond; or a substituted or unsubstituted arylene group, Lz11 and Lz12 are the same as or different from each other, and each independently a direct bond; a substituted or unsubstituted alkylene group; or a substituted or unsubstituted arylene group, Xz1 and Xz2 are the same as or different from each other, and each independently a curable group, Rz1 and Rz2 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group, Rz3 and Rz4 are the same as or different from each other, and each independently deuterium; a substituted or unsubstituted alkyl group; a substituted or unsubstituted alkoxy group; a substituted or unsubstituted aryl group; or a substituted or unsubstituted heteroaryl group, lz1 to lz3 are each independently 0 or 1, n1 and n2 are each independently an integer of 0 to 7, and when n1 and n2 are each 2 or greater, substituents in the two or more parentheses are the same as or different from each other, n3 and n4 are each independently an integer of 0 to 4, and when n3 and n4 are each 2 or greater, substituents in the two or more parentheses are the same as or different from each other, m1 and m2 are each independently an integer of 1 to 5, and m1+n3 is 5 or less, and m2+n4 is 5 or less.

Another embodiment of the present disclosure provides a coating composition including the compound.

In addition, one embodiment of the present disclosure provides an organic light emitting device including a first electrode; a second electrode; and one or more organic material layers provided between the first electrode and the second electrode, wherein one or more layers of the one or more organic material layers include the coating composition described above or a cured material thereof.

Lastly, one embodiment of the present disclosure provides a method for manufacturing an organic light emitting device, the method including preparing a first electrode; forming one or more organic material layers on the first electrode; and forming a second electrode on the one or more organic material layers, wherein the forming of one or more organic material layers includes forming one or more layers using the coating composition.

Advantageous Effects

A compound of Chemical Formula 1 of the present disclosure can be used as a material of an organic material layer of an organic light emitting device, and, while obtaining a device having low driving voltage, excellent light emission efficiency and/or lifetime properties, a device having a large area can be manufactured by using a solution process.

According to one embodiment of the present disclosure, the compound of Chemical Formula 1 has excellent solubility for an organic solvent by including fluorene and tricyclic or higher cyclic group together with one nitrogen atom in the molecule, and by forming a deep HOMO energy level, holes smoothly migrate, which enhances a lifetime of a device.

In addition, by the compound of Chemical Formula 1 of the present disclosure being substituted with two or more fluoro groups (—F), interfacial properties between a hole injection layer and a hole transfer layer are improved, and by increasing stability of the fluoro group-substituted phenyl group, device properties are improved.

DESCRIPTION OF DRAWINGS

The FIGURE illustrates an organic light emitting device according to one embodiment of the present disclosure.

REFERENCE NUMERAL

101: Substrate

201: First Electrode

301: Hole Injection Layer

401: Hole Transfer Layer

501: Light Emitting Layer

601: Electron Injection and Transfer Layer

701: Second Electrode

MODE FOR DISCLOSURE

Hereinafter, the present disclosure will be described in detail.

One embodiment of the present disclosure provides a compound represented by the following Chemical Formula 1.

[Chemical Formula 1]

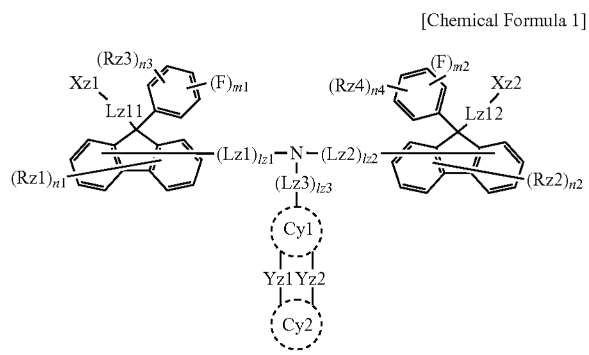

In Chemical Formula 1,

Yz1 and Yz2 are the same as or different from each other, and each independently a direct bond, O, S, CRaRb or SiRcRd, and when any one of Yz1 or Yz2 is a direct bond, the other one is O, S, CRaRb or SiRcRd, Ra, Rb, Rc and Rd are the same as or different from each other, and each independently hydrogen; deuterium; a substituted or unsubstituted alkyl group; a substituted or unsubstituted aryl group; a substituted or unsubstituted heteroaryl group, or bond to adjacent groups to form a substituted or unsubstituted ring, Cy1 and Cy2 are the same as or different from each other, and each independently a substituted or unsubstituted benzene ring; or a substituted or unsubstituted naphthalene ring, Lz1 to Lz3 are the same as or different from each other, and each independently a direct bond; or a substituted or unsubstituted arylene group, Lz11 and Lz12 are the same as or different from each other, and each independently a direct bond; a substituted or unsubstituted alkylene group; or a substituted or unsubstituted arylene group, Xz1 and Xz2 are the same as or different from each other, and each independently a curable group, Rz1 and Rz2 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group, Rz3 and Rz4 are the same as or different from each other, and each independently deuterium; a substituted or unsubstituted alkyl group; a substituted or unsubstituted alkoxy group; a substituted or unsubstituted aryl group; or a substituted or unsubstituted heteroaryl group, lz1 to lz3 are each independently 0 or 1, n1 and n2 are each independently an integer of 0 to 7, and when n1 and n2 are each 2 or greater, substituents in the two or more parentheses are the same as or different from each other, n3 and n4 are each independently an integer of 0 to 4, and when n3 and n4 are each 2 or greater, substituents in the two or more parentheses are the same as or different from each other, m1 and m2 are each independently an integer of 1 to 5, and m1+n3 is 5 or less, and m2+n4 is 5 or less.

The compound of Chemical Formula 1 according to one embodiment of the present disclosure includes an amine group to which a fluorene group, to which a curable group and a halogen group (specifically, a fluoro group) are introduced, bonds, and also includes a tricyclic or higher cyclic group therewith. Accordingly, the compound has increased stability by suppressing radical formation at the corresponding position, and has high HOMO (highest occupied molecular orbital) energy level value and excellent hole-mobility. As a result, when including the compound of Chemical Formula 1 in a hole injection layer in an organic light emitting device, holes are readily injected from the hole injection layer to a hole transfer layer, and an advantage of obtaining an organic light emitting device with long lifetime properties is obtained.

In the present disclosure, a description of a certain member (layer) being placed "on" another member (layer) includes not only a case of the certain member (layer) being in contact with the another member but a case of still another member (layer) being present between the two members (layers).

In the present specification, a description of a certain part "including" certain constituents means capable of further including other constituents, and does not exclude other constituents unless particularly stated on the contrary.

In the present disclosure, the "curable group" means a photocurable group or a thermal curable group, and may mean a reactive substituent crosslinking compounds by being exposed to heat and/or light. The crosslinking may be produced by linking radicals generated while a carbon-carbon multiple bond or a cyclic structure is decomposed by heat treatment or light irradiation.

Hereinafter, substituents of the present disclosure will be described in detail.

In the present disclosure, ---- and

each mean a site bonding to other substituents or bonding sites.

In the present disclosure, the term "substitution" means a hydrogen atom bonding to a carbon atom of a compound being changed to another substituent, and the position of substitution is not limited as long as it is a position at which the hydrogen atom is substituted, that is, a position at which a substituent is capable of substituting, and when two or more substituents substitute, the two or more substituents may be the same as or different from each other.

In the present disclosure, the term "substituted or unsubstituted" means being substituted with one or more substituents selected from the group consisting of deuterium, a halogen group, a nitrile group, an alkyl group, a cycloalkyl group, an alkoxy group, an aryl group and a heteroaryl group or being unsubstituted, or being substituted with a substituent linking two or more substituents among the substituents illustrated above or being unsubstituted. For example, the "substituent linking two or more substituents" may include a biphenyl group. In other words, a biphenyl group may be an aryl group, or interpreted as a substituent linking two phenyl groups.

In addition, in the present disclosure, the term "substituted or unsubstituted" means being substituted with one or more substituents selected from the group consisting of deuterium, a halogen group, a nitrile group, an alkyl group having 1 to 20 carbon atoms, a cycloalkyl group having 3 to 30 carbon atoms, an alkoxy group having 1 to 20 carbon atoms, an aryl group having 6 to 60 carbon atoms and a heteroaryl group having 2 to 60 carbon atoms or being unsubstituted, or being substituted with a substituent linking two or more substituents among the substituents illustrated above or being unsubstituted.

In the present disclosure, the halogen group is a fluoro group (—F), a chloro group (—Cl), a bromo group (—Br) or an iodo group (—I).

In the present disclosure, the alkyl group may be linear or branched, and although not particularly limited thereto, the number of carbon atoms may be from 1 to 20. According to another embodiment, the number of carbon atoms of the alkyl group is from 1 to 10. Specific examples of the alkyl group may include a methyl group, an ethyl group, an n-propyl group, an isopropyl group, an n-butyl group, an isobutyl group, a tert-butyl group, an n-pentyl group, an n-hexyl group, an n-heptyl group and the like, but are not limited thereto.

In the present disclosure, the cycloalkyl group is not particularly limited, but may have 3 to 60 carbon atoms, and according to one embodiment, the number of carbon atoms of the cycloalkyl group is from 3 to 30. According to another embodiment, the number of carbon atoms of the cycloalkyl group is from 3 to 20. Specific examples of the cycloalkyl group may include a cyclopropyl group, a cyclobutyl group, a cyclopentyl group, a cyclohexyl group, a cycloheptyl group, a cyclooctyl group and the like, but are not limited thereto.

In the present disclosure, the alkoxy group may be linear or branched. The number of carbon atoms of the alkoxy group is not particularly limited, but may be from 1 to 20. Specific examples of the alkoxy group may include a methoxy group, an ethoxy group, an n-propoxy group, an n-butoxy group, a tert-butoxy group, an n-pentyloxy group, an n-hexyloxy group, an n-octyloxy group, an n-nonyloxy group, an n-decyloxy group and the like, but are not limited thereto.

In the present disclosure, the aryl group is not particularly limited, but may have 6 to 60 carbon atoms, and the aryl group may be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. When the aryl group is a polycyclic aryl group, examples thereof may include a naphthyl group, an anthracenyl group, a phenanthrenyl group, a pyrenyl group, a perylenyl group, a triphenylenyl group, a chrysenyl group, a fluorenyl group and the like, but are not limited thereto.

In the present disclosure, the fluorenyl group may be substituted, and two substituents may bond to each other to form a spiro structure.

When the fluorenyl group is substituted, a spirofluorenyl group such as

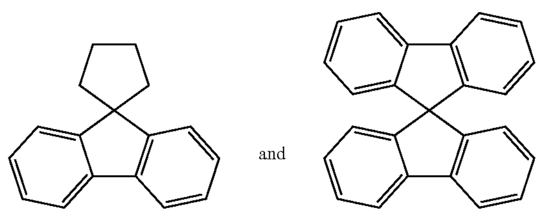

and a substituted fluorenyl group such as

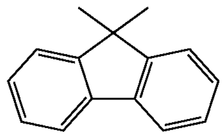

(9,9-dimethylfluorenyl group) and

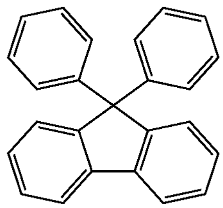 [SMILES: c1ccc(C2(c3ccccc3)c3ccccc3-c3ccccc32)cc1]

(9,9-diphenylfluorenyl group) may be included. However, the structure is not limited thereto.

In the present disclosure, the heteroaryl group is an aromatic cyclic group including one or more of N, O, P, S, Si or Se as a heteroatom, and although not particularly limited thereto, the number of carbon atoms may be from 2 to 60. According to one embodiment, the number of carbon atoms of the heteroaryl group is from 2 to 30. Examples of the heteroaryl group may include a pyridine group, a pyrrole group, a pyrimidine group, a pyridazine group, a furan group, a thiophene group, a benzothiophene group, a benzofuran group, a dibenzothiophene group, a dibenzofuran group and the like, but are not limited thereto.

In the present disclosure, the descriptions on the aryl group provided above may be applied to the arylene group except that the arylene group is divalent.

In the present disclosure, the "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other. In Chemical Formula 1 of the present disclosure, Ra and Rb may be adjacent groups, and Rc and Rd may be adjacent groups.

In the present disclosure, the "ring" in the substituted or unsubstituted ring formed by bonding to each other means a hydrocarbon ring; or a heteroring. The hydrocarbon ring may be aromatic, aliphatic, or a fused ring of aromatic and aliphatic. As for the heteroring, the descriptions on the heterocyclic group may be applied except for those that are divalent.

In the present disclosure, the descriptions on the aryl group provided above may be applied to the aromatic hydrocarbon ring except for those that are divalent.

In the present disclosure, the descriptions on the cycloalkyl group provided above may be applied to the aliphatic hydrocarbon ring except for those that are divalent.

In the present disclosure, the "energy level" means magnitude of energy. Accordingly, the energy level is interpreted to mean an absolute value of the corresponding energy value. For example, having a deep energy level means that the absolute value increases in a negative direction from a vacuum level.

In the present disclosure, a HOMO (highest occupied molecular orbital) means a molecular orbital function where electrons are in an area with highest energy among areas capable of participating in bonding, a LUMO (lowest unoccupied molecular orbital) means a molecular orbital function where electrons are in an area with lowest energy among anti-bonding areas, and a HOMO energy level means a distance from a vacuum level to the HOMO. In addition, a LUMO energy level means a distance from a vacuum level to the LUMO.

According to one embodiment of the present disclosure, the compound of Chemical Formula 1 preferably includes compounds having solubility for suitable organic solvents.

In addition, with the compound according to one embodiment of the present disclosure, an organic light emitting device may be manufactured using a solution coating method, and accordingly, a device having a large area may be manufactured.

According to one embodiment of the present disclosure, Chemical Formula 1 is represented by the following Chemical Formula 2.

[Chemical Formula 2]

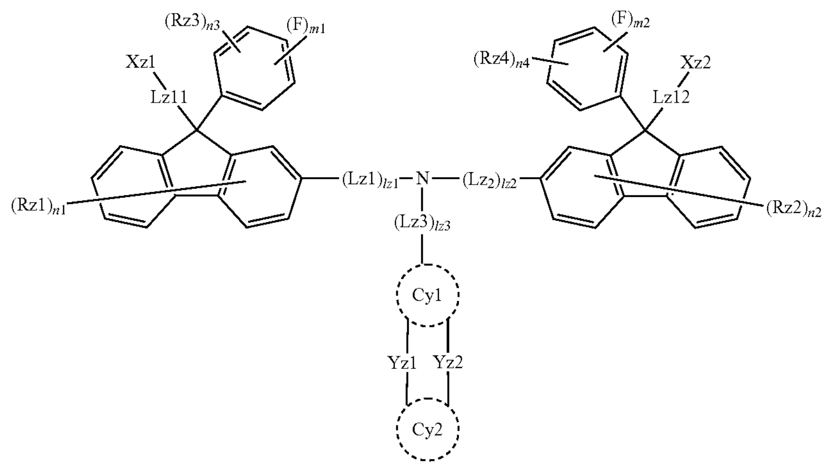

In Chemical Formula 2,

Lz1 to Lz3, Lz11, Lz12, Xz1, Xz2, Rz1 to Rz4, Yz1, Yz2, Cy1, Cy2, lz1 to lz3, n1 to n4, m1 and m2 have the same definitions as in Chemical Formula 1.

According to one embodiment of the present disclosure, Lz1 to Lz3 are the same as or different from each other, and each independently a direct bond; or a substituted or unsubstituted arylene group having 6 to 30 carbon atoms.

According to another embodiment, Lz1 to Lz3 are the same as or different from each other, and each independently a direct bond; a substituted or unsubstituted phenylene group; or a substituted or unsubstituted naphthylene group.

According to another embodiment, Lz1 and Lz2 are a direct bond.

According to another embodiment, Lz3 is a direct bond; a substituted or unsubstituted phenylene group; or a substituted or unsubstituted naphthylene group.

According to one embodiment of the present disclosure, Chemical Formula 1 is represented by any one of the following Chemical Formulae 3 to 5.

[Chemical Formula 3]

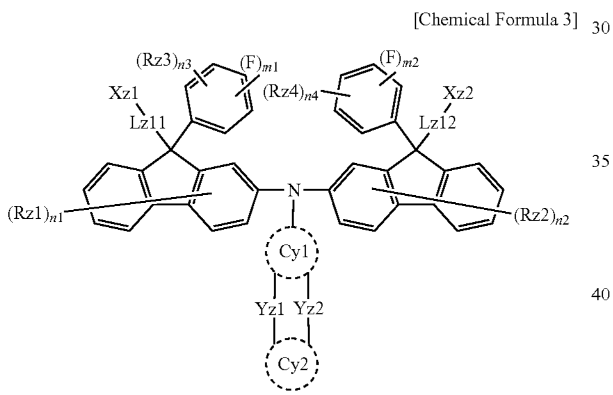

[Chemical Formula 4]

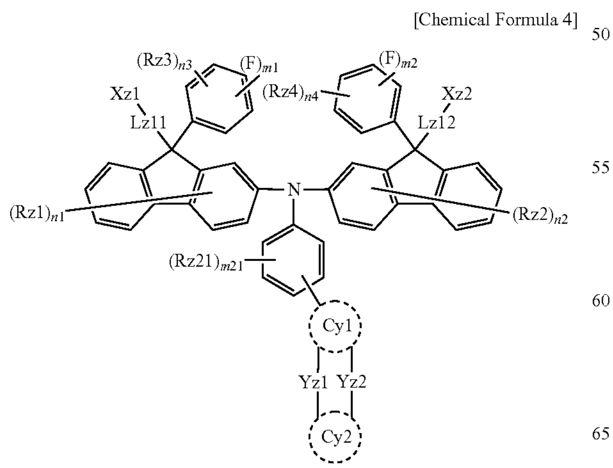

-continued

[Chemical Formula 5]

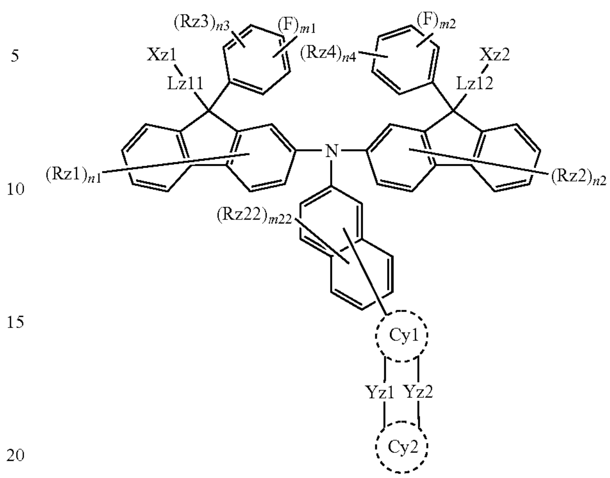

In Chemical Formulae 3 to 5,

Lz11, Lz12, Xz1, Xz2, Rz1 to Rz4, Cy1, Cy2, Yz1, Yz2, n1 to n4, m1 and m2 have the same definitions as in Chemical Formula 1, Rz21 and Rz22 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group, and m21 is an integer of 0 to 4, m22 is an integer of 0 to 6, and when m21 and m22 are each an integer of 2 or greater, substituents in the two or more parentheses are the same as or different from each other.

According to one embodiment of the present disclosure, m1 and m2 are each independently an integer of 1 to 5.

According to one embodiment of the present disclosure, n3 and n4 are each independently 0 or 1.

According to one embodiment of the present disclosure,

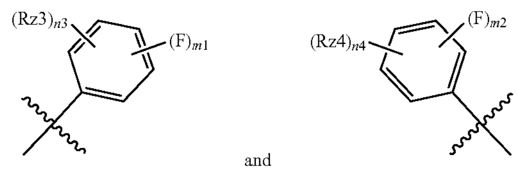

and are the same as or different from each other and may be each independently any one of the following structures, and

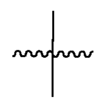

means a bonding position.

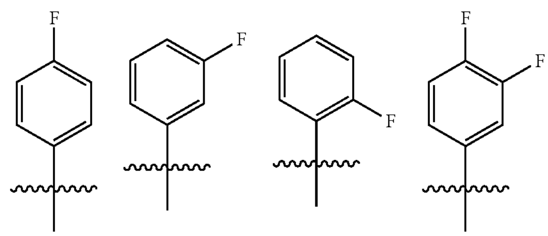

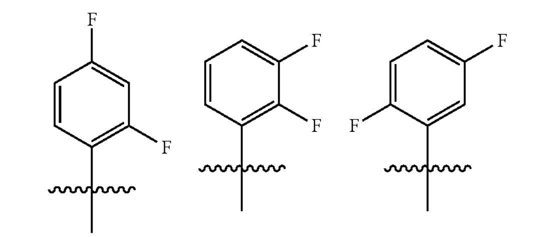

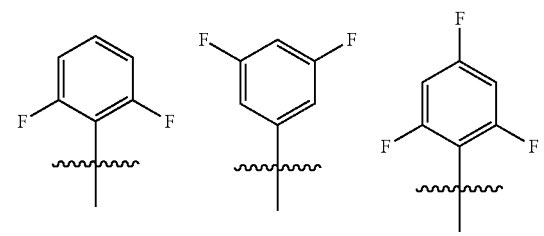

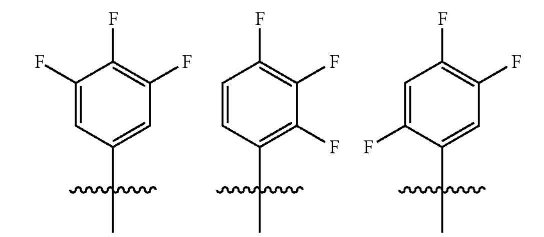

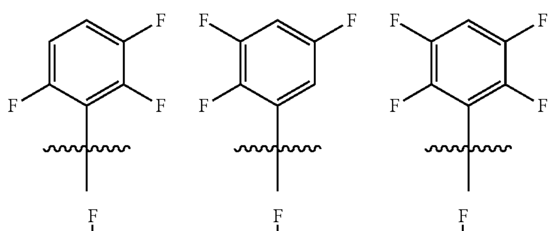

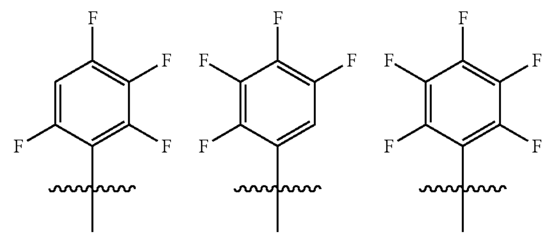

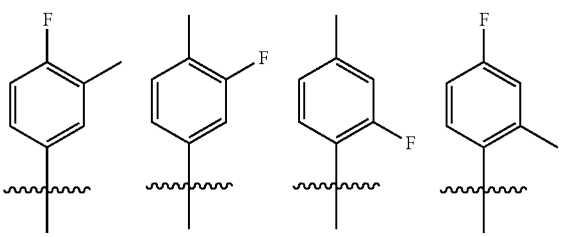

-continued

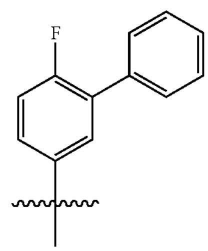

According to one embodiment of the present disclosure, Lz11 and Lz12 are the same as or different from each other, and each independently a direct bond; a substituted or unsubstituted alkylene group having 1 to 20 carbon atoms; or a substituted or unsubstituted arylene group having 6 to 30 carbon atoms.

According to another embodiment, Lz11 and Lz12 are the same as or different from each other, and each independently a direct bond; a substituted or unsubstituted butylene group; or a substituted or unsubstituted phenylene group.

According to one embodiment of the present disclosure, Xz1 and Xz2 are the same as or different from each other, and each independently a curable group.

According to one embodiment of the present disclosure, the curable group is any one selected from the group consisting of the following structures.

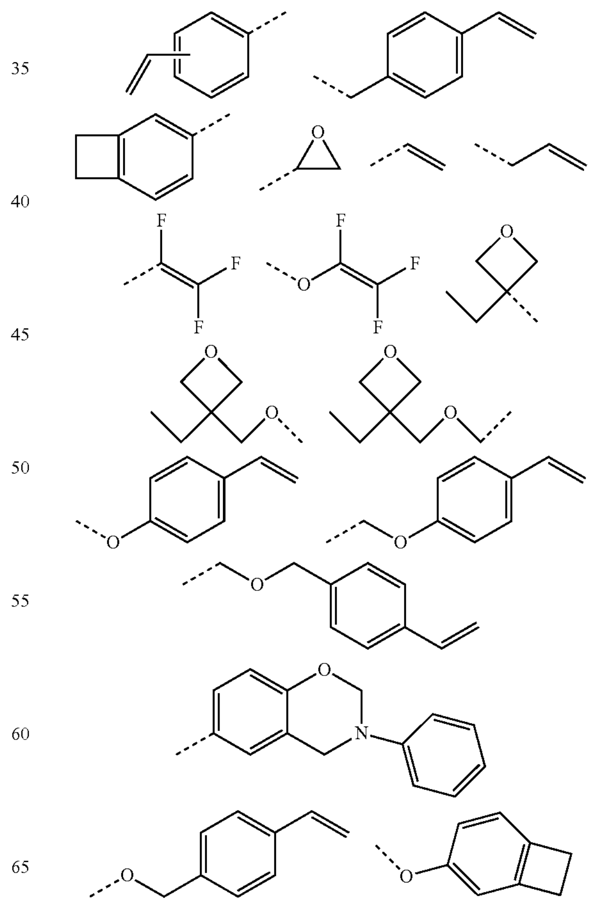

-continued

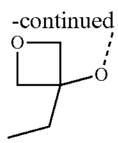

In the structures, ---- means a bonding position.

According to one embodiment of the present disclosure, Yz1 and Yz2 are the same as or different from each other, and each independently a direct bond, O, S, CRaRb or SiRcRd.

According to one embodiment of the present disclosure, when any one of Yz1 or Yz2 is a direct bond, the other one is O, S, CRaRb or SiRcRd.

According to one embodiment of the present disclosure, Yz1 and Yz2 are the same as or different from each other and each independently a direct bond, O, S, CRaRb or SiRcRd, and when any one of Yz1 or Yz2 is a direct bond, the other one is O, S, CRaRb or SiRcRd.

According to one embodiment of the present disclosure, Ra, Rb, Rc and Rd are the same as or different from each other, and each independently hydrogen; deuterium; a substituted or unsubstituted alkyl group; a substituted or unsubstituted aryl group; or a substituted or unsubstituted heteroaryl group, or bond to adjacent groups to form a substituted or unsubstituted ring.

According to one embodiment of the present disclosure, Ra, Rb, Rc and Rd are the same as or different from each other, and each independently hydrogen; deuterium; a substituted or unsubstituted alkyl group having 1 to 30 carbon atoms; a substituted or unsubstituted aryl group having 6 to 30 carbon atoms; or a substituted or unsubstituted heteroaryl group having 2 to 30 carbon atoms, or bond to adjacent groups to form a substituted or unsubstituted ring having 2 to 30 carbon atoms.

According to one embodiment of the present disclosure, Ra, Rb, Rc and Rd are the same as or different from each other, and each independently hydrogen; deuterium; a substituted or unsubstituted alkyl group having 1 to 10 carbon atoms; or a substituted or unsubstituted aryl group having 6 to 10 carbon atoms, or bond to adjacent groups to form a substituted or unsubstituted fluorene ring having 6 to 30 carbon atoms; or a substituted or unsubstituted heteroring having 2 to 30 carbon atoms.

According to one embodiment of the present disclosure, Ra, Rb, Rc and Rd are the same as or different from each other, and each independently hydrogen; deuterium; a substituted or unsubstituted alkyl group having 1 to 10 carbon atoms; or an aryl group having 6 to 10 carbon atoms unsubstituted or substituted with a halogen group, or bond to adjacent groups to form a substituted or unsubstituted fluorene ring having 6 to 30 carbon atoms; or a substituted or unsubstituted heteroring having 2 to carbon atoms.

According to one embodiment of the present disclosure, Ra, Rb, Rc and Rd are the same as or different from each other, and each independently a substituted or unsubstituted methyl group; or a substituted or unsubstituted phenyl group, or bond to adjacent groups to form a substituted or unsubstituted fluorene ring; or a substituted or unsubstituted xanthene ring.

According to one embodiment of the present disclosure, Ra, Rb, Rc and Rd are the same as or different from each other, and each independently a substituted or unsubstituted methyl group; or a phenyl group unsubstituted or substituted with a halogen group, or bond to adjacent groups to form a substituted or unsubstituted fluorene ring; or a substituted or unsubstituted xanthene ring.

According to one embodiment of the present disclosure, Cy1 and Cy2 are the same as or different from each other, and each independently a substituted or unsubstituted benzene ring; or a substituted or unsubstituted naphthalene ring.

According to one embodiment of the present disclosure, when any one of Cy1 or Cy2 is a substituted or unsubstituted benzene ring, the other one is a substituted or unsubstituted benzene ring; or a substituted or unsubstituted naphthalene ring.

According to one embodiment of the present disclosure, when any one of Cy1 or Cy2 is a substituted or unsubstituted naphthalene ring, the other one is a substituted or unsubstituted benzene ring.

According to one embodiment of the present disclosure, Cy1 and Cy2 are the same as or different from each other, and each independently a substituted or unsubstituted benzene ring; or a substituted or unsubstituted naphthalene ring, and at least one of Cy1 or Cy2 is a substituted or unsubstituted benzene ring.

According to one embodiment of the present disclosure, Cy1 and Cy2 are the same as or different from each other, and each independently any one selected from the group consisting of the following structures.

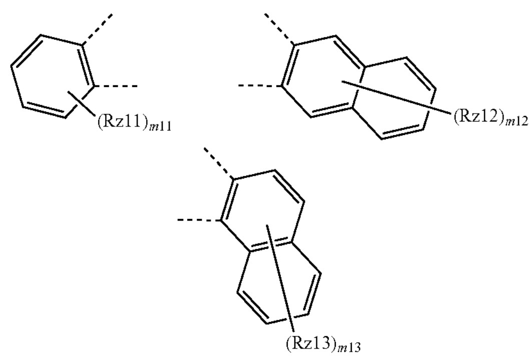

In the structures, ---- means a bonding position,

Rz11 to Rz13 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group, and m11 is an integer of 0 to 4, m12 and m13 are each independently an integer of 0 to 6, and when m11 to m13 are each an integer of 2 or greater, substituents in the two or more parentheses are the same as or different from each other.

According to one embodiment of the present disclosure, Rz11 to Rz13 are the same as or different from each other, and each independently deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to another embodiment, Rz11 to Rz13 are deuterium.

According to another embodiment, m11 to m13 are 0.

According to one embodiment of the present disclosure, m11 to m13 are each independently 0 or 1.

According to one embodiment of the present disclosure, Rz1 and Rz2 are the same as or different from each other, and each independently deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to another embodiment, Rz1 and Rz2 are deuterium.

According to another embodiment, n1 and n2 are 0.

According to one embodiment of the present disclosure, Rz3 and Rz4 are the same as or different from each other, and each independently deuterium; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to another embodiment, Rz3 and Rz4 are the same as or different from each other, and each independently an alkyl group having 1 to 20 carbon atoms; or an aryl group having 6 to carbon atoms.

According to another embodiment, Rz3 and Rz4 are the same as or different from each other, and each independently a substituted or unsubstituted methyl group; or a substituted or unsubstituted phenyl group.

According to another embodiment, Rz3 and Rz4 are the same as or different from each other, and each independently a methyl group; or a phenyl group.

According to one embodiment of the present disclosure, n1 and n2 are each independently 0 or 1.

According to one embodiment of the present disclosure, Rz21 and Rz22 are the same as or different from each other, and each independently deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to another embodiment, Rz21 and Rz22 are deuterium.

According to another embodiment, m21 and m22 are 0.

According to one embodiment of the present disclosure, Chemical Formula 1 is any one selected from the group consisting of the following compounds.

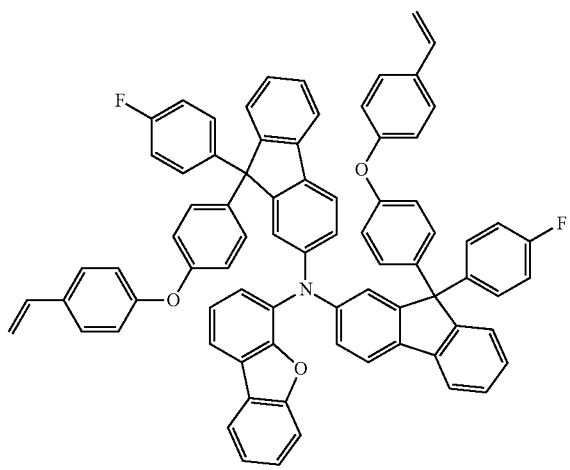

-continued

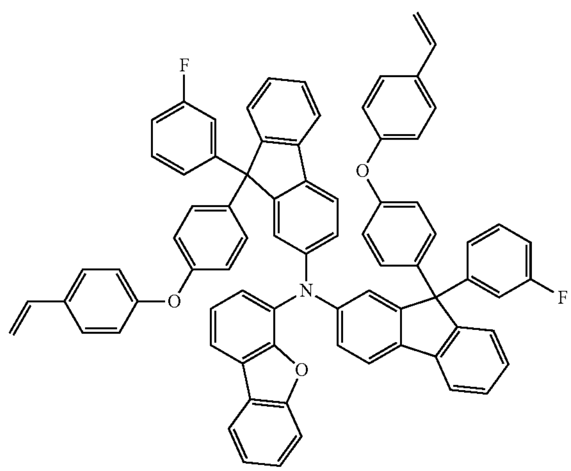

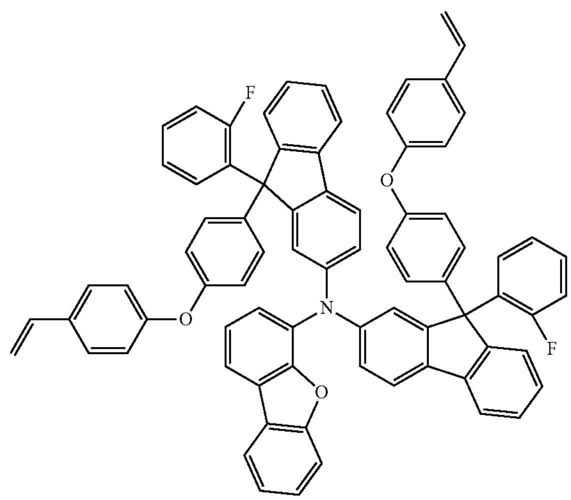

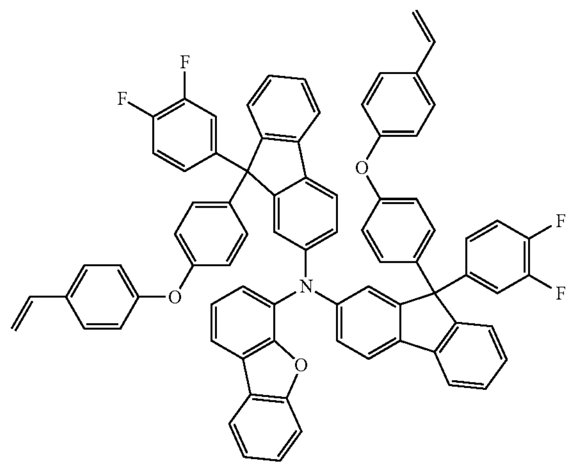

-continued
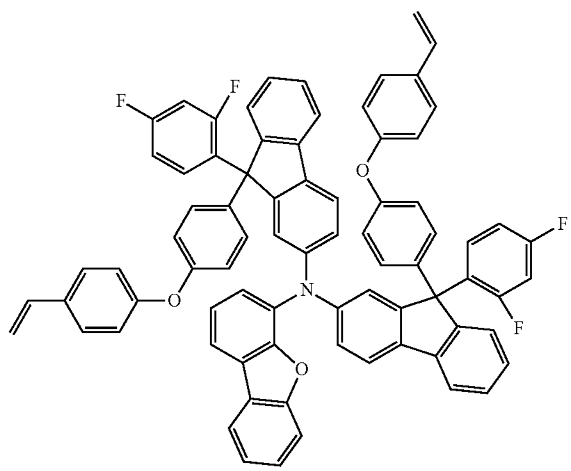
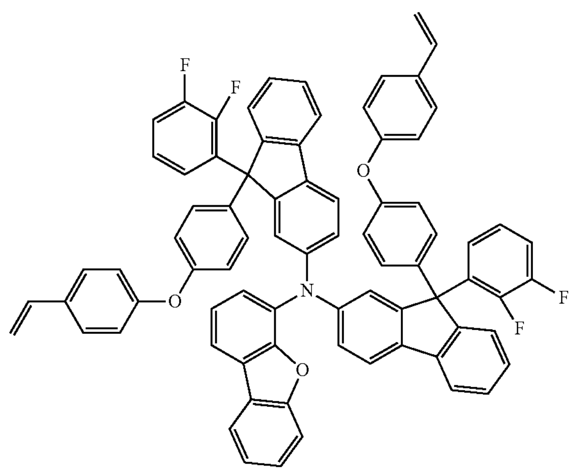
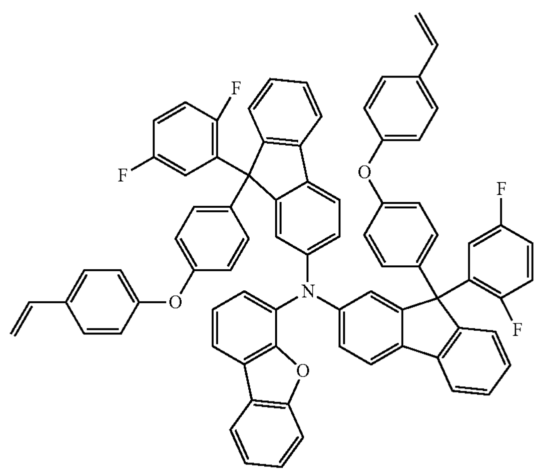
-continued
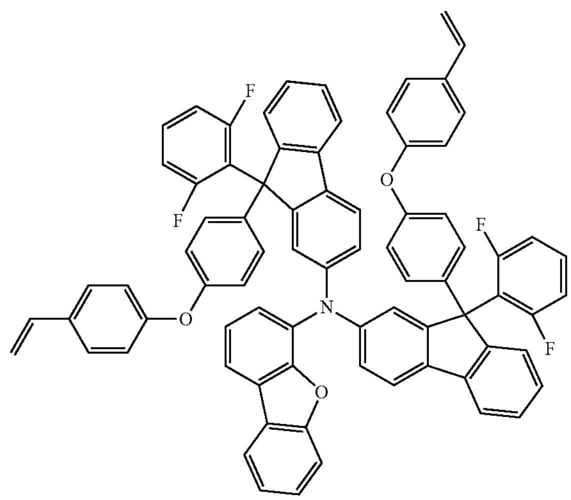
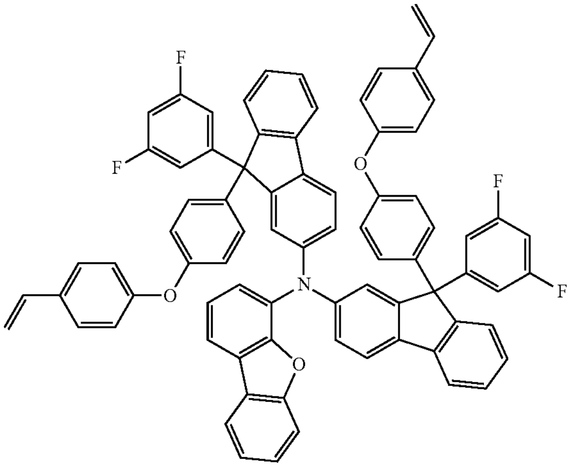
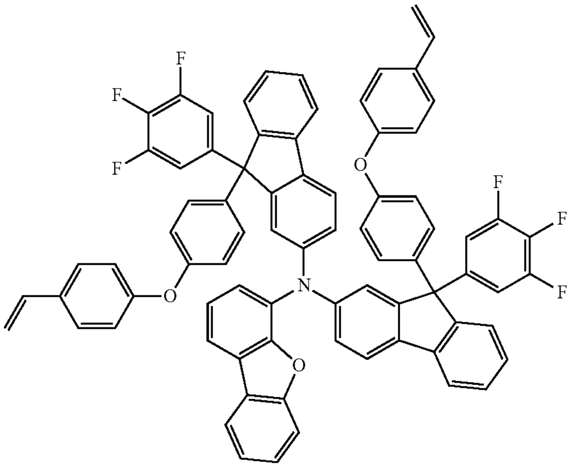

-continued
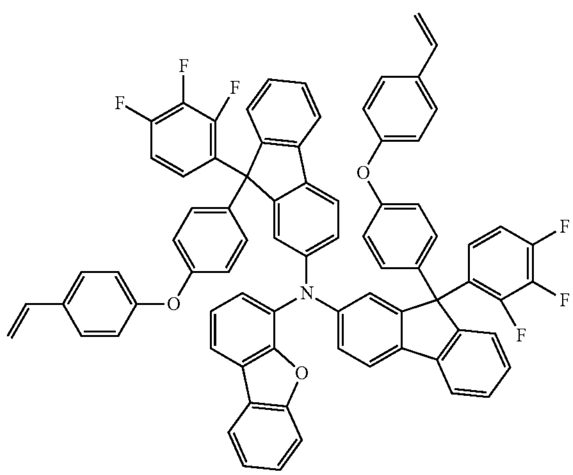
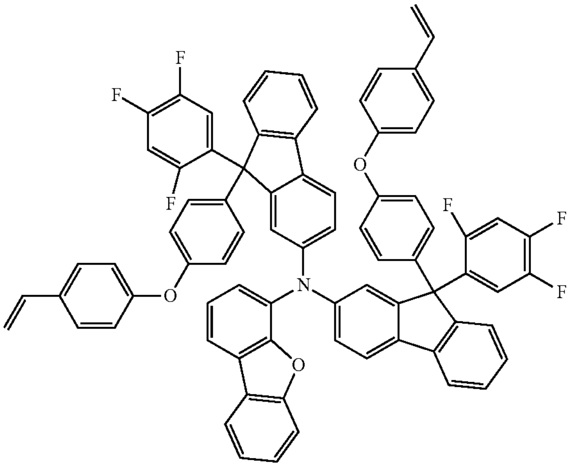
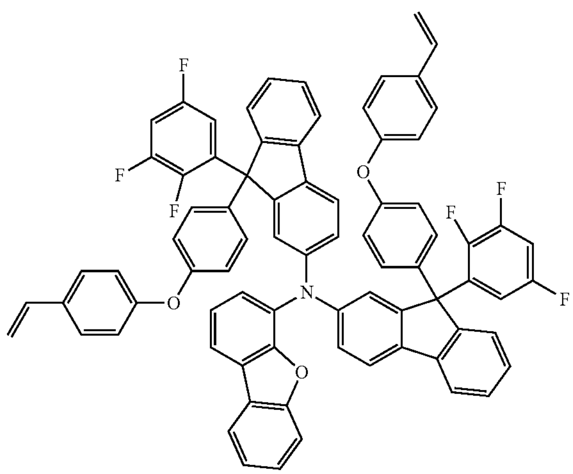
-continued
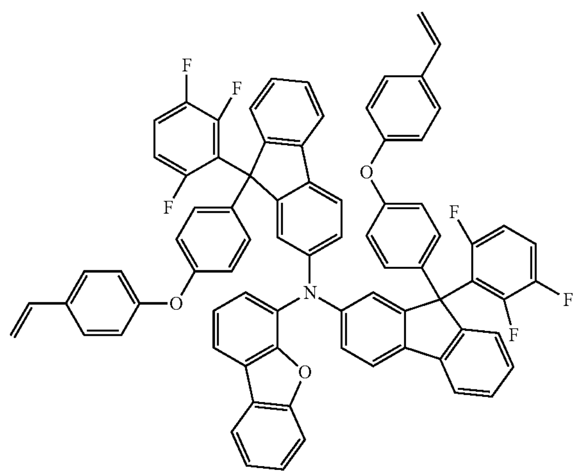
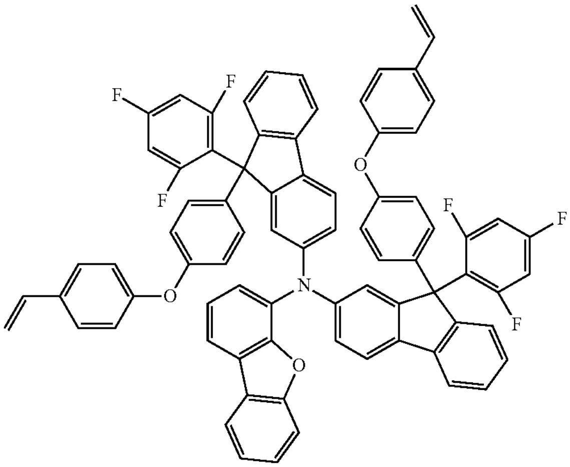
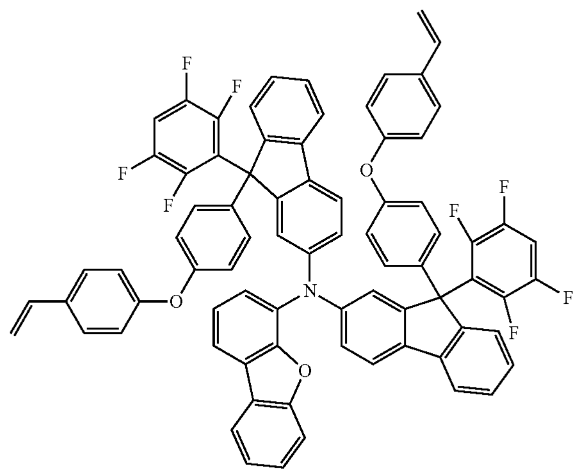

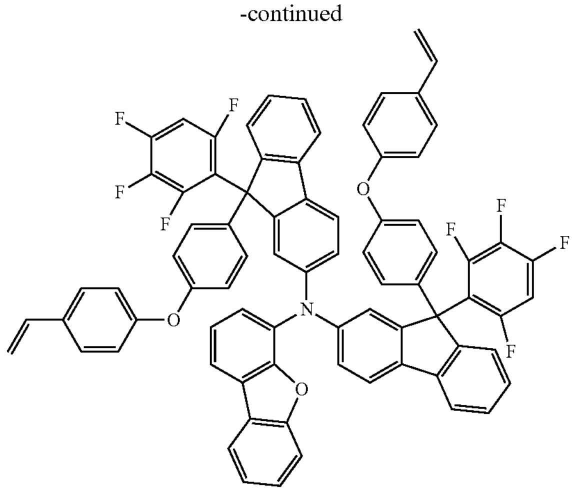
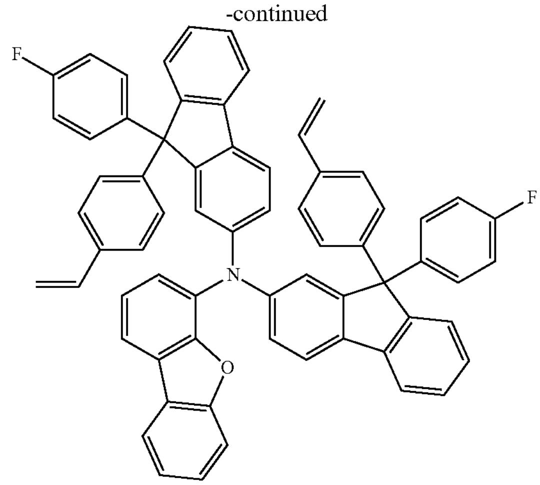
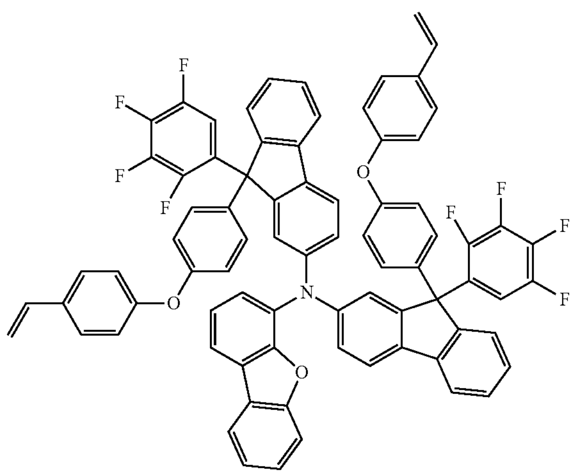
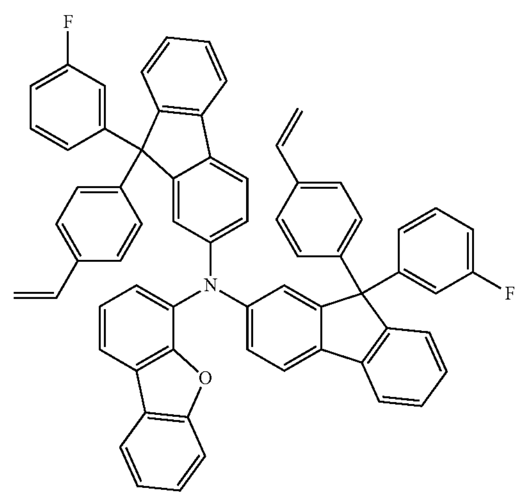
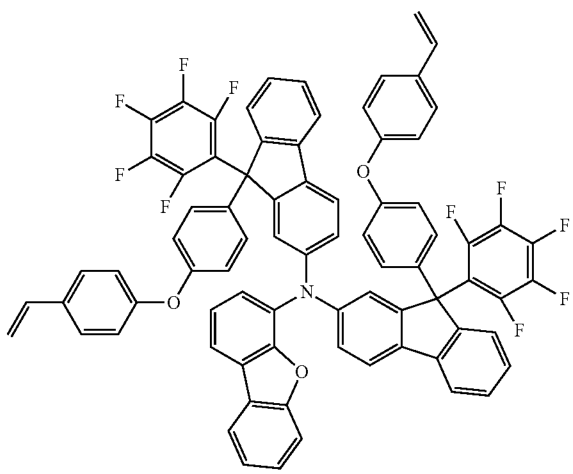
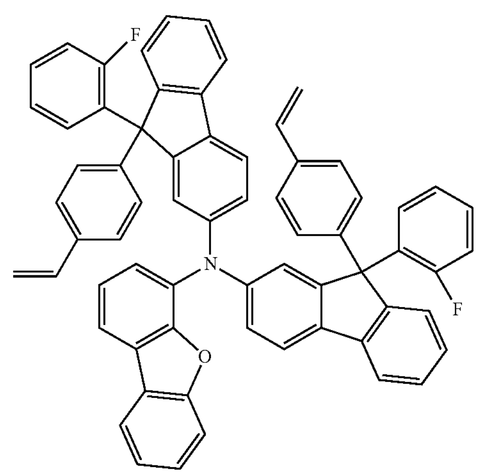

-continued
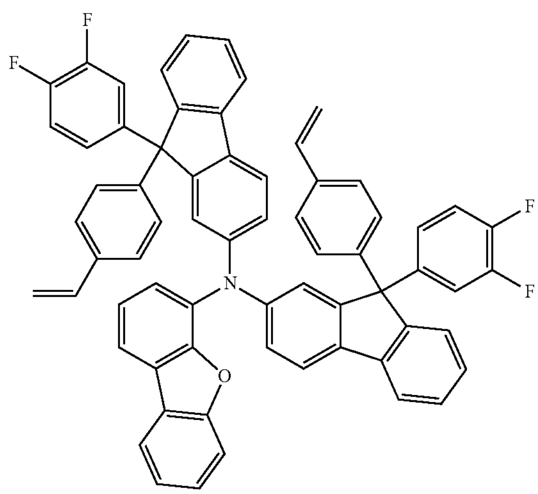
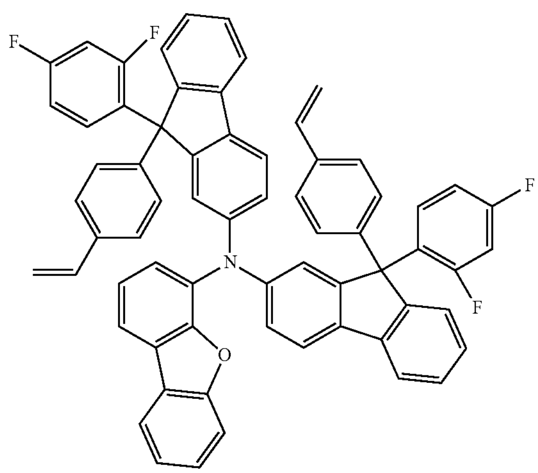
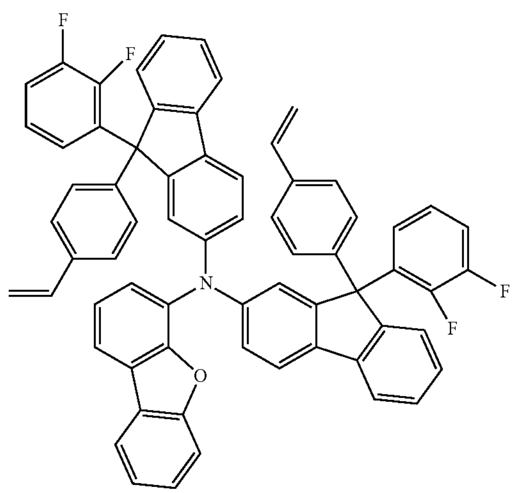
-continued
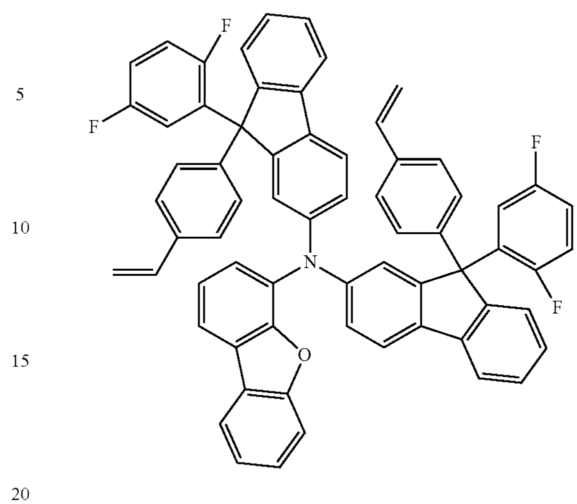
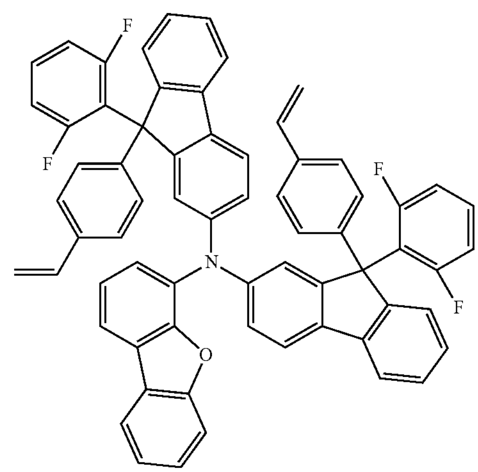
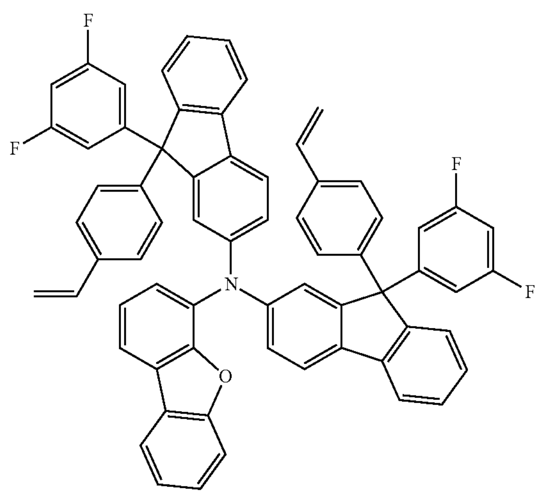

-continued
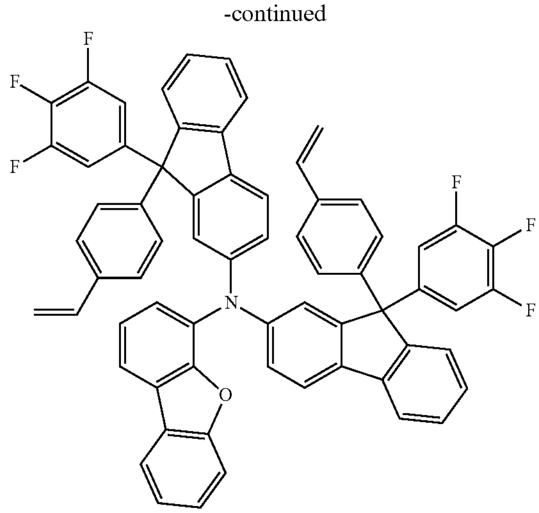
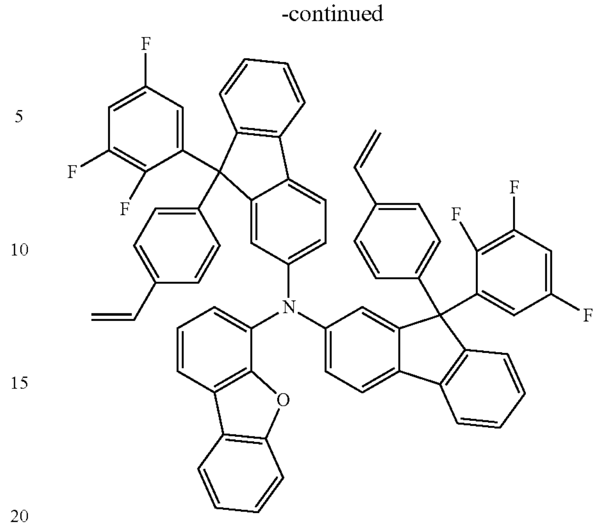
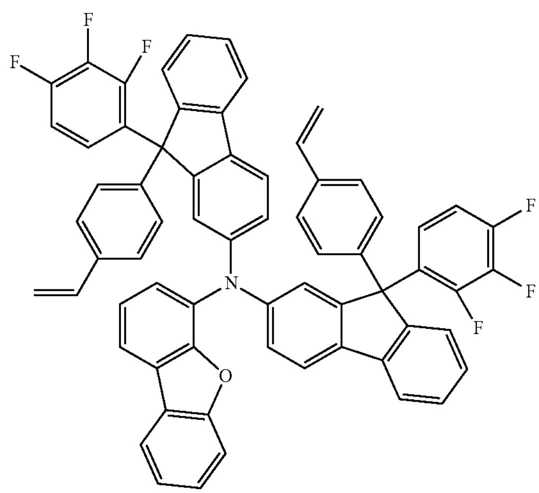
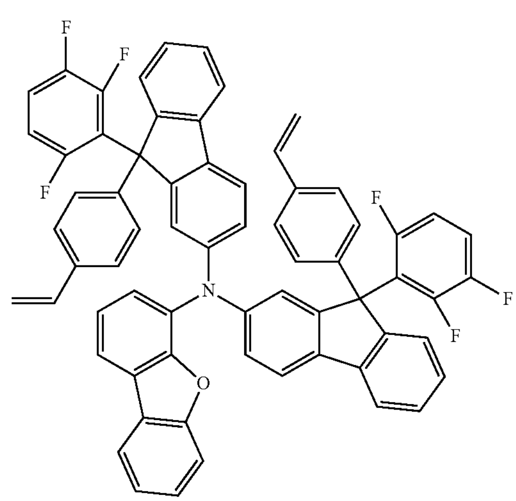
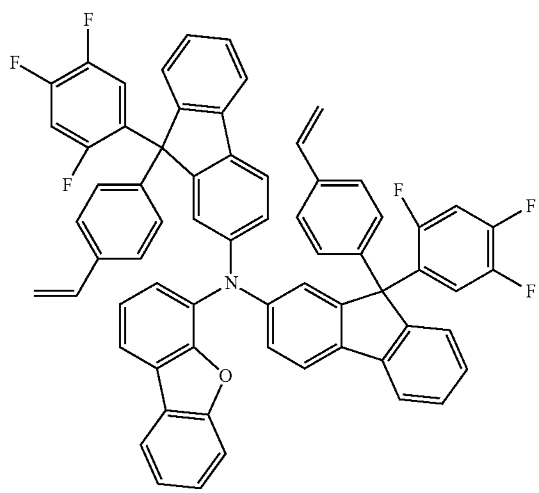
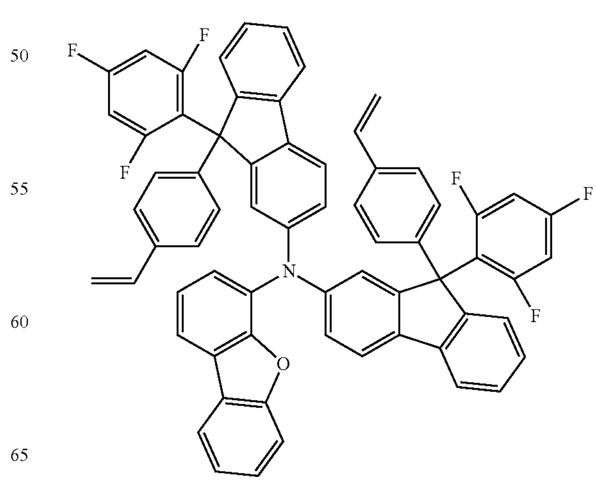
-continued -continued
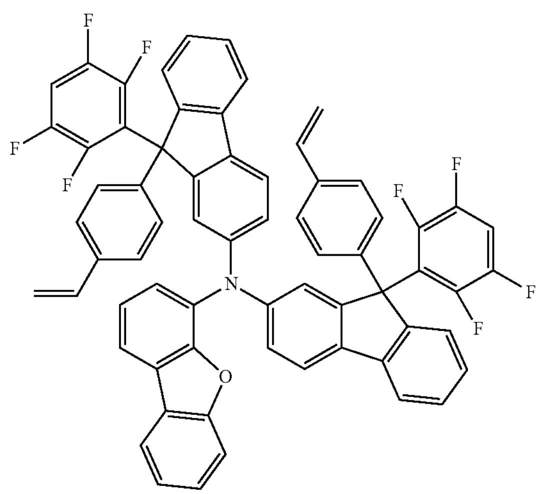
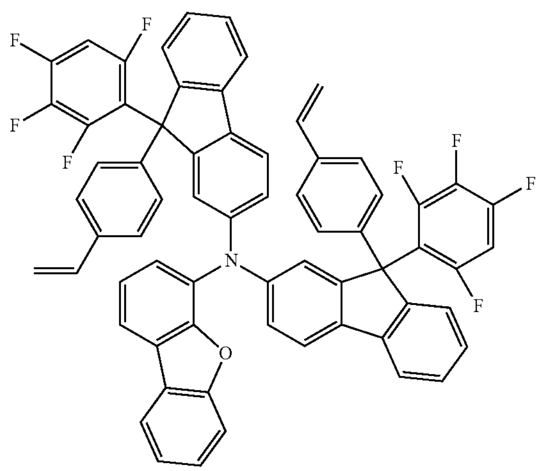
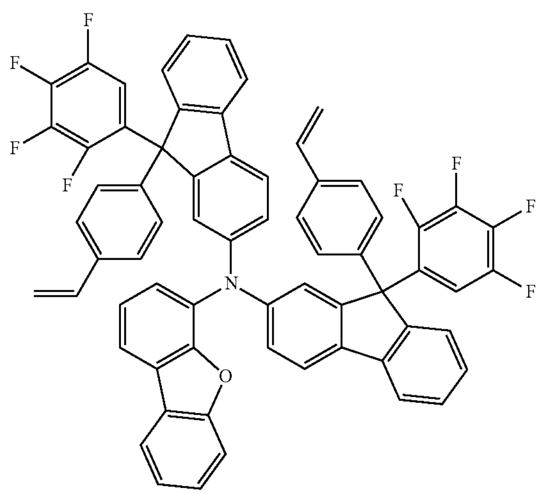
-continued
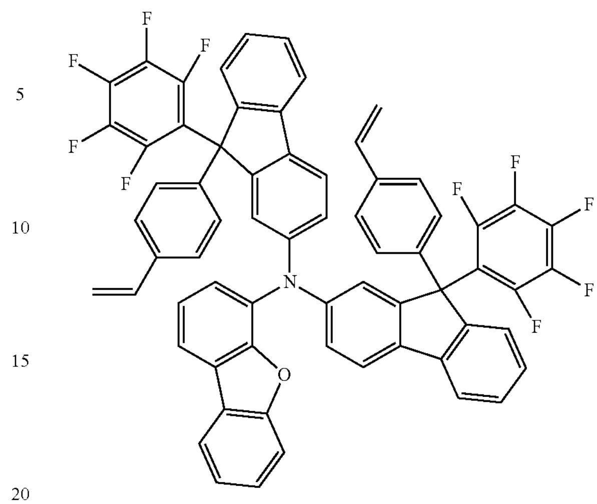
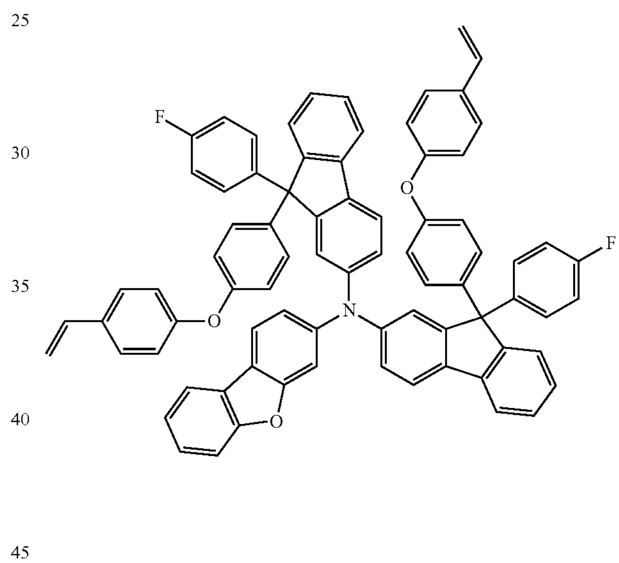
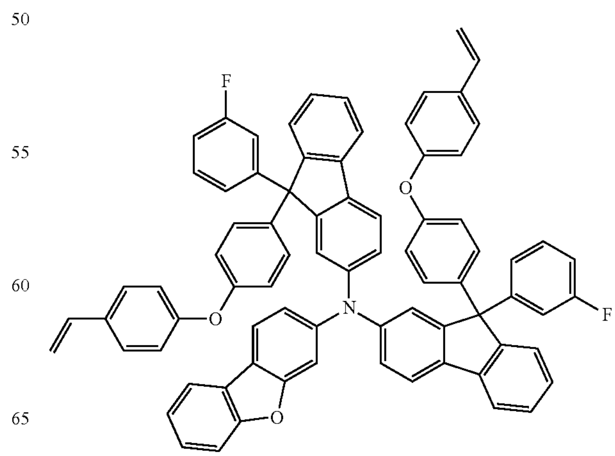

-continued
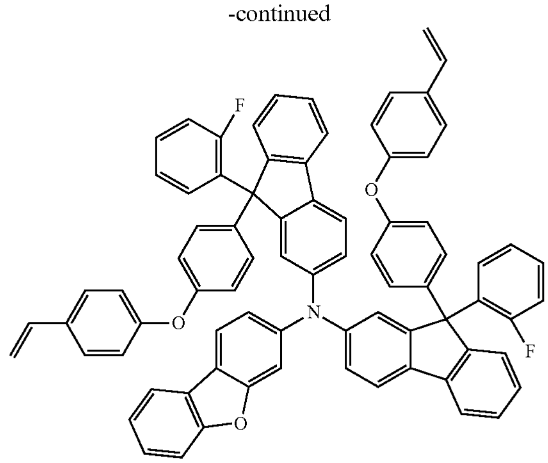
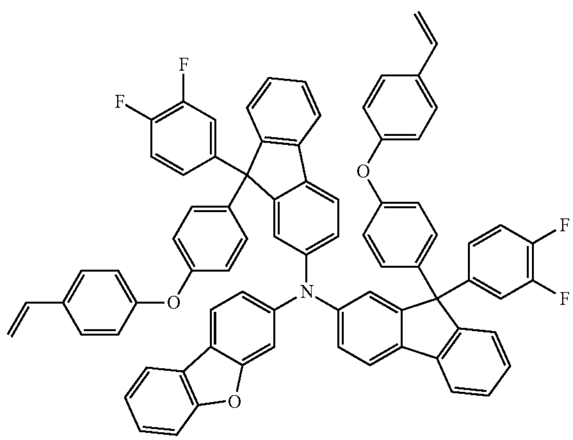
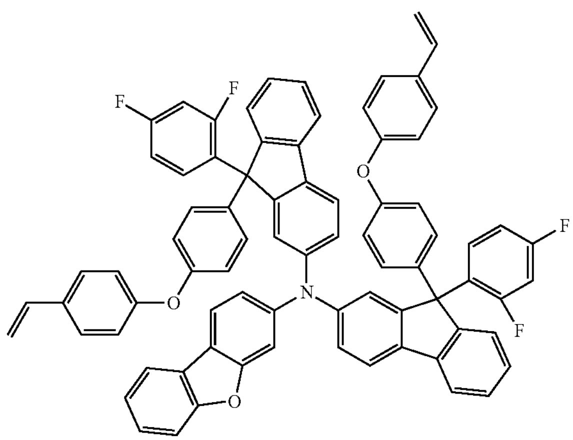
-continued
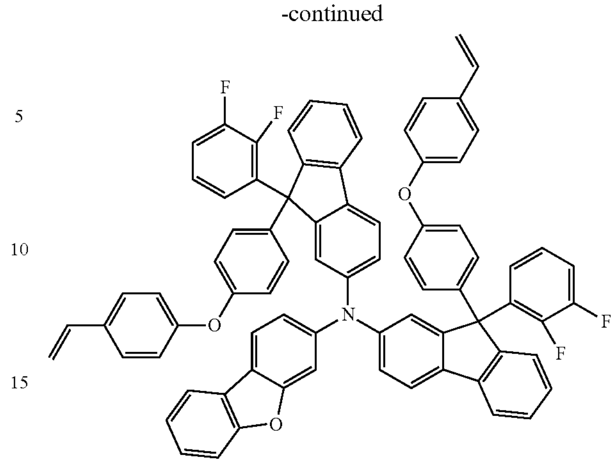
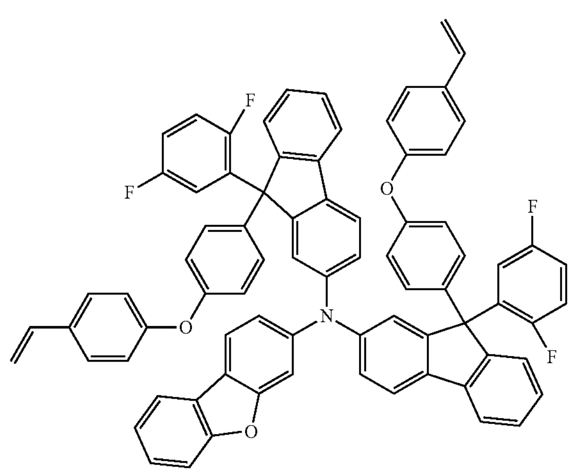
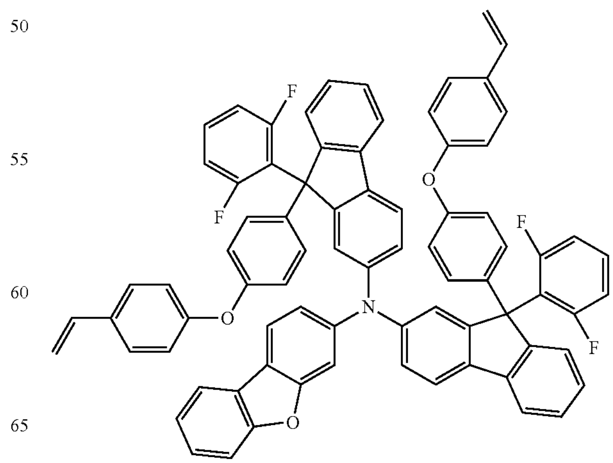

-continued
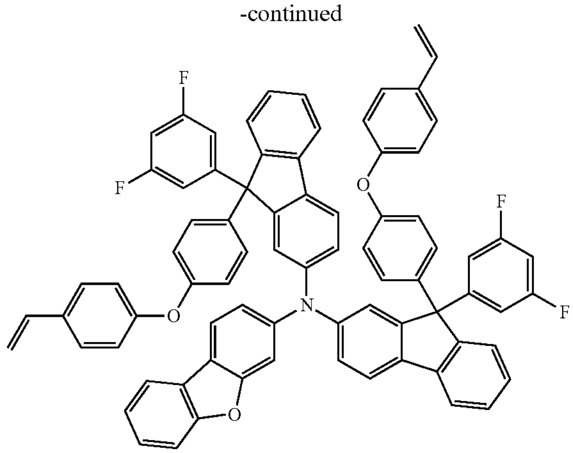
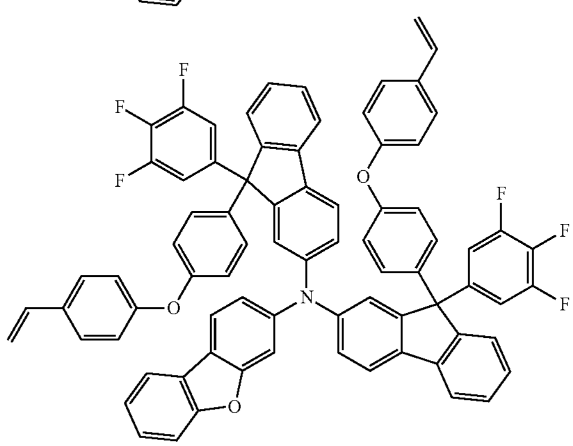
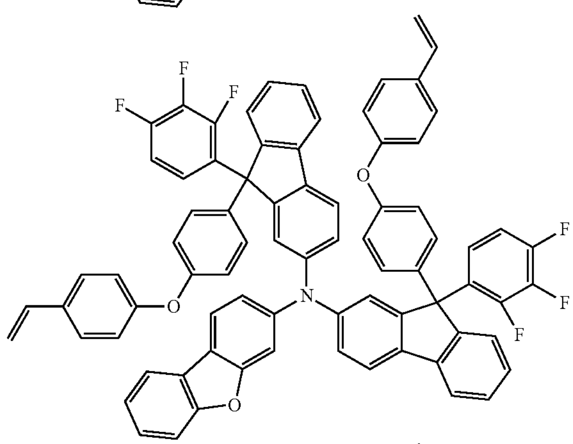
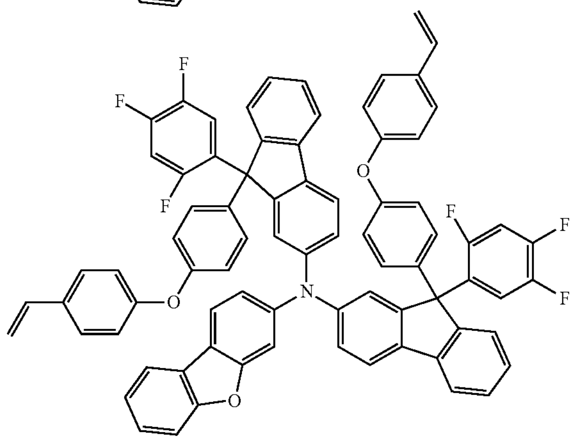
-continued
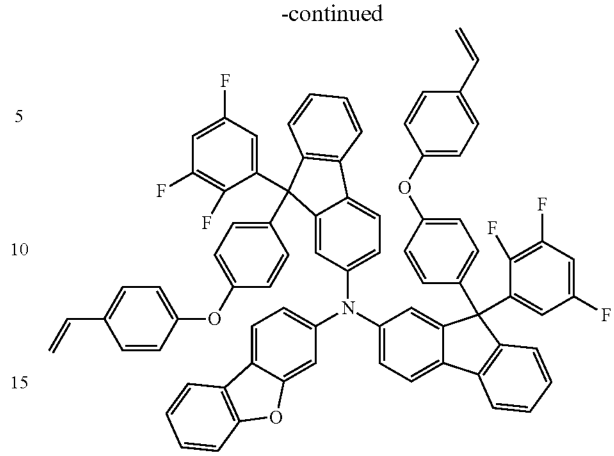
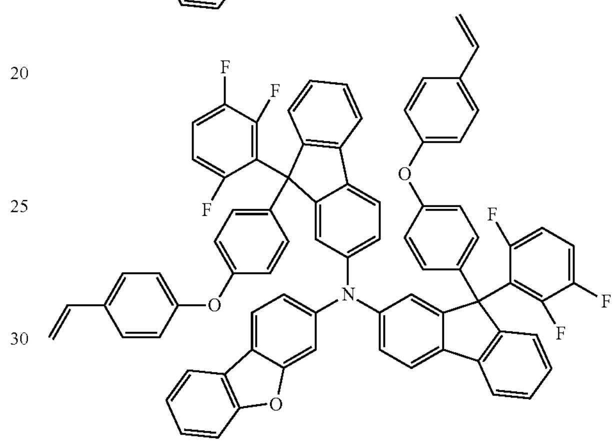
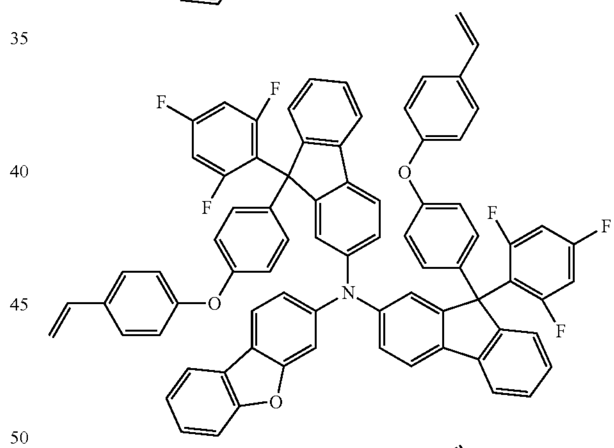
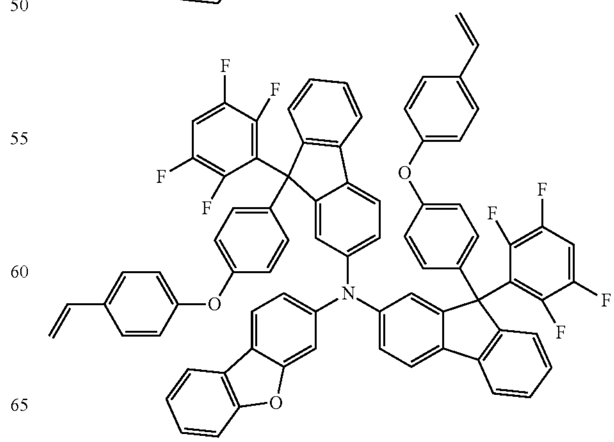

-continued
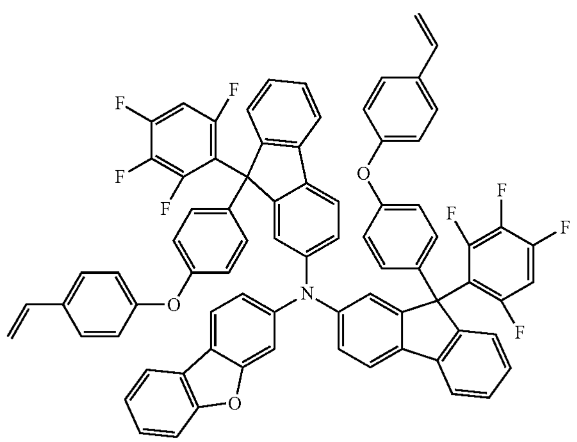
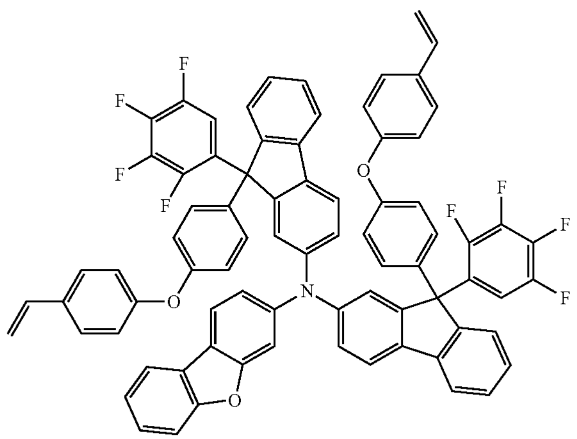
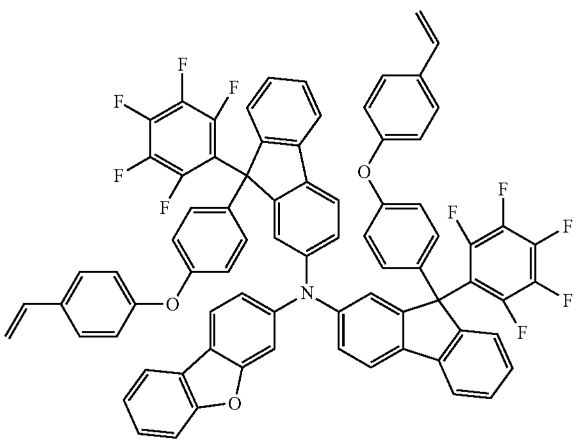
-continued
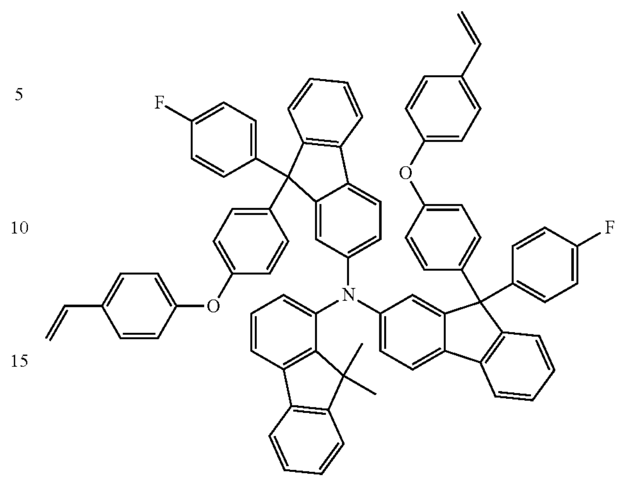
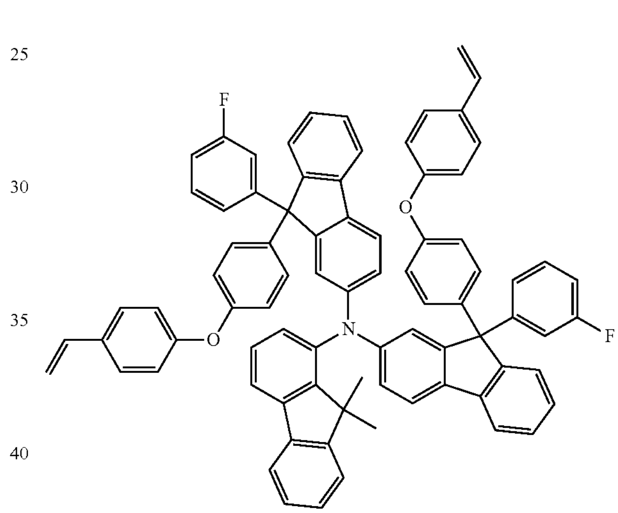
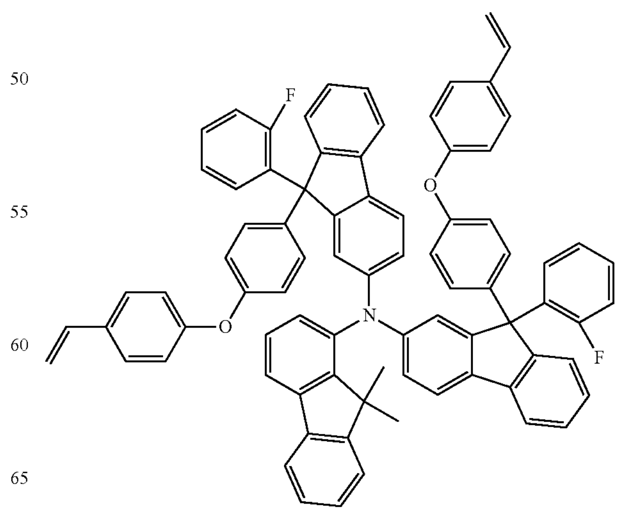

-continued
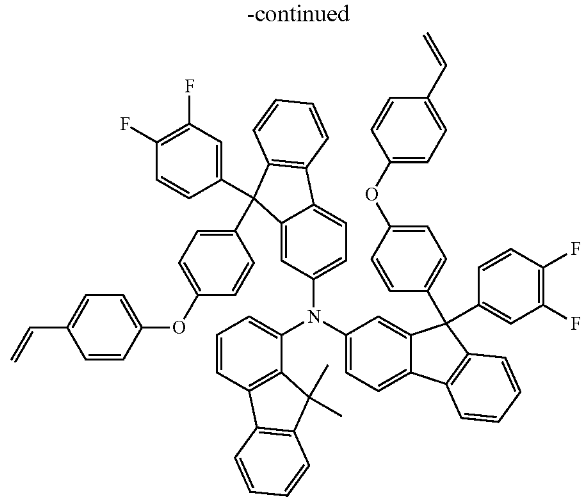
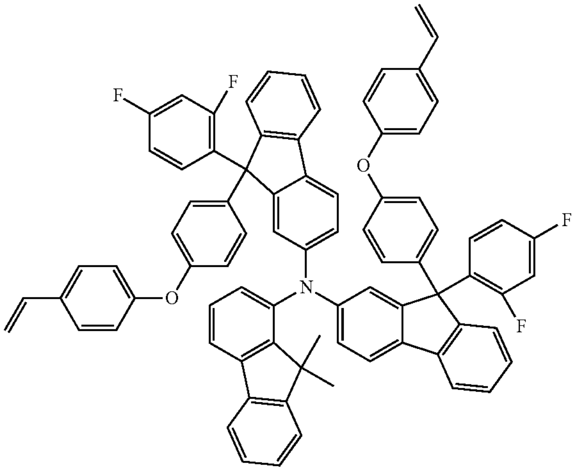
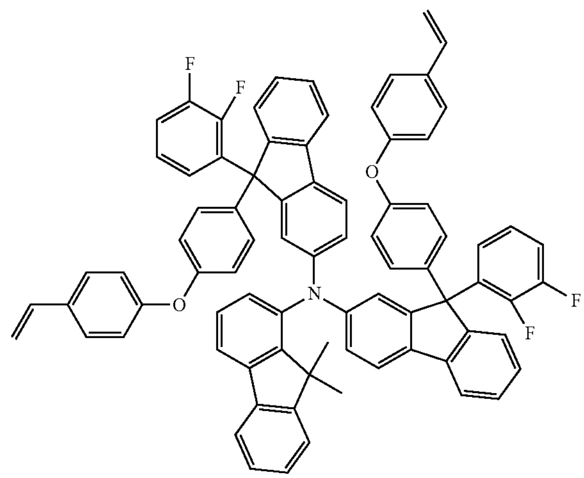
-continued
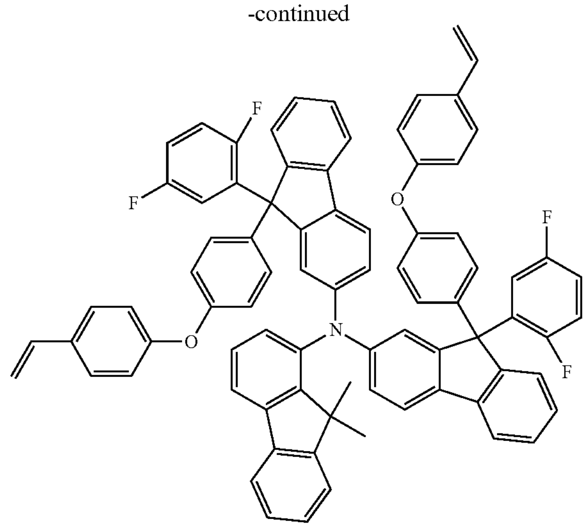
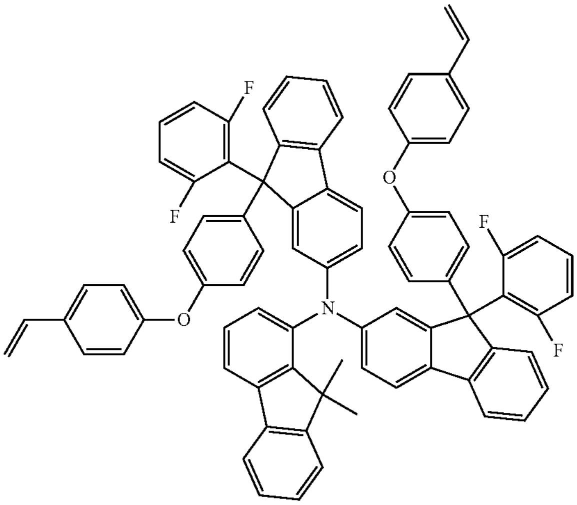
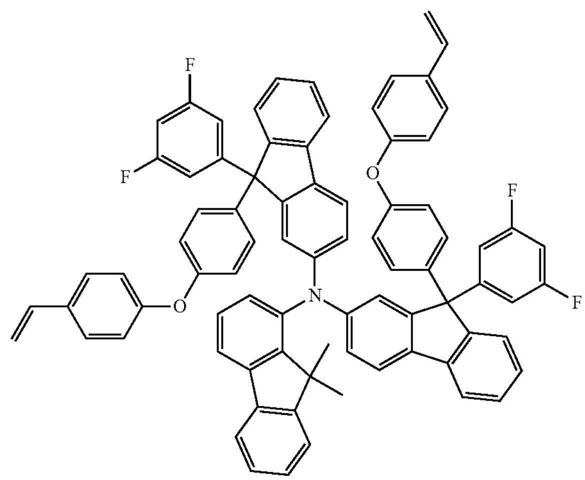

-continued
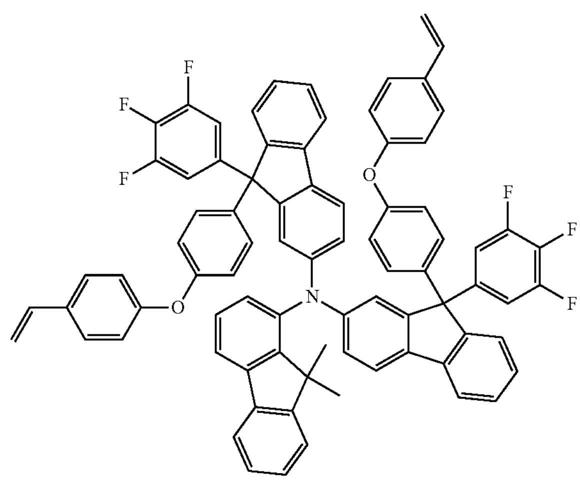
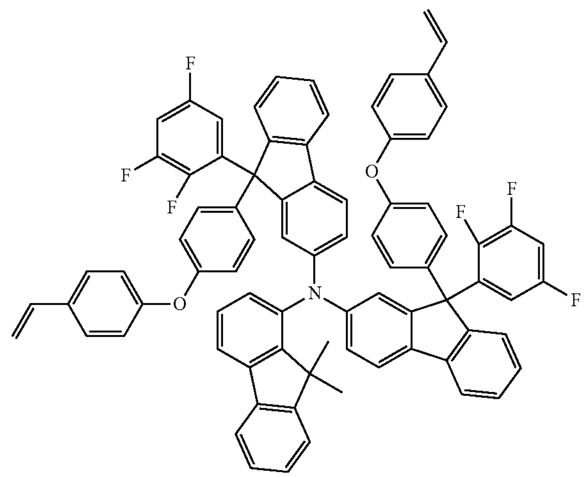
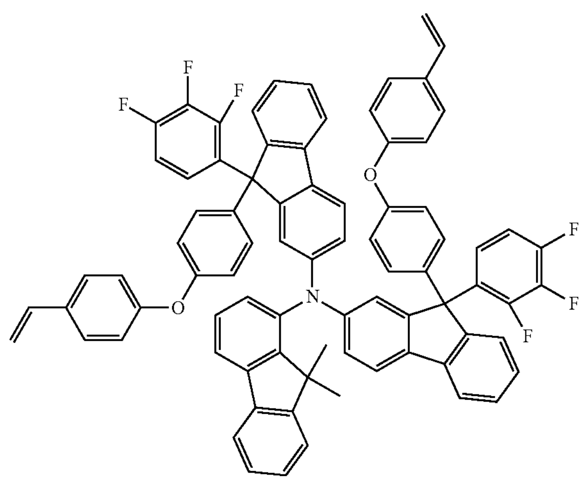
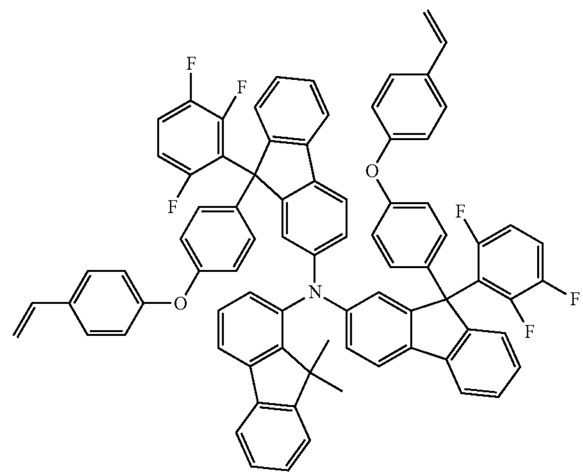
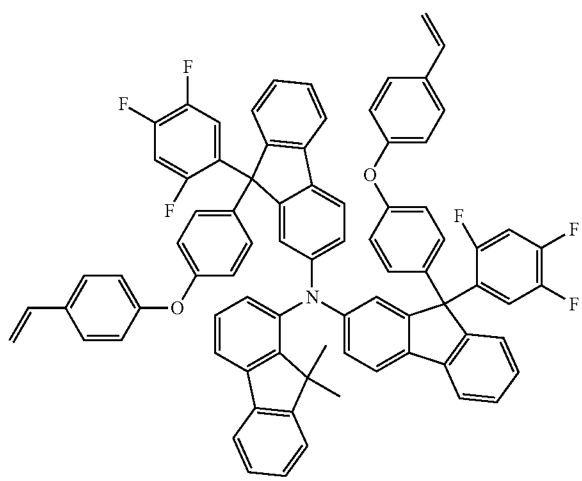
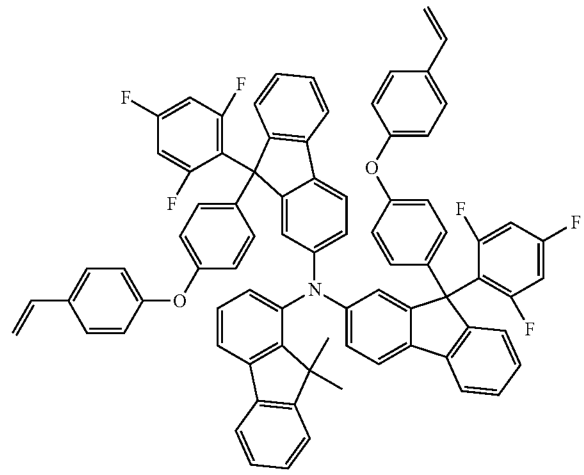
-continued -continued
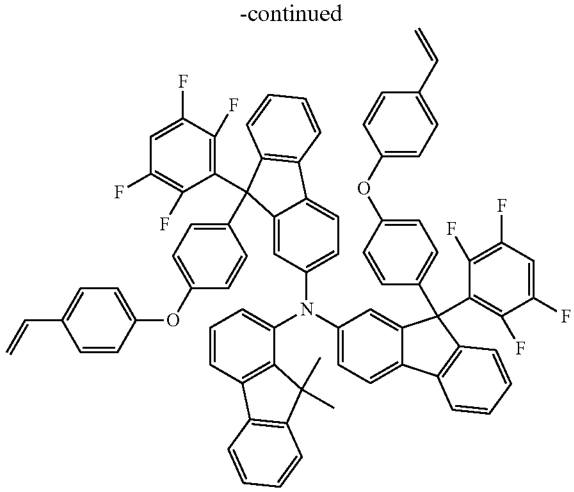
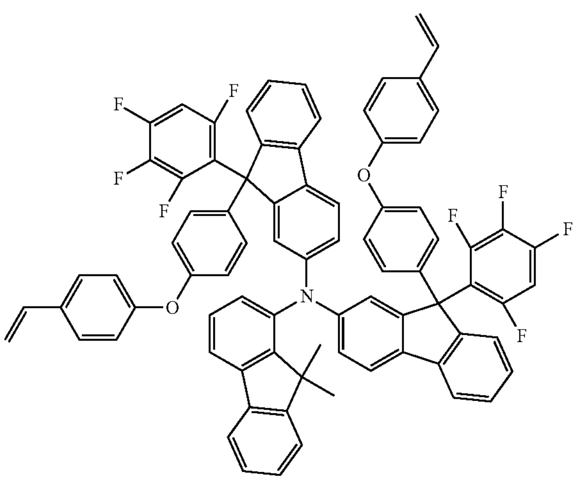
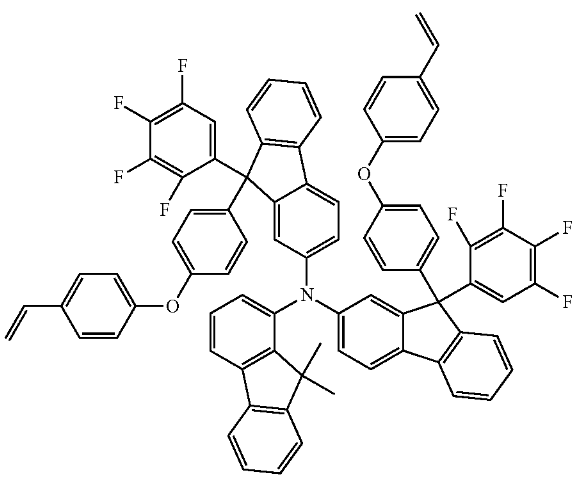
-continued
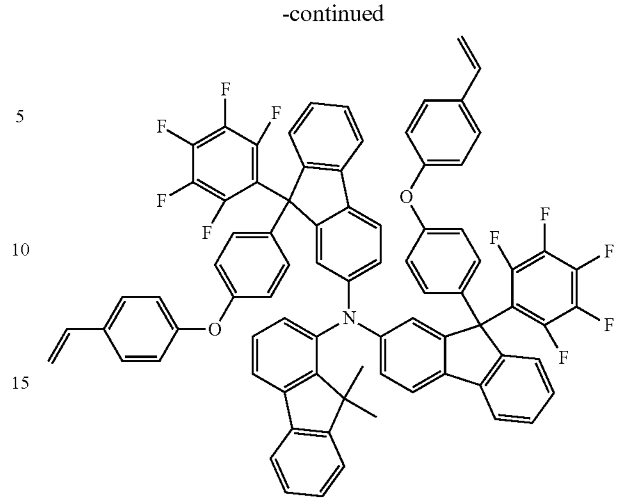
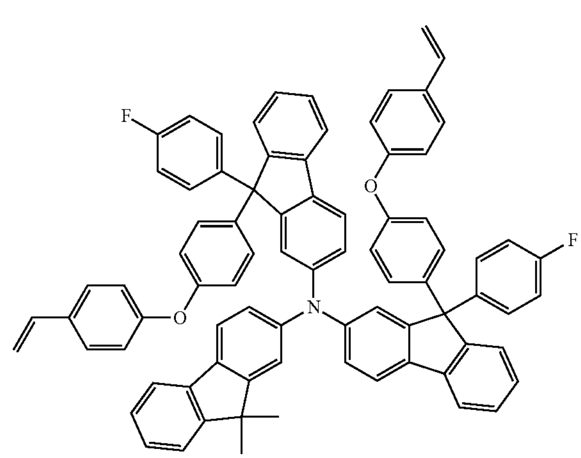
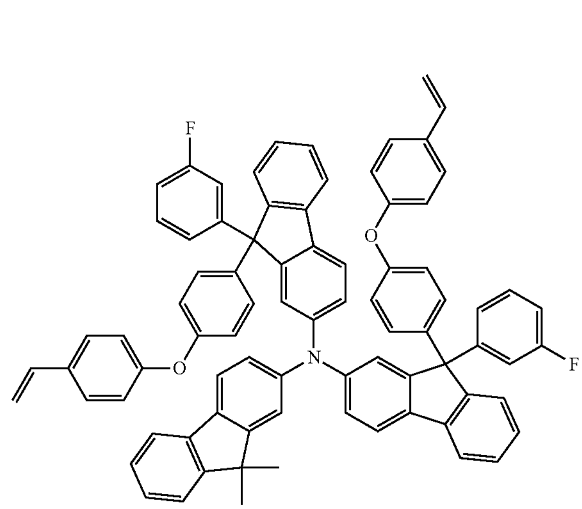

-continued
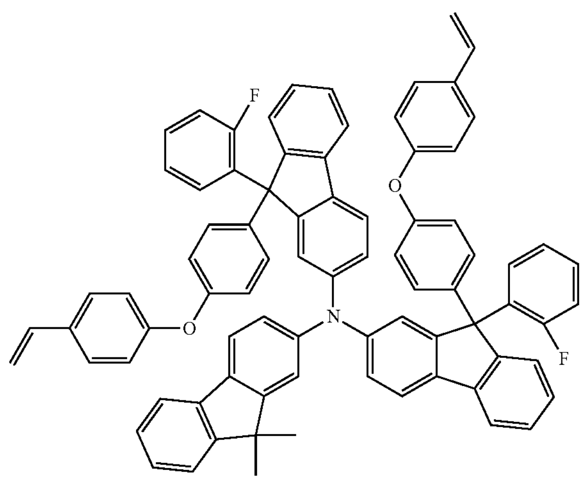
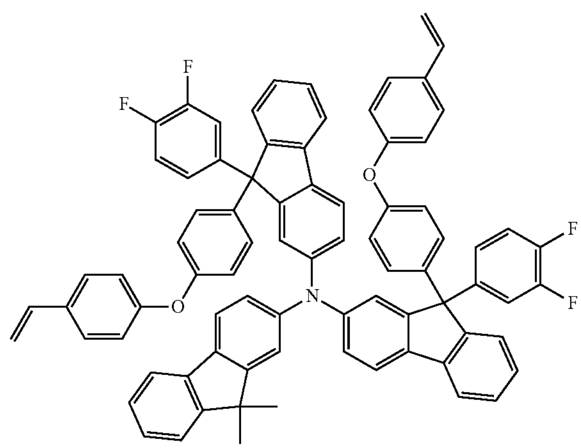
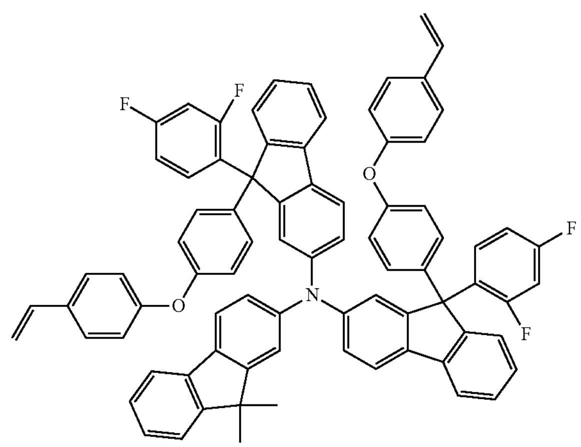
-continued
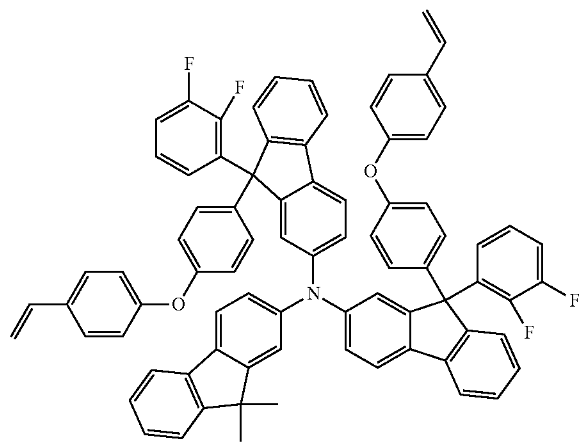
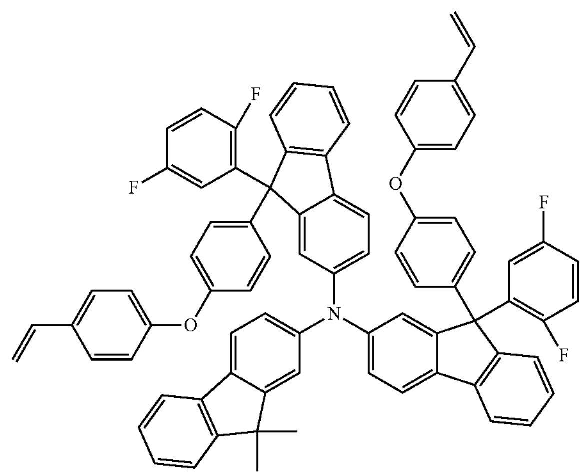
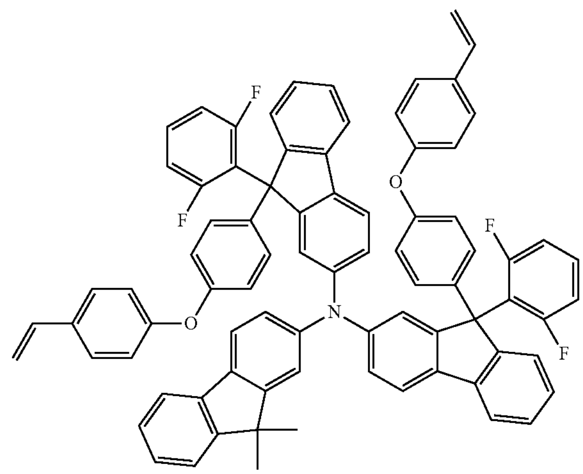

-continued
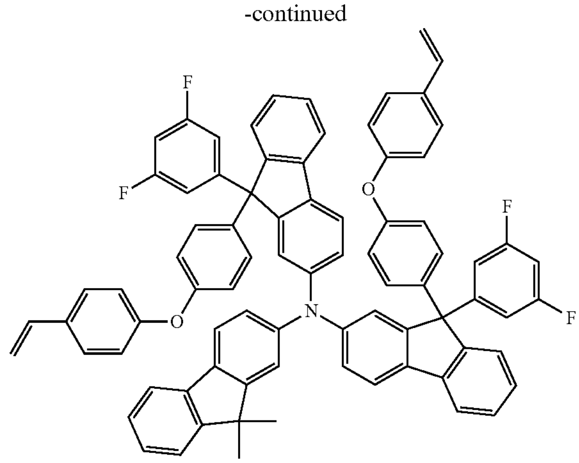
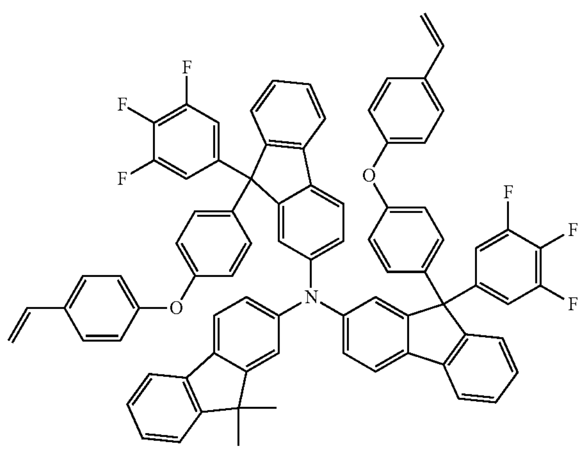
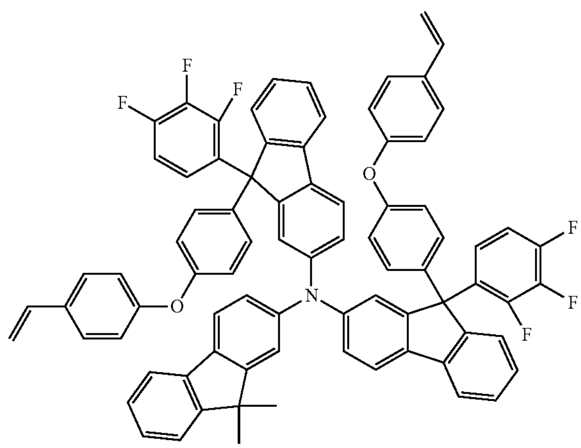
-continued
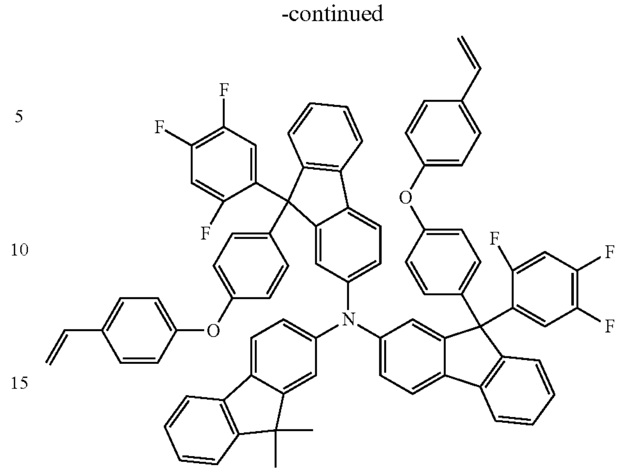
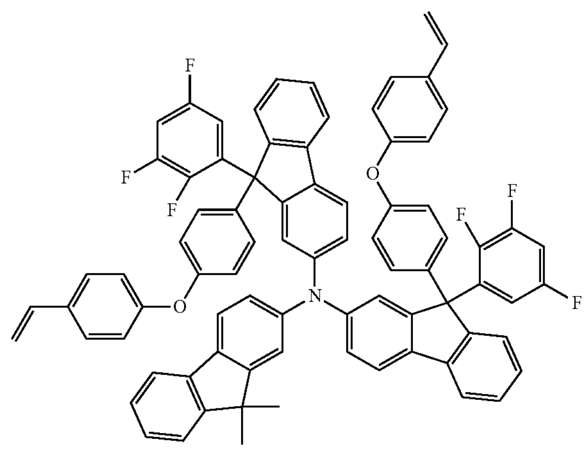
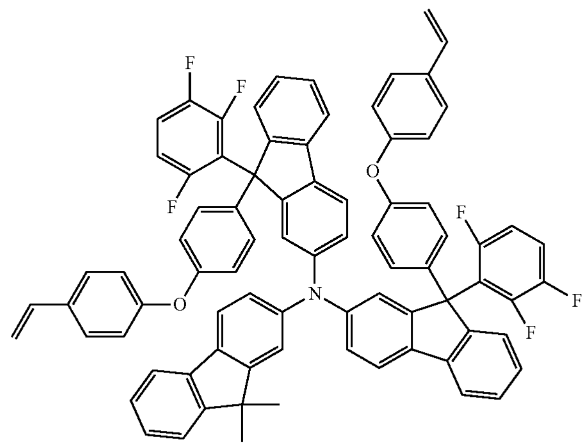

-continued
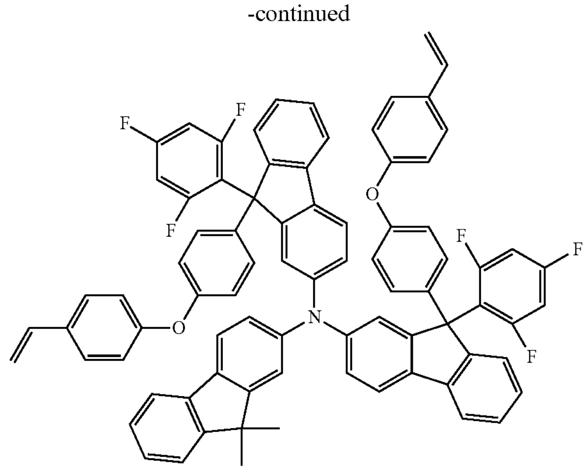
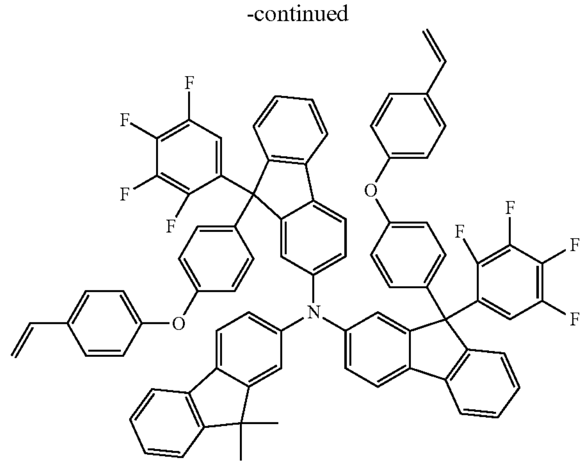
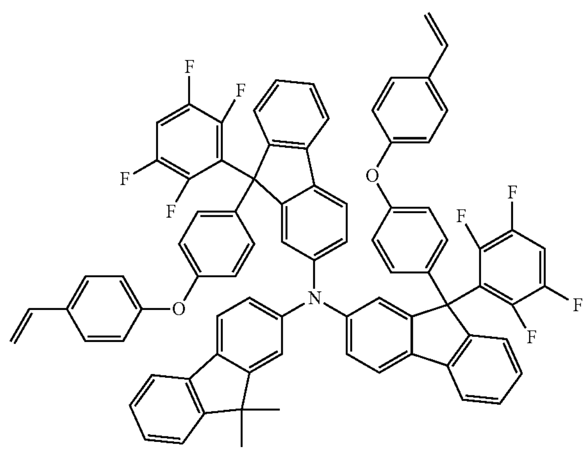
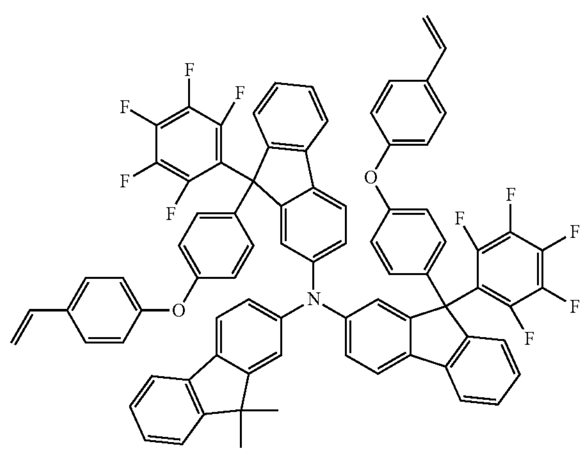
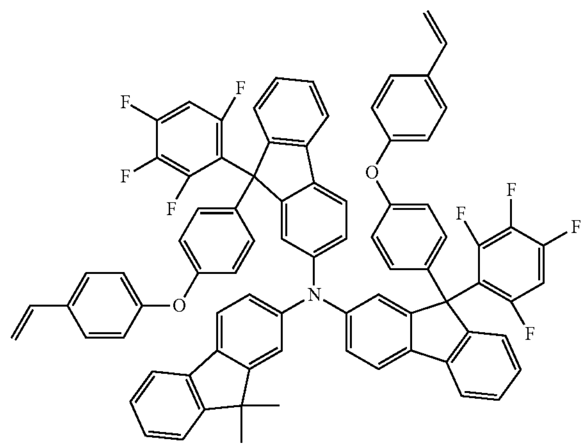
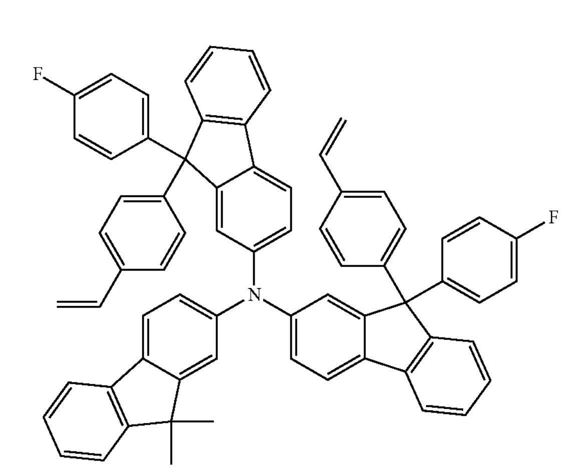
-continued -continued
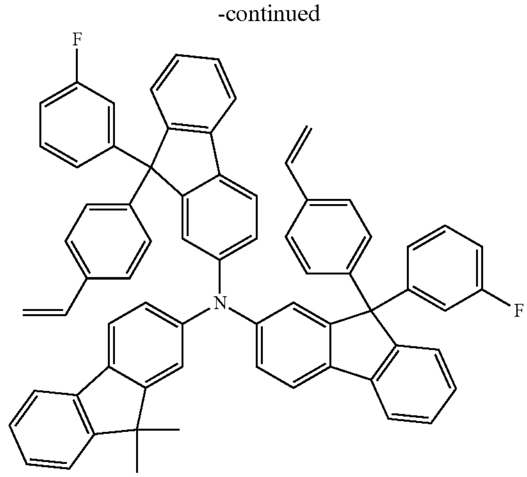
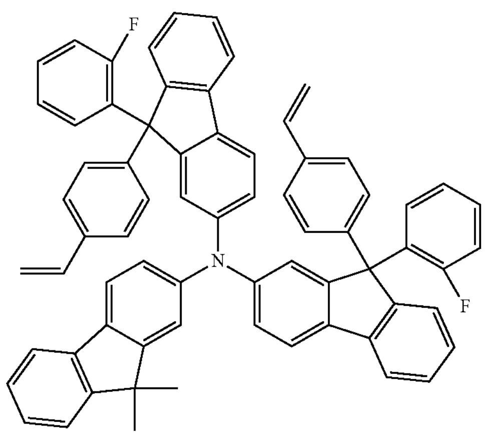
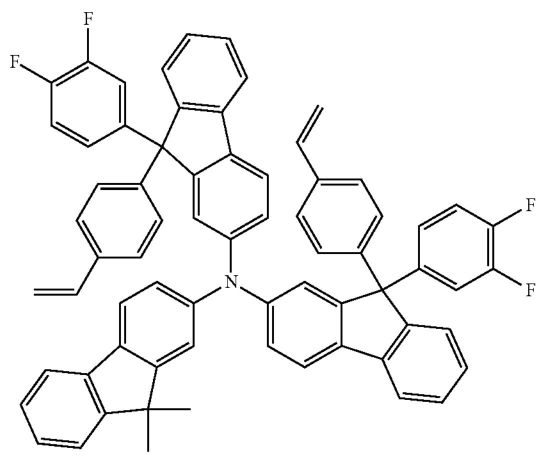
-continued
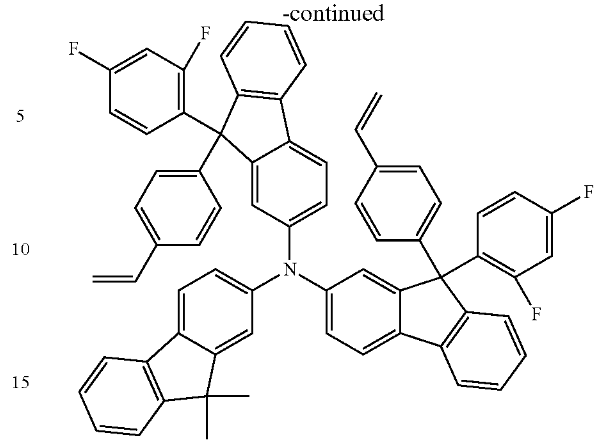
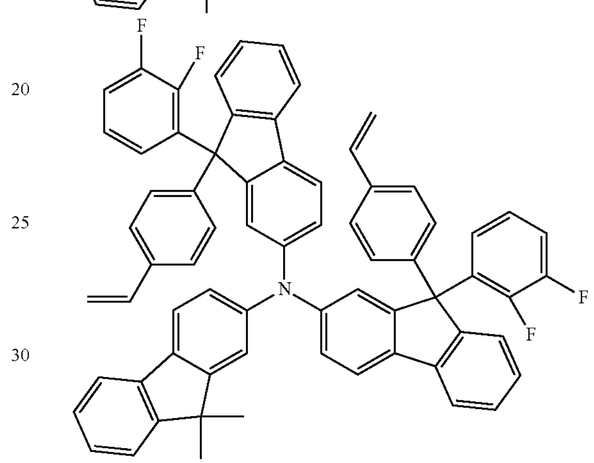
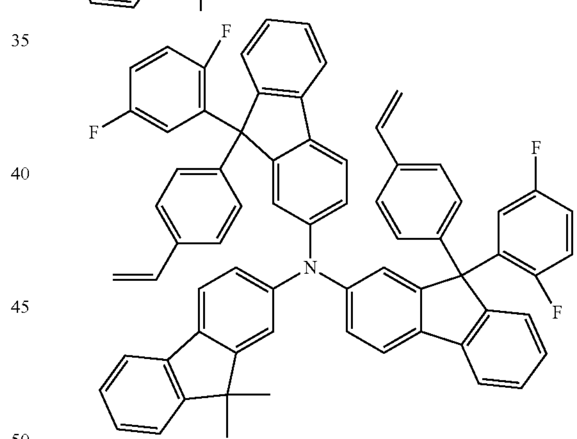
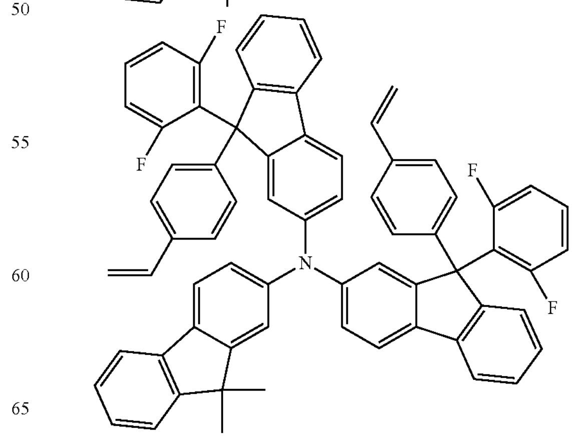

-continued
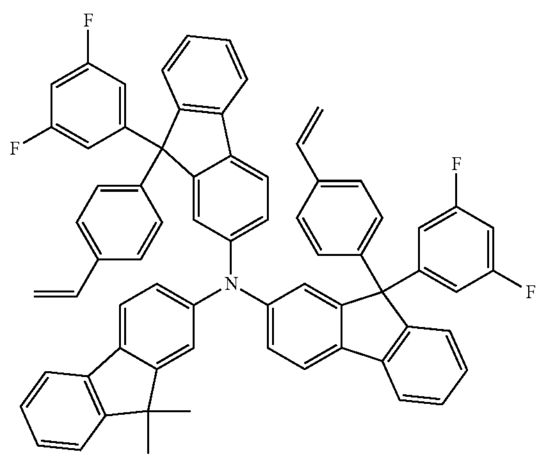
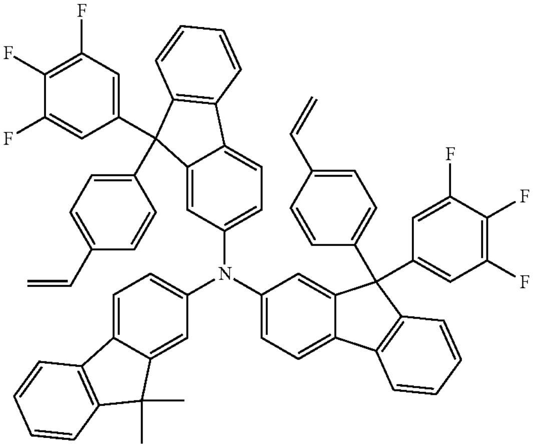
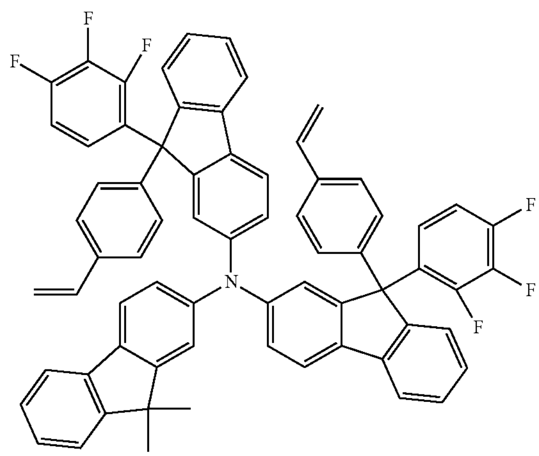
-continued
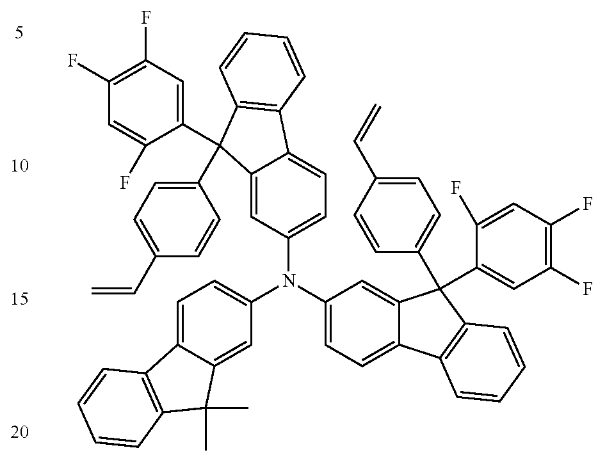
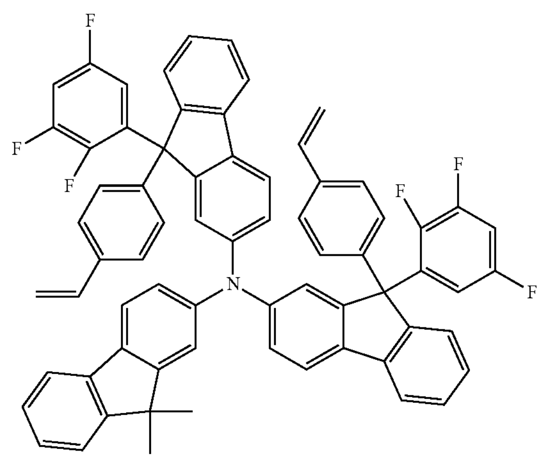

-continued
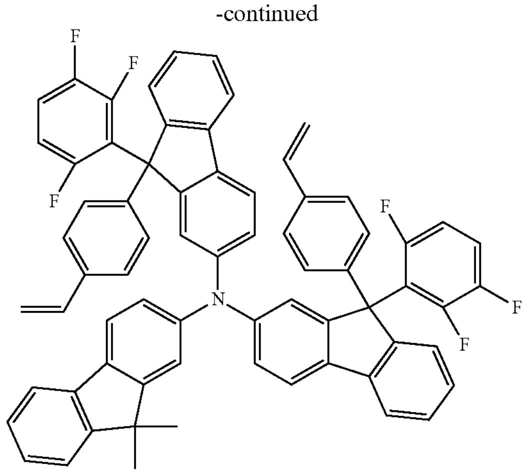
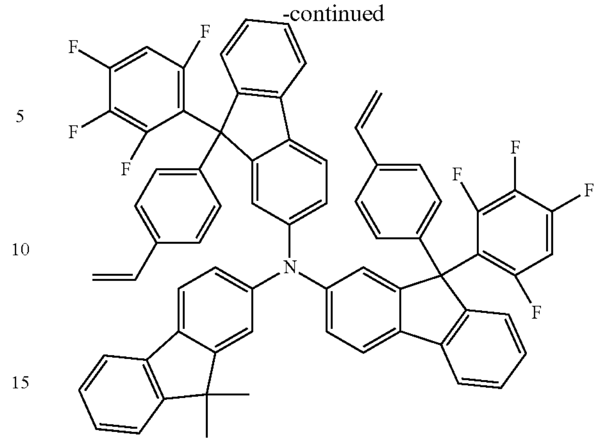
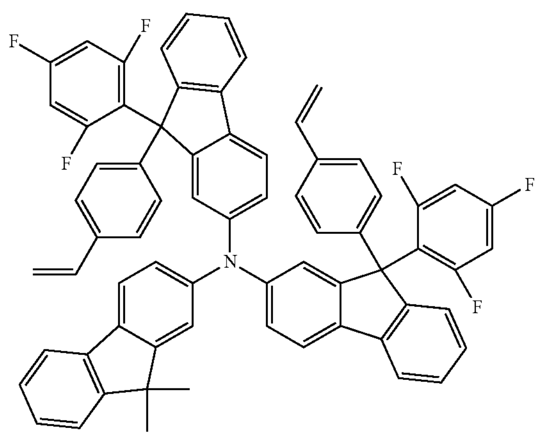
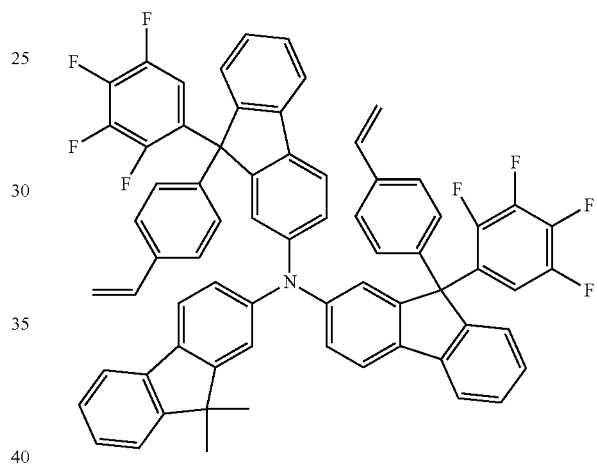
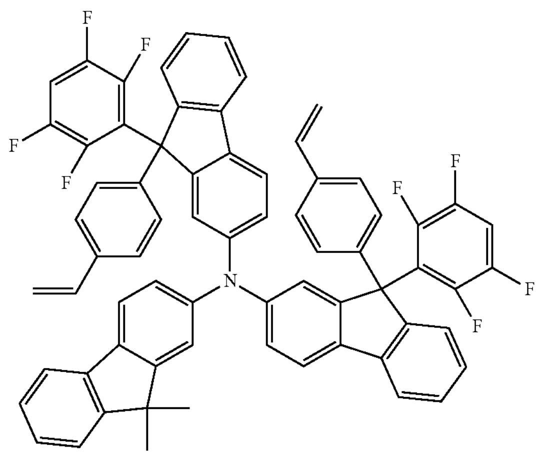
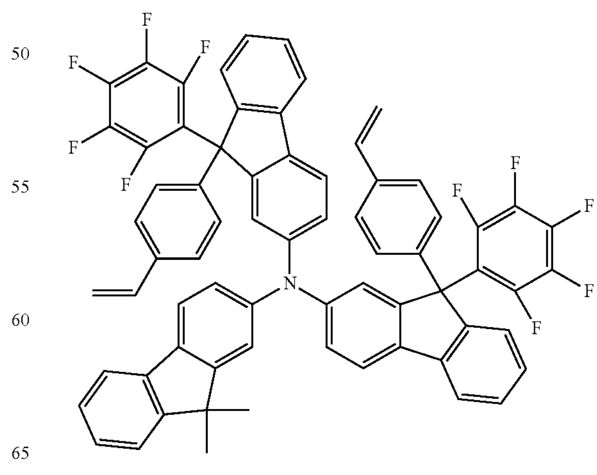

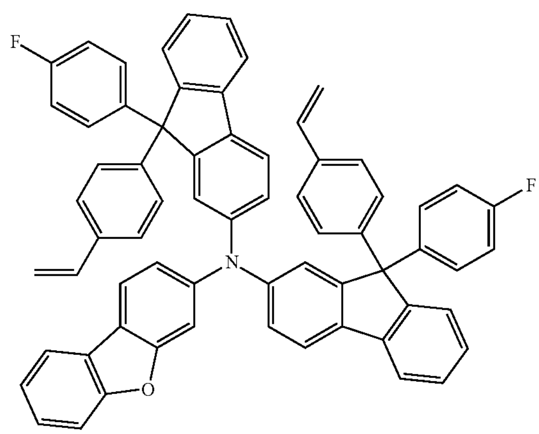
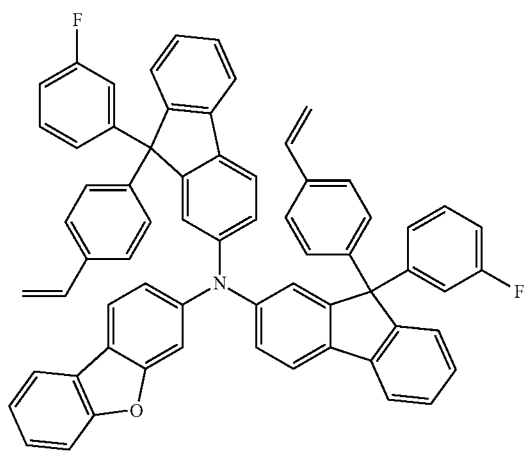
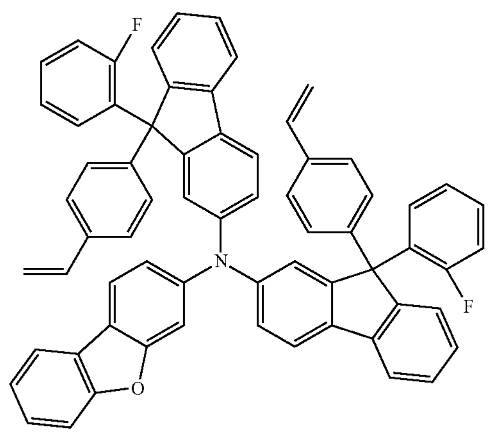
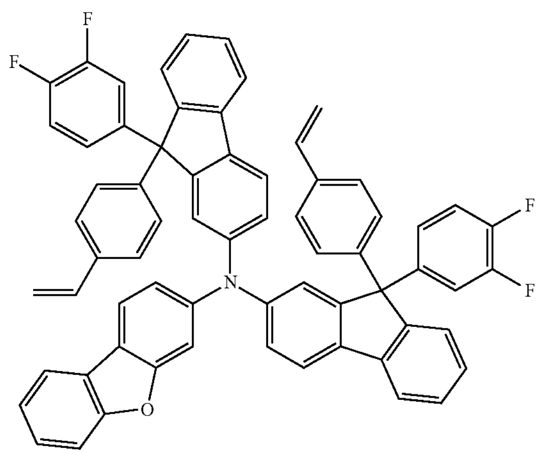
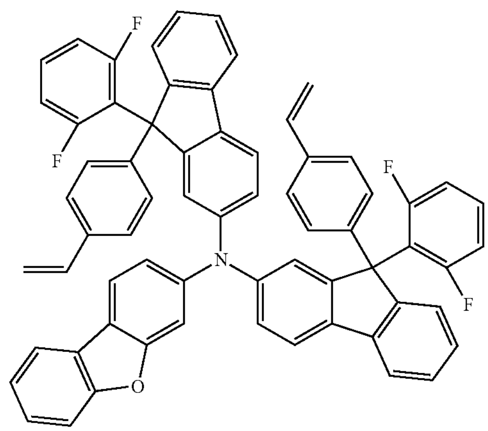
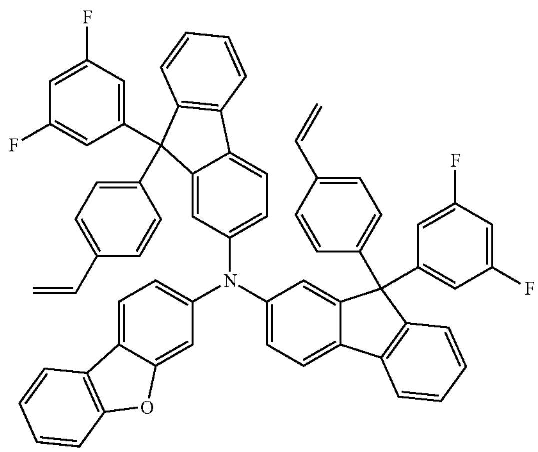

-continued
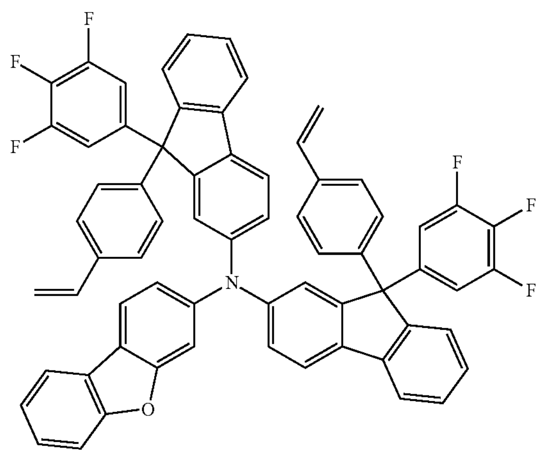
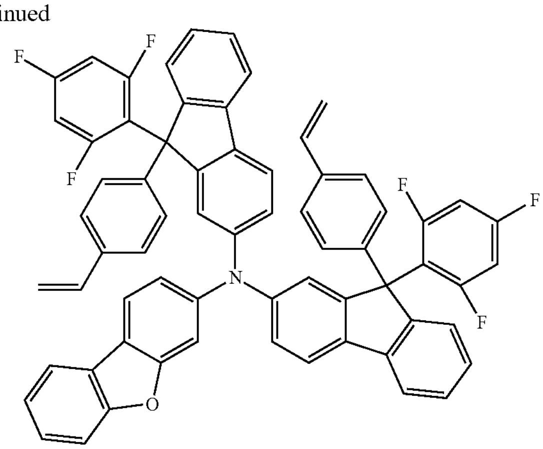
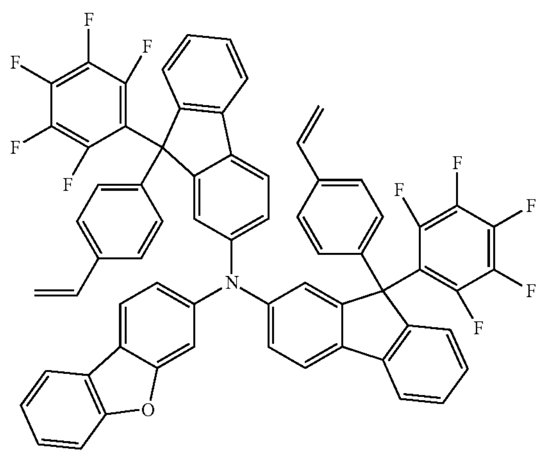
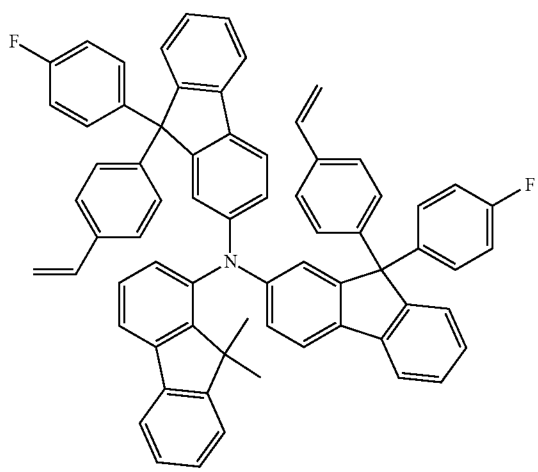
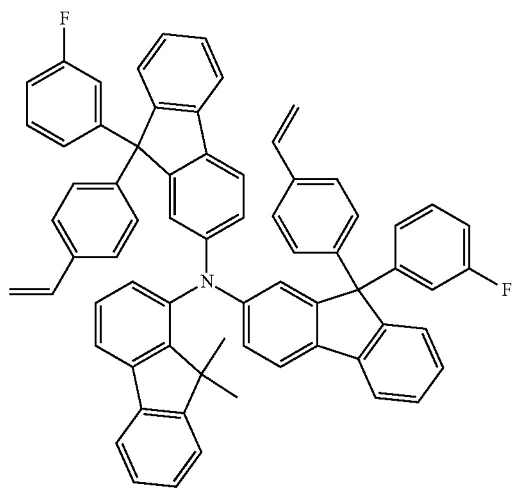
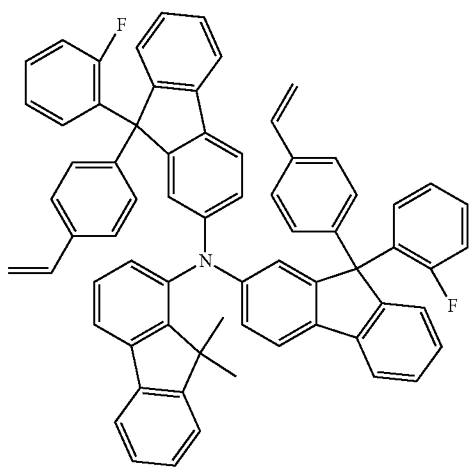

-continued
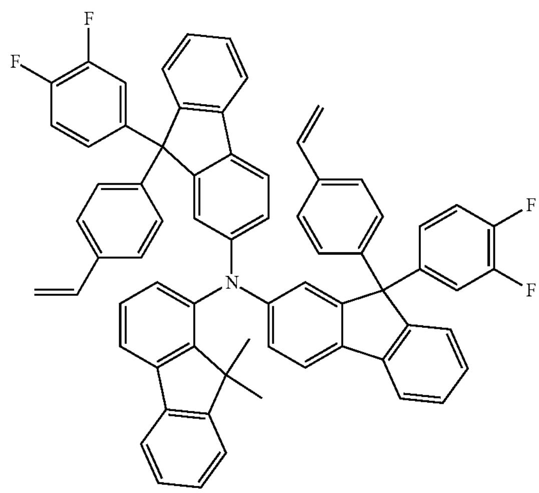
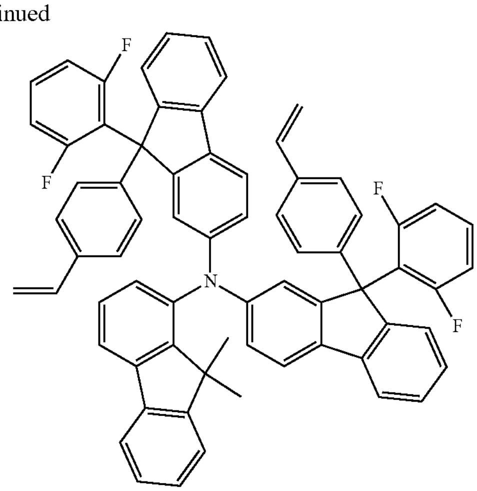
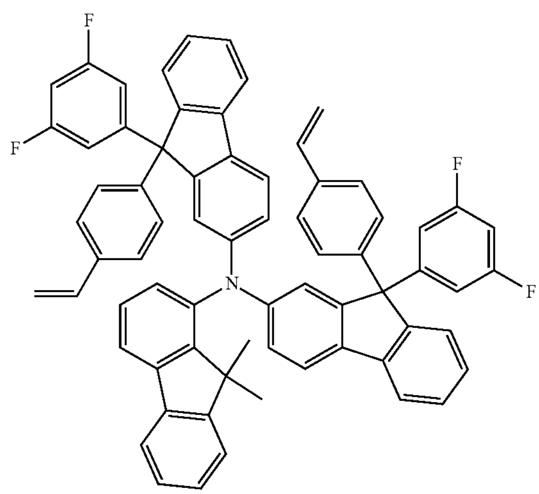
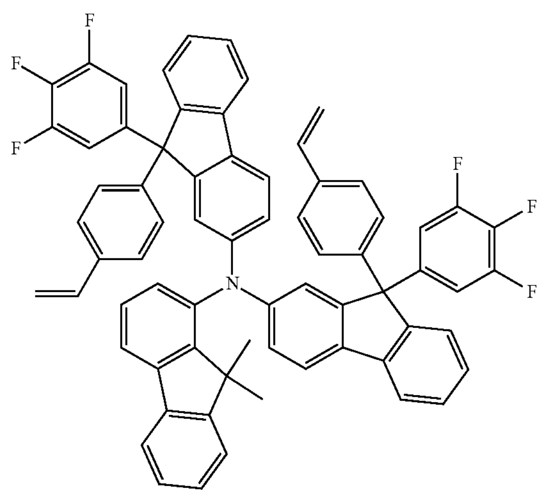
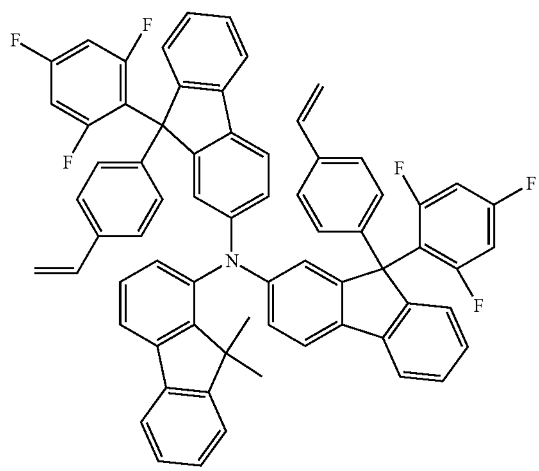
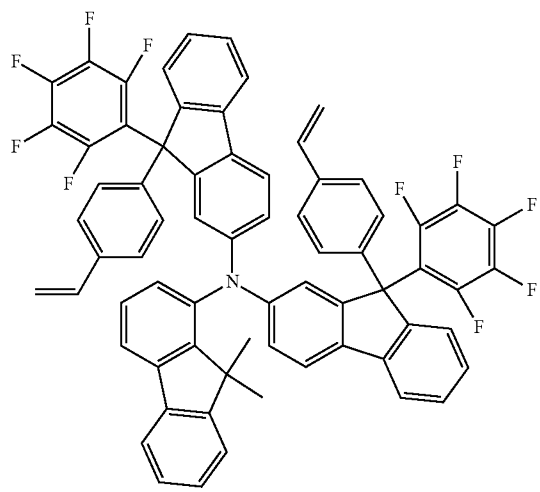

-continued
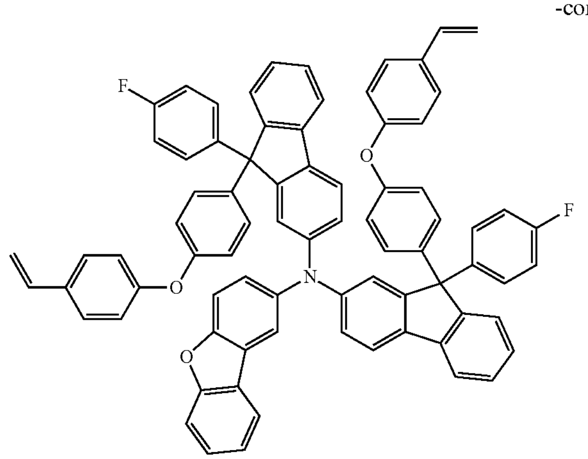
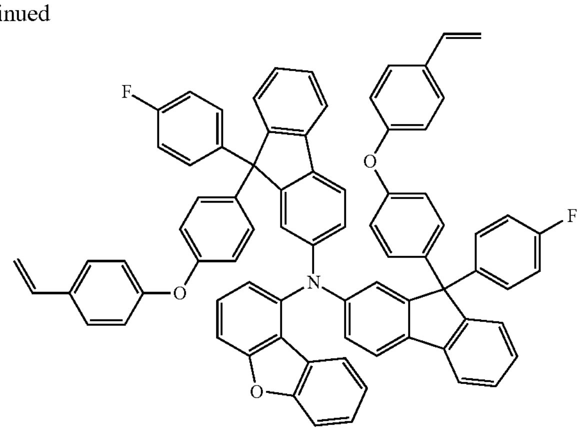
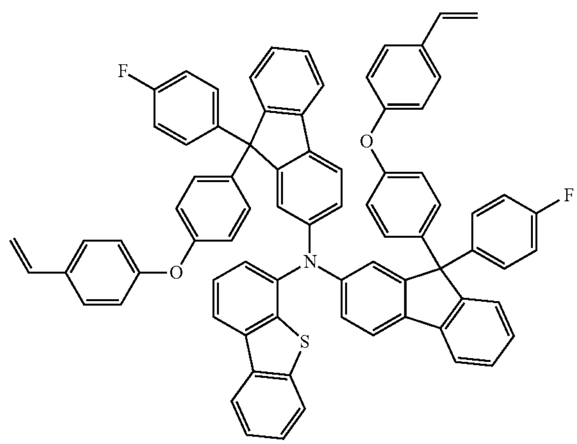
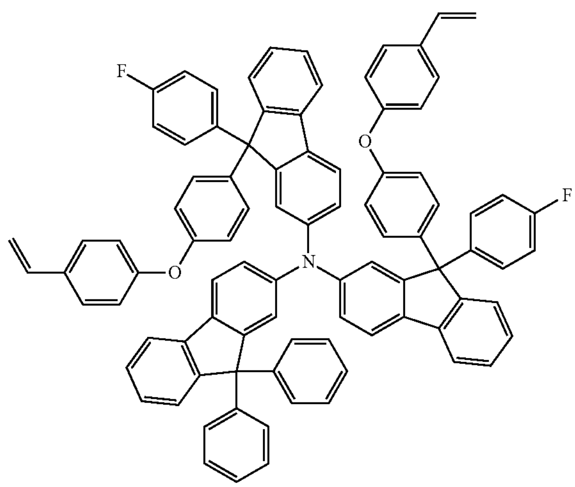
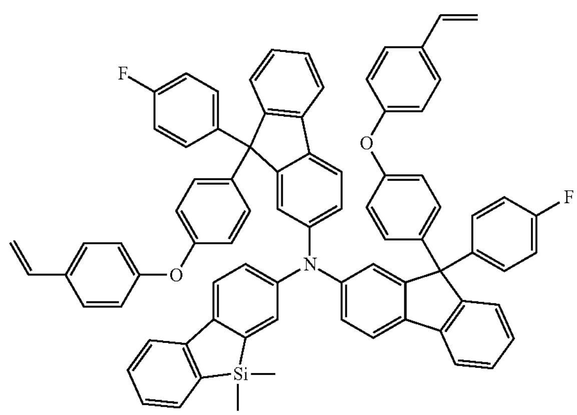
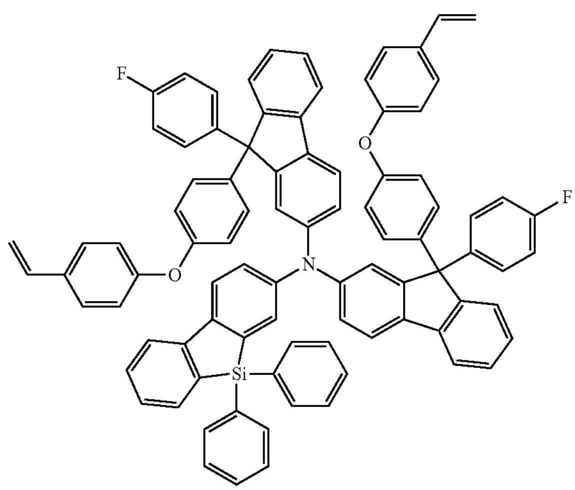

-continued
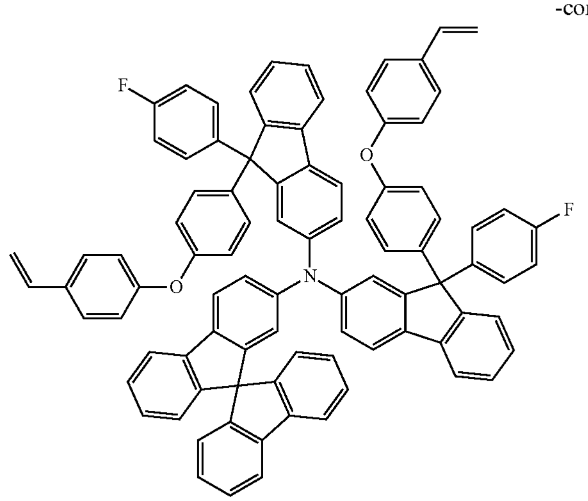
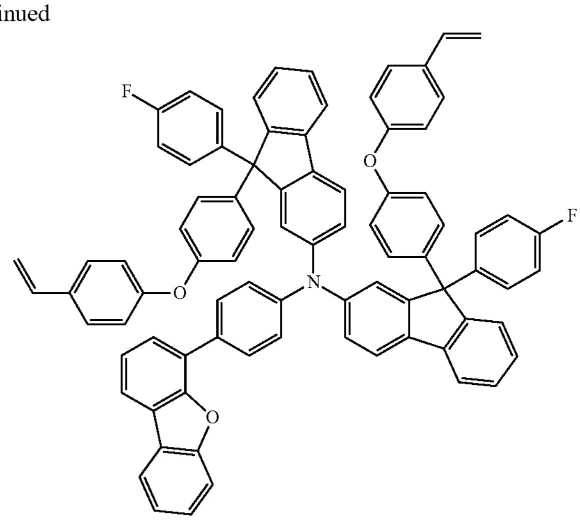
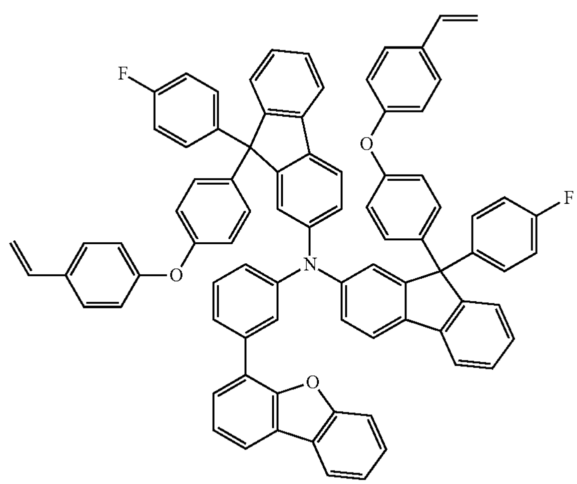
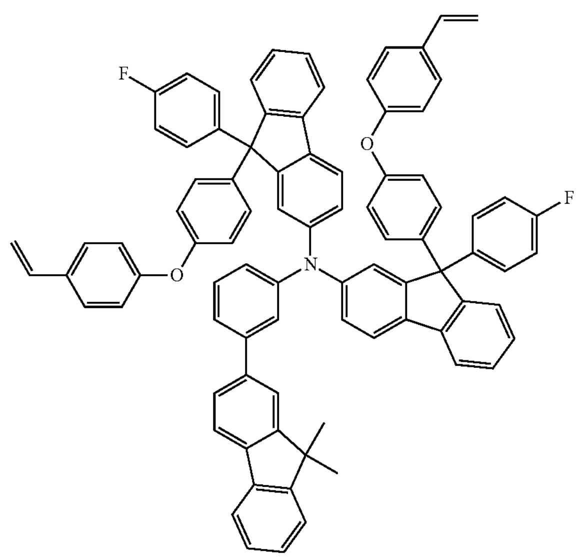
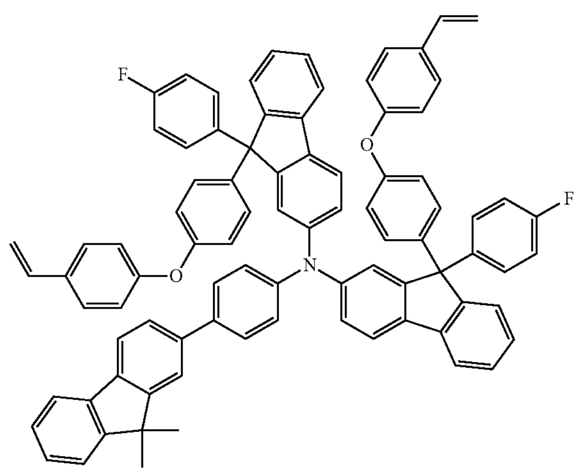
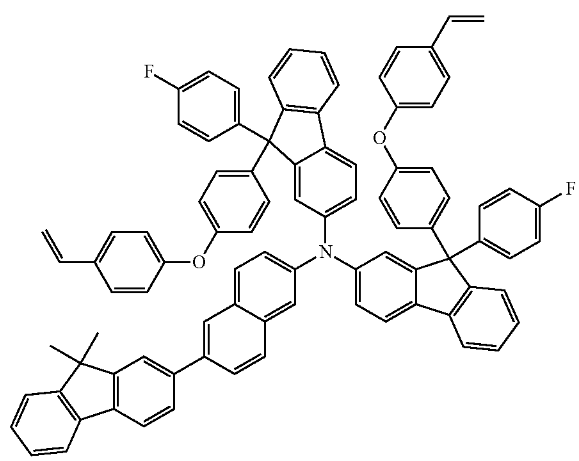

-continued
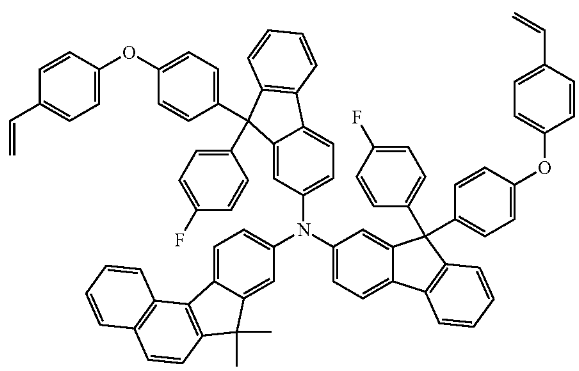
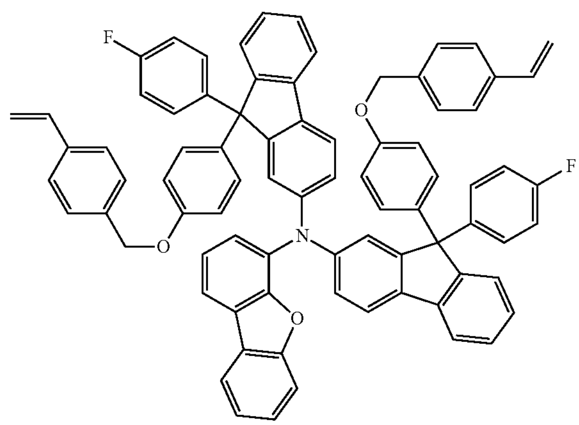
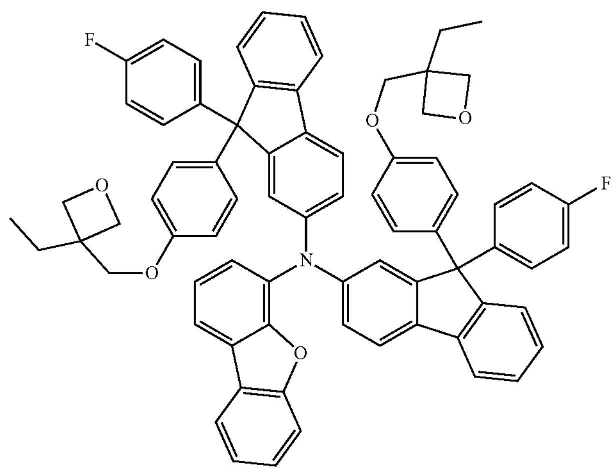
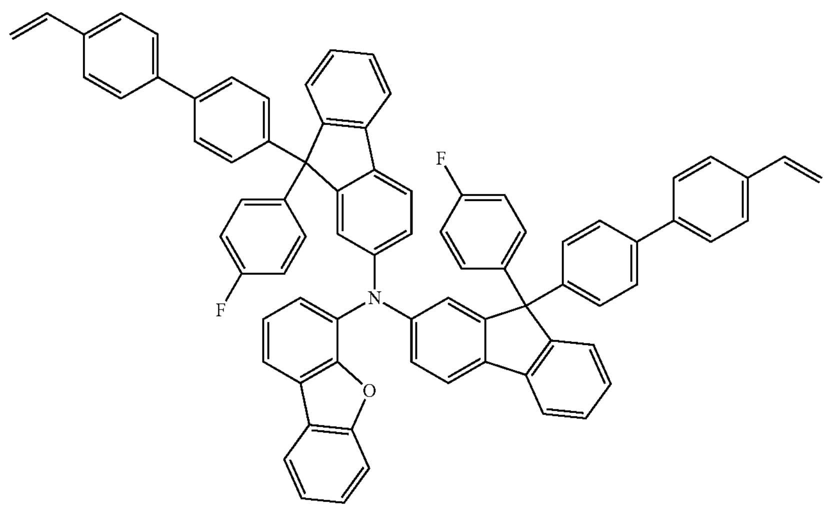

-continued
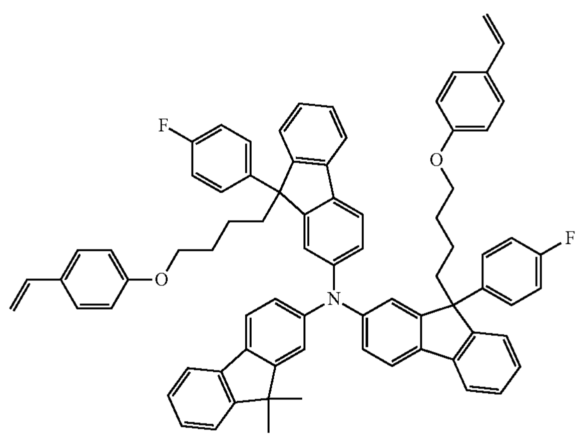
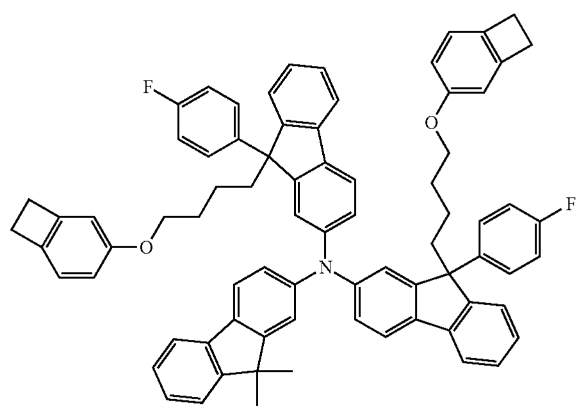
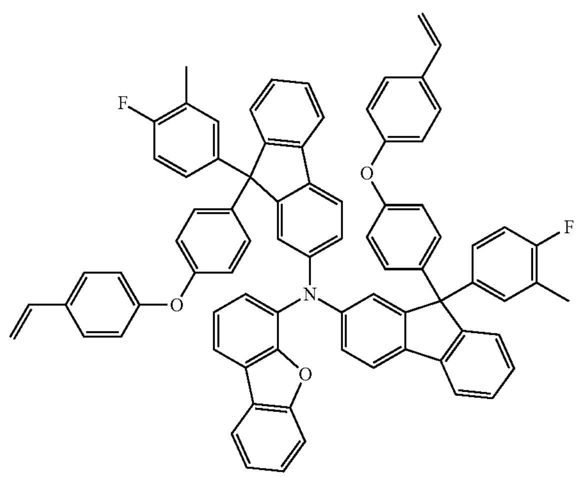
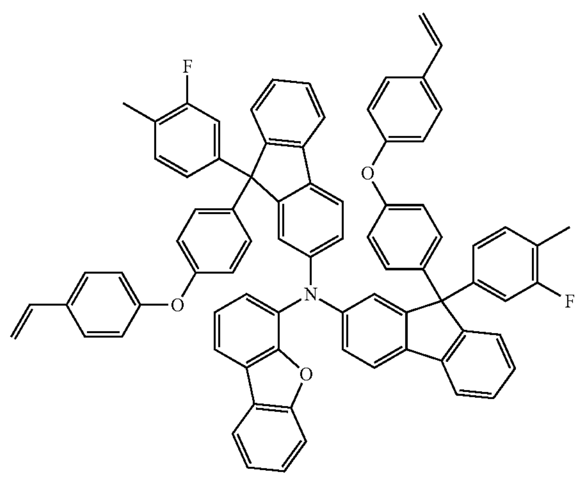
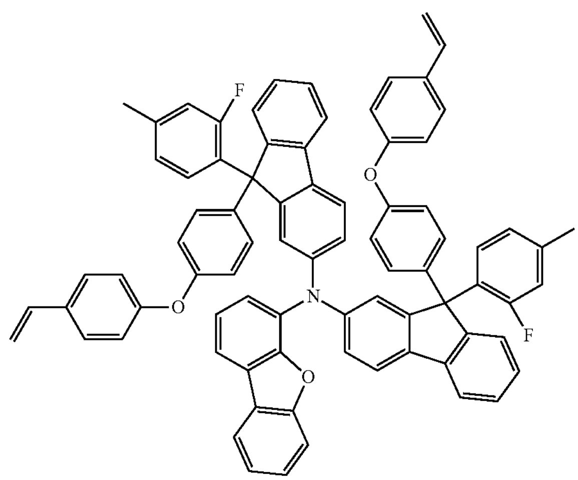
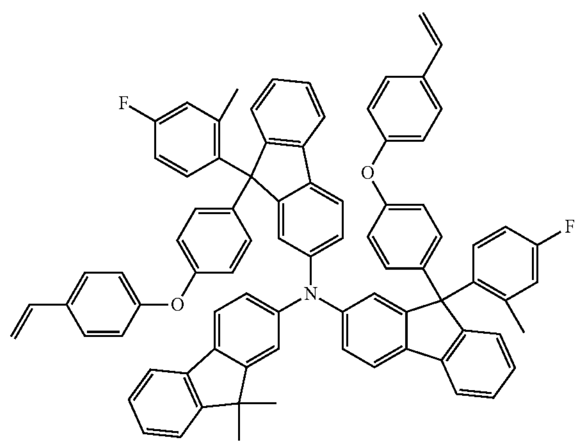

-continued
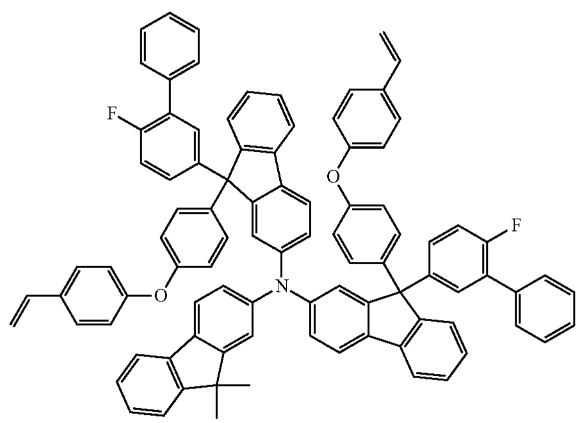
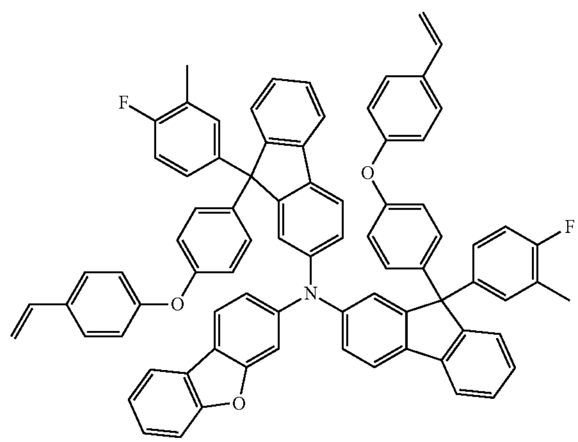
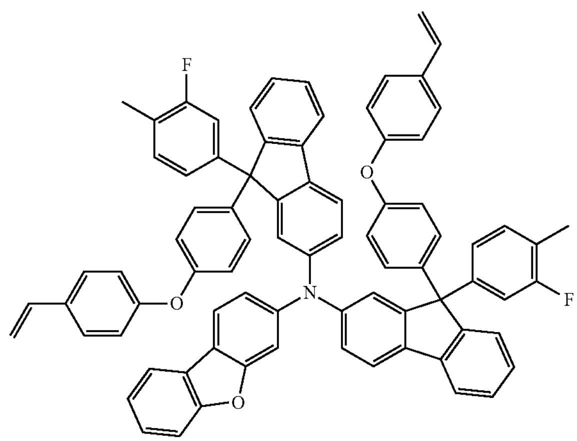
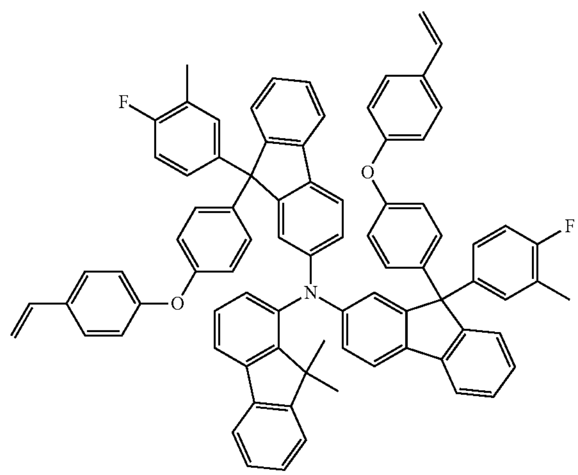
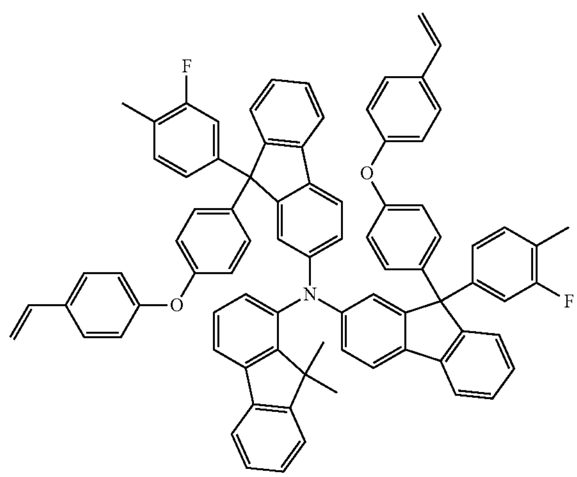
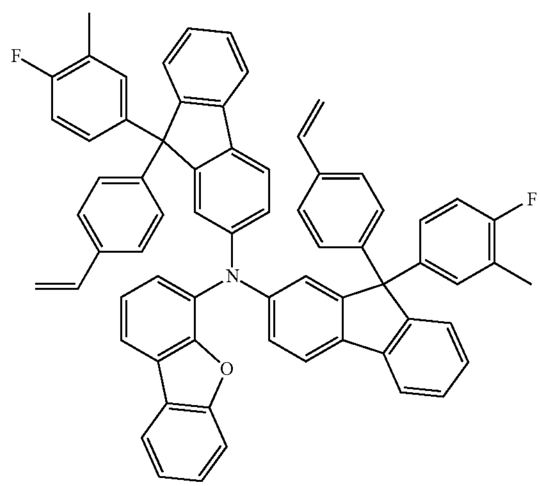

-continued
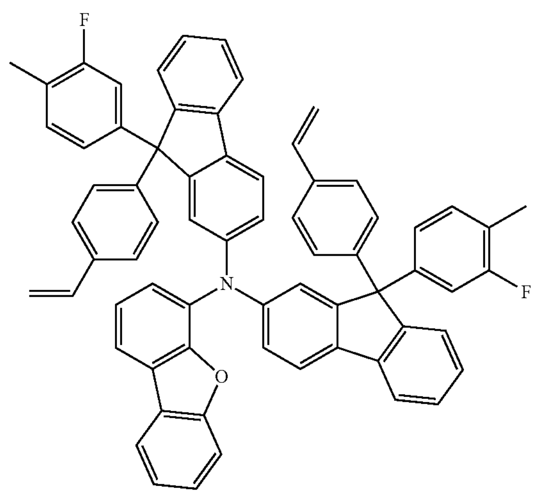
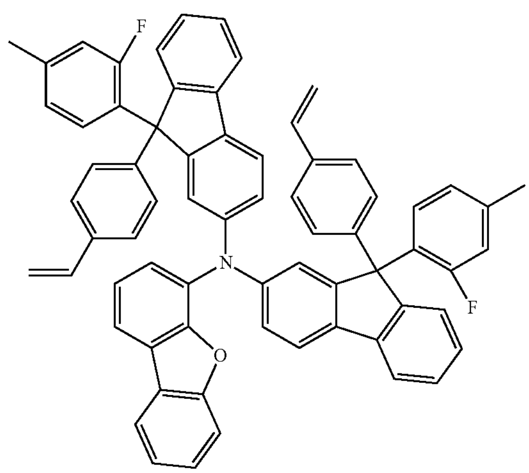
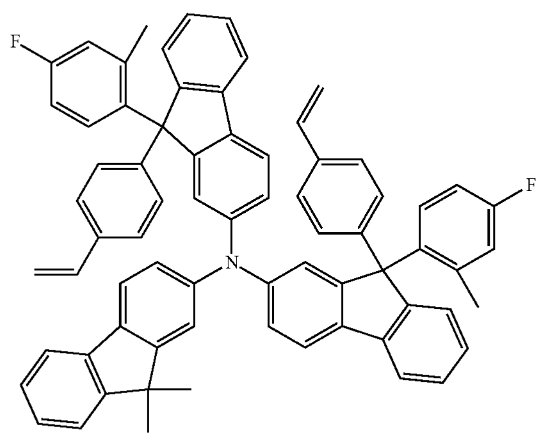
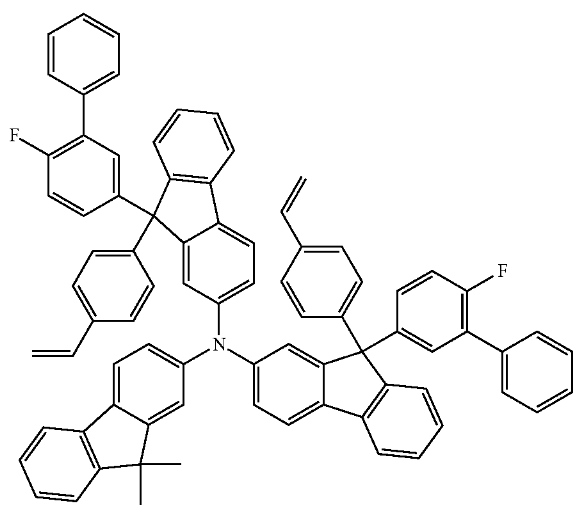
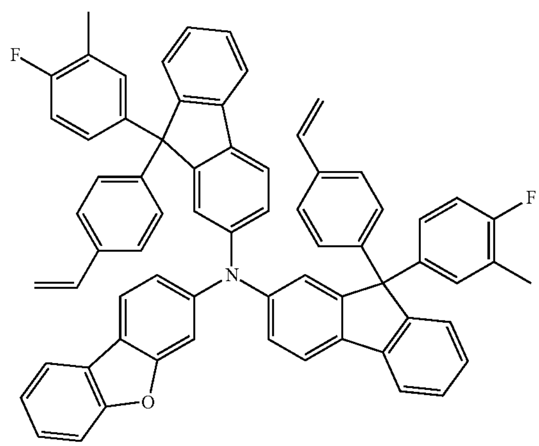
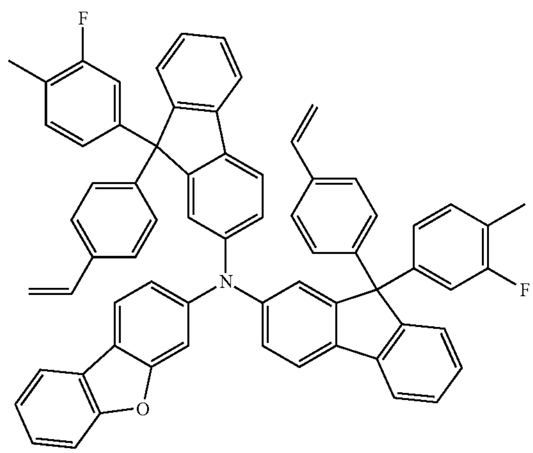

-continued
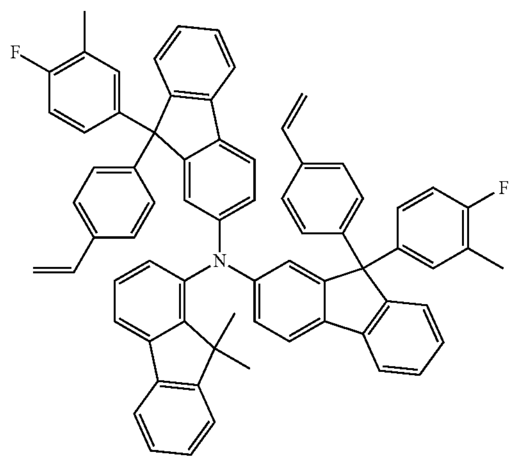
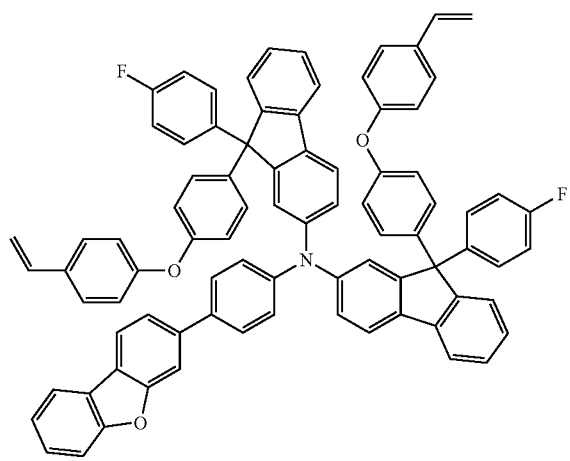
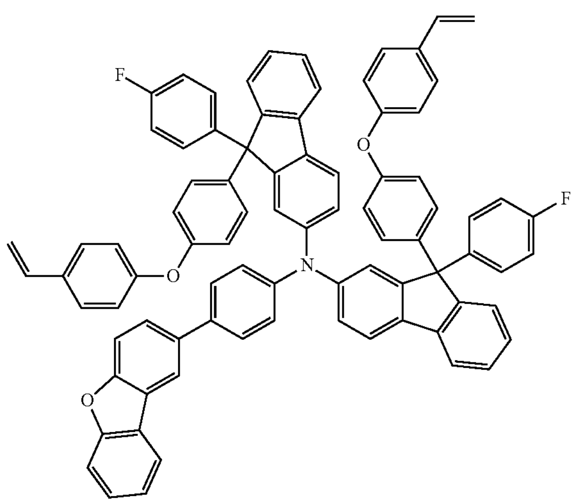
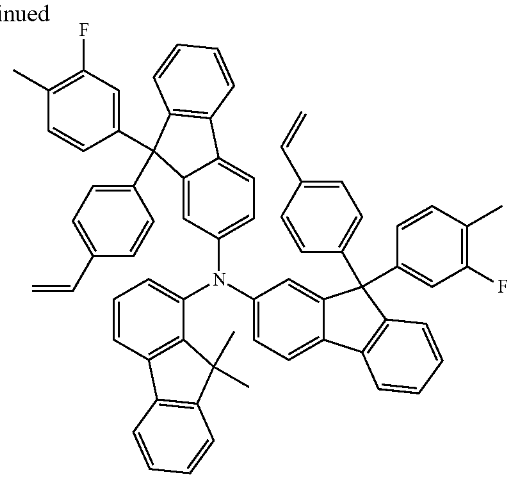
-continued
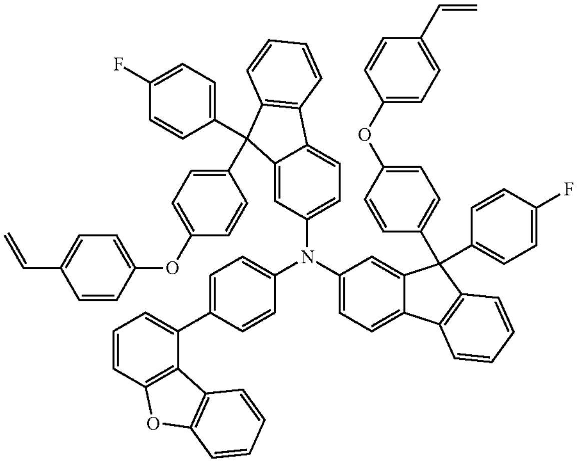
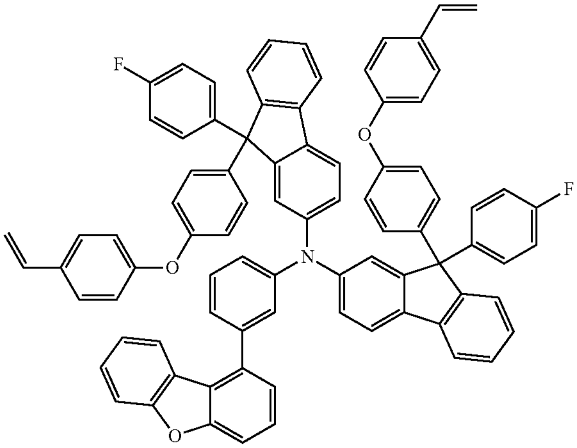

-continued
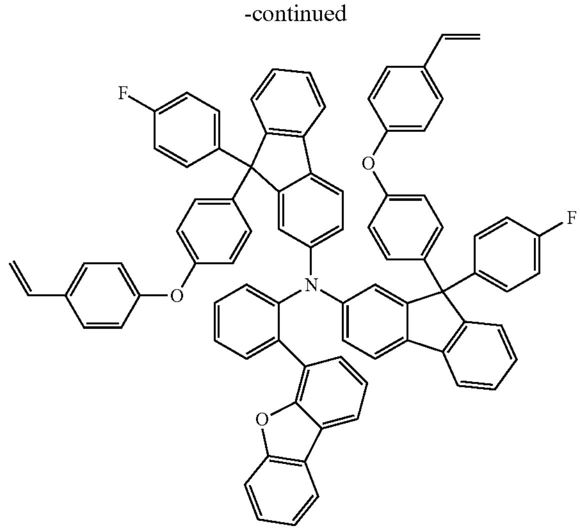
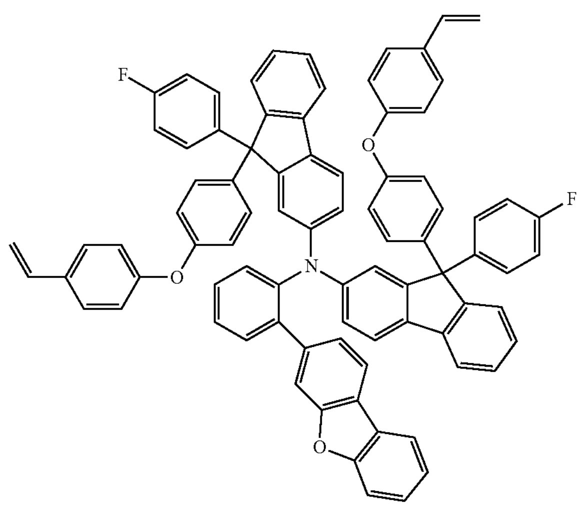
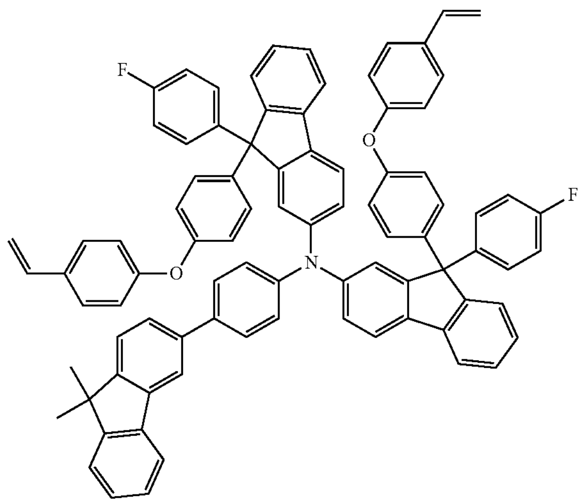
-continued
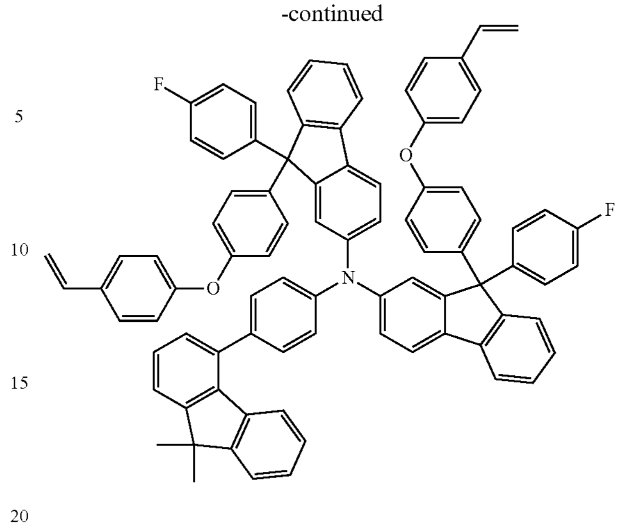
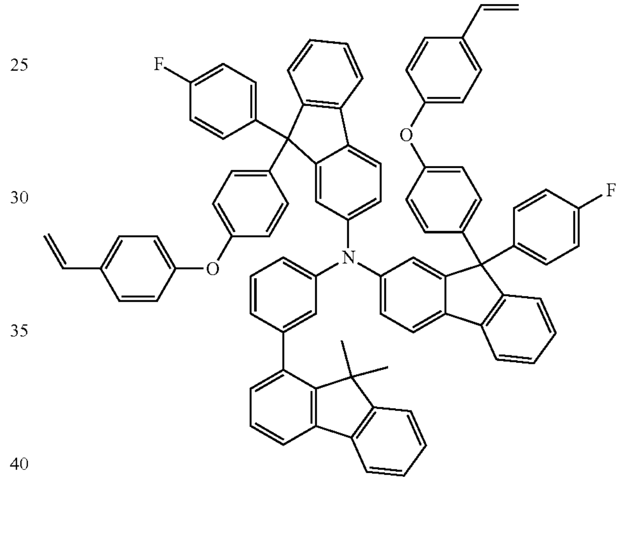
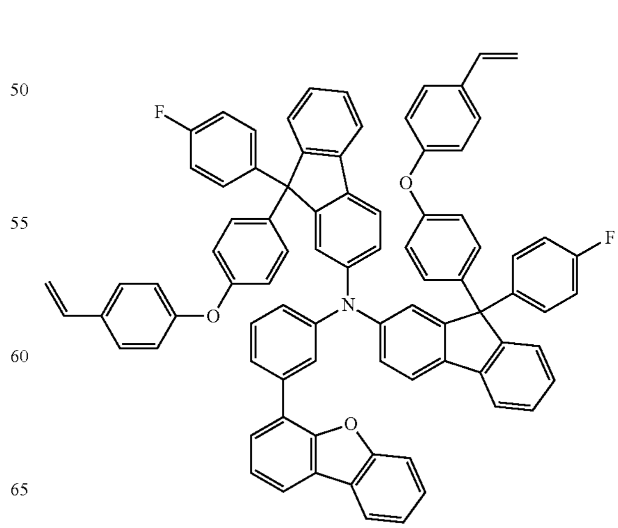

-continued
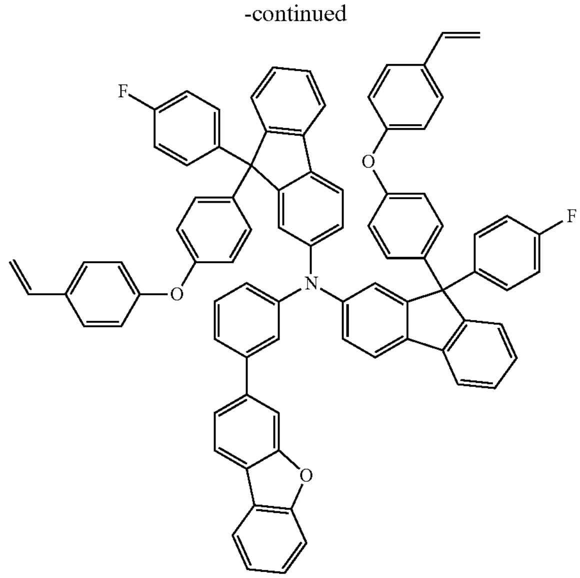
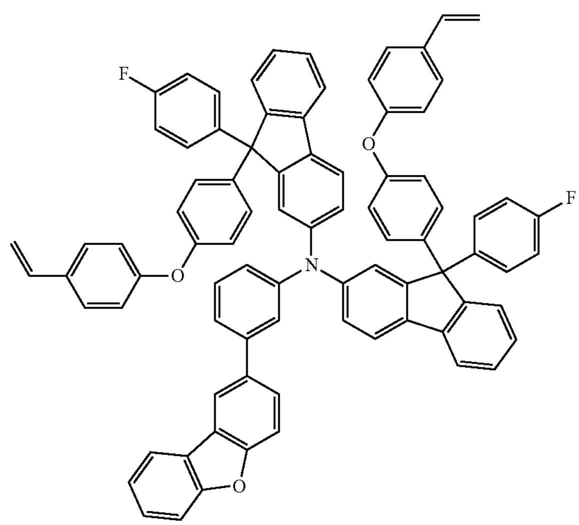
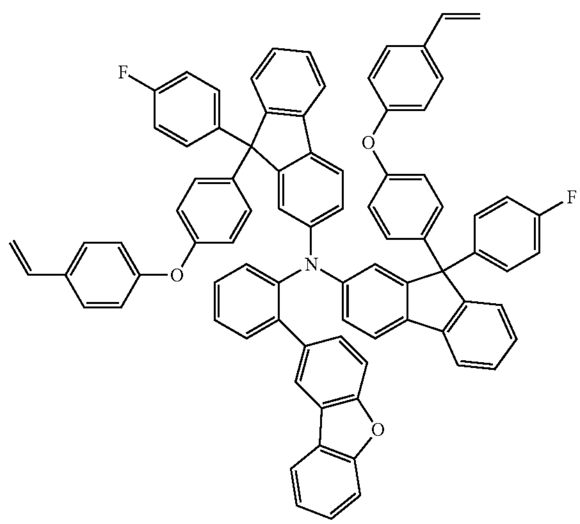
-continued
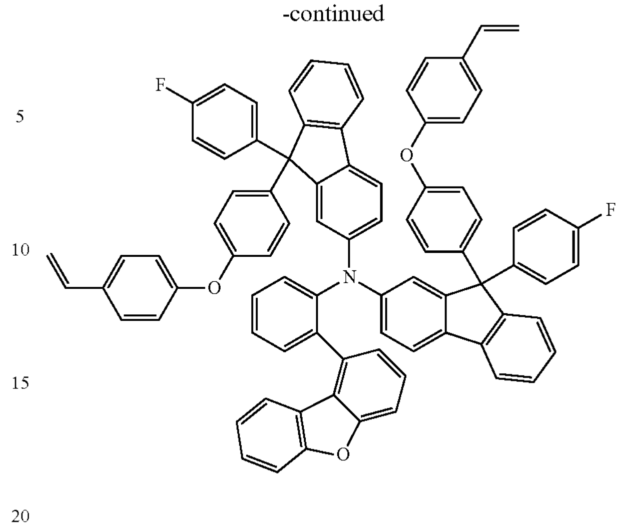
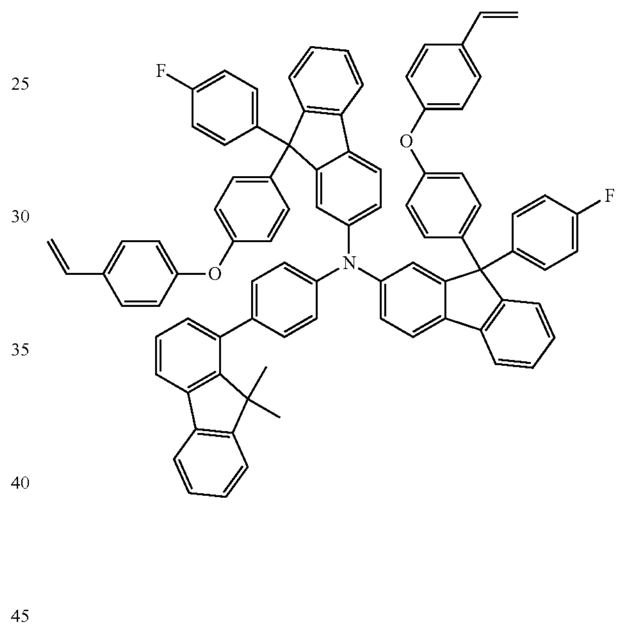
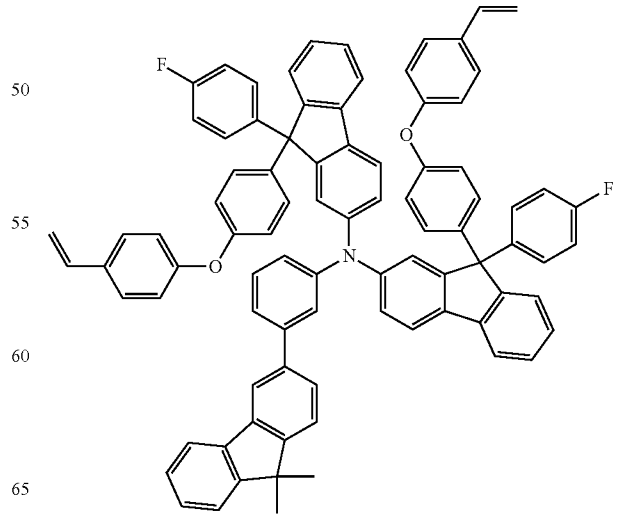

-continued
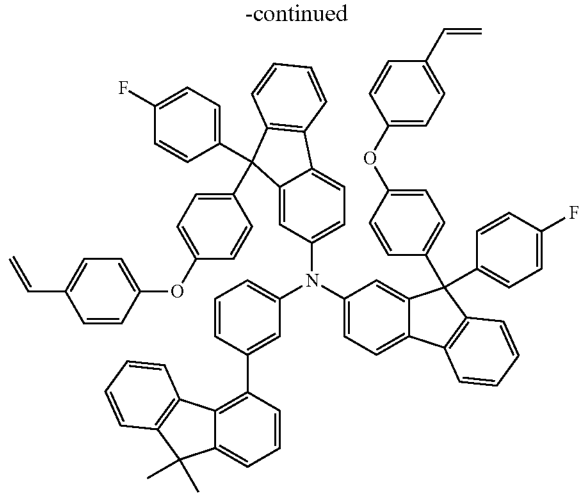
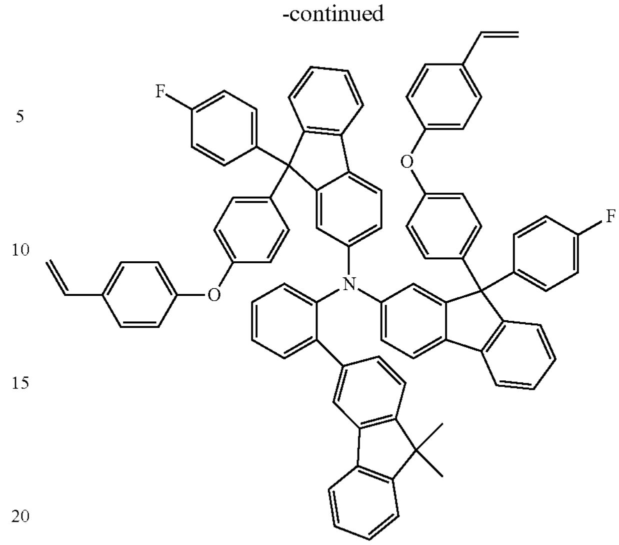
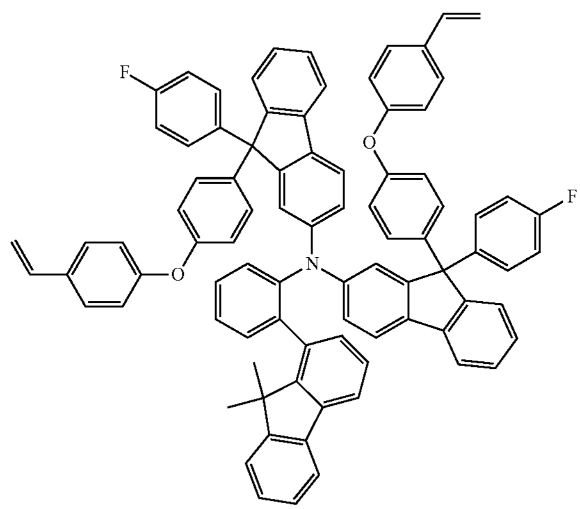
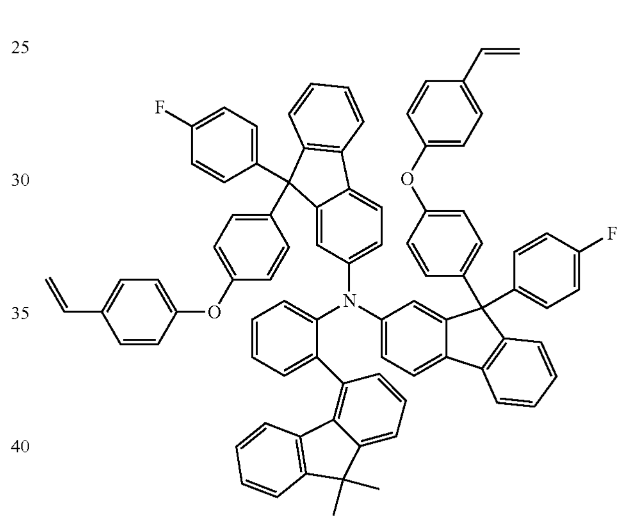
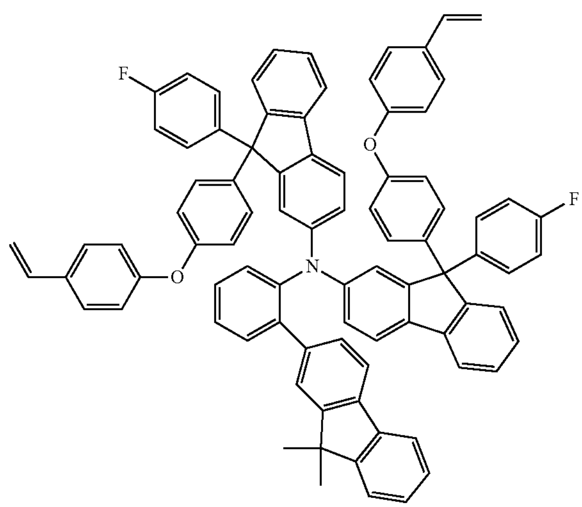
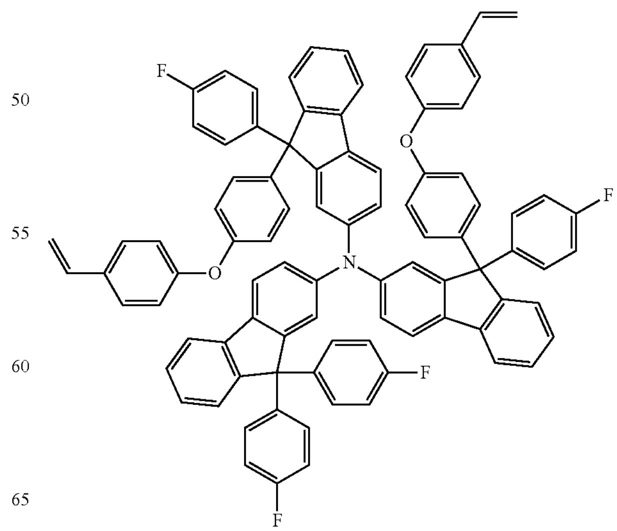
-continued -continued
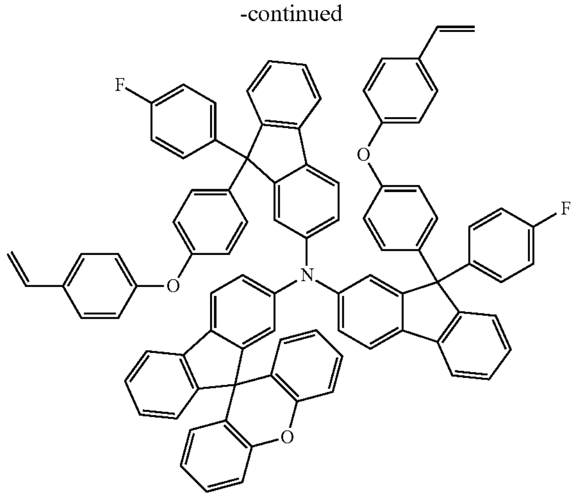
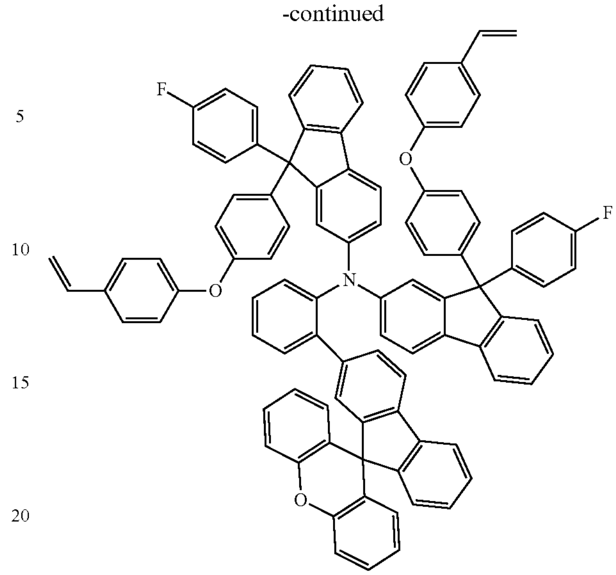
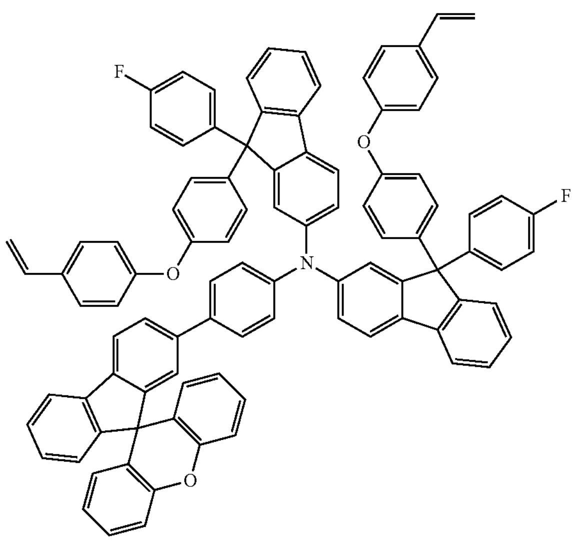
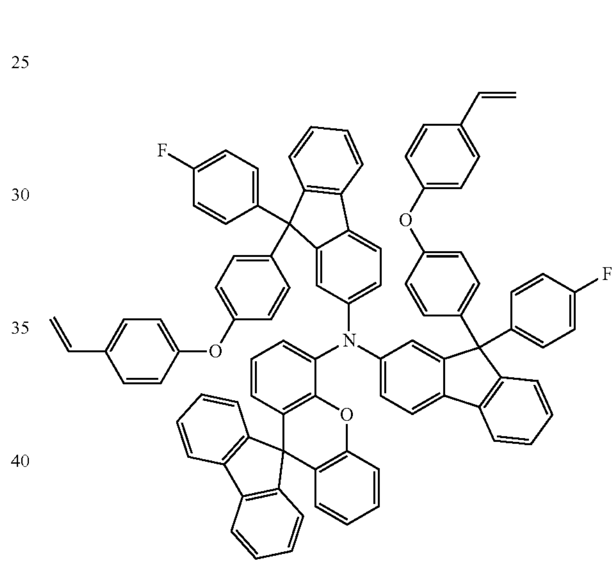
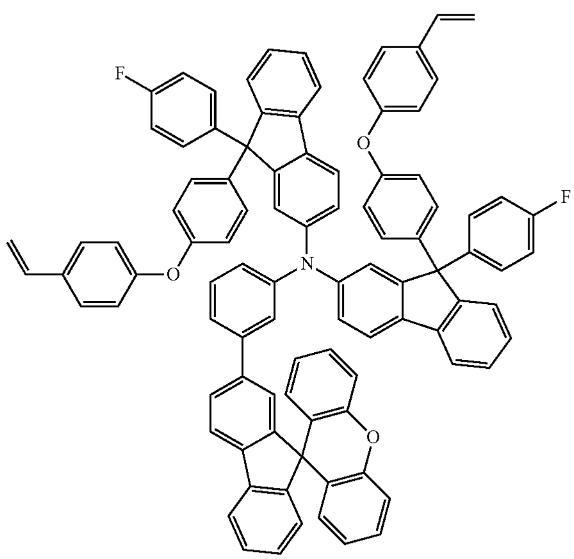
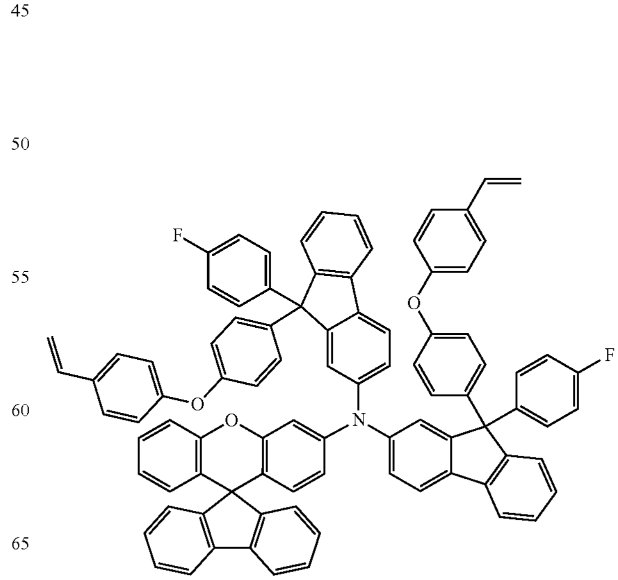
-continued -continued
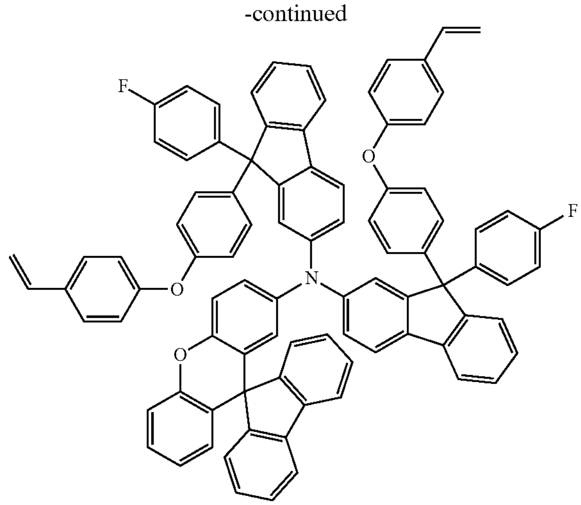
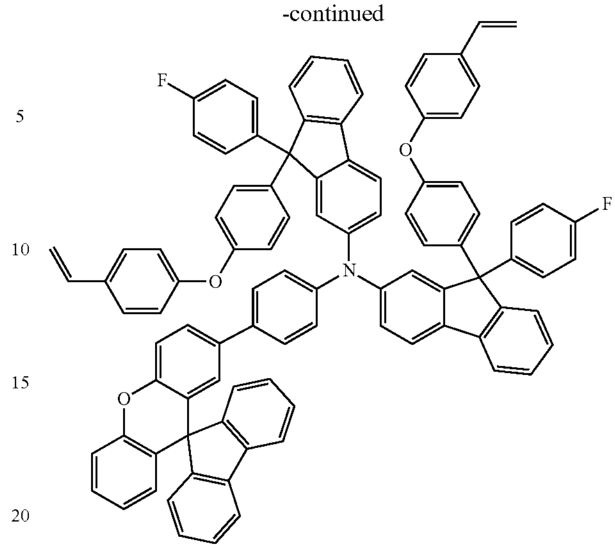
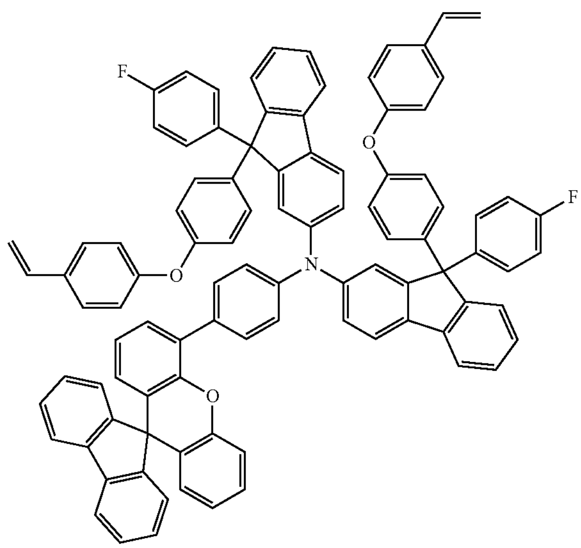
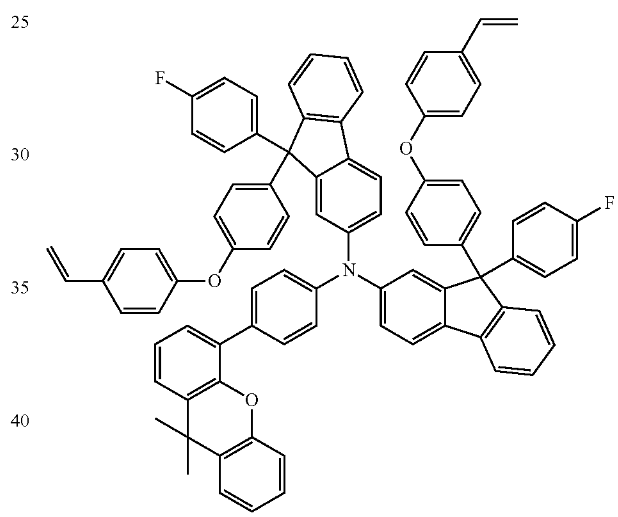
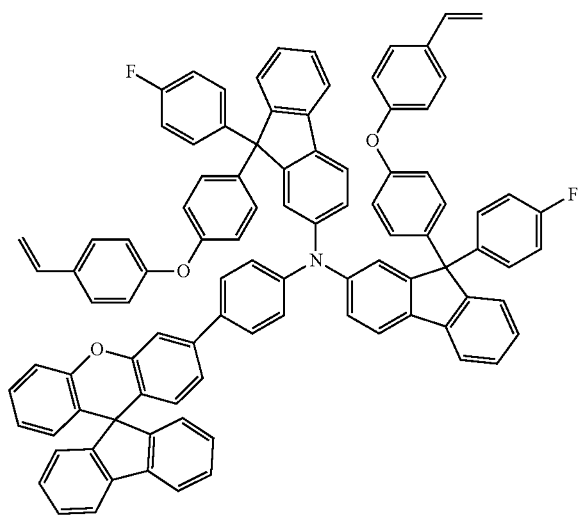
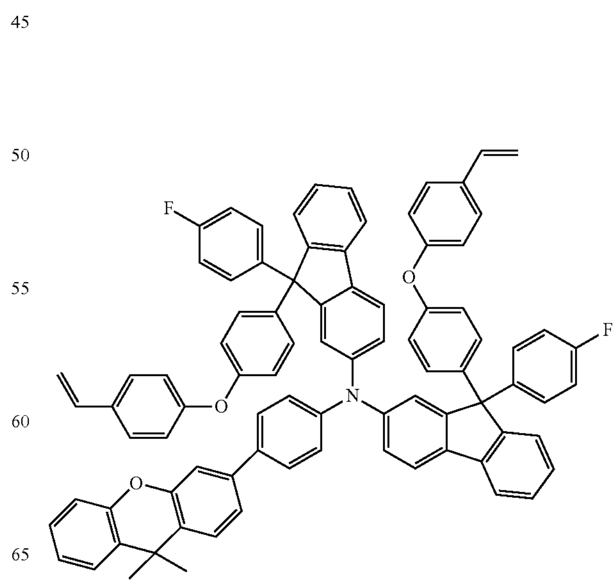

-continued
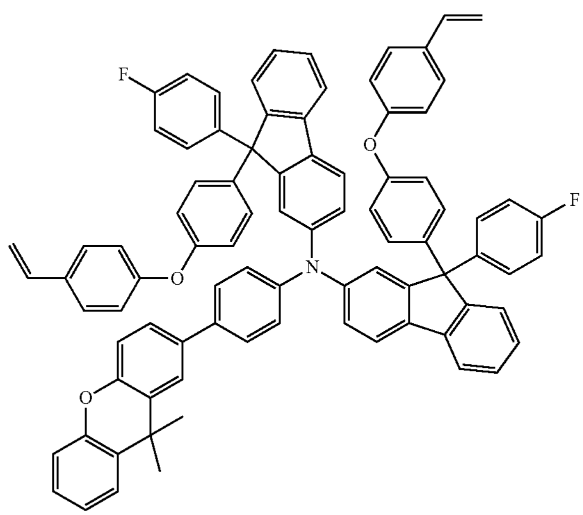 [SMILES: C=Cc1ccc(Oc2ccc(C3(c4ccc(F)cc4)c4ccccc4-c4ccc(N(c5ccc(-c6ccc7c(c6)C(C)(C)c6ccccc6O7)cc5)c5ccc6c(c5)C(c5ccc(F)cc5)(c5ccc(Oc7ccc(C=C)cc7)cc5)c5ccccc5-6)cc43)cc2)cc1]
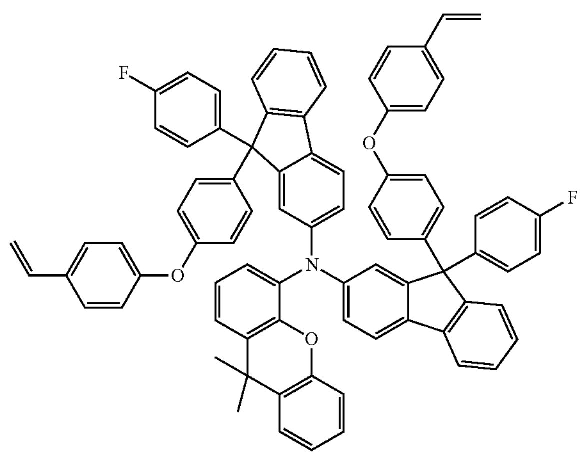
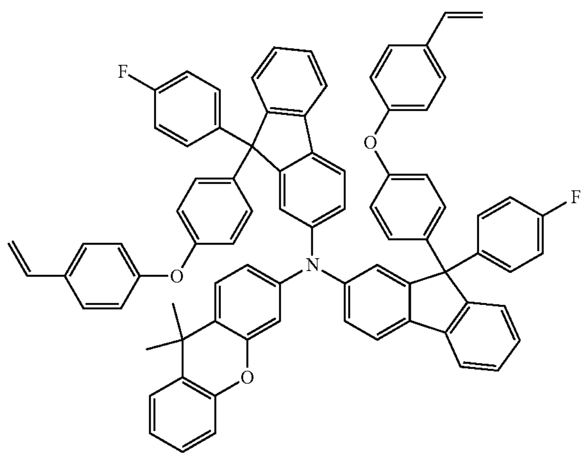
-continued
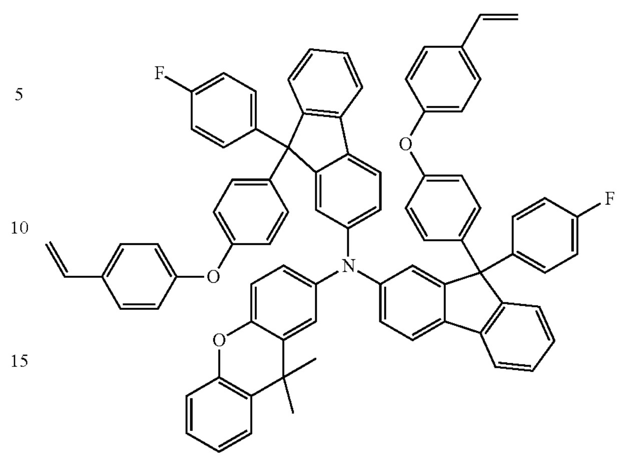
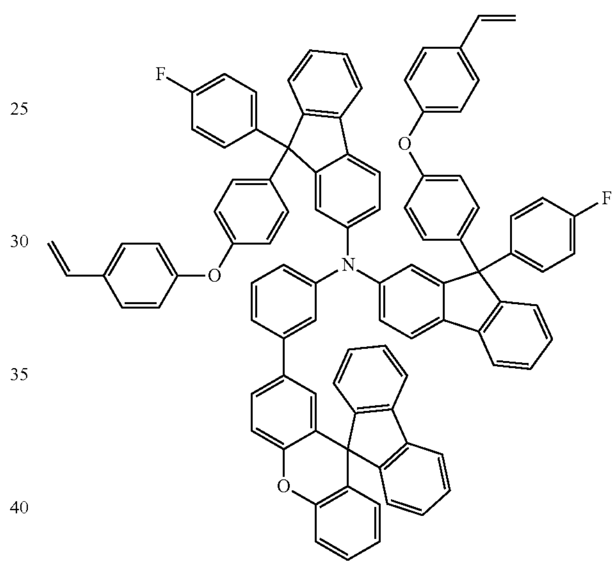
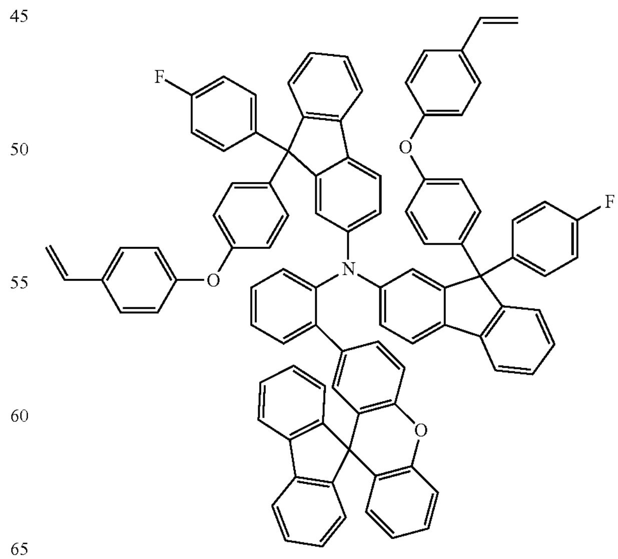

-continued

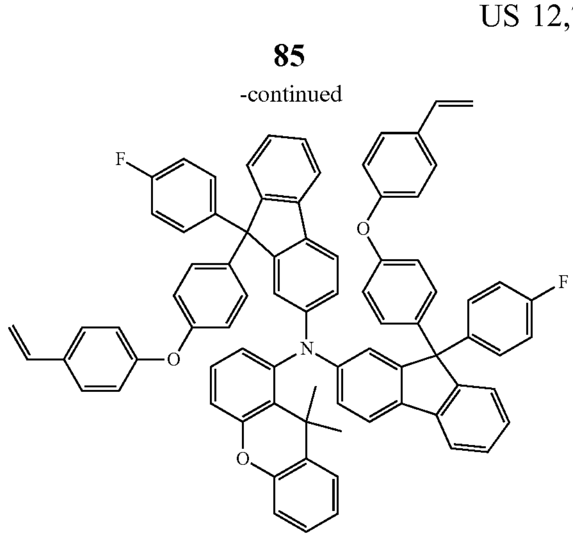

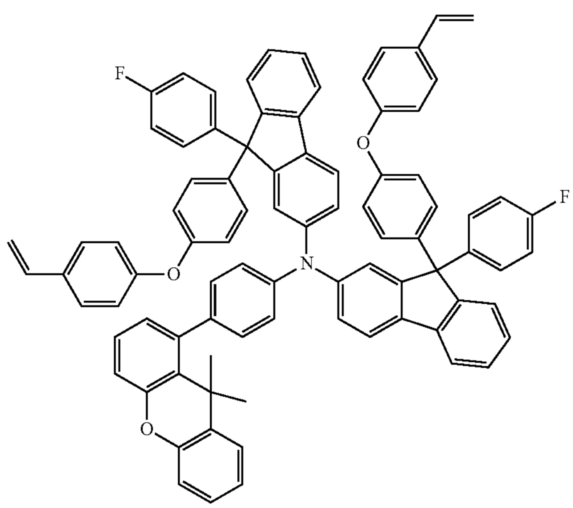

-continued

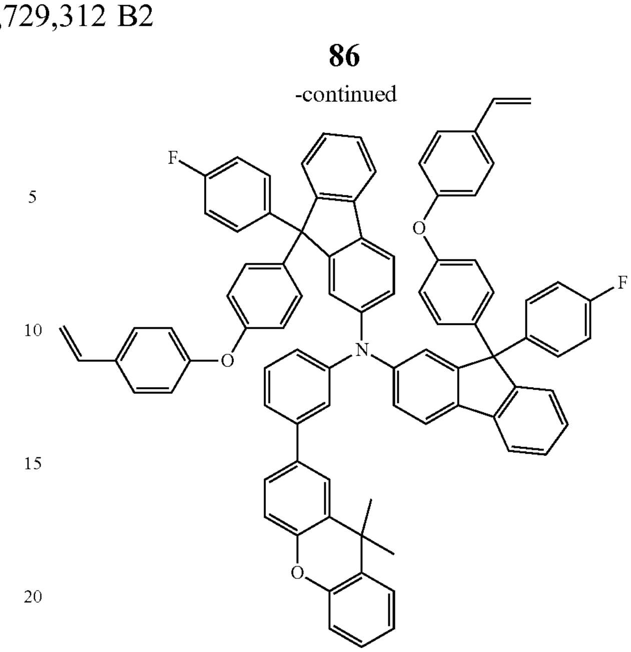

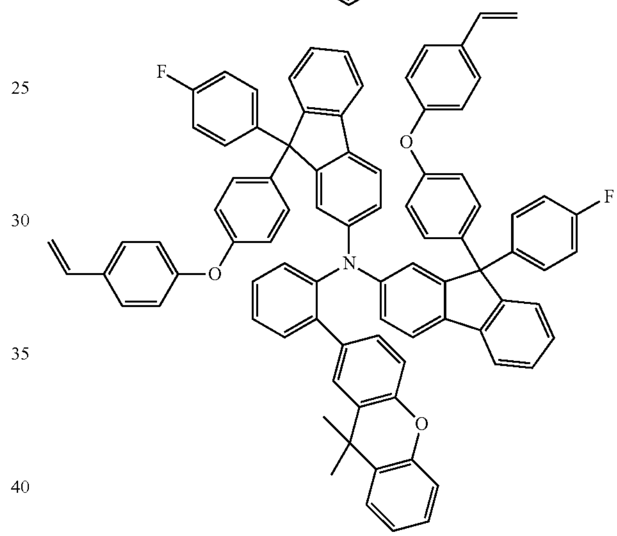

The compound of Chemical Formula 1 according to one embodiment of the present disclosure may have its core structure prepared as in the following Reaction Formula 1. In addition, substituents may bond thereto using methods known in the art, and types, positions and the number of the substituents may vary depending on techniques known in the art.

<Reaction Formula 1>

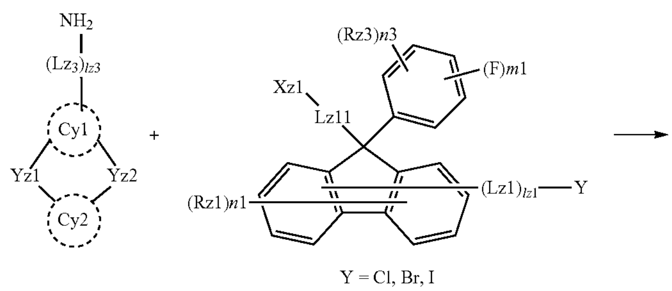

-continued

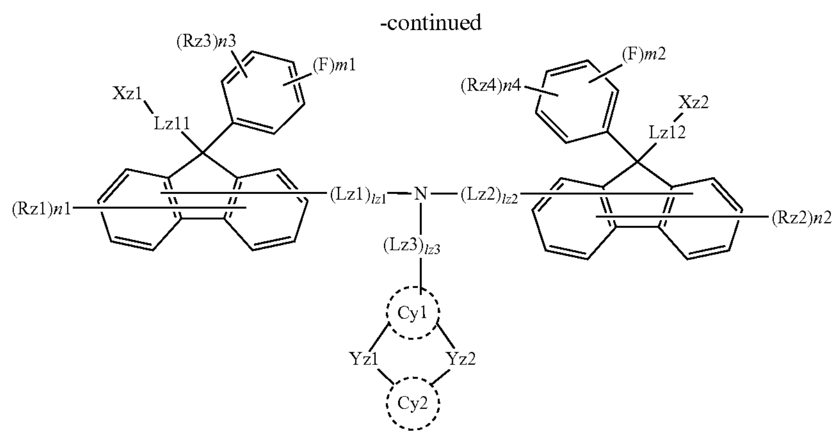

The reaction is an amine substitution reaction, and is preferably conducted under the presence of a palladium catalyst and a base, and reaction groups for the amine substitution reaction may vary as known in the art.

Substituents in Reaction Formula 1 have the same definitions as the substituents of Chemical Formula 1.

Hereinafter, a coating composition including the compound described above will be described in detail.

According to one embodiment of the present disclosure, the coating composition includes the compound of Chemical Formula 1 and a solvent.

According to one embodiment of the present disclosure, the coating composition may be a liquid phase.

According to one embodiment of the present disclosure, examples of the solvent may include chlorine-based solvents such as chloroform, methylene chloride, 1,2-dichloroethane, 1,1,2-trichloroethane, chlorobenzene and o-dichlorobenzene; ether-based solvents such as tetrahydrofuran and dioxane; aromatic hydrocarbon-based solvents such as toluene, xylene, trimethylbenzene and mesitylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, cyclohexanone, isophorone, tetralone, decalone and acetylacetone; ester-based solvents such as ethyl acetate, butyl acetate and ethyl cellosolve acetate; polyalcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol, and derivatives thereof; alcohol-based solvents such as methanol, ethanol, propanol, isopropanol and cyclohexanol; sulfoxide-based solvents such as dimethyl sulfoxide; amide-based solvents such as N-methyl-2-pyrrolidone and N,N-dimethylformamide; tetraline, and the like, however, the solvent is not limited thereto as long as it is a solvent capable of dissolving or dispersing the compound of Chemical Formula 1 according to one embodiment of the present disclosure.

According to one embodiment of the present disclosure, the solvent may be used either alone as one type, or as a mixture of two or more solvent types.

According to one embodiment of the present disclosure, the coating composition does not further include a p-doping material.

According to one embodiment of the present disclosure, the coating composition further includes a p-doping material.

In the present disclosure, the p-doping material means a material allowing a host material to have p-semiconductor properties. The p-semiconductor properties mean properties receiving or transferring holes at a HOMO (highest occupied molecular orbital) energy level, that is, properties of a material having high hole conductivity.

The p-doping material may be any one of the following structures, but is not limited thereto.

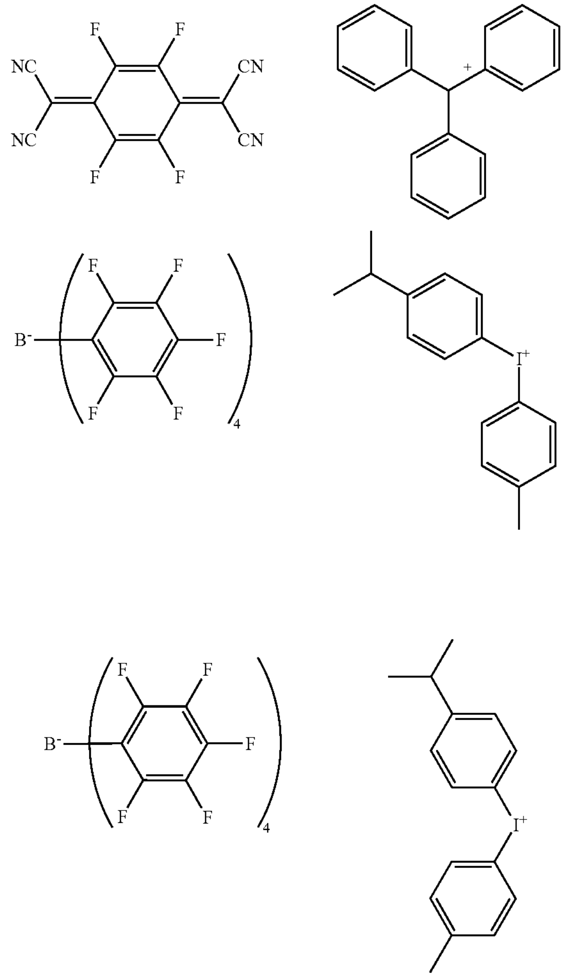

-continued

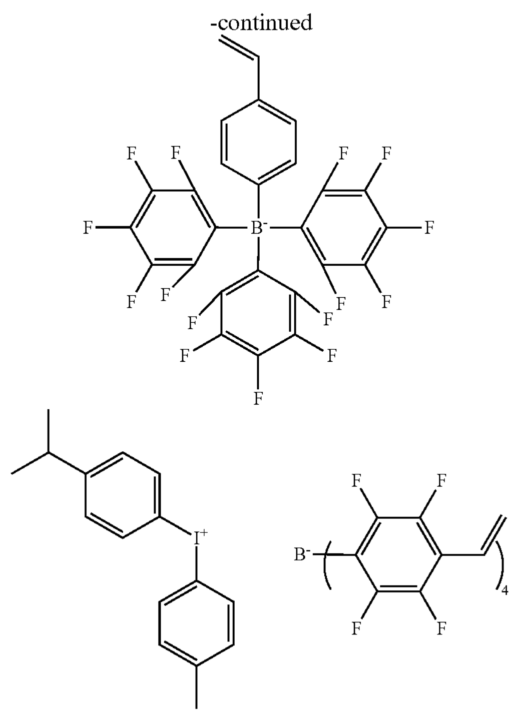

According to one embodiment of the present disclosure, a content of the p-doping material is from 0% by weight to 50% by weight; or from 10% by weight to 30% by weight based on the compound of Chemical Formula 1.

According to one embodiment of the present disclosure, the compound of Chemical Formula 1 and the p-doping material have a weight ratio of 9:1 to 1:9. As preferred one example, the compound of Chemical Formula 1 and the p-doping material have a weight ratio of 9:1 to 7:3. As specific one example, the compound of Chemical Formula 1 and the p-doping material have a weight ratio of 8:2.

According to one embodiment of the present disclosure, the p-doping material is included in 0% by weight to 30% by weight based on a total solid content of the coating composition.

According to one embodiment of the present disclosure, the p-doping material is preferably included in 1% by weight to 30% by weight based on a total solid content of the coating composition.

According to another embodiment of the present disclosure, the coating composition further includes a monomer including a photocurable group and/or a thermal curable group; or a monomer including an end group capable of forming a polymer by heat. The monomer including a photocurable group and/or a thermal curable group; or the monomer including an end group capable of forming a polymer by heat as above may be a compound having a molecular weight of 3,000 g/mol or less, however, the molecular weight is not limited to the example illustrated above.

The monomer including a photocurable group and/or a thermal curable group; or the monomer including an end group capable of forming a polymer by heat may mean aryl such as phenyl, biphenyl, fluorene or naphthalene; arylamine; or a monomer in which fluorene is substituted with a photocurable group and/or a thermal curable group or an end group capable of forming a polymer by heat.

According to one embodiment of the present disclosure, the coating composition has viscosity of 2 cP to 15 cP at room temperature. When satisfying the above-mentioned viscosity range, a device may be readily manufactured. Specifically, a uniform film may be formed when forming an organic material layer in an organic light emitting device.

According to one embodiment of the present disclosure, the coating composition is in a cured state by heat treatment or light treatment, and this is referred to as a cured material of the coating composition.

One embodiment of the present disclosure provides an organic light emitting device including the compound of Chemical Formula 1; or a coating composition including the compound of Chemical Formula 1 or a cured material thereof.

One embodiment of the present disclosure provides an organic light emitting device formed using the coating composition or a cured material thereof.

One embodiment of the present disclosure provides an organic light emitting device including a first electrode; a second electrode; and one or more organic material layers provided between the first electrode and the second electrode, wherein one or more layers of the one or more organic material layers include the coating composition described above or a cured material thereof. Herein, the cured material of the coating composition is the coating composition being in a cured state by heat treatment or light treatment.

Hereinafter, types of the organic material layer included in the organic light emitting device described above will be specifically described.

According to one embodiment of the present disclosure, the organic light emitting device includes one organic material layer, and the organic material layer includes the compound of Chemical Formula 1. As one example, the organic material layer including the compound of Chemical Formula 1 is a light emitting layer.

According to another embodiment of the present disclosure, the organic light emitting device includes two or more organic material layers, and the two or more organic material layers include the compound of Chemical Formula 1. For example, any one organic material layer of the two or more organic material layers includes the compound of Chemical Formula 1, and other one or more organic material layers are further included. The other one or more organic material layers according to one embodiment do not include the compound of Chemical Formula 1. The other one or more organic material layers according to another embodiment further include the compound of Chemical Formula 1. However, the structure is not limited to the above-described example.

The two or more organic material layers may include two or more layers selected from the group consisting of, for example, a hole injection layer, a hole transfer layer, a hole injection and transfer layer, an electron blocking layer, a light emitting layer, a hole blocking layer, an electron transfer layer, an electron injection layer, an electron injection and transfer layer, and the like. Herein, the hole injection and transfer layer means a layer carrying out hole injection and hole transfer at the same time, and the electron injection and transfer layer means a layer carrying out electron injection and electron transfer at the same time. However, the organic material layers forming the group are just one example, and are not limited to the example described above. In addition, the two or more organic material layers may include two or more layers performing the same role as necessary. The organic light emitting device according to one example includes a first hole injection layer and a second hole injection layer. However, the structure is not limited to the example described above.

According to one embodiment of the present disclosure, the organic material layer includes a light emitting layer. As one example, the light emitting layer includes the compound of Chemical Formula 1. As specific one example, the light emitting layer includes the compound of Chemical Formula 1 as a host of the light emitting layer. As specific another example, the light emitting layer includes the compound of Chemical Formula 1 as a dopant of the light emitting layer.

According to one embodiment of the present disclosure, the organic material layer includes a hole injection and transfer layer, a hole injection layer or a hole transfer layer. As one example, the hole injection and transfer layer, the hole injection layer or the hole transfer layer includes the compound of Chemical Formula 1.

According to one embodiment of the present disclosure, the organic material layer includes a hole injection layer. As one example, the hole injection layer includes the compound of Chemical Formula 1.

According to one embodiment of the present disclosure, the organic material layer further includes one or more layers selected from the group consisting of an electron blocking layer, a hole blocking layer, an electron transfer layer, an electron injection layer, and an electron injection and transfer layer.

As one example, one or more layers selected from the group consisting of the electron blocking layer, the hole blocking layer, the electron transfer layer, the electron injection layer, and the electron injection and transfer layer include the compound of Chemical Formula 1, the coating composition or a cured material thereof. As another example, the electron blocking layer, one or more layers selected from the group consisting of the hole blocking layer, the electron transfer layer, the electron injection layer, and the electron injection and transfer layer do not include the compound of Chemical Formula 1, the coating composition or a cured material thereof.

One embodiment of the present disclosure provides an organic light emitting device including a first electrode; a second electrode; and one or more organic material layers provided between the first electrode and the second electrode, wherein the organic material layer includes a light emitting layer and a hole injection layer, and the hole injection layer includes the compound of Chemical Formula 1, the coating composition or a cured material thereof.

Hereinafter, lamination structures of the organic material layers and the organic light emitting device including the same will be described in detail.

The organic material layer of the organic light emitting device according to one embodiment of the present disclosure has a single layer structure. For example, the organic material layer having a single layer structure is provided between the first electrode and the second electrode of the organic light emitting device, and the organic material layer includes the compound of Chemical Formula 1. According to specific one embodiment, the organic material layer forming in a single layer structure is a light emitting layer, and the light emitting layer herein includes the compound of Chemical Formula 1.

The organic material layer of the organic light emitting device according to another embodiment of the present disclosure has a multilayer structure in which two or more organic material layers are laminated. For example, the organic material layer having a multilayer structure is provided between the first electrode and the second electrode of the organic light emitting device.

According to one embodiment of the present disclosure, the organic material layer having a multilayer structure includes a light emitting layer, and organic material layers other than the light emitting layer. As one example, the light emitting layer is provided between the first electrode and the second electrode, and the organic material layers other than the light emitting layer are provided between the first electrode and the light emitting layer. As another example, the light emitting layer is provided between the first electrode and the second electrode, and the organic material layers other than the light emitting layer are provided between the light emitting layer and the second electrode. As still another example, the light emitting layer is provided between the first electrode and the second electrode, any one organic material layer other than the light emitting layer is provided between the first electrode and the light emitting layer, and any other organic material layer other than the light emitting layer is provided between the light emitting layer and the second electrode. However, the structures are just an example, and the structure is not limited to the structure described above. In addition, the organic material layers other the light emitting layer may include one or more layers selected from the group consisting of, for example, a hole injection and transfer layer, a hole injection layer, a hole transfer layer, an electron blocking layer, a hole blocking layer, an electron transfer layer, an electron injection layer, an electron injection and transfer layer, and the like, but are not limited thereto.

In a general organic light emitting device, a hole injection layer, a hole transfer layer or an electron-blocking layer is provided between an anode and a light emitting layer. As a specific example, a hole injection layer is provided on an anode, a hole transfer layer is provided on the hole injection layer, and an electron blocking layer is provided on the hole injection layer, however, the structure is not limited to the example described above.

In addition, in a general organic light emitting device, an electron injection layer, an electron transfer layer or a hole blocking layer is provided between a cathode and a light emitting layer. As a specific example, a hole blocking layer is provided on a light emitting layer, an electron transfer layer is provided on the hole blocking layer, and an electron injection layer is provided on the electron transfer layer, however, the structure is not limited to the example described above.

The organic material layer having a multilayer structure included in the organic light emitting device according to one embodiment of the present disclosure includes one or more layers selected from the group consisting of a hole injection and transfer layer, a hole injection layer, a hole transfer layer, an electron blocking layer, a hole blocking layer, an electron transfer layer, an electron injection layer, and an electron injection and transfer layer; and a light emitting layer, wherein the light emitting layer is provided between the first electrode and the second electrode, the one or more layers are provided between the first electrode and the light emitting layer, and the one or more layers include the compound of Chemical Formula 1.

A structure of the organic light emitting device according to one embodiment of the present disclosure is illustrated in the FIGURE. In the FIGURE, a structure of the organic light emitting device in which a first electrode (201), a hole injection layer (301), a hole transfer layer (401), a light emitting layer (501), an electron injection and transfer layer (601) and a second electrode (701) are consecutively laminated on a substrate (101) is illustrated. The hole injection layer (301) and/or the hole transfer layer (401) of the FIGURE include the compound of Chemical Formula 1; or the coating composition including the compound of Chemical Formula 1 or a cured material thereof, or may be formed using the coating composition. Herein, the forming of the hole injection layer (301) and/or the hole transfer layer (401) of the FIGURE using the coating composition will be described later in specific descriptions on the organic material layers, and materials and preparation methods thereof. In addition, the FIGURE illustrates the organic light emitting device according to one embodiment of the present disclosure, and the organic light emitting device is not limited thereto.

The organic light emitting device having the organic material layer in a single layer or multilayer structure as above may have, for example, lamination structures as below, however, the lamination structure is not limited thereto.

(1) an anode/a hole transfer layer/a light emitting layer/a cathode (2) an anode/a hole injection layer/a hole transfer layer/a light emitting layer/a cathode (3) an anode/a hole injection layer/a hole buffer layer/a hole transfer layer/a light emitting layer/a cathode (4) an anode/a hole transfer layer/a light emitting layer/an electron transfer layer/a cathode (5) an anode/a hole transfer layer/a light emitting layer/an electron transfer layer/an electron injection layer/a cathode (6) an anode/a hole injection layer/a hole transfer layer/a light emitting layer/an electron transfer layer/a cathode (7) an anode/a hole injection layer/a hole transfer layer/a light emitting layer/an electron transfer layer/an electron injection layer/a cathode (8) an anode/a hole injection layer/a hole buffer layer/a hole transfer layer/a light emitting layer/an electron transfer layer/a cathode (9) an anode/a hole injection layer/a hole buffer layer/a hole transfer layer/a light emitting layer/an electron transfer layer/an electron injection layer/a cathode

(10) an anode/a hole transfer layer/an electron blocking layer/a light emitting layer/an electron transfer layer/a cathode

(11) an anode/a hole transfer layer/an electron blocking layer/a light emitting layer/an electron transfer layer/an electron injection layer/a cathode

(12) an anode/a hole injection layer/a hole transfer layer/an electron blocking layer/a light emitting layer/an electron transfer layer/a cathode

(13) an anode/a hole injection layer/a hole transfer layer/an electron blocking layer/a light emitting layer/an electron transfer layer/an electron injection layer/a cathode

(14) an anode/a hole transfer layer/a light emitting layer/a hole blocking layer/an electron transfer layer/a cathode

(15) an anode/a hole transfer layer/a light emitting layer/a hole blocking layer/an electron transfer layer/an electron injection layer/a cathode

(16) an anode/a hole injection layer/a hole transfer layer/a light emitting layer/a hole blocking layer/an electron transfer layer/a cathode

(17) an anode/a hole injection layer/a hole transfer layer/a light emitting layer/a hole blocking layer/an electron transfer layer/an electron injection layer/a cathode

(18) an anode/a hole injection layer/a hole transfer layer/a light emitting layer/a hole blocking layer/an electron transfer layer/an electron injection layer/a cathode/a capsule

(19) an anode/a hole injection layer/a first hole transfer layer/a second hole transfer layer/a light emitting layer/a hole blocking layer/an electron transfer layer/an electron injection layer/a cathode/a capsule According to one embodiment of the present disclosure, the first electrode is an anode, and the second electrode is a cathode.

According to another embodiment of the present disclosure, the first electrode is a cathode, and the second electrode is an anode.

According to one embodiment of the present disclosure, the organic light emitting device may be an organic light emitting device having a structure in a normal direction in which an anode, one or more organic material layers and a cathode are consecutively laminated on a substrate (normal type).

According to another embodiment of the present disclosure, the organic light emitting device may be an organic light emitting device having a structure in a reverse direction in which a cathode, one or more organic material layers and an anode are consecutively laminated on a substrate (inverted type).

Hereinafter, specific descriptions on the organic material layers described above, and materials and preparation methods thereof will be described. However, the organic light emitting device of the present disclosure may be manufactured using materials and methods known in the art, except that the organic material layers include the above-described compound.

In the organic light emitting device according to one embodiment of the present disclosure, one or more layers of the organic material layers are formed using the coating composition including the compound of Chemical Formula 1. Other than this, the organic light emitting device according to one embodiment of the present disclosure may be manufactured using materials and methods known in the art.

For example, the organic light emitting device of the present disclosure may be manufactured by consecutively laminating an anode, an organic material layer and a cathode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, forming an organic material layer including one or more of a hole injection layer, a hole transfer layer, a light emitting layer, an electron injection layer, an electron transfer layer, a hole injection and transfer layer or an electron injection and transfer layer thereon through a solution process, a deposition process or the like, and then depositing a material usable as a cathode thereon. In addition to such a method, the organic light emitting device may also be manufactured by consecutively depositing a cathode material, an organic material layer and an anode material on a substrate.

In addition, one embodiment of the present disclosure provides a method for manufacturing an organic light emitting device formed using the coating composition.

Specifically, according to one embodiment of the present disclosure, the method includes preparing a first electrode; forming one or more organic material layers on the first electrode; and forming a second electrode on the one or more organic material layers, wherein the forming of one or more organic material layers includes forming organic material layers using the coating composition.

According to one embodiment of the present disclosure, the forming of one or more organic material layers using the coating composition uses a spin coating method.

According to another embodiment of the present disclosure, the forming of one or more organic material layers using the coating composition uses a printing method.

According to one embodiment of the present disclosure, the printing method may include, for example, inkjet printing, nozzle printing, offset printing, transfer printing, screen printing or the like, however, the printing method is not limited to the printing methods listed above.

The coating composition according to one embodiment of the present disclosure may be formed using a printing method since a solution process is suited due to its structural properties, which is economically effective in terms of time and costs when manufacturing the device.

According to one embodiment of the present disclosure, the forming of one or more organic material layers using the coating composition includes coating the coating composition; and heat treating or light treating the coated coating composition.

According to one embodiment of the present disclosure, the forming of one or more organic material layers using the coating composition includes coating the coating composition on the first electrode or one or more organic material layers; and heat treating or light treating the coated coating composition.

According to one embodiment of the present disclosure, the heat treating may be conducted through heat treatment, and a temperature of the heat treatment in the heat treating may be from 85° C. to 250° C., may be from 100° C. to 250° C. according to one embodiment, and may be from 150° C. to 250° C. in another embodiment.

According to one embodiment of the present disclosure, a time of the heat treatment in the heat treating may be from 1 minute to 2 hours, may be from 1 minute to 1 hour according to one embodiment, and may be from 10 minutes to 1 hour in another embodiment. As preferred one example, a time of the heat treatment in the heat treating may be from 20 minutes to 40 minutes.

When including the heat treating or light treating in the forming of one or more organic material layers formed using the coating composition, a plurality of the compounds included in the coating composition form crosslinks, and an organic material layer including a thin-filmed structure may be provided. This may prevent the organic material layer formed using the coating composition from being dissolved by a solvent, being morphologically influenced or being decomposed when laminating other layers on the surface of the organic material layer.

Accordingly, when the organic material layer formed using the coating composition is formed including the heat treating or light treating, resistance for a solvent increases, and a multilayer may be formed by repeatedly performing solution deposition and crosslinking methods, and lifetime properties of the device may be enhanced by increasing stability.

Hereinafter, materials of the anode, the cathode and the specific organic material layers described above will be described in detail.

As the anode material, materials having large work function are normally preferred so that hole injection to an organic material layer is smooth. Examples thereof include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene](PEDOT), polypyrrole and polyaniline, and the like, but are not limited thereto.

As the cathode material, materials having small work function are normally preferred so that electron injection to an organic material layer is smooth. Examples thereof include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The light emitting layer may include a host material and/or a dopant material.

The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes dibenzofuran derivatives, ladder-type furan compounds, pyrimidine derivatives and the like, however, the material is not limited thereto.

According to one embodiment of the present disclosure, as the host material, two or more host materials selected from among the host materials described above may be mixed and used. As one example, an anthracene derivative and a pyrene derivative may be mixed in a weight ratio of 1:99 to 99:1 and used. As more specific one example, an anthracene derivative and a pyrene derivative may be mixed in a weight ratio of 92:8 and used.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like. In addition, the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, however, the styrylamine compound is not limited thereto. In addition, the metal complex includes iridium complexes, platinum complexes or the like, but is not limited thereto.

The hole injection layer is a layer receiving holes from an electrode. As the hole injection material, materials having a hole transferring ability, and thereby having a hole receiving effect from an anode and an excellent hole injection effect for a light emitting layer or a light emitting material are preferred. In addition, materials having an excellent ability of preventing excitons generated in the light emitting layer from moving to an electron injection layer or an electron injection material are preferred. In addition, materials having an excellent thin film forming ability are preferred. In addition, the HOMO of the hole injection material is preferably in between the work function of an anode material and the HOMO of surrounding organic material layers. Specific examples of the hole injection material include metal porphyrin, oligothiophene, arylamine-based organic materials, hexanitrile hexaazatriphenylene-based organic materials; quinacridone-based organic materials; perylene-based organic materials; polythiophene-based conductive polymers such as anthraquinone and polyaniline, but are not limited thereto. According to one embodiment of the present disclosure, the hole injection material is the compound of Chemical Formula 1; or the coating composition including the compound of Chemical Formula 1 or a cured material thereof.

The hole transfer layer is a layer that receives holes from a hole injection layer and transfers the holes to a light emitting layer, and may have a single layer structure or a multilayer structure of two or more layers. As the hole transfer material, materials capable of receiving holes from an anode or a hole injection layer, moving the holes to a light emitting layer, and having high mobility for the holes are preferred. In the present disclosure, the compound of Chemical Formula 1 described above may be included as the hole transfer material. In addition, other hole transfer materials may be further included in addition to the compound of Chemical Formula 1 as necessary. Specific examples thereof include arylamine-based organic materials, carbazole-based compounds, conductive polymers, block copolymers having conjugated parts and non-conjugated parts together, and the like, but are not limited thereto. According to one embodiment of the present disclosure, the hole transfer material is the compound of Chemical Formula 1; or the coating composition including the compound of Chemical Formula 1 or a cured material thereof.

The electron transfer layer is a layer that receives electrons from an electron injection layer and transfers the electrons to a light emitting layer. As the electron transfer material, materials capable of favorably receiving electrons from a cathode, moving the electrons to a light emitting layer, and having high mobility for the electrons are preferred. Specific examples thereof include Al complexes of 8-hydroxyquinoline; complexes including $Alq_3$; organic radical compounds; hydroxyflavon-metal complexes, and the like, but are not limited thereto. The electron transfer layer may be used together with any desired cathode material as used in the art. Particularly, the suitable cathode material is a common material that has small work function, and in which an aluminum layer or a silver layer follows. Specifically, the cathode material includes cesium, barium, calcium, ytterbium, samarium and the like, and in each case, an aluminum layer or a silver layer follows.

The electron injection layer is a layer that receives electrons from an electrode. As the electron injection material, materials having an excellent ability to transfer electrons, having an electron receiving effect from a cathode, and having an excellent electron injection effect for a light emitting layer or a light emitting material are preferred. In addition, materials preventing excitons generated in the light emitting layer from moving to a hole injection layer, and having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited there. The metal complex compound includes 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato) gallium and the like, but is not limited thereto.

The electron blocking layer is a layer capable of enhancing lifetime or efficiency of a device by preventing electrons injected from an electron injection layer from passing through a light emitting layer and entering a hole injection layer. The electron blocking layer may be formed using the compound of Chemical Formula 2 described above between the light emitting layer and the hole injection layer, or between the light emitting layer and a layer carrying out hole injection and hole transfer at the same time. In addition, as necessary, other known electron blocking materials other than the compound of Chemical Formula 2 may be further included.

The hole blocking layer is a layer blocking holes from reaching a cathode, and may be generally formed under the same condition as an electron injection layer. Specific examples of the hole blocking layer material may include oxadiazole derivatives or triazole derivatives, phenanthroline derivatives, aluminum complexes and the like, but are not limited thereto.

The hole injection and transfer layer may include the materials of the hole injection layer and the hole transfer layer described above.

The electron injection and transfer layer may include the materials of the electron injection layer and the electron transfer layer described above.

When the organic light emitting device includes a plurality of organic material layers, the organic material layers may be formed with materials the same as or different from each other.

The organic light emitting device according to the present disclosure may be a top-emission type, a bottom-emission type or a dual-emission type depending on the materials used.

One embodiment of the present disclosure provides an electronic device including an organic light emitting device including an organic material layer including the compound of Chemical Formula 1; or the coating composition including the compound of Chemical Formula 1 or a cured material thereof, or formed using the coating composition.

The electronic device may include all of an interlayer insulating film of a semiconductor device, a color filter, a black matrix, an overcoat, a column spacer, a passivation film, a buffer coat film, an insulating film for a multilayer print substrate, a cover coat of a flexible copper clad plate, an insulating film solder resist film for a multilayer print substrate, an insulating film of an OLED, a protective film of a thin film transistor of a liquid crystal display device, an electrode protective film of an organic EL device and a semiconductor protective film, an insulating film of an OLED, an insulating film of an LCD, an insulating film of a semiconductor, a solar cell module, a touch panel, a display device such as a display panel, and the like, but is not limited thereto.

Hereinafter, the present disclosure will be described in detail with reference to examples in order to specifically describe the present disclosure. However, the examples according to the present disclosure may be modified to various different forms, and the scope of the present disclosure is not to be construed as being limited to the examples described below.

Examples of the present disclosure are provided in order to more fully describe the present disclosure to those having average knowledge in the art.

Preparation Example

Preparation Example 1. Preparation of Compound 1

1) Synthesis of Intermediate 1-1

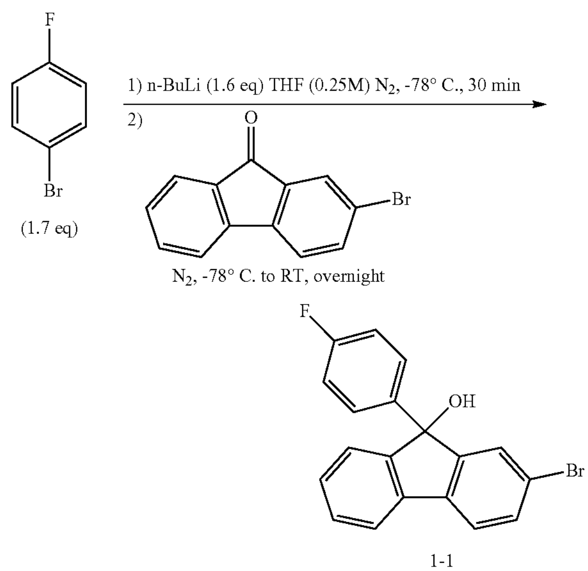

1-1

1-Bromo-4-fluorobenzene (27.9 mL, 255 mmol) was introduced to tetrahydrofuran (THF, hereinafter referred to as THF) (500 mL). The flask was substituted with nitrogen and cooled to −78° C. n-BuLi (2.5 M Hex) (96 mL, 240 mmol) was introduced to a dropping funnel, and then slowly introduced to the reaction mixture. The result was stirred for 30 minutes at −78° C. 2-Bromofluorenone (38.9 g, 150 mmol) was introduced thereto. The result was stirred overnight while slowly raising the temperature to room temperature. The reaction was terminated by introducing distilled water thereto, and the result was extracted with ethyl acetate and water. The organic layer was collected, dried using $MgSO_4$, and filtered. The filtrate was dried using a vacuum rotary concentrator to remove the organic solvent, and used for the next reaction.

2) Synthesis of Intermediate 1-2

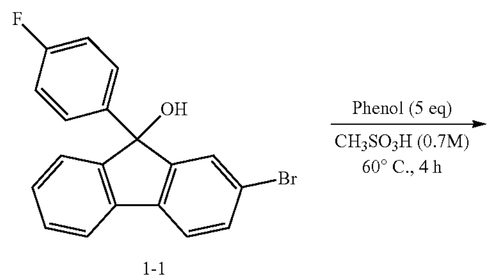

1-1

-continued

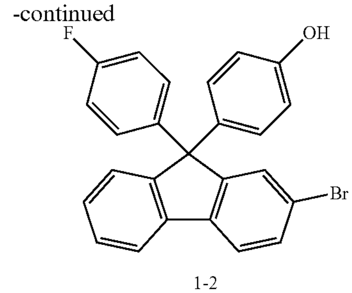

1-2

Intermediate 1-1 (~53 g, 150 mmol) and phenol (70.6 g, 750 mmol) were introduced to a round bottom flask (RBF, hereinafter referred to as RBF). $CH_3SO_3H$ (214 mL) was introduced thereto, and the mixture was stirred for 4 hours at 60° C. Ice water was introduced thereto, and the result was extracted with ethyl acetate and water. The organic layer was collected, dried using $MgSO_4$, and filtered. The filtrate was dried using a vacuum rotary concentrator to remove the organic solvent. The result was column purified, and then crystallized under a condition of dichloromethane (DCM)/heptane to secure Intermediate 1-2 (40.6 g).

3) Synthesis of Intermediate 1-3

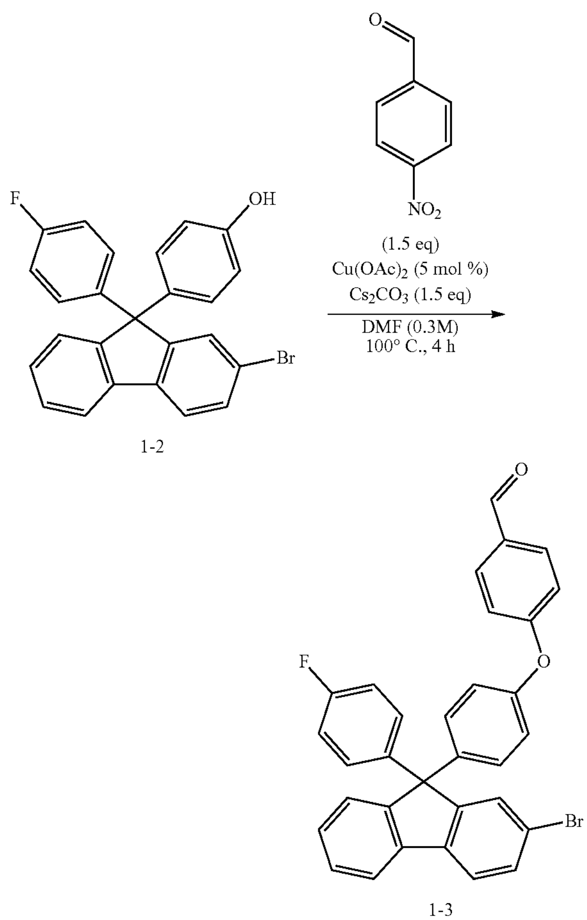

1-2

1-3

Intermediate 1-2 (40 g, 92.7 mmol), 4-nitrobenzaldehyde (21.2 g, 139 mmol), $Cu(OAc)_2$ (842 mg, 4.64 mmol) and $Cs_2CO_3$ (45.3 g, 139 mmol) were introduced to RBF. Dimethylformamide (DMF, hereinafter referred to as DMF) (310 mL) was introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 1-3 (38.7 g).

4) Synthesis of Intermediate 1-4

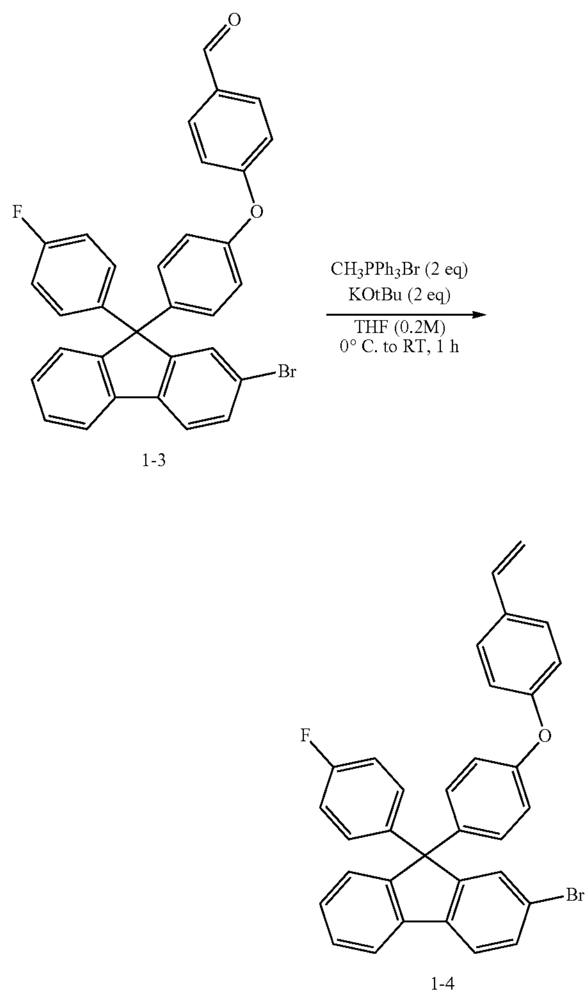

1-3

1-4

$CH_3PPh_3Br$ (51.6 g, 144.6 mmol), potassium tert-butoxide [KOtBu](16.2 g, 144.6 mmol) and THF (217 mL) were introduced to RBF, and cooled to 0° C. A solution obtained by dissolving Intermediate 1-3 (38.7 g, 72.3 mmol) in THF (144 mL) was introduced to the reaction mixture. The result was stirred for 1 hour while raising the temperature to room temperature. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Intermediate 1-4 (33.7 g).

5) Synthesis of Compound 1

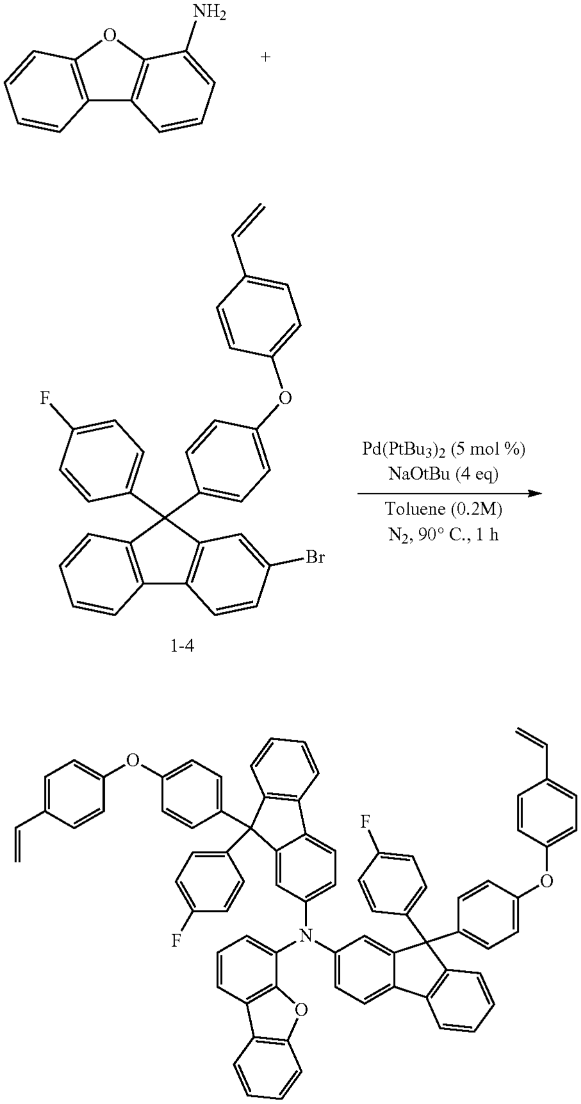

1-4

Compound 1

4-Aminodibenzofuran (513 mg, 2.8 mmol), Intermediate 1-4 (3.1 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 1 (2.9 g). Synthesis of the compound was identified through LC-MS and NMR. MS: $[M+H]^+=1088$ NMR measurement values of Compound 1: $^1H$ NMR (500 MHz, DMSO-d6) δ 8.07 (dd, 1H), 7.92 (d, 1H), 7.82 (dd, 4H), 7.46 (dd, 4H), 7.39-7.24 (m, 10H), 7.21 (dd, 1H), 7.10 (m, 2H), 6.97-6.83 (m, 18H), 6.72 (dd, 2H), 6.65 (d, 4H), 5.75 (d, 2H), 5.21 (d, 2H)

Preparation Example 2. Preparation of Compound 2

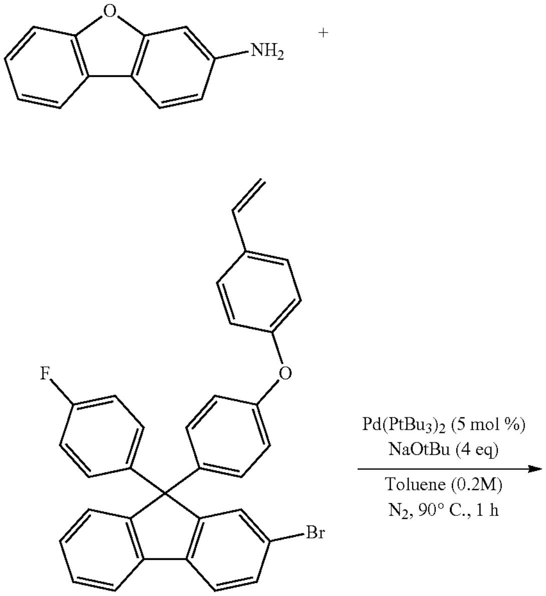

1-4

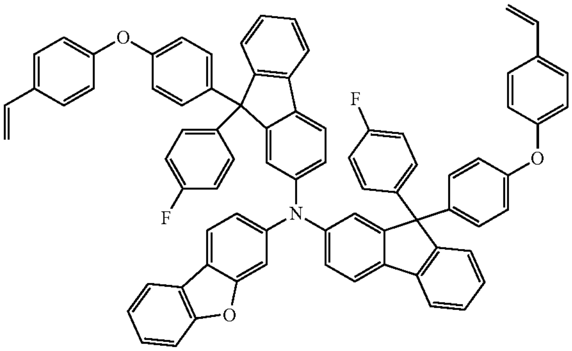

Compound 2

3-Aminodibenzofuran (513 mg, 2.8 mmol), Intermediate 1-4 (3.1 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 2 (2.5 g). Synthesis of the compound was identified through LC-MS and NMR. MS: $[M+H]^+$=1088

NMR measurement values of Compound 2: 1H NMR (500 MHz, DMSO-d6) δ 8.11 (s, 1H), 8.07 (dd, 1H), 7.85 (d, 1H), 7.82 (dd, 4H), 7.46 (dd, 4H), 7.39-7.20 (m, 10H), 7.08 (m, 2H), 6.97-6.83 (m, 18H), 6.72 (dd, 2H), 6.65 (d, 4H), 5.75 (d, 2H), 5.21 (d, 2H)

Preparation Example 3. Preparation of Compound 3

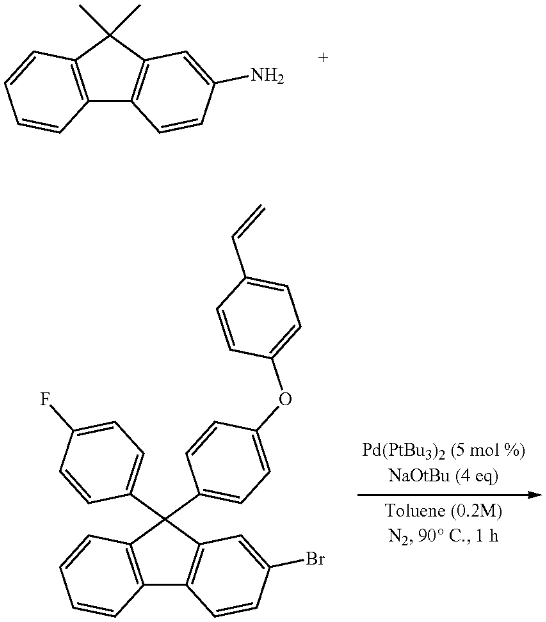

1-4

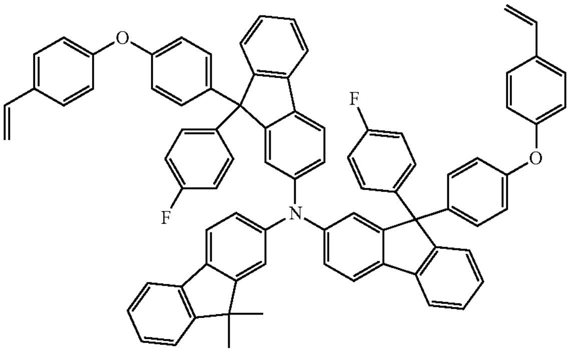

Compound 3

2-Amino-9,9-dimethylfluorene (586 mg, 2.8 mmol), Intermediate 1-4 (3.1 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 3 (2.6 g). Synthesis of the compound was identified through LC-MS and NMR. MS: $[M+H]^+$=1114

NMR measurement values of Compound 3: 1H NMR (500 MHz, DMSO-d6) δ 7.95 (dd, 1H), 7.90 (dd, 1H), 7.84 (dd, 4H), 7.46 (dd, 4H), 7.39-7.20 (m, 11H), 7.08 (m, 2H), 6.97-6.83 (m, 18H), 6.72 (dd, 2H), 6.65 (d, 4H), 5.75 (d, 2H), 5.21 (d, 2H), 1.68 (s, 6H)

Preparation Example 4. Preparation of Compound 4

1) Preparation of Intermediate 4-1

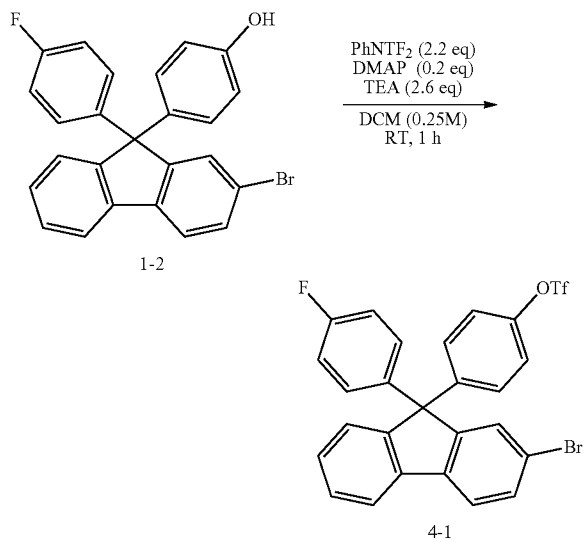

1-2

4-1

Intermediate 1-2 (45 g, 104 mmol), phenyl triflimide (81.8 g, 229 mmol) and DMAP (4-dimethylaminopyridine) (2.54 g, 21 mmol) were introduced to a round bottom flask. Dichloromethane (416 mL) and triethylamine (37.7 mL, 270 mmol) were introduced thereto, and the mixture was stirred for 1 hour at room temperature. The result was extracted with dichloromethane and a 3% aqueous HCl solution, and the organic layer was collected, dried using $MgSO_4$ and filtered. The filtrate was dried using a vacuum rotary concentrator to remove the organic solvent. The result was crystallized under a condition of dichloromethane/heptane to prepare Intermediate 4-1 (52.5 g).

3) Preparation of Intermediate 4-2

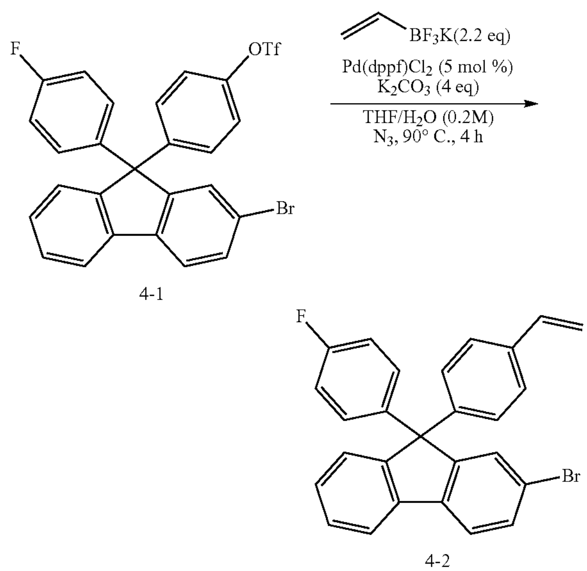

4-1

4-2

Intermediate 4-1 (52.2 g, 92.7 mmol), potassium vinyltrifluoroborate (27.3 g, 204 mmol), $Pd(dppf)Cl_2$ (3.4 g, 4.6 mmol) and $K_2CO_3$ (51.2 g, 971 mmol) were introduced to a round bottom flask. The flask was substituted with nitrogen, THF (371 mL) and $H_2O$ (93 mL) were introduced thereto, and the mixture was stirred for 4 hours at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to prepare Intermediate 4-2 (34 g).

5) Preparation of Compound 4

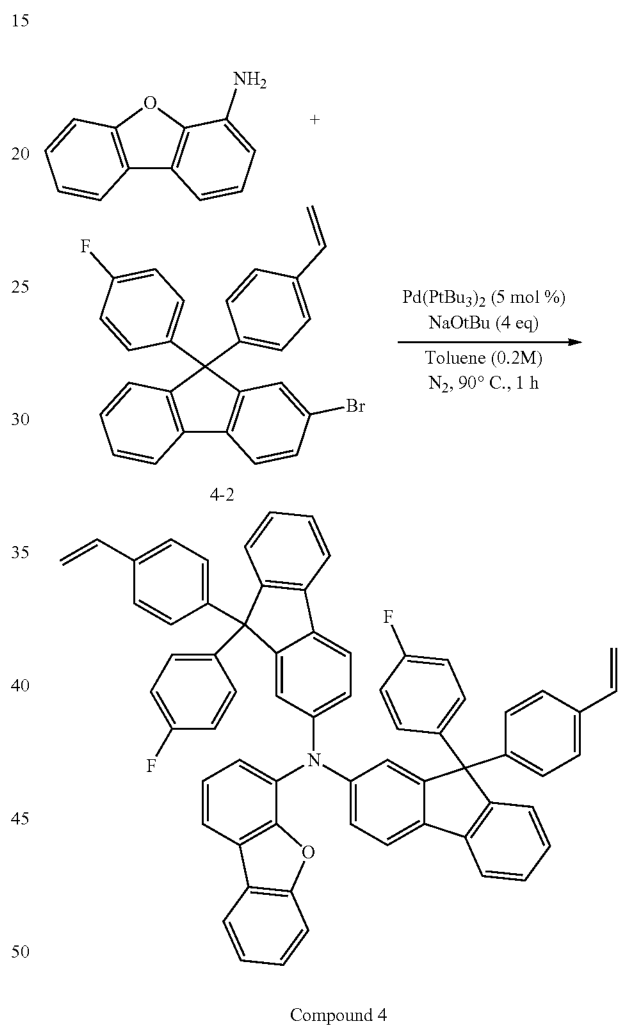

+

4-2

Compound 4

4-Aminodibenzofuran (513 mg, 2.8 mmol), Intermediate 4-2 (2.53 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 4 (2.0 g). Synthesis of the compound was identified through LC-MS and NMR. MS: $[M+H]^+=904$ NMR measurement values of Compound 4: 1H NMR (500 MHz, DMSO-d6) δ 8.07 (dd, 1H), 7.92 (d, 1H), 7.63 (dd, 4H), 7.39-7.24 (m, 10H), 7.21 (dd, 1H), 7.10 (m, 2H), 6.97-6.83 (m, 18H), 6.72 (dd, 2H), 5.75 (d, 2H), 5.21 (d, 2H)

Preparation Example 5. Preparation of Compound 5

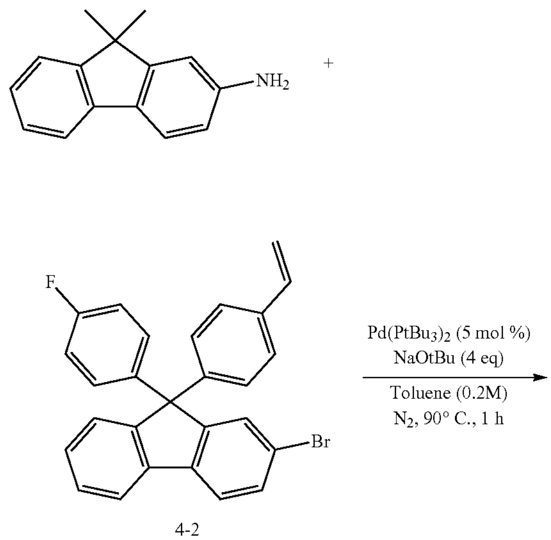

4-2

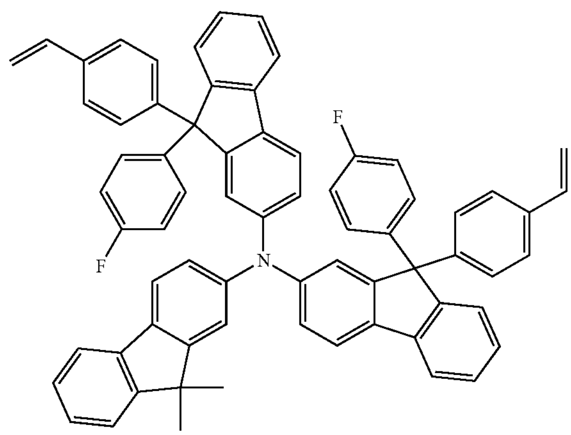

Compound 5

2-Amino-9,9-dimethylfluorene (586 mg, 2.8 mmol), Intermediate 4-2 (2.53 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound (2.1 g). Synthesis of the compound was identified through LC-MS and NMR. MS: $[M+H]^+=930$ NMR measurement values of Compound 5: $^1H$ NMR (500 MHz, DMSO-d6) δ 7.95 (dd, 1H), 7.90 (dd, 1H), 7.84 (dd, 4H), 7.39-7.20 (m, 11H), 7.08 (m, 2H), 6.97-6.83 (m, 18H), 6.72 (dd, 2H), 5.75 (d, 2H), 5.21 (d, 2H), 1.68 (s, 6H)

Preparation Example 6. Preparation of Compound 6

1) Preparation of Intermediate 6-1

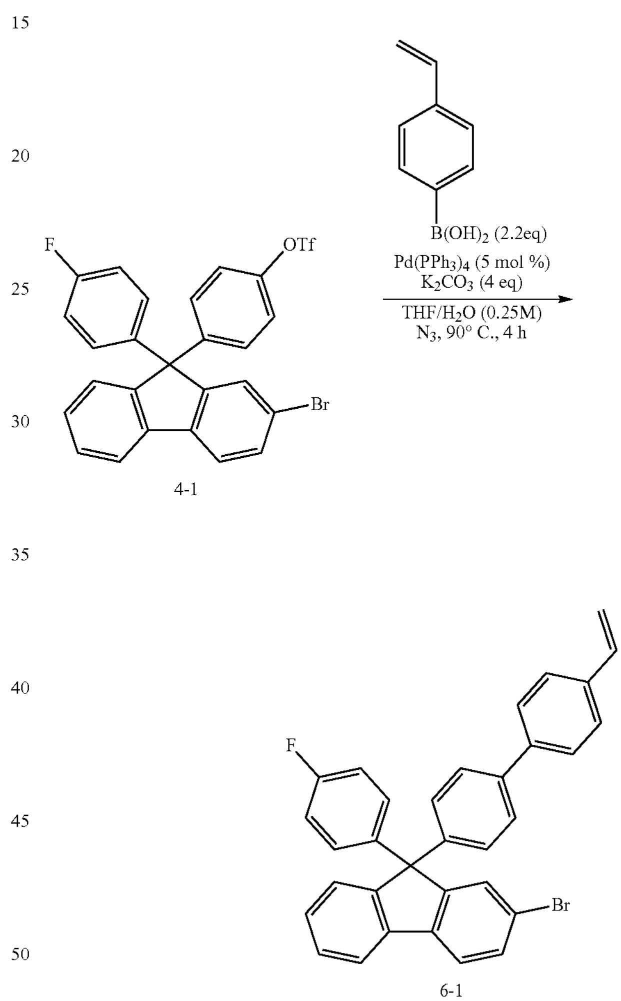

4-1

6-1

Intermediate 4-1 (11.3 g, 20 mmol), 4-vinylphenylboronic acid (6.51 g, 44 mmol), $Pd(PPh_3)_4$ (1.16 g, 1 mmol) and $K_2CO_3$ (11 g, 80 mmol) were introduced to a round bottom flask. After that, the flask was substituted with nitrogen, and THF (64 mL) and $H_2O$ (16 mL) were introduced thereto. The mixture was stirred for 4 hours at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to prepare Intermediate 6-1 (7 g).

2) Preparation of Compound 6

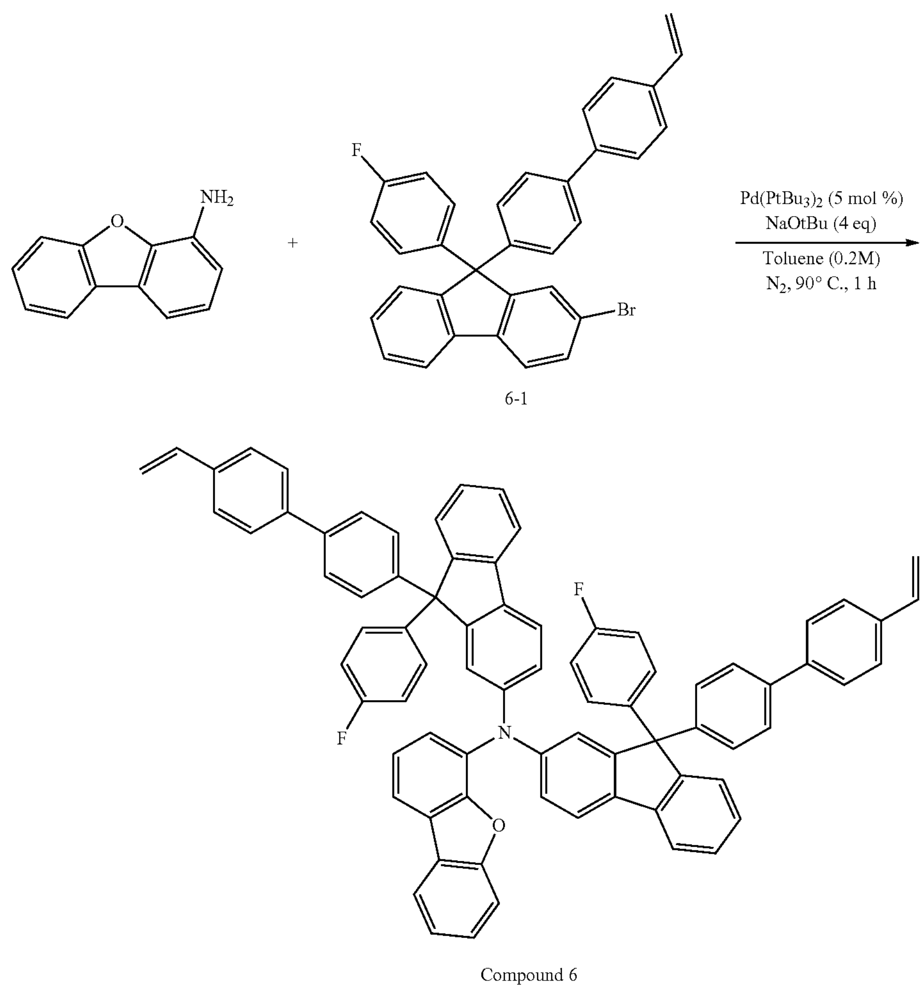

6-1

Compound 6

4-Aminodibenzofuran (513 mg, 2.8 mmol), Intermediate 6-1 (2.97 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 6 (2.8 g). Synthesis of the compound was identified through LC-MS and NMR. MS: $[M+H]^+=1056$ NMR measurement values of Compound 6: $^1H$ NMR (500 MHz, DMSO-d6) δ 8.07 (dd, 1H), 7.92 (d, 1H), 7.63 (dd, 4H), 7.63-7.50 (m, 12H), 7.40-7.27 (m, 17H), 6.97-6.80 (m, 10H), 6.72 (dd, 2H), 5.75 (d, 2H), 5.21 (d, 2H)

Preparation Example 7. Preparation of Compound 7

1) Synthesis of Intermediate 7-1

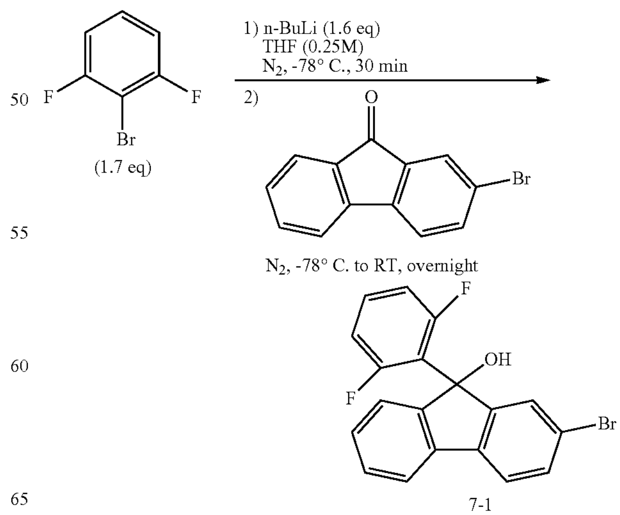

7-1

1-Bromo-2,6-difluorobenzene (29.4 mL, 255 mmol) was introduced to THF (500 mL). The flask was substituted with nitrogen, and cooled to −78° C. n-BuLi (2.5 M Hex) (96 mL, 240 mmol) was introduced to a dropping funnel, and then slowly introduced to the reaction mixture. The result was stirred for 30 minutes at −78° C. 2-Bromofluorenone (38.9 g, 150 mmol) was introduced thereto, and the result was stirred overnight while slowly raising the temperature to room temperature. The reaction was terminated by introducing distilled water thereto, and the result was extracted with ethyl acetate and water. The organic layer was collected, dried using $MgSO_4$, and filtered. The filtrate was dried using a vacuum rotary concentrator to remove the organic solvent, and used for the next reaction.

2) Synthesis of Intermediate 7-2

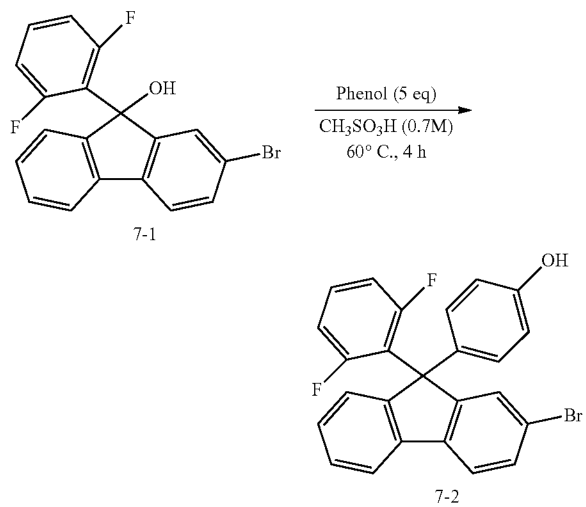

7-1

7-2

Intermediate 7-1 (56 g, 150 mmol) and phenol (70.6 g, 750 mmol) were introduced to RBF. $CH_3SO_3H$ (214 mL) was introduced thereto, and the mixture was stirred for 4 hours at 60° C. Ice water was introduced thereto, and the result was extracted with ethyl acetate and water. The organic layer was collected, dried using $MgSO_4$, and filtered. The filtrate was dried using a vacuum rotary concentrator to remove the organic solvent. The result was column purified, and then crystallized under a condition of DCM/heptane to secure Intermediate 7-2 (45.2 g).

3) Synthesis of Intermediate 7-3

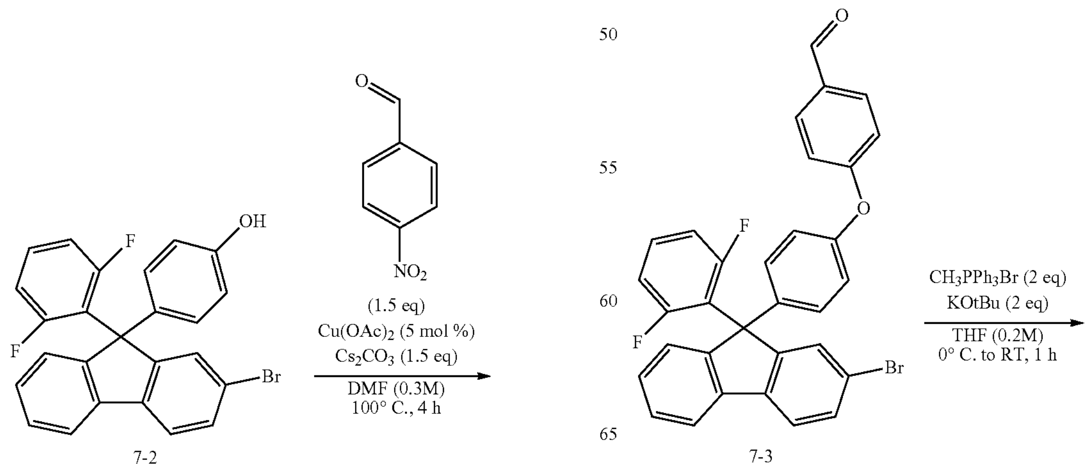

7-2

7-3

-continued

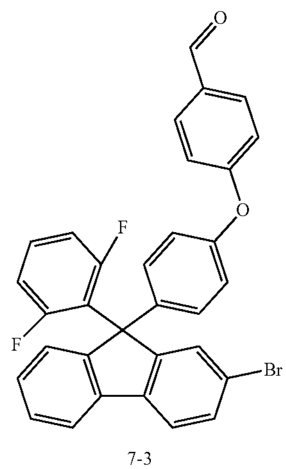

7-3

Intermediate 7-2 (45.2 g, 100 mmol), 4-nitrobenzaldehyde (22.8 g, 150 mmol), $Cu(OAc)_2$ (908 mg, 5 mmol) and $Cs_2CO_3$ (48.9 g, 150 mmol) were introduced to RBF. DMF (333 mL) was introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 7-3 (39.8 g).

4) Synthesis of Intermediate 7-4

-continued

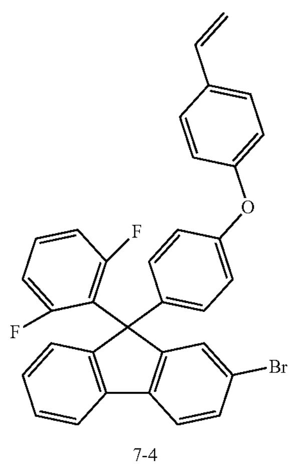

7-4

CH$_3$PPh$_3$Br (51.4 g, 144 mmol), KOtBu (16.2 g, 144 mmol) and THF (216 mL) were introduced to RBF, and cooled to 0° C. A solution obtained by dissolving Intermediate 7-3 (39.8 g, 72 mmol) in THF (144 mL) was introduced to the reaction mixture, and the result was stirred for 1 hour while raising the temperature to room temperature. The result was extracted with ethyl acetate and water, and the organic layer was collected, dried using MgSO$_4$ and filtered. The filtrate was dried using a vacuum rotary concentrator to remove the organic solvent. The result was column purified, and then crystallized under a condition of DCM/EtOH to secure Intermediate 7-4 (34.8 g).

5) Synthesis of Compound 7

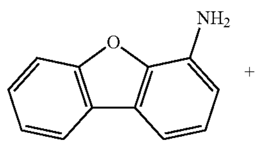

+

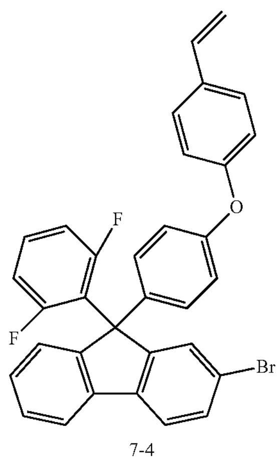

7-4

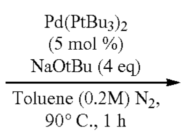

-continued

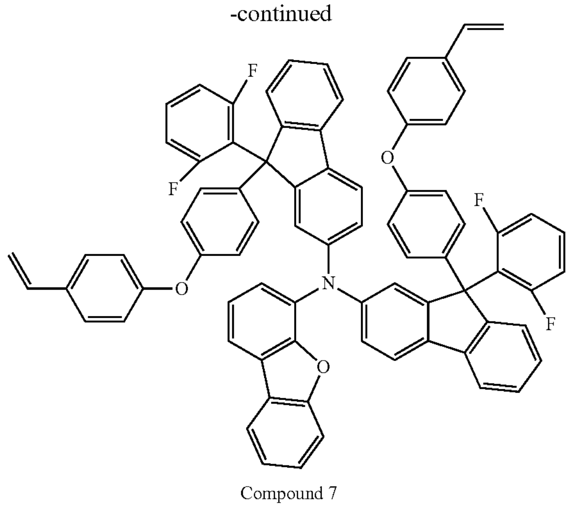

Compound 7

4-Aminodibenzofuran (513 mg, 2.8 mmol), Intermediate 7-4 (3.2 g, 5.74 mmol), Pd(PtBu$_3$)$_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using MgSO$_4$ and filtered. The filtrate was dried using a vacuum rotary concentrator to remove the organic solvent. The result was column purified, and then crystallized under a condition of DCM/EtOH to secure Compound 7 (2.7 g). Synthesis of the compound was identified through LC-MS and NMR. MS: $[M+H]^+=1124$ NMR measurement values of Compound 7: $^1$H NMR (500 MHz, DMSO-d6) δ 8.04 (dd, 1H), 7.90 (d, 1H), 7.78 (dd, 4H), 7.48-7.41 (m, 6H), 7.34 (t, 2H), 7.28-7.18 (m, 8H), 7.14-7.05 (m, 5H), 6.97 (dd, 4H), 6.88-6.81 (m, 8H), 6.72 (dd, 2H), 6.60 (dd, 4H), 5.74 (d, 2H), 5.21 (d, 2H)

Preparation Example 8. Preparation of Compound 8

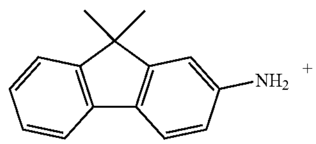

+

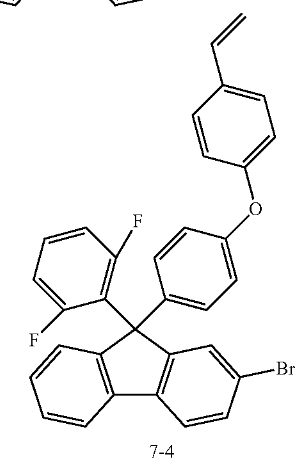

7-4

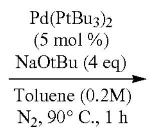

-continued

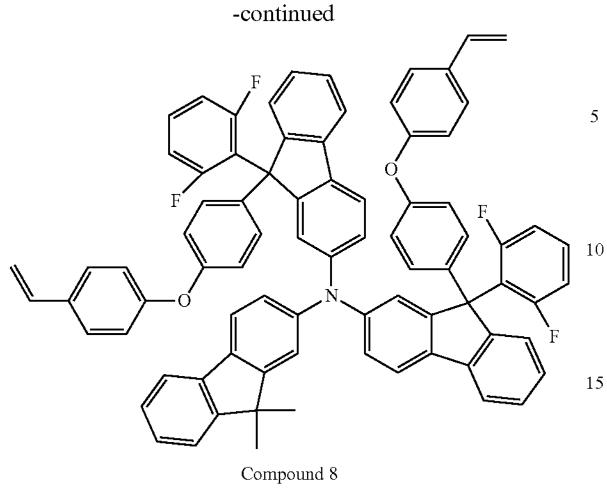

Compound 8

2-Amino-9,9-dimethylfluorene (586 mg, 2.8 mmol), Intermediate 7-4 (3.2 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 8 (2.1 g). Synthesis of the compound was identified through LC-MS and NMR. MS: $[M+H]^+=1150$ NMR measurement values of Compound 8: $^1H$ NMR (500 MHz, DMSO-d6) δ 7.95 (dd, 1H), 7.90 (dd, 1H), 7.84 (dd, 4H), 7.46 (dd, 4H), 7.39-7.20 (m, 11H), 7.08 (m, 2H), 6.97-6.85 (m, 16H), 6.73 (dd, 2H), 6.60 (dd, 4H), 5.75 (d, 2H), 5.21 (d, 2H), 1.68 (s, 6H)

Preparation Example 9. Preparation of Compound 9

1) Synthesis of Intermediate 9-1

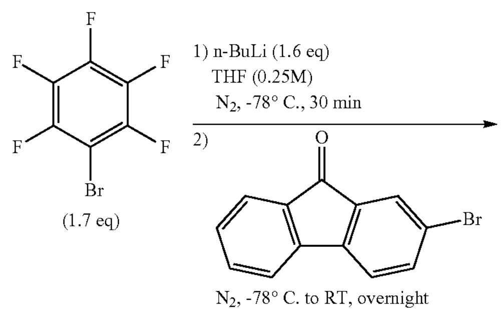

-continued

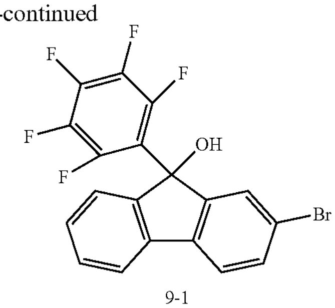

9-1

1-Bromo-2,3,4,5,6-pentafluorobenzene (31.8 mL, 255 mmol) was introduced to THF (500 mL), and the flask was substituted with nitrogen and cooled to −78° C. n-BuLi (2.5 M Hex) (96 mL, 240 mmol) was introduced to a dropping funnel, then slowly introduced to the reaction mixture, and the result was stirred for 30 minutes at −78° C. 2-Bromo-fluorenone (38.9 g, 150 mmol) was introduced thereto. The result was stirred overnight while slowly raising the temperature to room temperature. The reaction was terminated by introducing distilled water thereto, and the result was extracted with ethyl acetate and water. The organic layer was collected, dried using $MgSO_4$, and filtered. The filtrate was dried using a vacuum rotary concentrator to remove the organic solvent, and used for the next reaction.

2) Synthesis of Intermediate 9-2

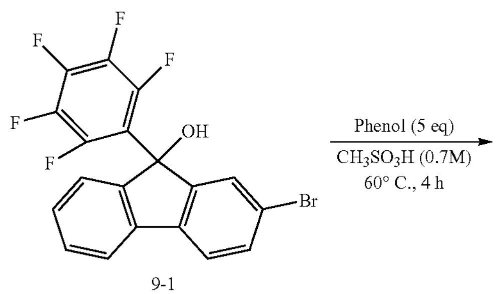

9-1

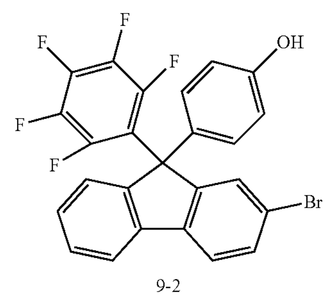

9-2

Intermediate 9-1 (64.1 g, 150 mmol) and phenol (70.6 g, 750 mmol) were introduced to RBF. $CH_3SO_3H$ (214 mL) was introduced thereto, and the mixture was stirred for 4 hours at 60° C. Ice water was introduced thereto, and the result was extracted with ethyl acetate and water. The organic layer was collected, dried using $MgSO_4$, and filtered. The filtrate was dried using a vacuum rotary concentrator to remove the organic solvent. The result was column purified, and then crystallized under a condition of DCM/heptane to secure Intermediate 9-2 (52.8 g).

3) Synthesis of Intermediate 9-3

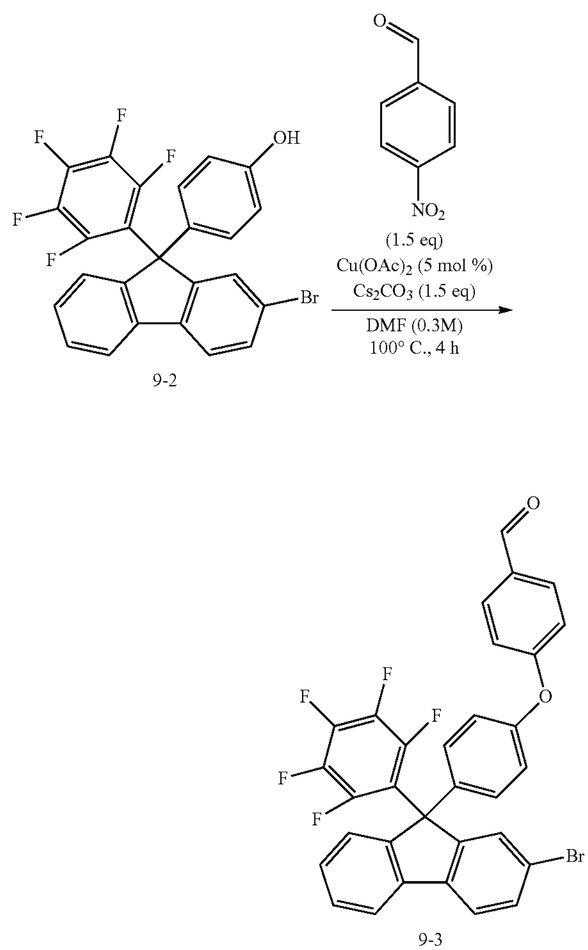

9-2

9-3

Intermediate 9-2 (50.3 g, 100 mmol), 4-nitrobenzaldehyde (22.8 g, 150 mmol), $Cu(OAc)_2$ (908 mg, 5 mmol) and $Cs_2CO_3$ (48.9 g, 150 mmol) were introduced to RBF. DMF (333 mL) was introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 9-3 (48.6 g).

4) Synthesis of Intermediate 9-4

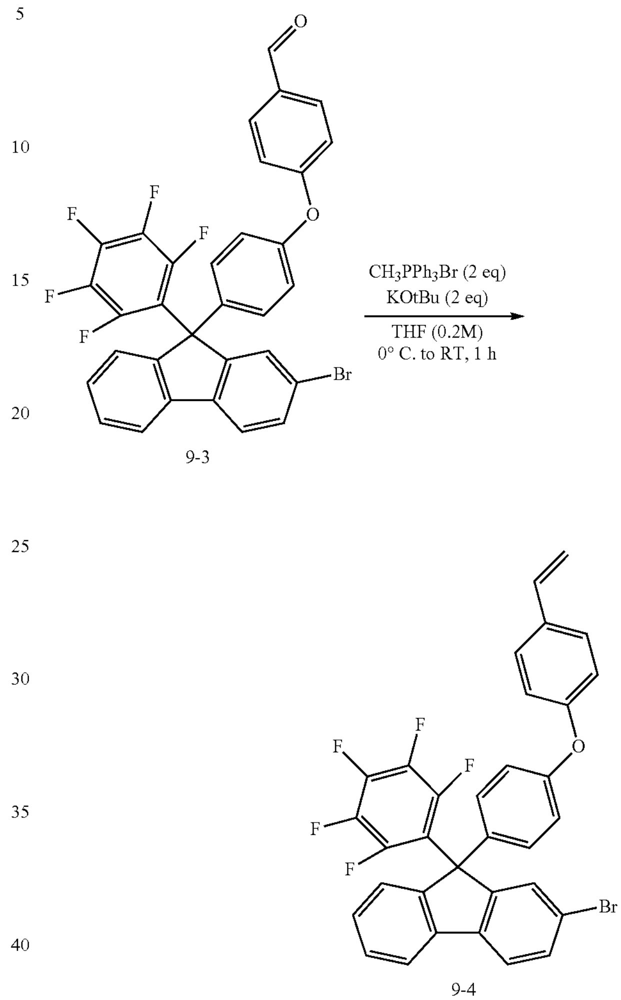

9-3

9-4

$CH_3PPh_3Br$ (51.4 g, 144 mmol), KOtBu (16.2 g, 144 mmol) and THF (216 mL) were introduced to RBF, and cooled to 0° C. A solution obtained by dissolving Intermediate 9-3 (43.7 g, 72 mmol) in THF (144 mL) was introduced to the reaction mixture, and the result was stirred for 1 hour while raising the temperature to room temperature. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Intermediate 9-4 (31 g).

5) Synthesis of Compound 9

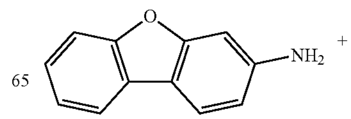
+

-continued

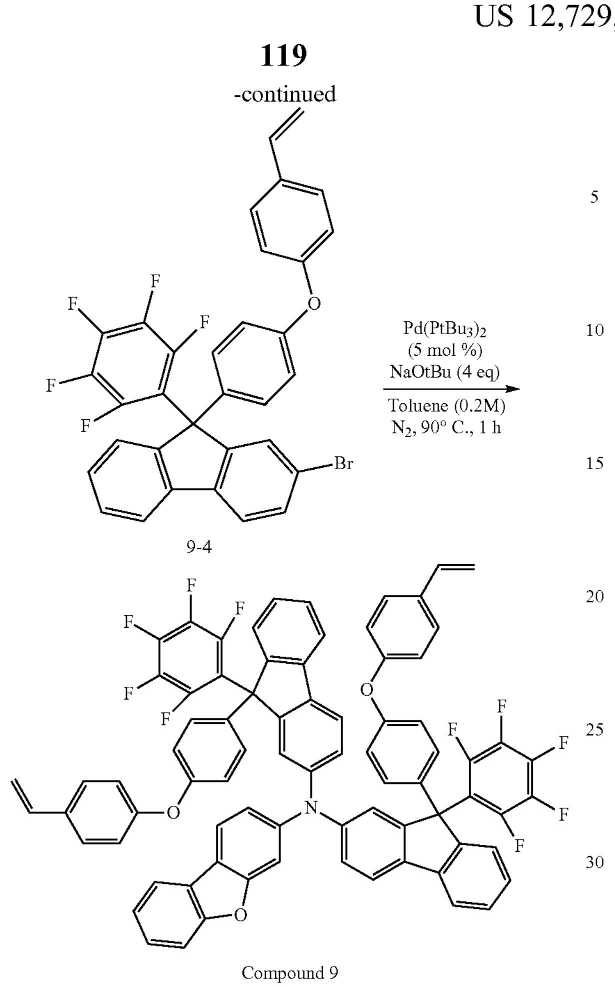

9-4

Compound 9

3-Aminodibenzofuran (513 mg, 2.8 mmol), Intermediate 9-4 (3.5 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 9 (2.3 g). Synthesis of the compound was identified through LC-MS and NMR. MS: $[M+H]^+=1232$ NMR measurement values of Compound 9: $^1H$ NMR (500 MHz, DMSO-d6) δ 8.04 (dd, 1H), 7.90 (d, 1H), 7.78 (dd, 4H), 7.48-7.41 (m, 6H), 7.34 (t, 2-H), 7.28-7.18 (m, 8H), 7.14-7.05 (m, 5H), 6.97-6.88 (m, 6H), 6.72 (dd, 2H), 6.60 (dd, 4H), 5.74 (d, 2H), 5.21 (d, 2H)

Preparation Example 10. Preparation of Compound 10

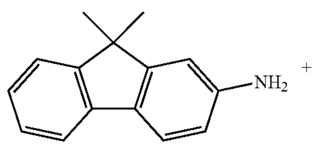

-continued

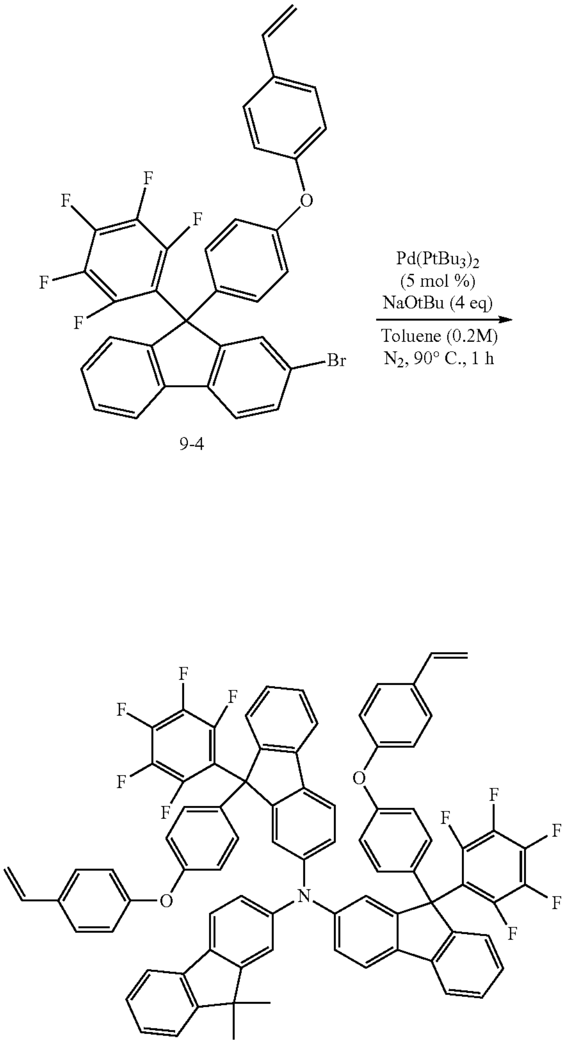

9-4

Compound 10

2-Amino-9,9-dimethylfluorene (586 mg, 2.8 mmol), Intermediate 9-4 (3.5 g, 5.74 mmol), $Pd(PtBu_3)_2$ (72 mg, 0.14 mmol) and sodium tert-butoxide [NaOtBu](1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 10 (2.1 g). Synthesis of the compound was identified through LC-MS and NMR. MS: $[M+H]^+=1258$ NMR measurement values of Compound 10: 1H NMR (500 MHz, DMSO-d6) δ 7.95 (dd, 1H), 7.90 (dd, 1H), 7.82 (dd, 4H), 7.46 (dd, 4H), 7.39-7.20 (m, 11H), 7.08 (m, 2H), 6.90-6.83 (m, 10H), 6.72 (dd, 2H), 6.64 (d, 4H), 5.75 (d, 2H), 5.21 (d, 2H), 1.68 (s, 6H)

Preparation Example 11. Preparation of Compound 11

1) Synthesis of Intermediate 11-1

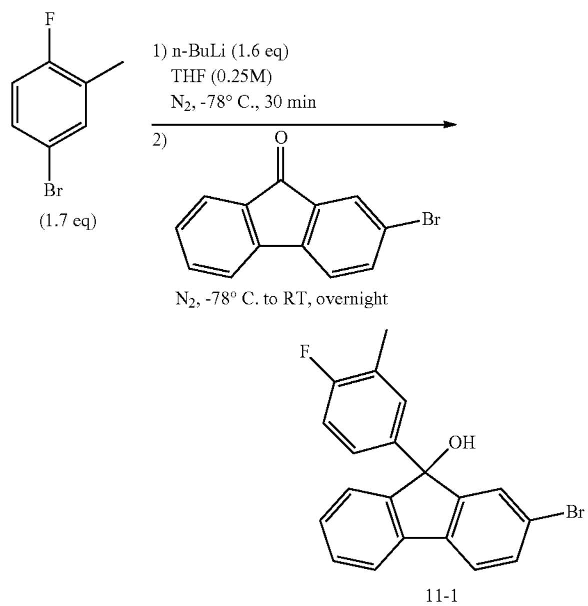

11-1

5-Bromo-2-fluoromethylbenzene (31.7 mL, 255 mmol) was introduced to THF (500 mL), and the flask was substituted with nitrogen and cooled to −78° C. n-BuLi (2.5 M Hex) (96 mL, 240 mmol) was introduced to a dropping funnel, then slowly introduced to the reaction mixture, and the result was stirred for 30 minutes at −78° C. 2-Bromofluorenone (38.9 g, 150 mmol) was introduced thereto. The result was stirred overnight while slowly raising the temperature to room temperature. The reaction was terminated by introducing distilled water thereto, and the result was extracted with ethyl acetate and water. The organic layer was collected, dried using $MgSO_4$, and filtered. The filtrate was dried using a vacuum rotary concentrator to remove the organic solvent to secure Intermediate 11-1, which was used for the next reaction.

2) Synthesis of Intermediate 11-2

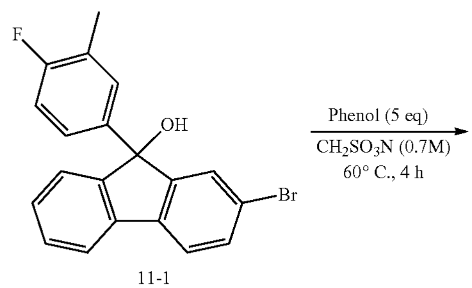

11-1

-continued

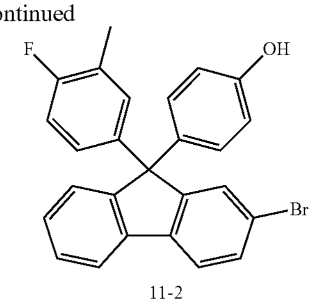

11-2

Intermediate 11-1 (55.4 g, 150 mmol) and phenol (70.6 g, 750 mmol) were introduced to RBF. $CH_3SO_3H$ (214 mL) was introduced thereto, and the mixture was stirred for 4 hours at 60° C. Ice water was introduced thereto, and the result was extracted with ethyl acetate and water. The organic layer was collected, dried using $MgSO_4$, and filtered. The filtrate was dried using a vacuum rotary concentrator to remove the organic solvent. The result was column purified, and then crystallized under a condition of DCM/heptane to secure Intermediate 11-2 (44.8 g).

3) Synthesis of Intermediate 11-3

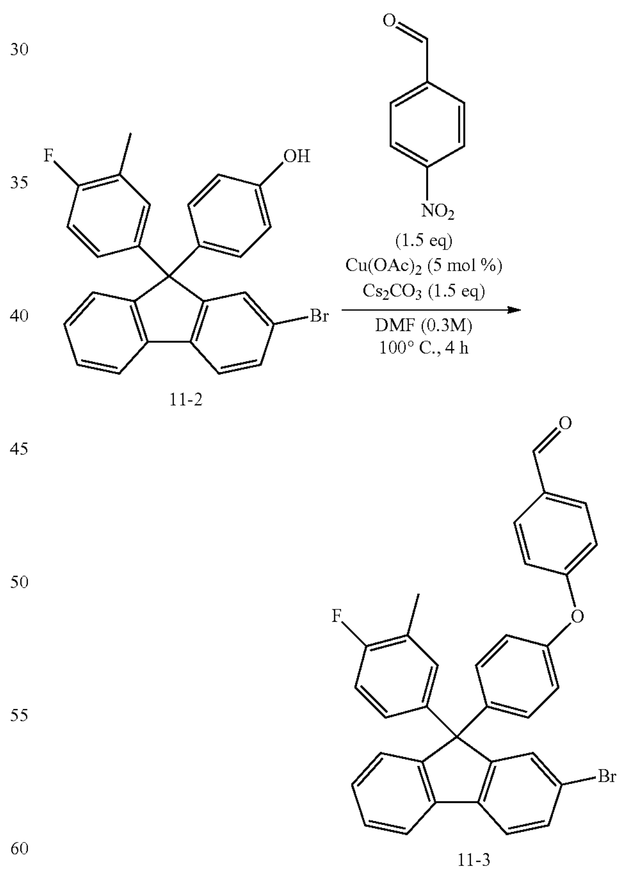

11-2

11-3

Intermediate 11-2 (44.5 g, 100 mmol), 4-nitrobenzaldehyde (22.8 g, 150 mmol), $Cu(OAc)_2$ (908 mg, 5 mmol) and $Cs_2CO_3$ (48.9 g, 150 mmol) were introduced to RBF. DMF (333 mL) was introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 11-3 (45 g).

4) Synthesis of Intermediate 11-4

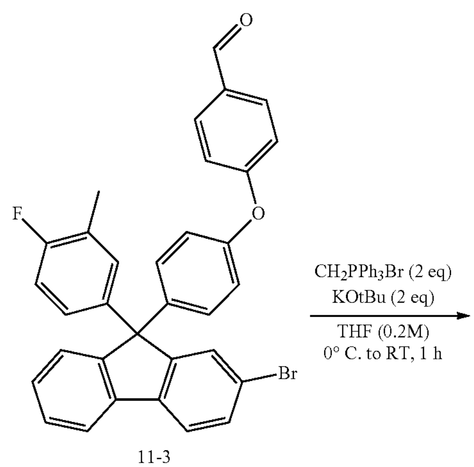

11-3

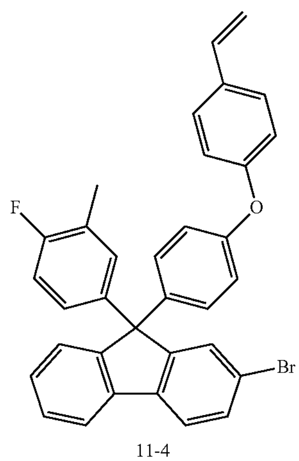

11-4

$CH_3PPh_3Br$ (51.4 g, 144 mmol), KOtBu (16.2 g, 144 mmol) and THE (216 mL) were introduced to RBF, and cooled to 0° C. A solution obtained by dissolving Intermediate 11-3 (39.6 g, 72 mmol) in THE (144 mL) was introduced to the reaction mixture, and the result was stirred for 1 hour while raising the temperature to room temperature. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Intermediate 11-4 (35.9 g).

5) Synthesis of Compound 11

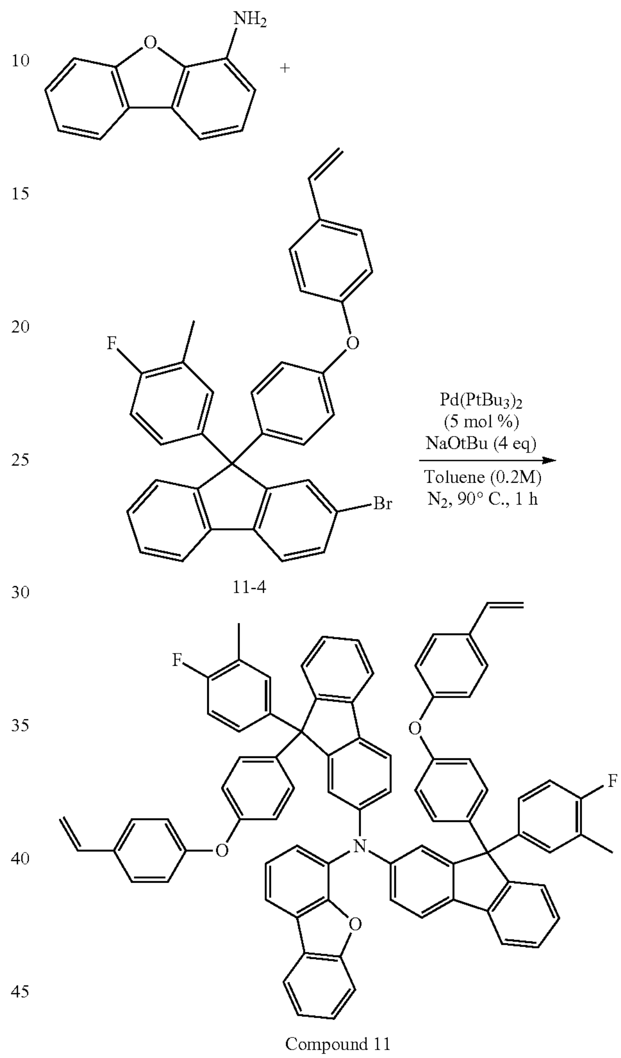

11-4

Compound 11

4-Aminodibenzofuran (513 mg, 2.8 mmol), Intermediate 11-4 (3.14 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 11 (2.6 g). Synthesis of the compound was identified through LC-MS and NMR. MS: $[M+H]^+$=1116

NMR measurement values of Compound 11: 1H NMR (500 MHz, DMSO-d6) δ 8.07 (dd, 1H), 7.92 (d, 1H), 7.82 (dd, 4H), 7.46 (dd, 4H), 7.39-7.24 (m, 10H), 7.21 (dd, 1H), 7.10 (m, 2H), 6.97-6.83 (m, 16H), 6.72 (dd, 2H), 6.65 (d, 4H), 5.75 (d, 2H), 5.21 (d, 2H), 2.31 (s, 6H)

Preparation Example 12. Preparation of Compound 12

(1) Synthesis of Intermediate 12-1

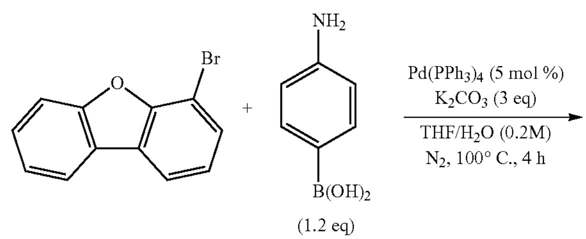

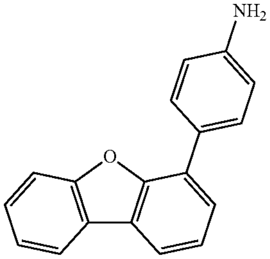

12-1

4-Bromodibenzofuran (2.47 g, 10 mmol), 4-aminophenylboronic acid (1.64 g, 12 mmol), $Pd(PPh_3)_4$ (578 mg, 0.5 mmol) and $K_2CO_3$ (4.15 g, 30 mmol) were introduced to RBF. The flask was substituted with nitrogen, THF (25 mL) and water (25 mL) were introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 12-1 (2.1 g).

(2) Synthesis of Compound 12

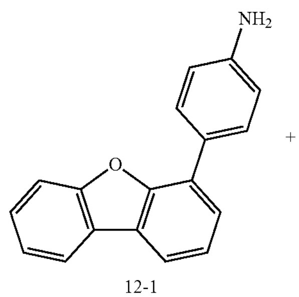

12-1

+

-continued

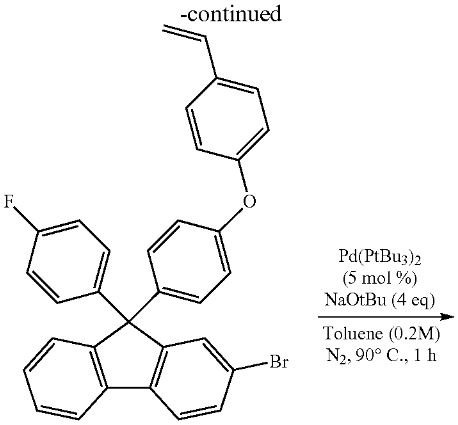

1-4

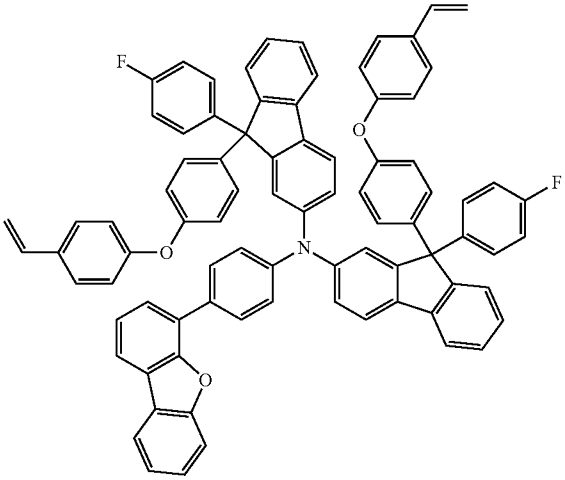

Compound 12

Intermediate 12-1 (648 mg, 2.5 mmol), Intermediate 1-4 (2.8 g, 5.25 mmol), $Pd(PtBu_3)_2$ (64 mg, 0.125 mmol) and NaOtBu (961 mg, mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 12 (2 g). Synthesis of the compound was identified through LC-MS and NMR. MS: $[M+H]^+$=1164

NMR measurement values of Compound 12: $^1H$ NMR (500 MHz, DMSO-d6) δ 8.02 (dd, 1H), 7.91 (d, 1H), 7.79 (dd, 4H), 7.46 (dd, 4H), 7.42-7.22 (m, 14H), 7.21 (dd, 1H), 7.10 (m, 2H), 6.97-6.83 (m, 18H), 6.72 (dd, 2H), 6.65 (d, 4H), 5.75 (d, 2H), 5.21 (d, 2H)

Preparation Example 13. Preparation of Compound 13

(1) Synthesis of Intermediate 13-1

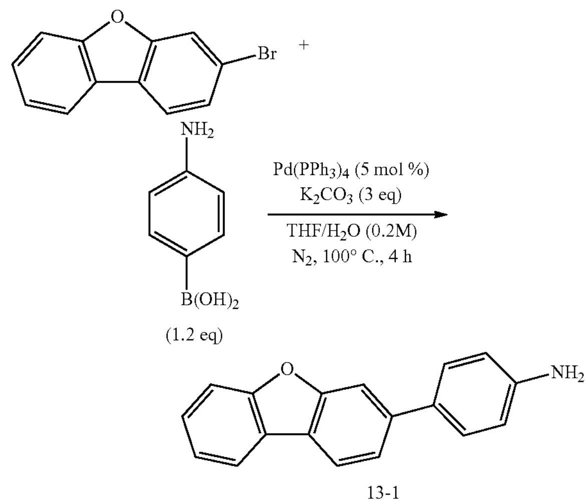

(1.2 eq)

13-1

3-Bromodibenzofuran (2.47 g, 10 mmol), 4-aminophenylboronic acid (1.64 g, 12 mmol), $Pd(PPh_3)_4$ (578 mg, 0.5 mmol) and $K_2CO_3$ (4.15 g, 30 mmol) were introduced to RBF. The flask was substituted with nitrogen, THF (25 mL) and water (25 mL) were introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 13-1 (2.2 g).

(2) Synthesis of Compound 13

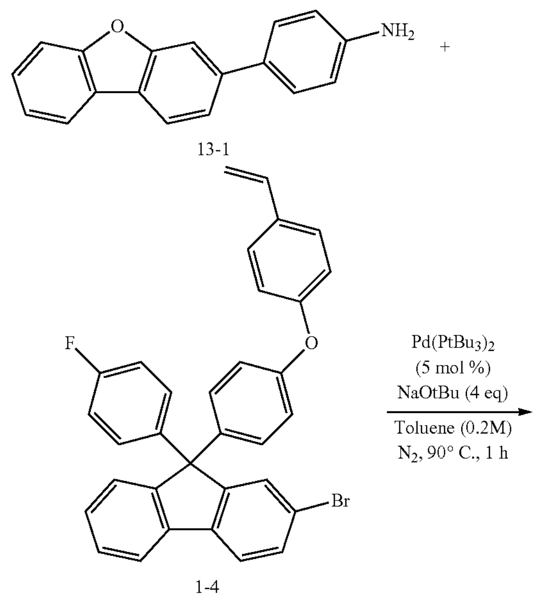

13-1

1-4

-continued

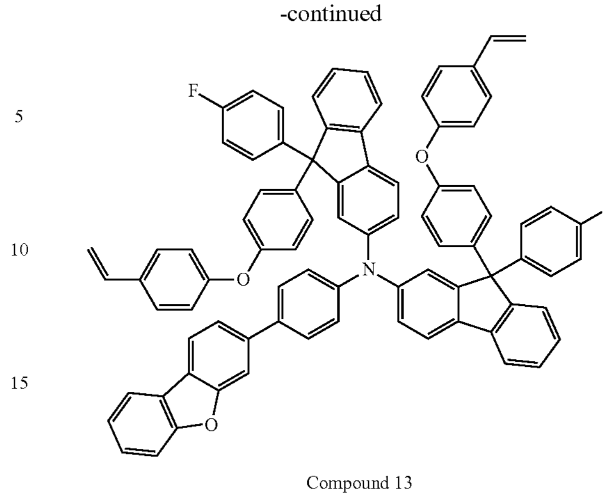

Compound 13

Intermediate 13-1 (648 mg, 2.5 mmol), Intermediate 1-4 (2.8 g, 5.25 mmol), $Pd(PtBu_3)_2$ (64 mg, 0.125 mmol) and NaOtBu (961 mg, mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 13 (2.2 g). Synthesis of the compound was identified through LC-MS and NMR. MS: $[M+H]^+$=1164

NMR measurement values of Compound 13: 1H NMR (500 MHz, DMSO-d6) δ 8.05 (s, 1H), 8.00 (dd, 1H), 7.85 (d, 1H), 7.80 (dd, 4H), 7.46 (dd, 4H), 7.39-7.20 (m, 14H), 7.08 (m, 2H), 6.97-6.83 (m, 18H), 6.72 (dd, 2H), 6.65 (d, 4H), 5.75 (d, 2H), 5.21 (d, 2H)

Preparation Example 14. Preparation of Compound 14

(1) Synthesis of Intermediate 14-1

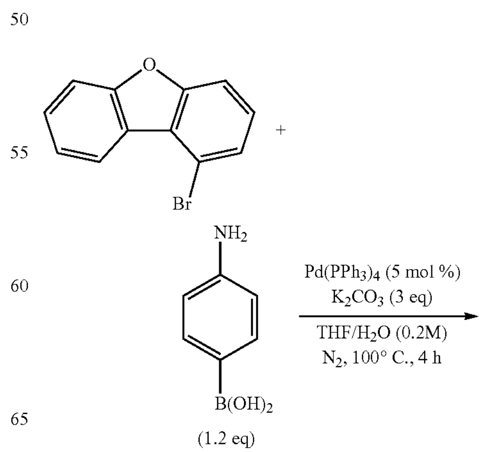

(1.2 eq)

-continued

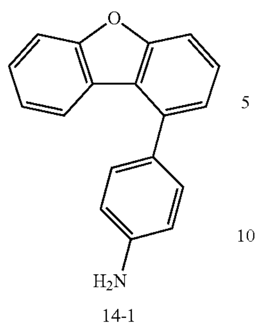

14-1

1-Bromodibenzofuran (2.47 g, 10 mmol), 4-aminophenylboronic acid (1.64 g, 12 mmol), $Pd(PPh_3)_4$ (578 mg, 0.5 mmol) and $K_2CO_3$ (4.15 g, 30 mmol) were introduced to RBF. The flask was substituted with nitrogen, THF (25 mL) and water (25 mL) were introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 14-1 (2.1 g).

(2) Synthesis of Compound 14

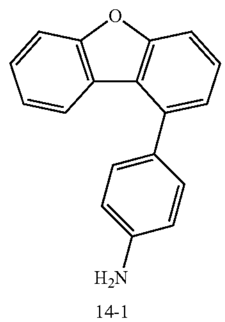

14-1

+

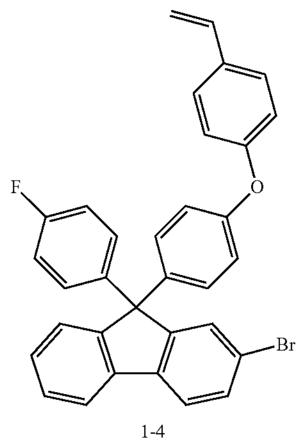

1-4

Pd(PtBu3)2
(5 mol %)
NaOtBu (4 eq)
Toluene (0.2M)
N2, 90° C., 1 h

-continued

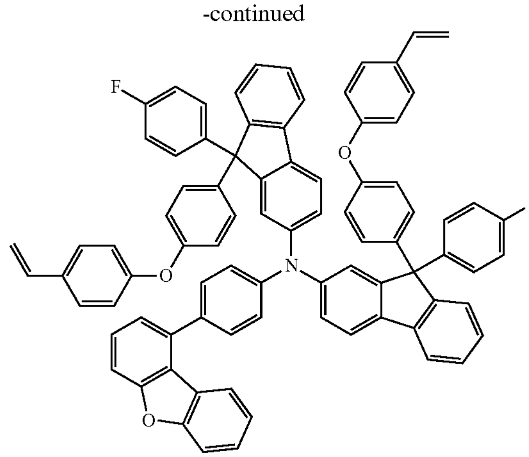

Compound 14

Intermediate 14-1 (648 mg, 2.5 mmol), Intermediate 1-4 (2.8 g, 5.25 mmol), $Pd(PtBu_3)_2$ (64 mg, 0.125 mmol) and NaOtBu (961 mg, mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 14 (2.1 g). Synthesis of the compound was identified through LC-MS and NMR. MS: $[M+H]^+$=1164

NMR measurement values of Compound 14: $^1$H NMR (500 MHz, DMSO-d6) δ 8.05 (dd, 1H), 7.92 (d, 1H), 7.79 (dd, 4H), 7.46 (dd, 4H), 7.42-7.22 (m, 14H), 7.21 (dd, 1H), 7.10 (m, 2H), 6.97-6.83 (m, 18H), 6.72 (dd, 2H), 6.65 (d, 4H), 5.75 (d, 2H), 5.21 (d, 2H)

Preparation Example 15. Preparation of Compound 15

(1) Synthesis of Intermediate 15-1

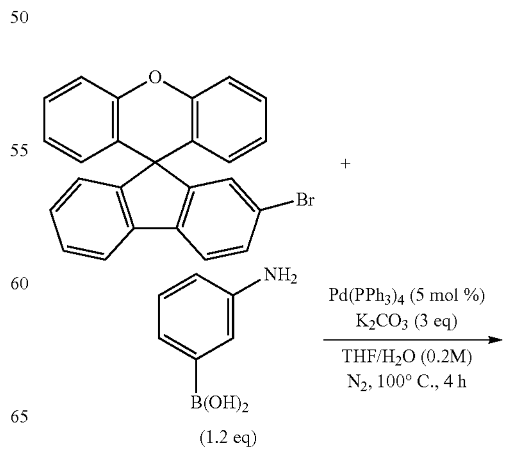

-continued

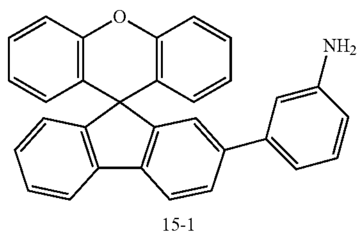

15-1

2-Bromospiro[fluorene-9,9'-xanthene](4.11 g, 10 mmol), 3-aminophenylboronic acid (1.64 g, 12 mmol), $Pd(PPh_3)_4$ (578 mg, 0.5 mmol) and $K_2CO_3$ (4.15 g, 30 mmol) were introduced to RBF. The flask was substituted with nitrogen, THF (25 mL) and water (25 mL) were introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 15-1 (3.5 g).

(2) Synthesis of Compound 15

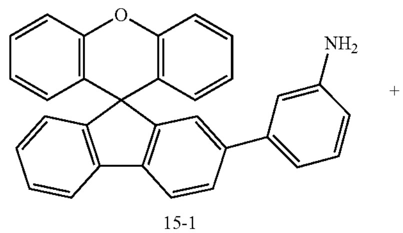

15-1

+

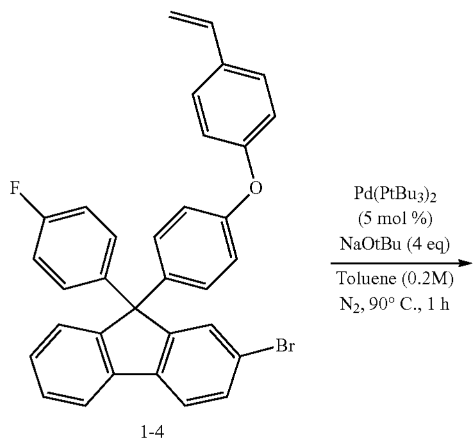

1-4

-continued

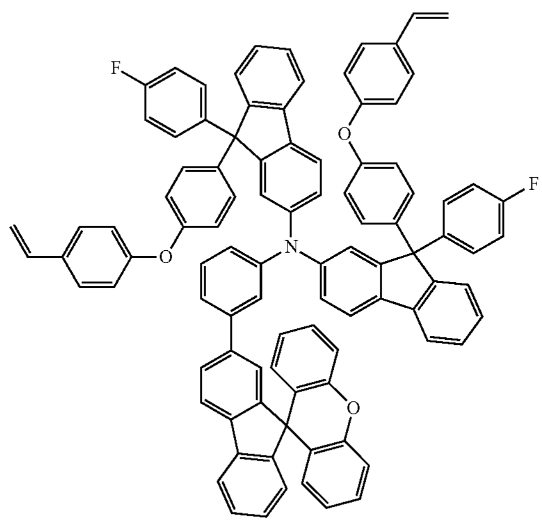

Compound 15

Intermediate 15-1 (1.06 g, 2.5 mmol), Intermediate 1-4 (2.8 g, 5.25 mmol), $Pd(PtBu_3)_2$ (64 mg, 0.125 mmol) and NaOtBu (961 mg, mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 15 (2.3 g). Synthesis of the compound was identified through LC-MS and NMR. MS: $[M+H]^+=1328$ NMR measurement values of Compound 15: $^1H$ NMR (500 MHz, DMSO-d6) δ 8.05 (dd, 1H), 7.94 (d, 1H), 7.75 (dd, 4H), 7.46 (dd, 4H), 7.42-7.22 (m, 16H), 7.15 (dd, 1H), 7.10 (m, 2H), 7.01-6.80 (m, 24H), 6.72 (dd, 2H), 6.65 (d, 4H), 5.75 (d, 2H), 5.21 (d, 2H)

Preparation Example 16. Preparation of Compound 16

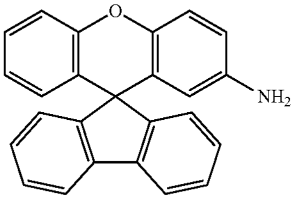

+

-continued

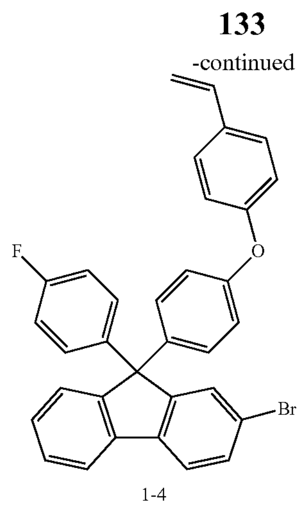

Pd(PtBu3)2
(5 mol %)
NaOtBu (4 eq)
Toluene (0.2M)
$N_2$, 90° C., 1 h 1-4

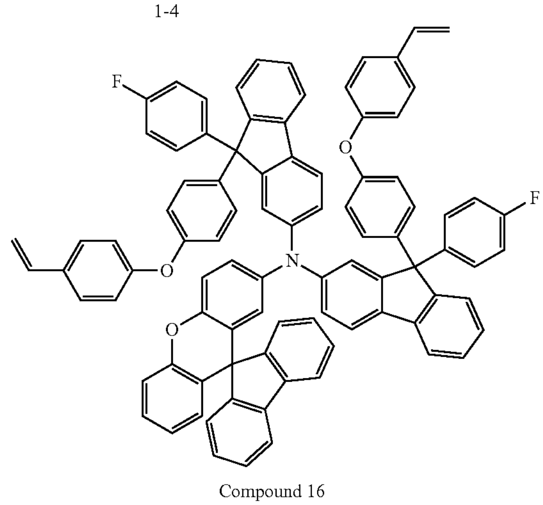

Compound 16

Spiro[fluorene-9,9'-xanthen]-2'-amine (869 mg, 2.5 mmol), Intermediate 1-4 (2.8 g, 5.25 mmol), $Pd(PtBu_3)_2$ (64 mg, 0.125 mmol) and NaOtBu (961 mg, 10 mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered.

The filtrate was dried using a vacuum rotary concentrator to remove the organic solvent. The result was column purified, and then crystallized under a condition of DCM/EtOH to secure Compound 16 (2.1 g). Synthesis of the compound was identified through LC-MS and NMR. MS: $[M+H]^+$=1252

NMR measurement values of Compound 16: $^1$H NMR (500 MHz, DMSO-d6) δ 8.03 (dd, 1H), 7.92 (d, 1H), 7.74 (dd, 4H), 7.45 (dd, 4H), 7.42-7.22 (m, 12H), 7.15 (dd, 1H), 7.10 (m, 2H), 7.01-6.80 (m, 24H), 6.72 (dd, 2H), 6.65 (d, 4H), 5.75 (d, 2H), 5.21 (d, 2H)

Preparation Example 17. Preparation of Compound 17

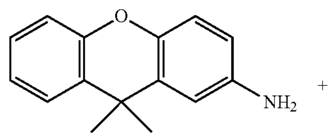

+

-continued

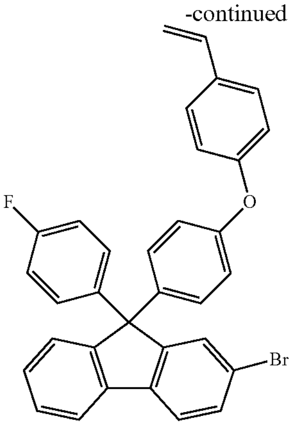

Pd(PtBu3)2
(5 mol %)
NaOtBu (4 eq)
Toluene (0.2M)
$N_2$, 90° C., 1 h 1-4

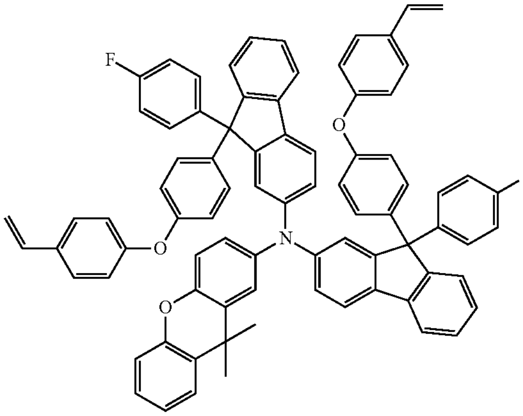

Compound 17

9,9-Dimethyl-9H-xanthen-2-amine (563 mg, 2.5 mmol), Intermediate 1-4 (2.8 g, 5.25 mmol), $Pd(PtBu_3)_2$ (64 mg, 0.125 mmol) and NaOtBu (961 mg, 10 mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 17 (1.7 g). Synthesis of the compound was identified through LC-MS and NMR. MS: $[M+H]^+$=1130

NMR measurement values of Compound 17: $^1$H NMR (500 MHz, DMSO-d6) δ 8.02 (dd, 1H), 7.94 (dd, 1H), 7.85 (dd, 4H), 7.46 (dd, 4H), 7.39-7.20 (m, 11H), 7.08 (m, 2H), 6.97-6.83 (m, 18H), 6.72 (dd, 2H), 6.65 (d, 4H), 5.75 (d, 2H), 5.21 (d, 2H), 1.69 (s, 6H)

Preparation Example 18. Compound 18

(1) Synthesis of Intermediate 18-1

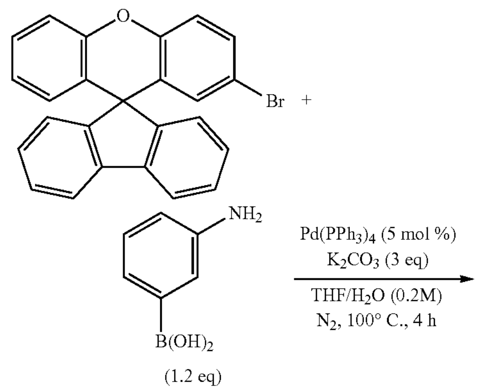

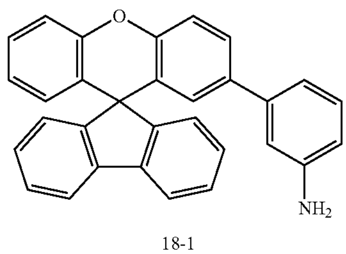

18-1

2'-Bromospiro[fluorene-9,9'-xanthene](4.11 g, 10 mmol), 3-aminophenylboronic acid (1.64 g, 12 mmol), $Pd(PPh_3)_4$ (578 mg, 0.5 mmol) and $K_2CO_3$ (4.15 g, 30 mmol) were introduced to RBF. The flask was substituted with nitrogen, THF (25 mL) and water (25 mL) were introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 18-1 (3.0 g).

(2) Synthesis of Compound 18

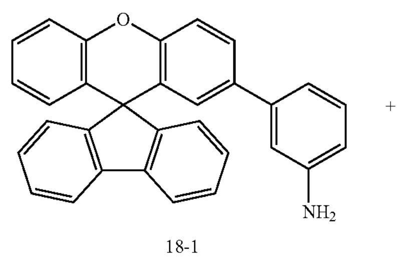

18-1

-continued

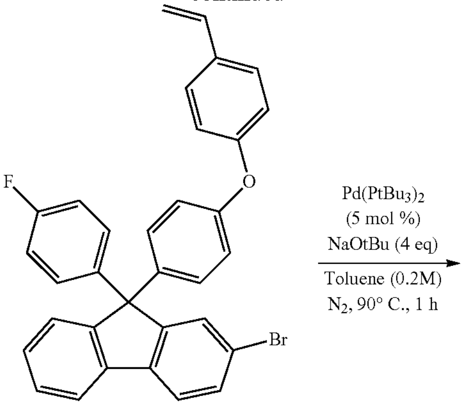

1-4

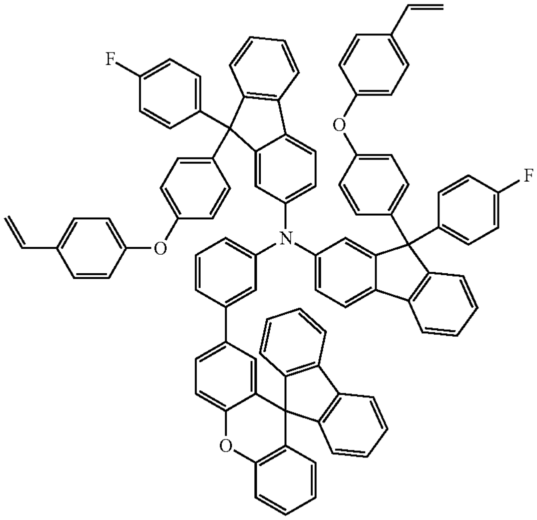

Compound 18

Intermediate 18-1 (1.06 g, 2.5 mmol), Intermediate 1-4 (2.8 g, 5.25 mmol), $Pd(PtBu_3)_2$ (64 mg, 0.125 mmol) and NaOtBu (961 mg, mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 18 (2.4 g). Synthesis of the compound was identified through LC-MS and NMR. MS: $[M+H]^+$=1328

NMR measurement values of Compound 18: 1H NMR (500 MHz, DMSO-d6) δ 8.04 (dd, 1H), 7.93 (d, 1H), 7.74 (dd, 4H), 7.46 (dd, 4H), 7.42-7.22 (m, 16H), 7.15 (dd, 1H), 7.10 (m, 2H), 7.01-6.80 (m, 24H), 6.72 (dd, 2H), 6.65 (d, 4H), 5.75 (d, 2H), 5.21 (d, 2H)

Preparation Example 19. Preparation of Compound 19

(1) Synthesis of Intermediate 19-1

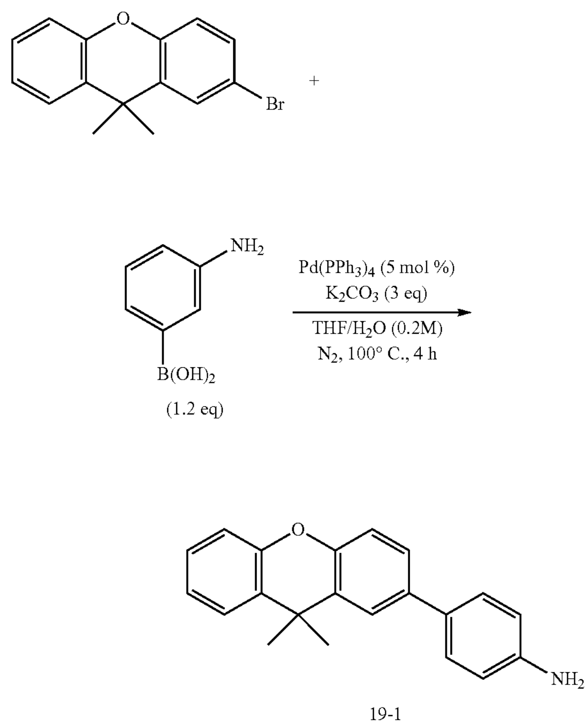

(1.2 eq)

19-1

2-Bromo-9,9-dimethyl-9H-xanthene (4.11 g, 10 mmol), 4-aminophenylboronic acid (1.64 g, 12 mmol), $Pd(PPh_3)_4$ (578 mg, 0.5 mmol) and $K_2CO_3$ (4.15 g, 30 mmol) were introduced to RBF. The flask was substituted with nitrogen, THF (25 mL) and water (25 mL) were introduced thereto, and the mixture was stirred for 4 hours at 100° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/heptane to secure Intermediate 19-1 (2.3 g).

(2) Synthesis of Compound 19

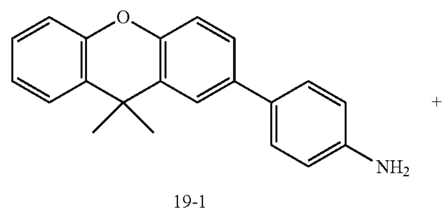

19-1

-continued

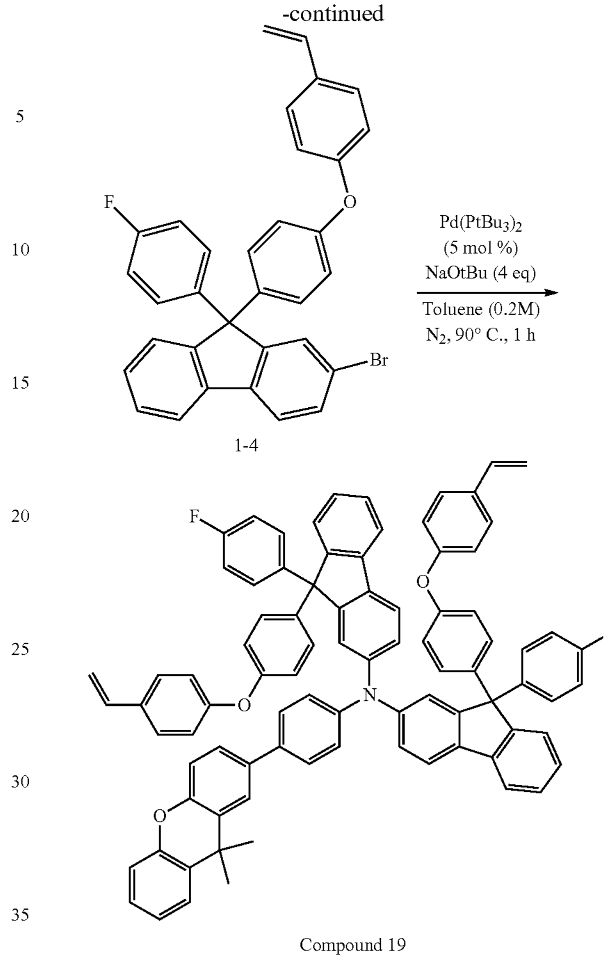

1-4

Compound 19

Intermediate 19-1 (753 mg, 2.5 mmol), Intermediate 1-4 (2.8 g, 5.25 mmol), $Pd(PtBu_3)_2$ (64 mg, 0.125 mmol) and NaOtBu (961 mg, mmol) were introduced to RBF. The flask was substituted with nitrogen, toluene (12.5 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 19 (2.2 g). Synthesis of the compound was identified through LC-MS and NMR. MS: $[M+H]^+$=1206

NMR measurement values of Compound 19: $^1H$ NMR (500 MHz, DMSO-d6) δ 8.02 (dd, 1H), 7.95 (dd, 1H), 7.80 (dd, 4H), 7.46 (dd, 4H), 7.40-7.20 (m, 15H), 7.08 (m, 2H), 6.97-6.83 (m, 18H), 6.72 (dd, 2H), 6.65 (d, 4H), 5.75 (d, 2H), 5.21 (d, 2H), 1.69 (s, 6H)

Preparation Example 20. Preparation of Compound 20

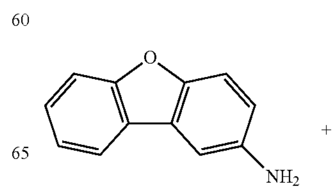

+

-continued

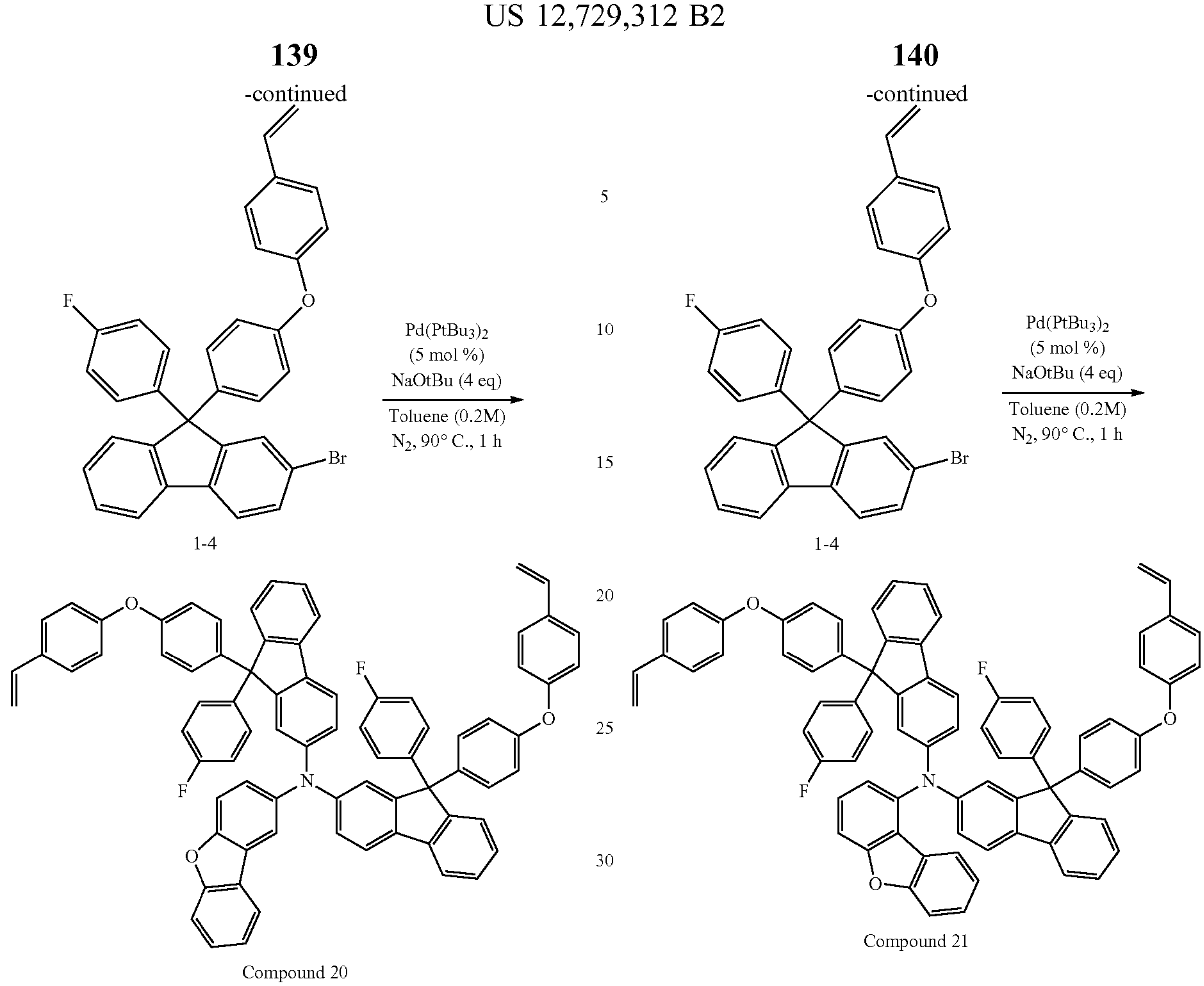

Compound 20

Compound 21

2-Aminodibenzofuran (513 mg, 2.8 mmol), Intermediate 1-4 (3.1 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 20 (2.2 g). Synthesis of the compound was identified through LC-MS and NMR. MS: $[M+H]^+=1088$ NMR measurement values of Compound 20: 1H NMR (500 MHz, DMSO-d6) δ 8.00 (d, 1H), 7.92 (d, 1H), 7.83 (d, 4H), 7.50 (m, 1H), 7.44-7.28 (m, 10H), 7.28 (t, 2H), 7.18 (dd, 1H), 7.13 (m, 2H), 7.08-6.97 (m, 15H), 6.92 (d, 4H), 6.84 (t, 4H), 6.68 (dd, 2H), 5.71 (d, 2H), 5.19 (d, 2H)

Preparation Example 21. Preparation of Compound 21

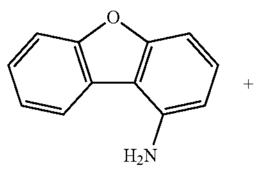

1-Aminodibenzofuran (513 mg, 2.8 mmol), Intermediate 1-4 (3.1 g, 5.74 mmol), $Pd(PtBu_3)_2$ (72 mg, 0.14 mmol) and NaOtBu (1.08 g, 11.2 mmol) were introduced to RBF. The flask was substituted with nitrogen, toluene (14 mL) was introduced thereto, and the mixture was stirred for 1 hour at 90° C. The result was extracted with ethyl acetate and water, and the organic layer was collected, dried using $MgSO_4$ and filtered. The filtrate was dried using a vacuum rotary concentrator to remove the organic solvent. The result was column purified, and then crystallized under a condition of DCM/EtOH to secure Compound 21 (2.4 g). Synthesis of the compound as identified through LC-MS and NMR. MS: $[M+H]^+=1088$ NMR measurement values of Compound 21: 1H NMR (500 MHz, DMSO-d6) δ 7.77 (m, 0.4H), 7.57 (m, 2H), 7.51-7.46 (m, 5H), 7.36-7.29 (m, 5H), 7.24 (t, 2H), 7.03-6.68 (m, 29H), 5.74 (d, 2H), 5.20 (d, 2H)

Device Example

Example 1

A glass substrate on which indium tin oxide (ITO) was coated as a thin film to a thickness of 1,500 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol and acetone, dried, then washed for 5 minutes, and then transported to a glove box.

On the transparent ITO electrode, a 2 wt % cyclohexanone ink including Compound 1 prepared in Preparation Example 1 and the following Compound G in a weight ratio of 8:2 was spin coated on the ITO surface, and heat treated for 30 minutes at 220° C. to form a hole injection layer having a thickness of 400 Å.

On the hole injection layer, a 2 wt % toluene ink of the following Compound A was spin coated and heat treated for 10 minutes at 120° C. to form a hole transfer layer having a thickness of 200 Å. The following Compound B and Compound C were vacuum deposited on the hole transfer layer in a weight ratio of 92:8 to form a light emitting layer having a thickness of 200 Å. The following Compound D was vacuum deposited on the light emitting layer to form an electron injection and transfer layer having a thickness of 350 Å. On the electron injection and transfer layer, LiF and aluminum were consecutively deposited to thicknesses of 10 Å and 1000 Å, respectively, to form a cathode.

Compound G

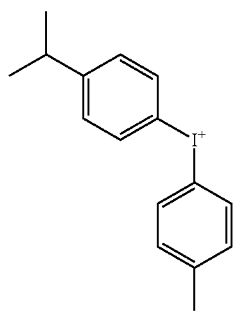

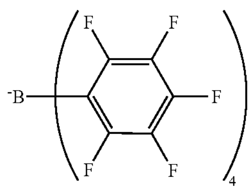

Compound A

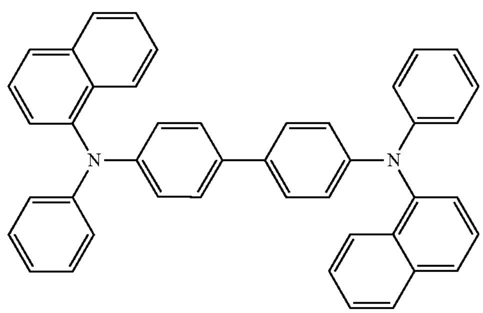

Compound B

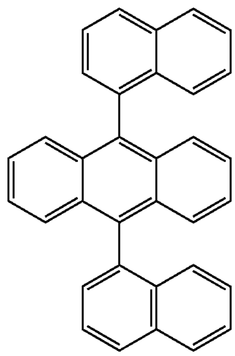

-continued

Compound C

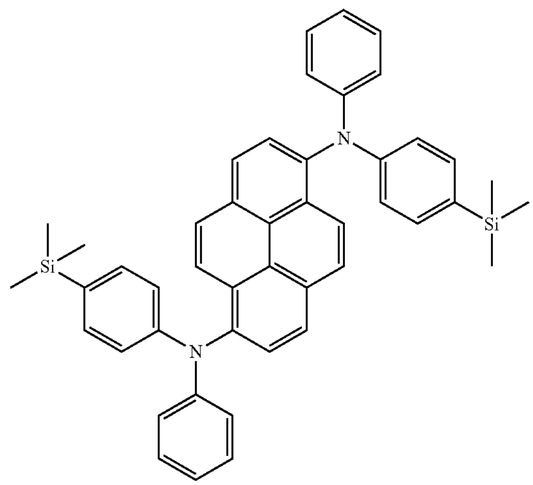

Compound D

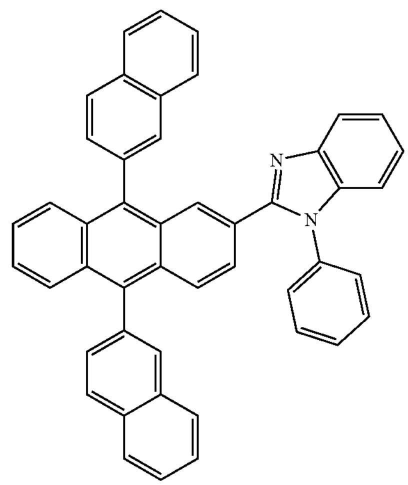

In the above-mentioned process, the deposition rates of the organic materials were maintained at 0.4 Å/sec to 0.7 Å/sec, the deposition rates of the lithium fluoride and the aluminum of the cathode were maintained at 0.3 Å/sec and 2 Å/sec, respectively, and the degree of vacuum during the deposition was maintained at $5\times10^{-8}$ torr to $2\times10^{-7}$ torr.

Examples 2 to 21

Organic light emitting devices were manufactured in the same manner as in Example 1 except that compounds described in the following Table 1 were used instead of Compound 1 when preparing the hole injection layer.

Comparative Experimental Examples 1 to 4

Organic light emitting devices were manufactured in the same manner as in Example 1 except that any one compound of the following Compounds CE1 to CE4 was used as described in the following Table 1 instead of Compound 1 when preparing the hole injection layer.

CE1
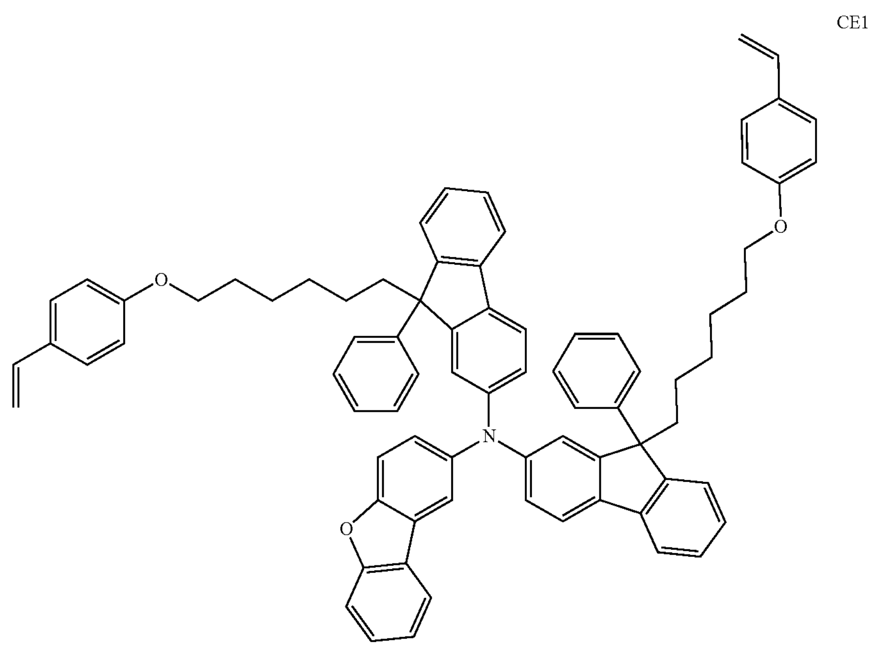
CE2
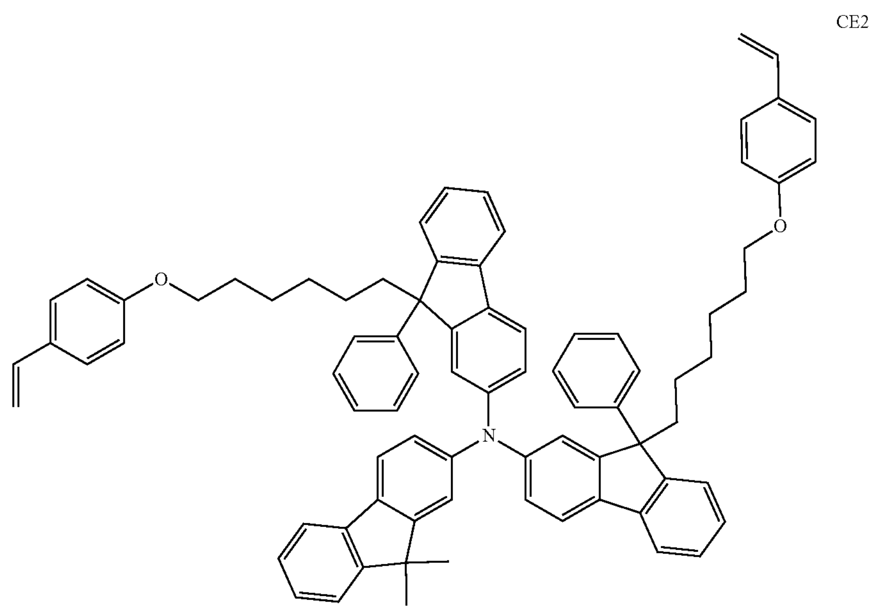

-continued

CE3

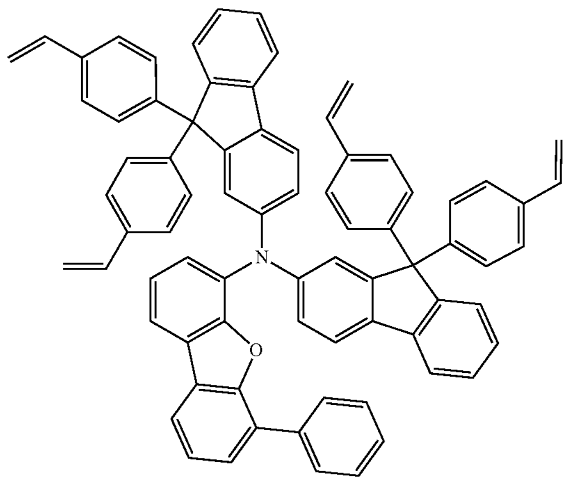

CE4

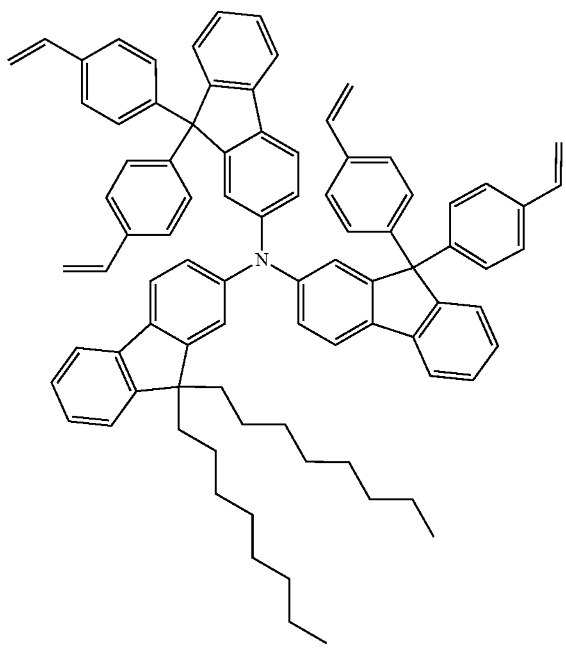

For each of the organic light emitting devices manufactured in the examples and the comparative experimental examples, driving voltage, external quantum efficiency, luminance and lifetime were measured at current density of 10 mA/cm$^2$, and the results are shown in the following Table 1. The external quantum efficiency was obtained by (the number of emitted photons)/(the number of injected charge carriers). T95 means time (hr) taken for luminance to decrease to 95% from initial luminance (500 nit).

TABLE 1

| | HIL Host | Driving Voltage (V) | External Quantum Efficiency (%) | Luminance (cd/m$^2$) | T95 (hr) @500 nit |
|---|---|---|---|---|---|
| Example 1 | Compound 1 | 4.63 | 5.6 | 586 | 194 |
| Example 2 | Compound 2 | 4.61 | 5.2 | 609 | 136 |
| Example 3 | Compound 3 | 4.75 | 5.8 | 612 | 148 |
| Example 4 | Compound 4 | 4.70 | 5.3 | 512 | 115 |
| Example 5 | Compound 5 | 4.86 | 5.2 | 593 | 181 |
| Example 6 | Compound 6 | 4.80 | 5.5 | 534 | 110 |
| Example 7 | Compound 7 | 4.63 | 5.7 | 523 | 123 |
| Example 8 | Compound 8 | 4.70 | 5.2 | 548 | 186 |
| Example 9 | Compound 9 | 4.54 | 5.4 | 567 | 170 |

TABLE 1-continued

| | HIL Host | Driving Voltage (V) | External Quantum Efficiency (%) | Luminance ($cd/m^2$) | T95 (hr) @500 nit |
|---|---|---|---|---|---|
| Example 10 | Compound 10 | 4.58 | 5.4 | 522 | 171 |
| Example 11 | Compound 11 | 4.65 | 5.3 | 559 | 162 |
| Example 12 | Compound 12 | 4.68 | 5.5 | 618 | 155 |
| Example 13 | Compound 13 | 4.71 | 5.6 | 559 | 148 |
| Example 14 | Compound 14 | 4.85 | 5.8 | 638 | 152 |
| Example 15 | Compound 15 | 4.65 | 5.5 | 600 | 142 |
| Example 16 | Compound 16 | 4.79 | 5.7 | 598 | 149 |
| Example 17 | Compound 17 | 4.68 | 5.5 | 581 | 153 |
| Example 18 | Compound 18 | 4.83 | 5.2 | 586 | 152 |
| Example 19 | Compound 19 | 4.81 | 5.3 | 570 | 158 |
| Example 20 | Compound 20 | 4.63 | 5.6 | 592 | 198 |
| Example 21 | Compound 21 | 4.62 | 5.5 | 570 | 172 |
| Comparative Experimental Example 1 | CE1 | 6.80 | 4.2 | 423 | 72 |
| Comparative Experimental Example 2 | CE2 | 6.73 | 4.6 | 468 | 61 |
| Comparative Experimental Example 3 | CE3 | 6.11 | 5.1 | 475 | 55 |
| Comparative Experimental Example 4 | CE4 | 6.14 | 5.3 | 480 | 51 |

As shown in Table 1, it was identified that the organic light emitting devices according to the examples using the compound represented by Chemical Formula 1 according to the present disclosure as a host of the hole injection layer had significantly reduced driving voltage and significantly enhanced lifetime compared to the comparative experimental examples.

In addition, most of the organic light emitting devices of the examples had increased efficiency and luminance compared to the organic light emitting devices of the comparative experimental examples. Through this, it was identified that film and interfacial properties were improved by the fluoro group (—F) introduced into the molecule, and hole mobility and hole/electron balance were improved due to the change in the HOMO level, which improved performance of the organic light emitting device.

The invention claimed is:

1. A compound represented by Chemical Formula 1:

[Chemical Formula 1]

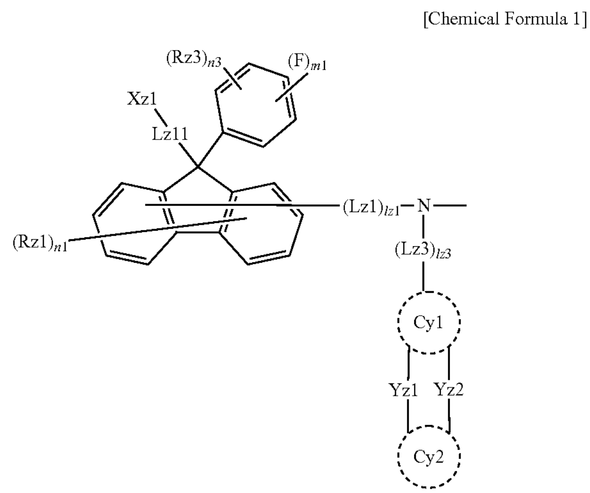

-continued

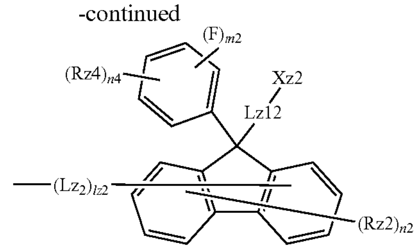

wherein, in Chemical Formula 1,

Yz1 and Yz2 are the same as or different from each other, and each independently a direct bond, O, S, CRaRb or SiRcRd, and when any one of Yz1 or Yz2 is a direct bond, the other one is O, S, CRaRb or SiRcRd;

Ra, Rb, Rc and Rd are the same as or different from each other, and each independently hydrogen; deuterium; a substituted or unsubstituted alkyl group; a substituted or unsubstituted aryl group; a substituted or unsubstituted heteroaryl group, or bond to adjacent groups to form a substituted or unsubstituted ring;

Cy1 and Cy2 are the same as or different from each other, and each independently a substituted or unsubstituted benzene ring; or a substituted or unsubstituted naphthalene ring;

Lz1 to Lz3 are the same as or different from each other, and each independently a direct bond; or a substituted or unsubstituted arylene group;

Lz11 and Lz12 are the same as or different from each other, and each independently a direct bond; a substituted or unsubstituted alkylene group; or a substituted or unsubstituted arylene group;

Xz1 and Xz2 are the same as or different from each other, and each independently a curable group;

Rz1 and Rz2 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group;

Rz3 and Rz4 are the same as or different from each other, and each independently deuterium; a substituted or unsubstituted alkyl group; a substituted or unsubstituted alkoxy group; a substituted or unsubstituted aryl group; or a substituted or unsubstituted heteroaryl group;

lz1 to lz3 are each independently 0 or 1;

n1 and n2 are each independently an integer of 0 to 7, and when n1 and n2 are each independently 2 or greater, each occurrence of Rz1 and Rz2 is the same as or different from each other;

n3 and n4 are each independently an integer of 0 to 4, and when n3 and n4 are each independently 2 or greater, each occurrence of Rz3 and Rz4 is the same as or different from each other;

m1 and m2 are each independently an integer of 1 to 5; and m1+n3 is 5 or less, and m2+n4 is 5 or less.

2. The compound of claim 1, wherein the curable group is any one selected from the group consisting of the following structures:

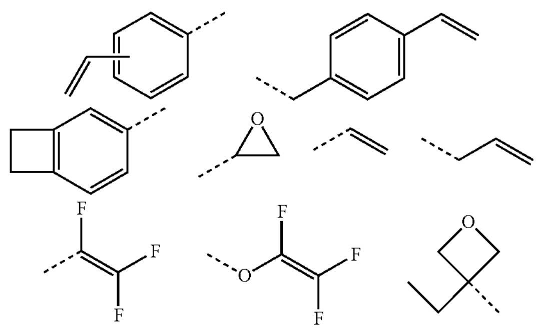

-continued

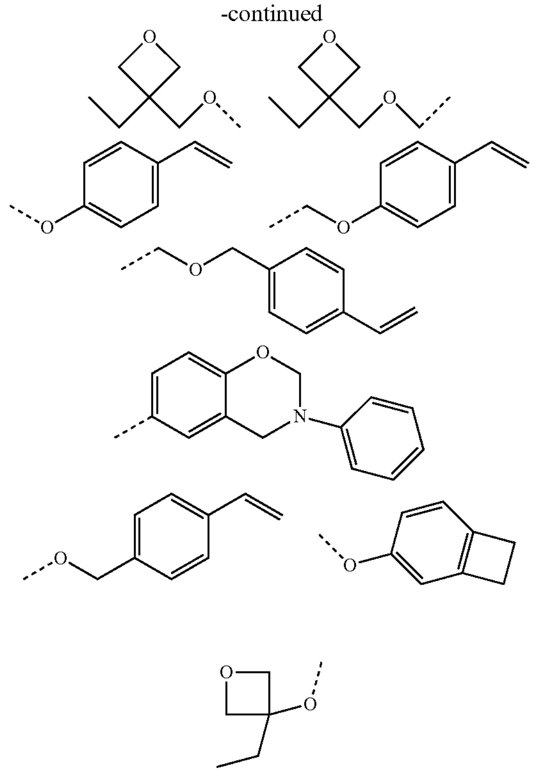

in the structures,

---- means a position bonding to Chemical Formula 1.

3. The compound of claim 1, wherein Chemical Formula 1 is represented by Chemical Formula 2:

[Chemical Formula 2]

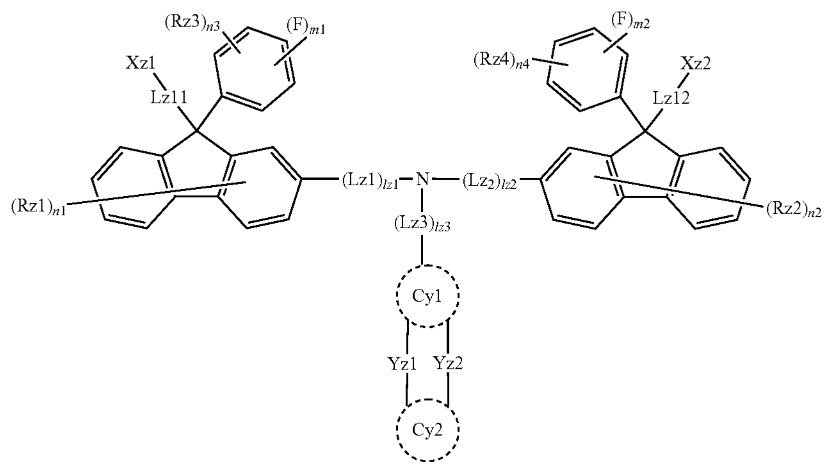

in Chemical Formula 2,

Lz1 to Lz3, Lz11, Lz12, Xz1, Xz2, Rz1 to Rz4, Yz1, Yz2, Cy1, Cy2, lz1 to lz3, n1 to n4, m1 and m2 have the same definitions as in Chemical Formula 1.

4. The compound of claim 1, wherein Chemical Formula 1 is represented by any one of Chemical Formulae 3 to 5:

[Chemical Formula 3]

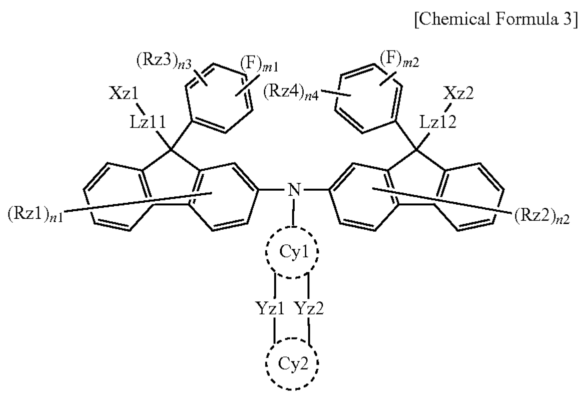

[Chemical Formula 4]

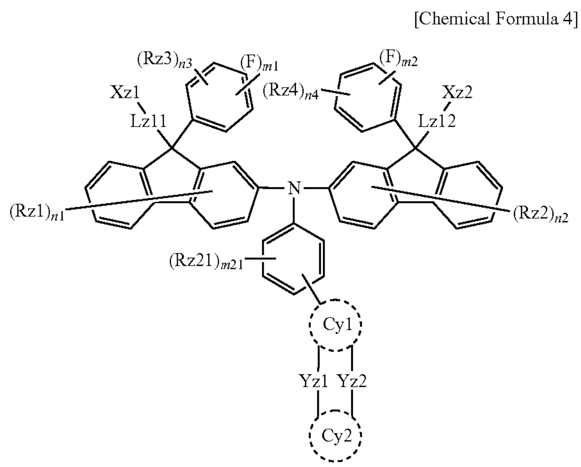

[Chemical Formula 5]

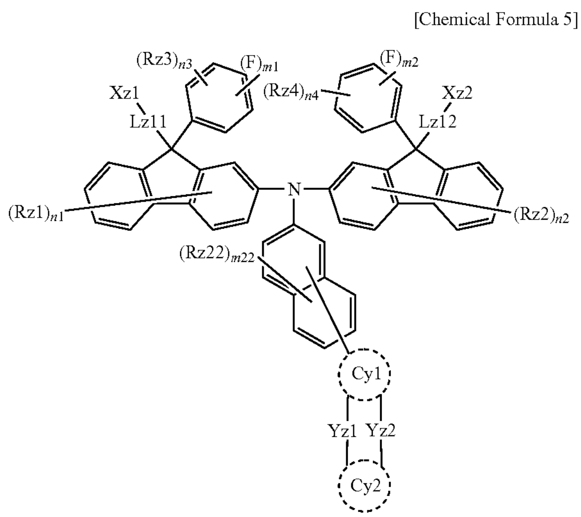

in Chemical Formulae 3 to 5,

Lz11, Lz12, Xz1, Xz2, Rz1 to Rz4, Cy1, Cy2, Yz1, Yz2, n1 to n4, m1 and m2 have the same definitions as in Chemical Formula 1;

Rz21 and Rz22 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group; and m21 is an integer of 0 to 4, m22 is an integer of 0 to 6, and when m21 and m22 are each an integer of 2 or greater, each occurrence of Rz21 and Rz22 is the same as or different from each other.

5. The compound of claim 1, wherein Cy1 and Cy2 are the same as or different from each other, and each independently represented by any one of the following structures:

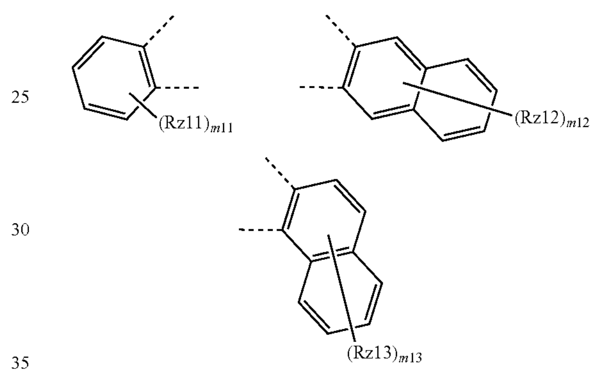

in the structures,

---- means a bonding position;

Rz11 to Rz13 are the same as or different from each other, and each independently deuterium; a halogen group; a substituted or unsubstituted alkyl group; a substituted or unsubstituted alkoxy group; a substituted or unsubstituted aryl group; or a substituted or unsubstituted heteroaryl group;

m11 is an integer of 0 to 4; and m12 and m13 are each independently an integer of 0 to 6, and when m11 to m13 are each an integer of 2 or greater, each occurrence of Rz11 to Rz13 is the same as or different from each other.

6. The compound of claim 1, wherein Lz11 and Lz12 are the same as or different from each other, and each independently a direct bond; a substituted or unsubstituted alkylene group having 1 to 20 carbon atoms; or a substituted or unsubstituted arylene group having 6 to 30 carbon atoms.

7. The compound of claim 1, wherein Ra, Rb, Rc and Rd are the same as or different from each other, and each independently a substituted or unsubstituted methyl group; or a substituted or unsubstituted phenyl group, or bond to adjacent groups to form a substituted or unsubstituted fluorene ring; or a substituted or unsubstituted xanthene ring.

8. The compound of claim 1, wherein the compound of Chemical Formula 1 is any one selected from the group consisting of the following compounds:

-continued
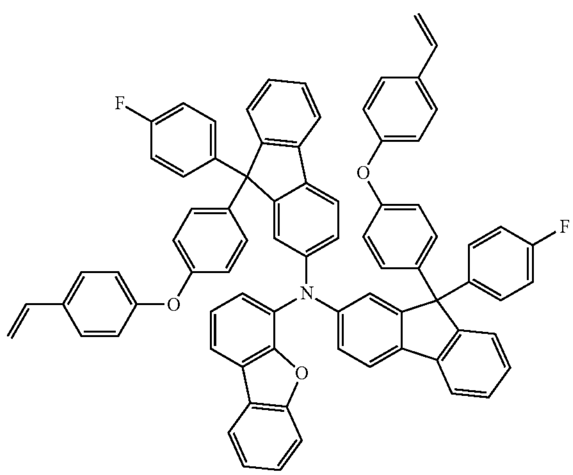
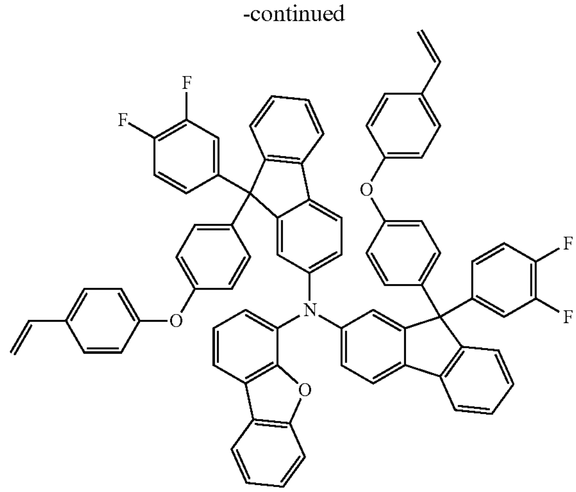
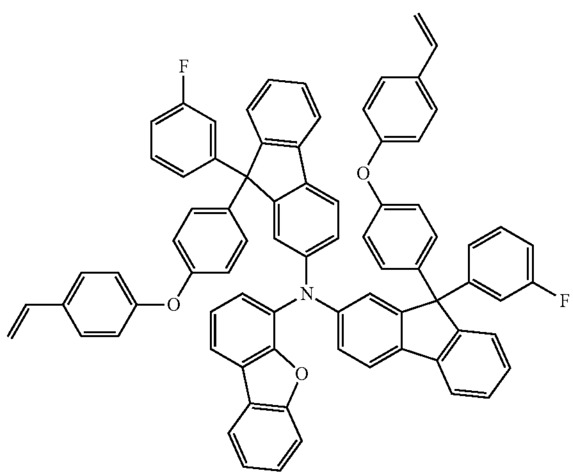
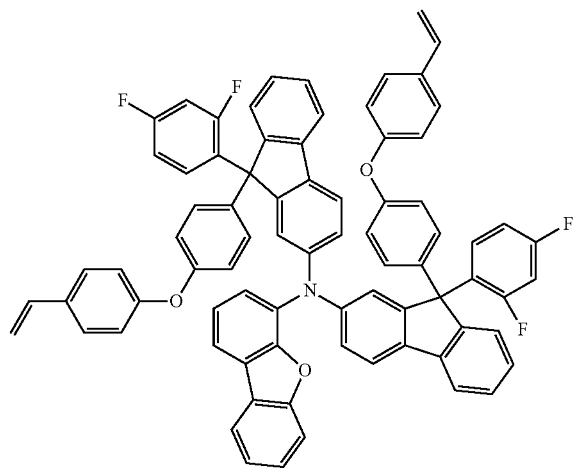
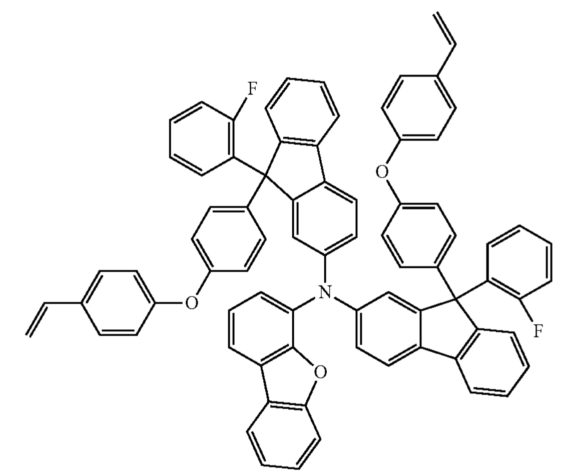
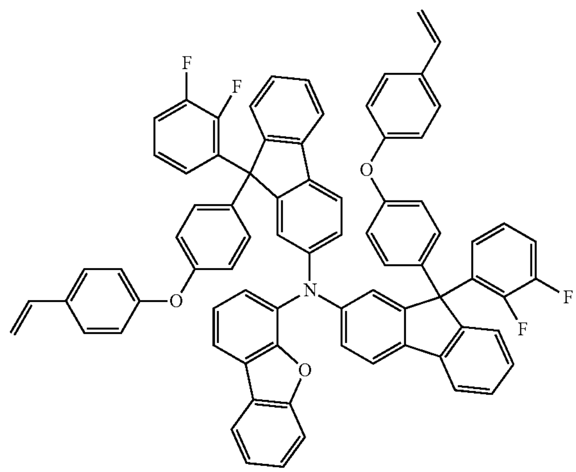

-continued
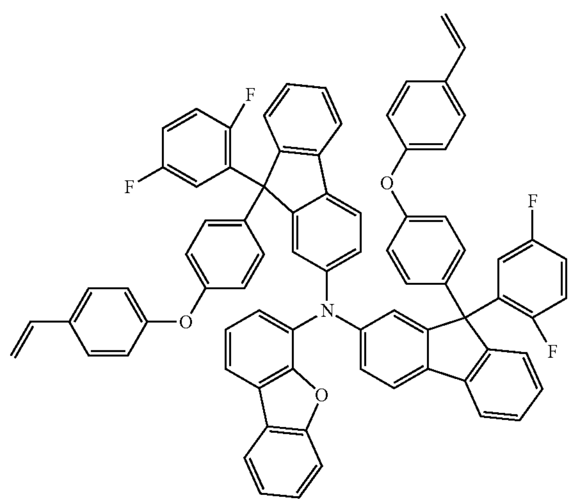
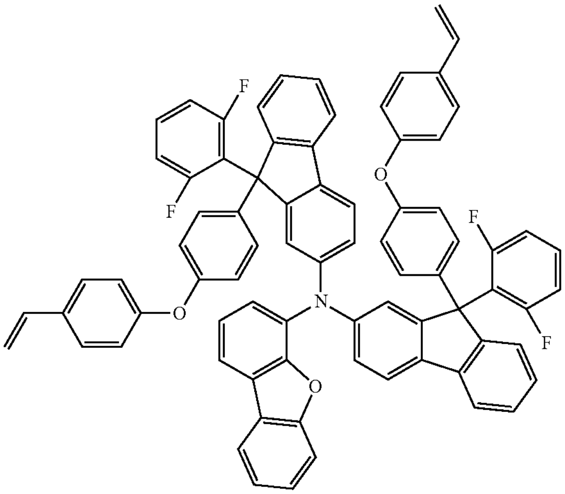
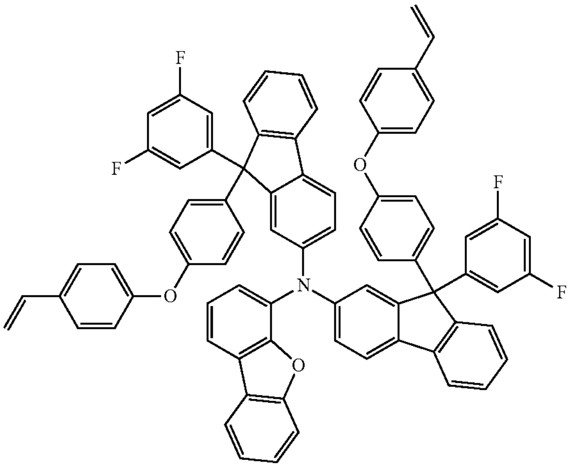
-continued
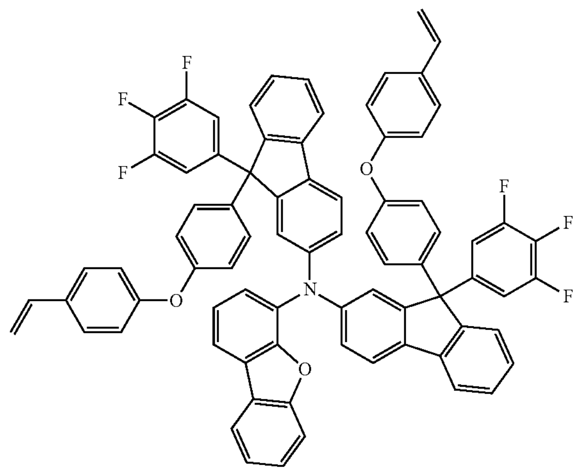
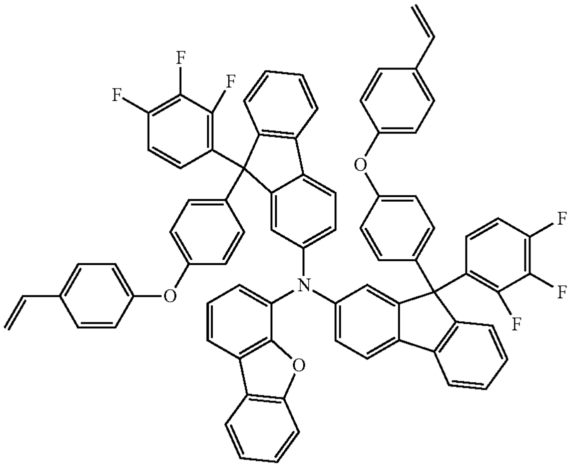
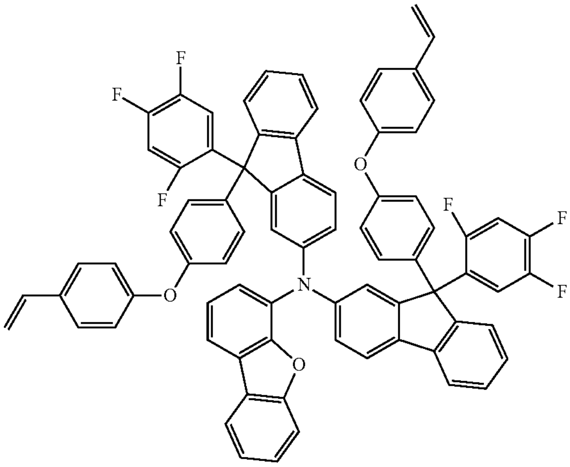

-continued
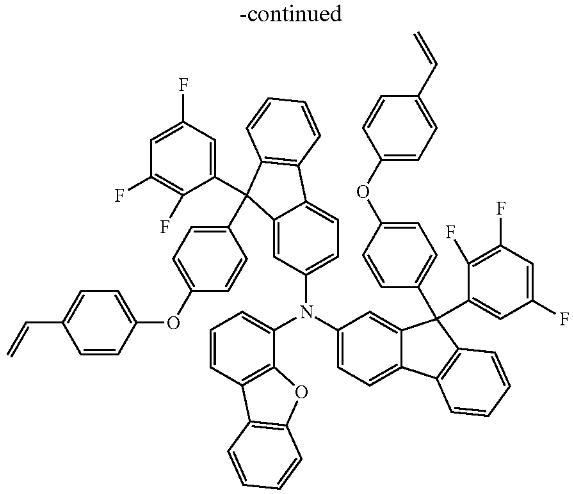
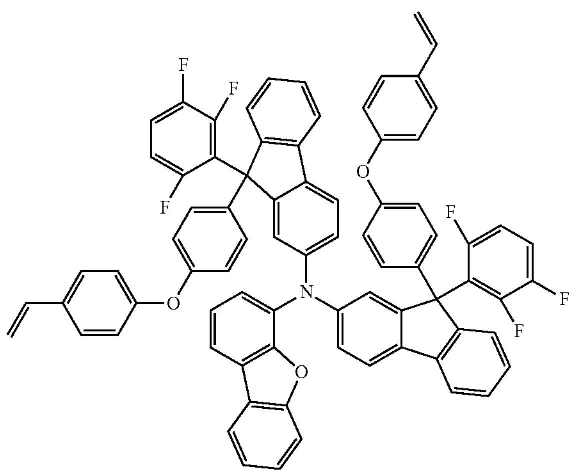
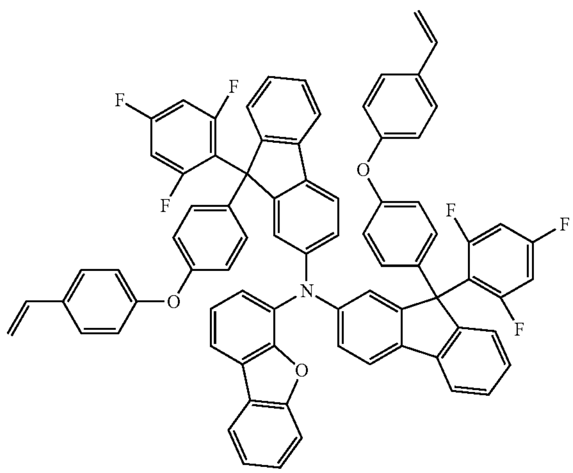
-continued
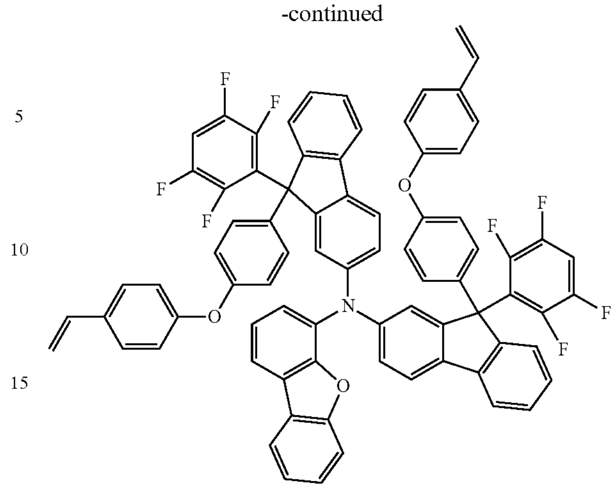
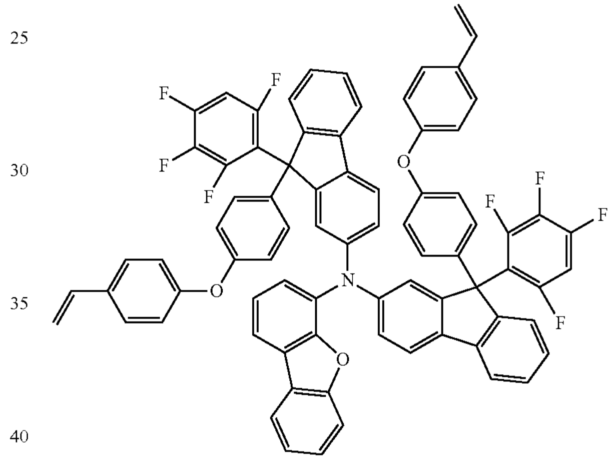
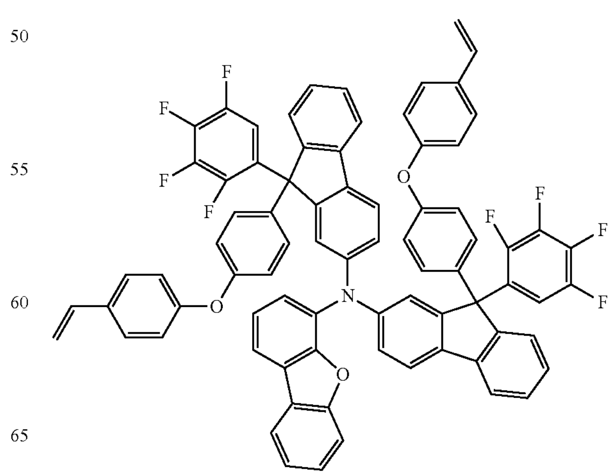

-continued
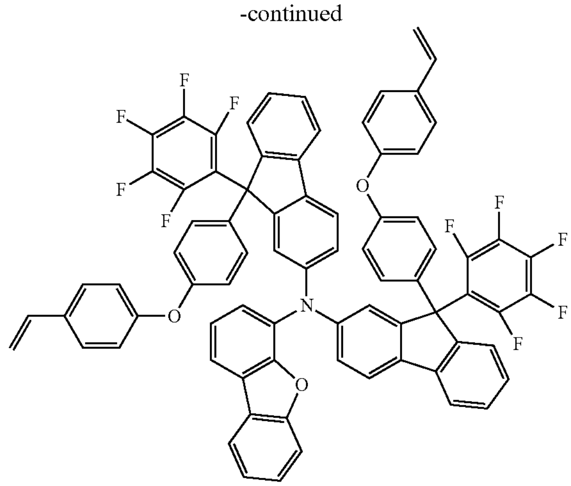
-continued
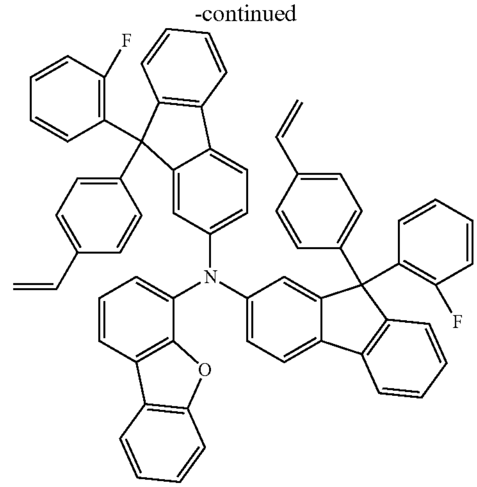
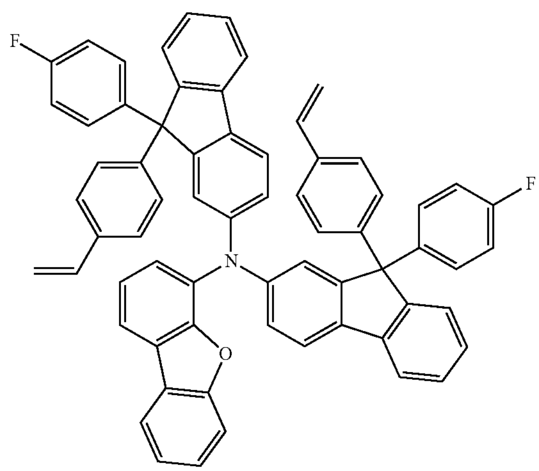
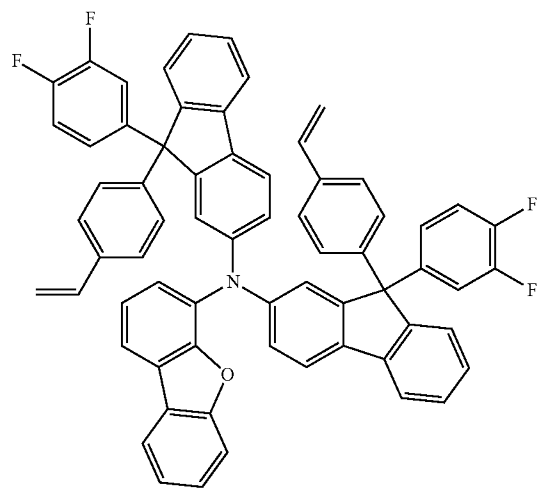
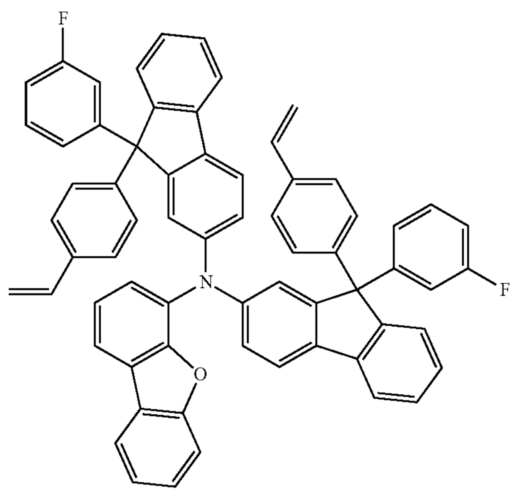
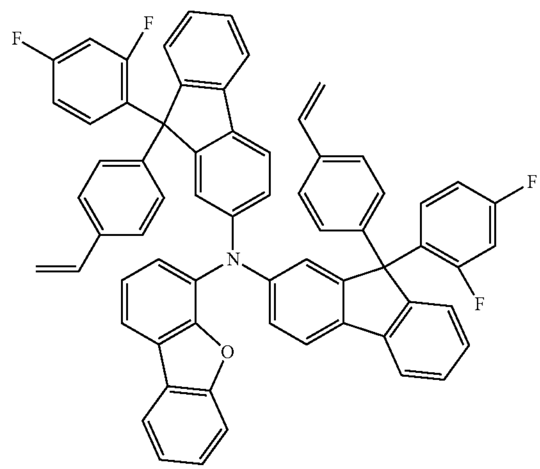

-continued
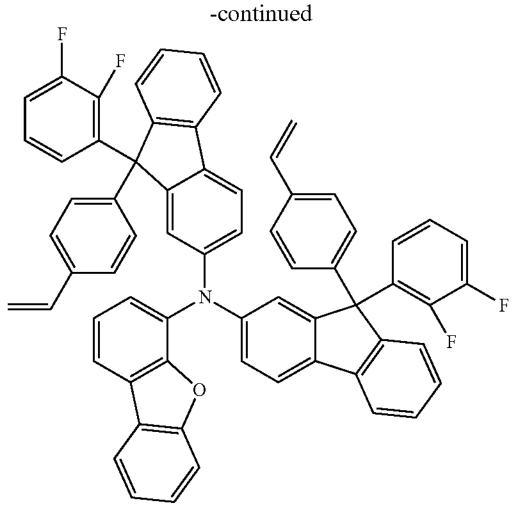
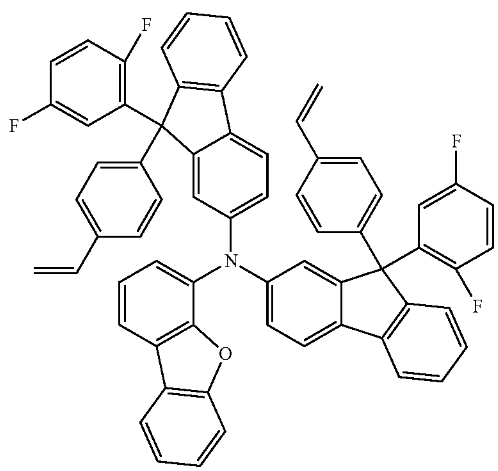
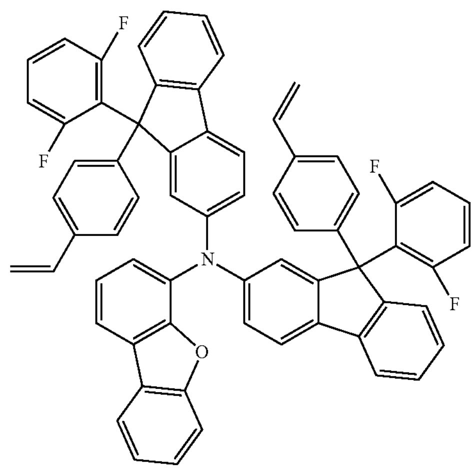
-continued
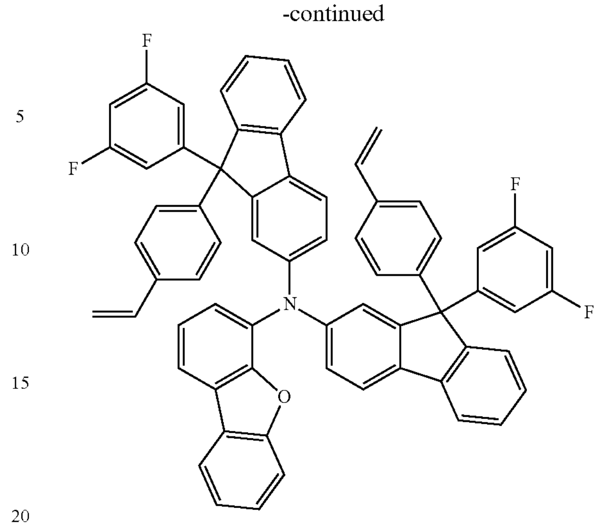
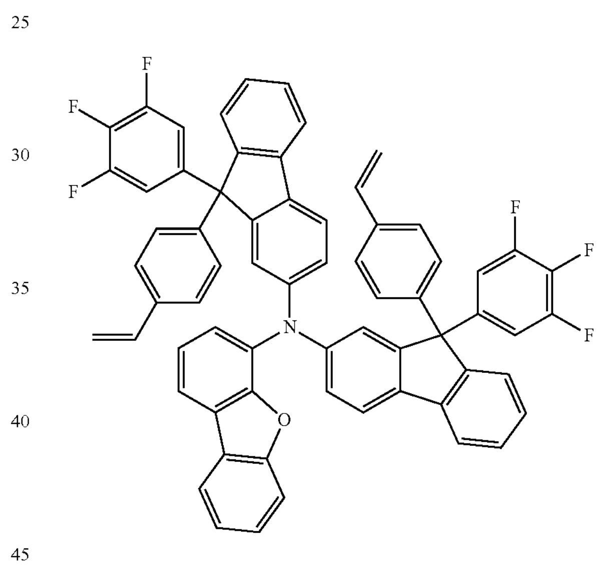
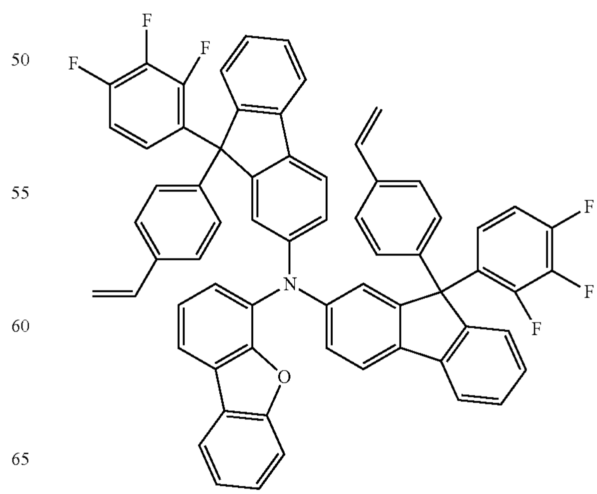

-continued
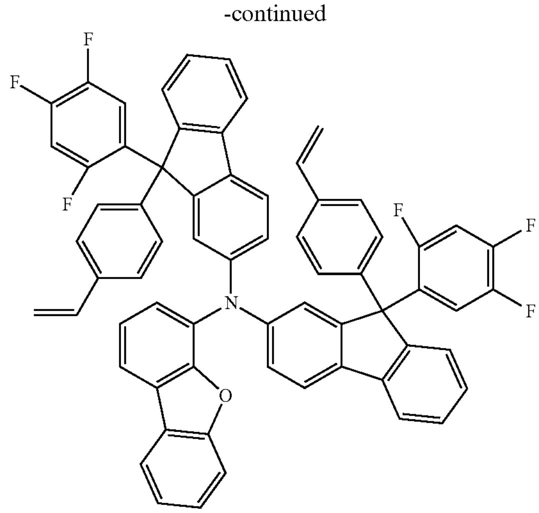
-continued
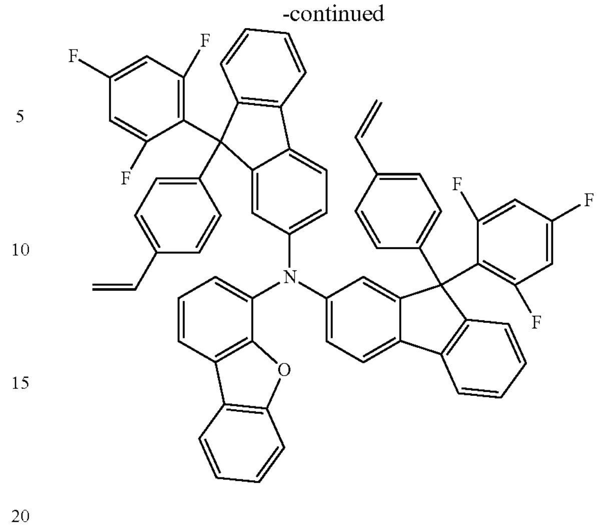
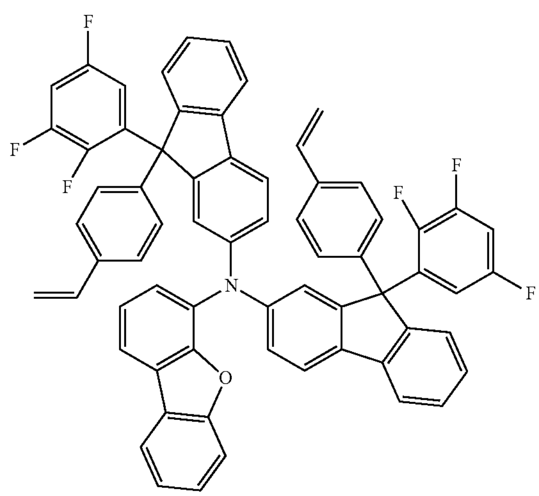
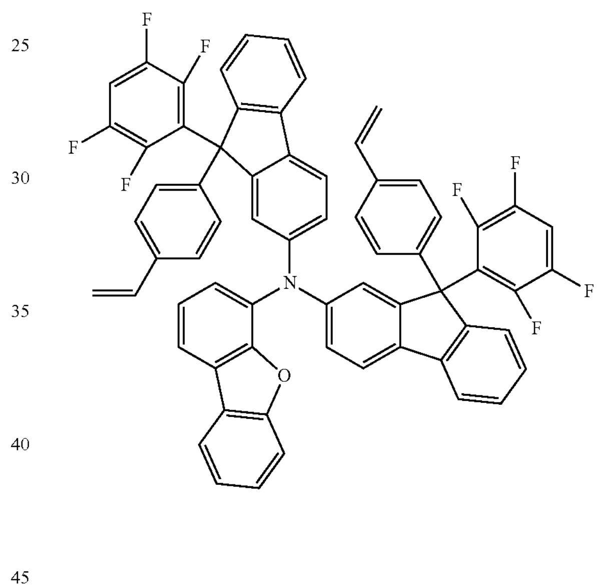
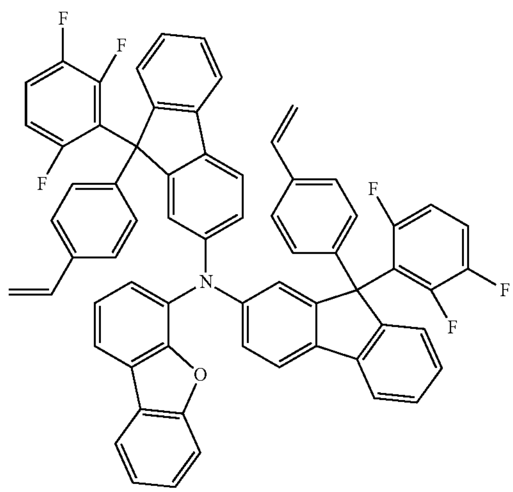
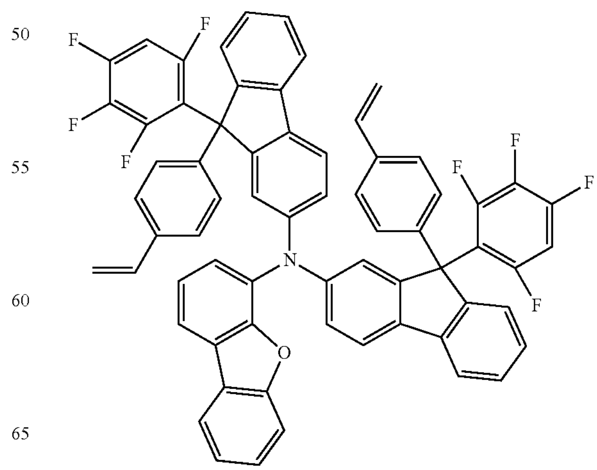

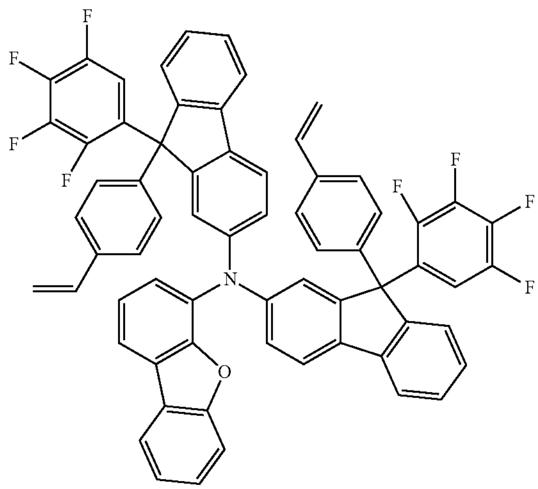
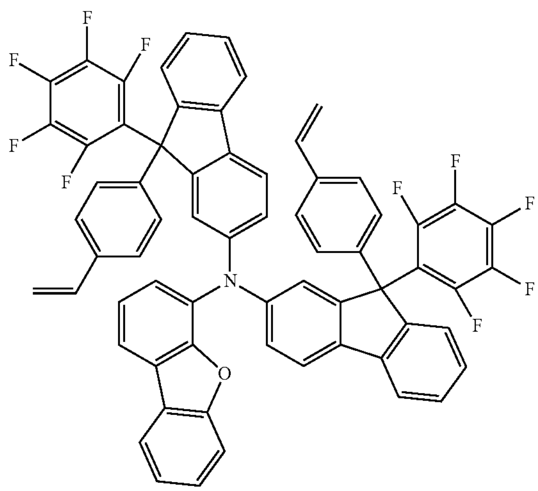
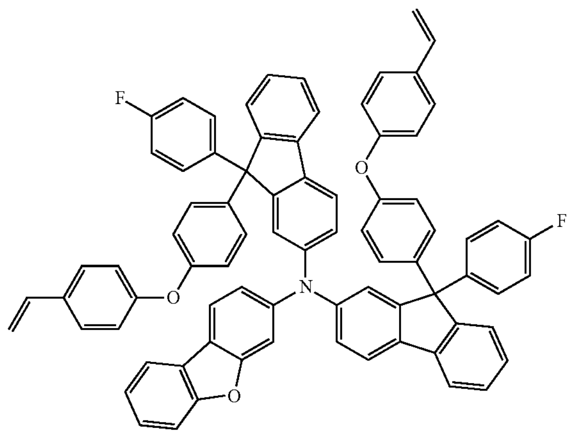
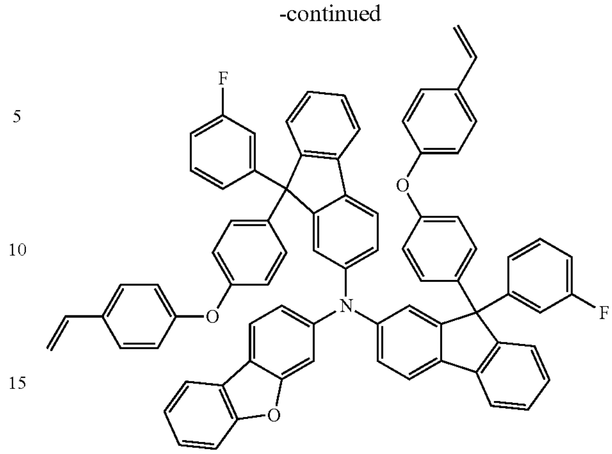
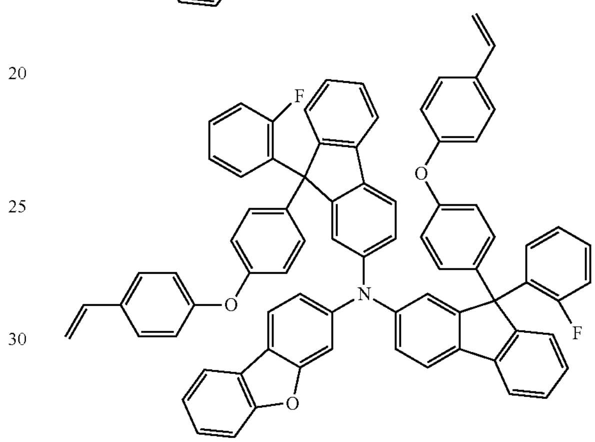
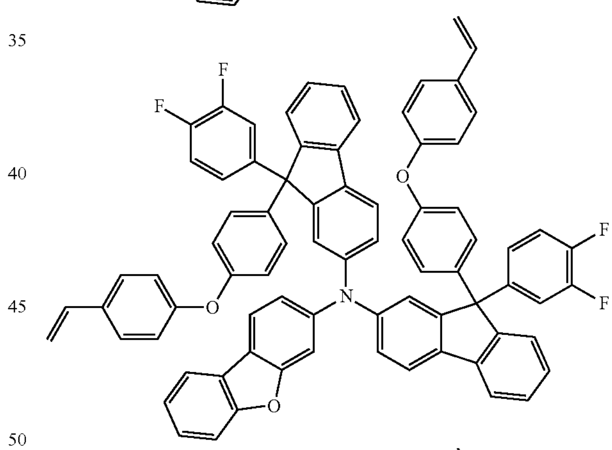
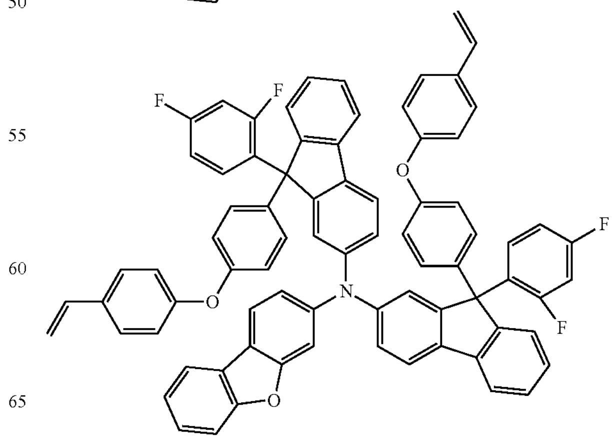

-continued
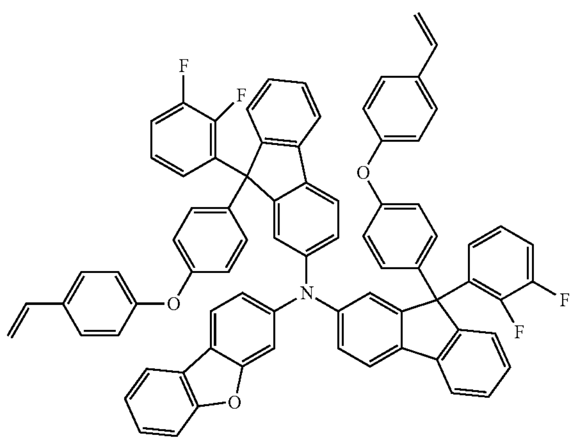
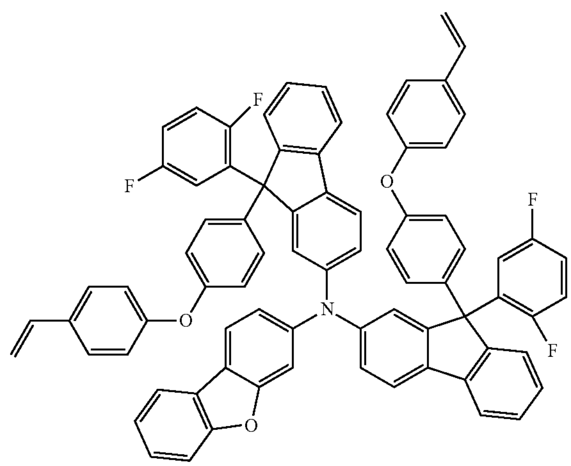
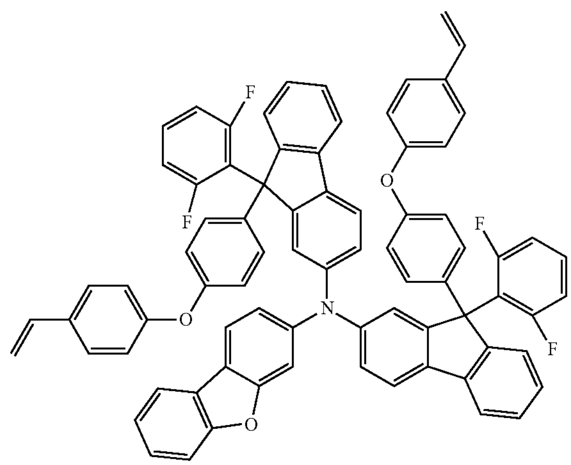
-continued
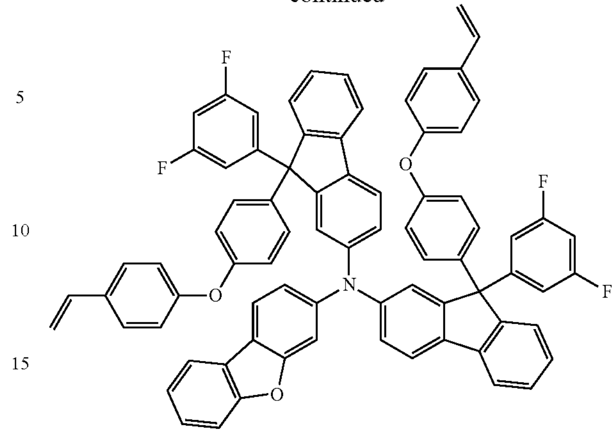
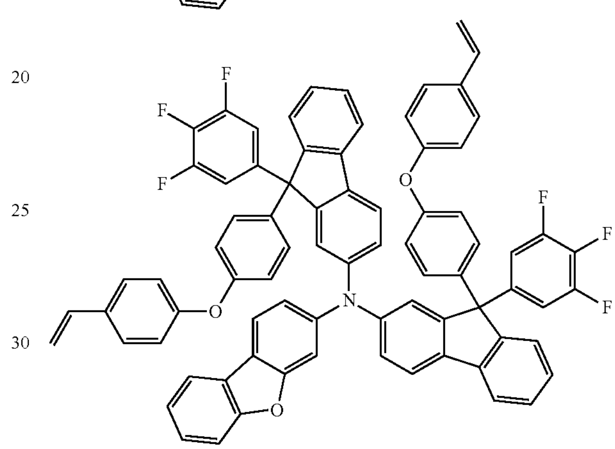
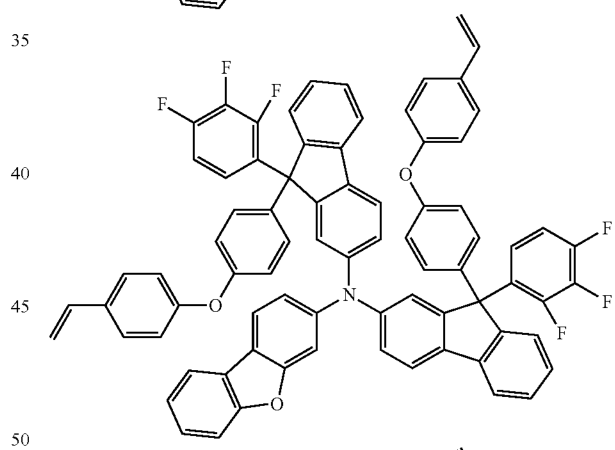
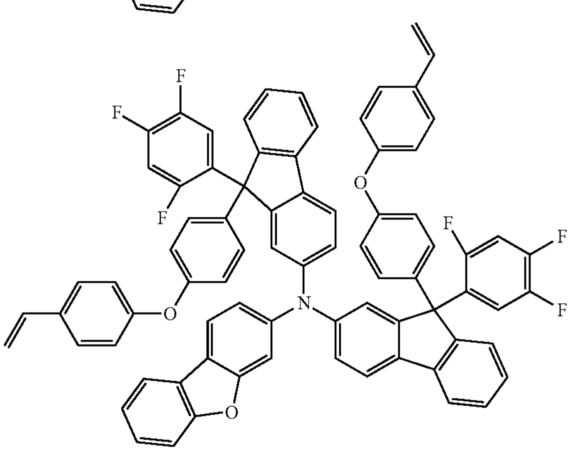

-continued
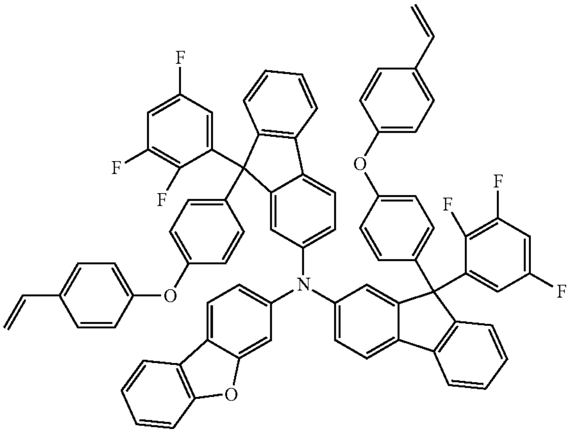
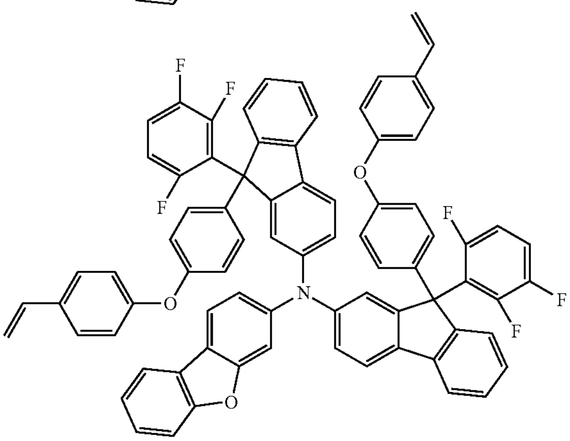
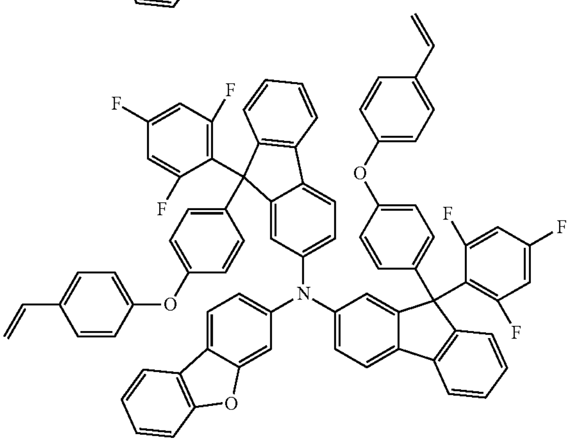
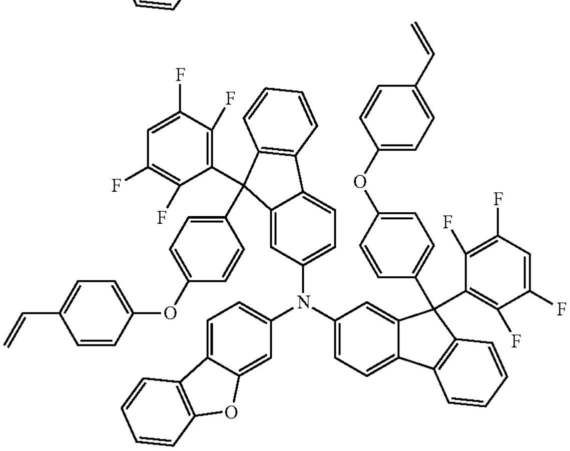
-continued
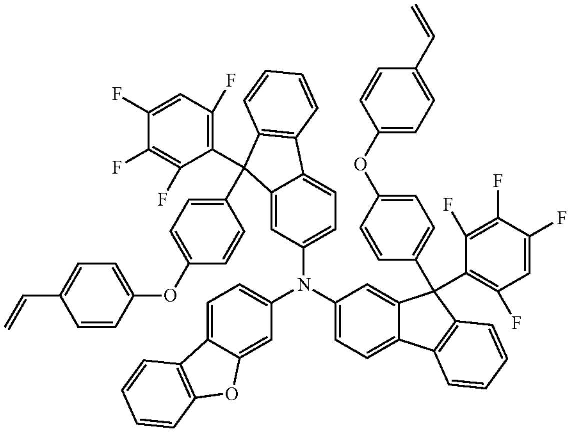
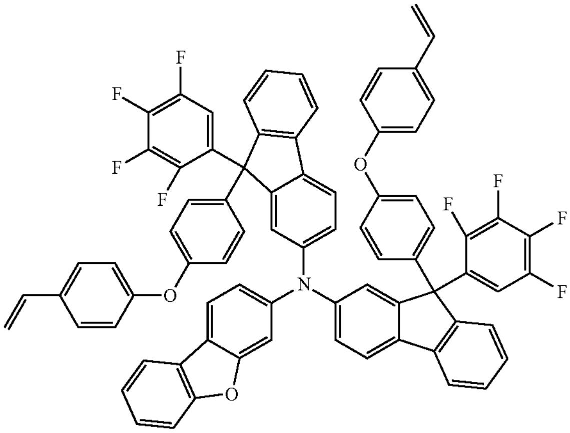
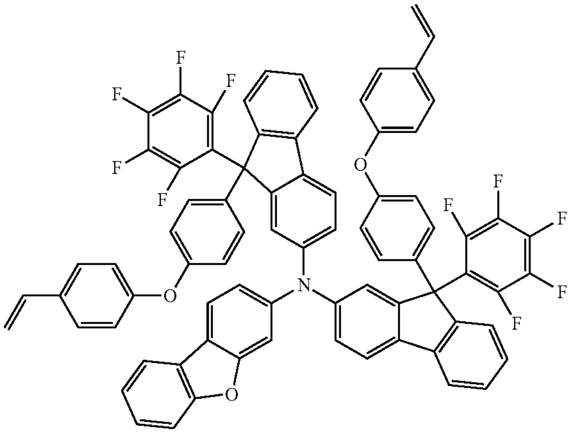

-continued
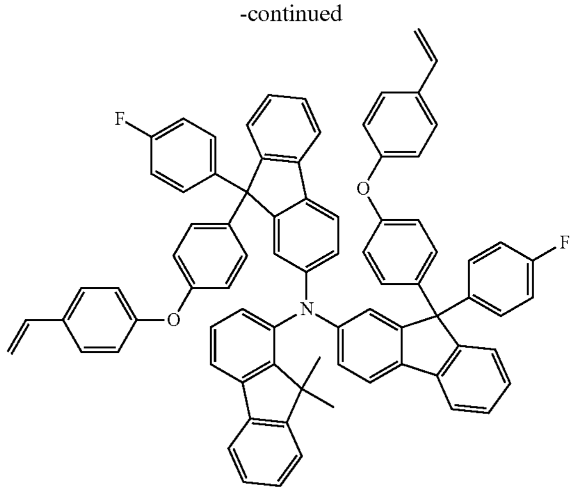
-continued
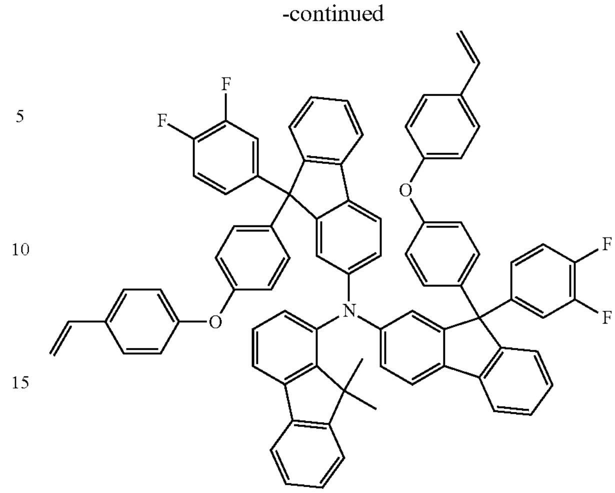
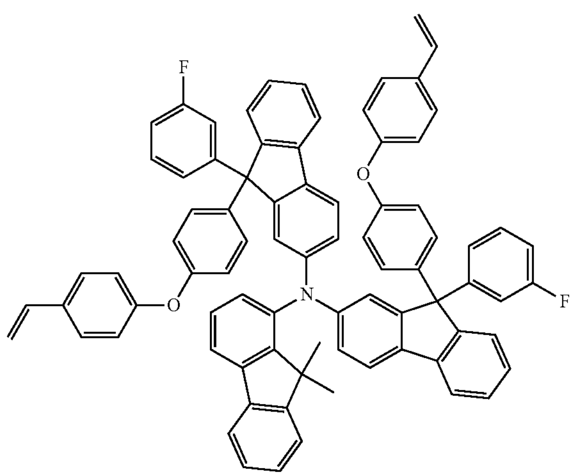
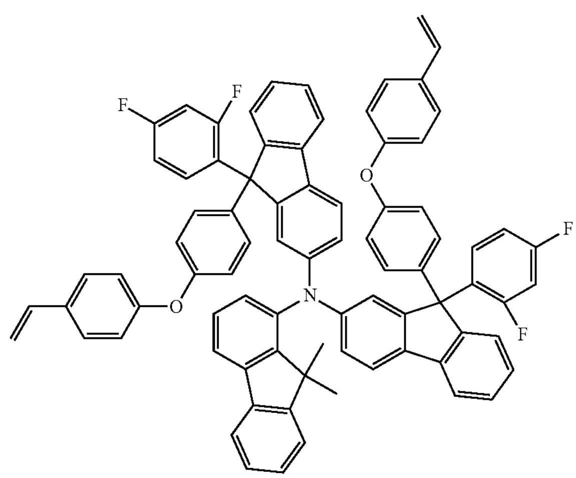
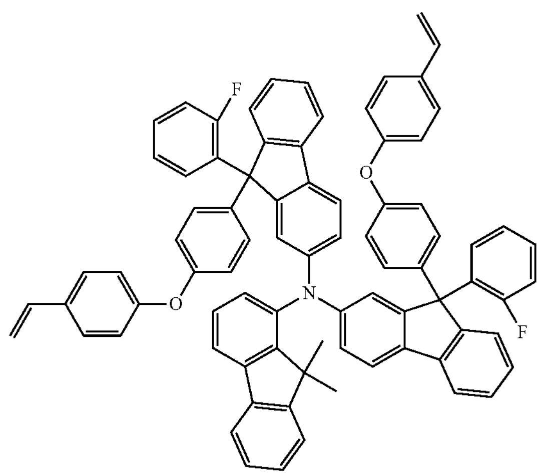
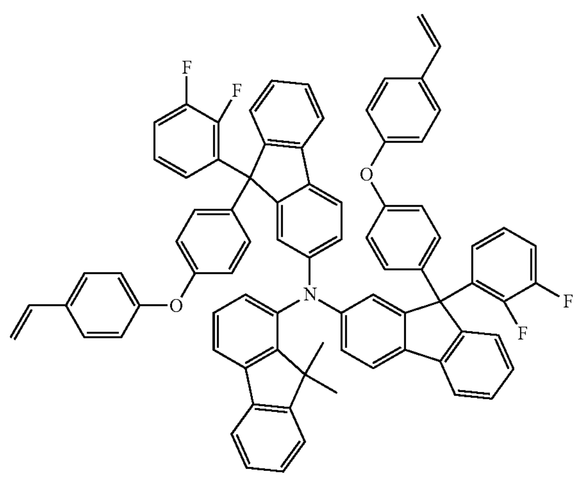

-continued
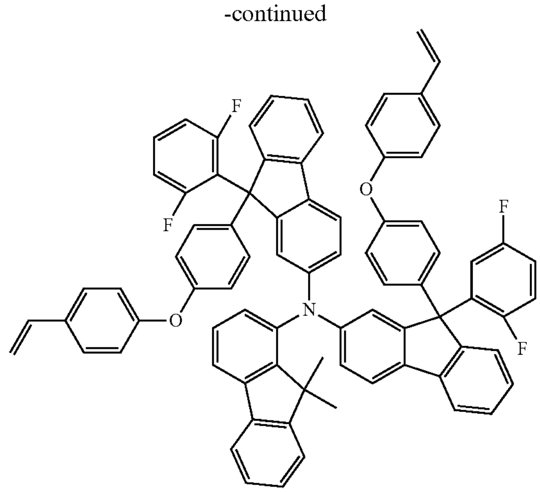
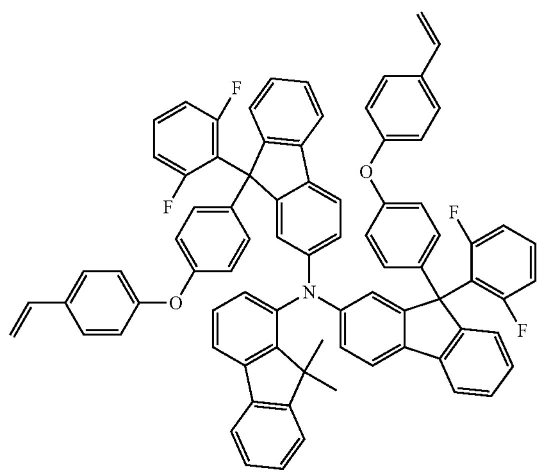
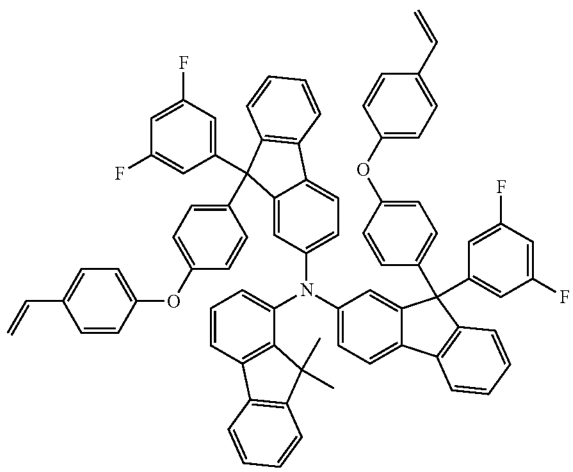
-continued
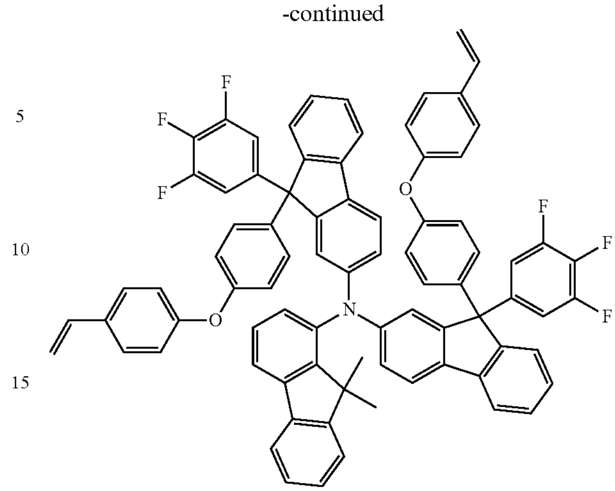
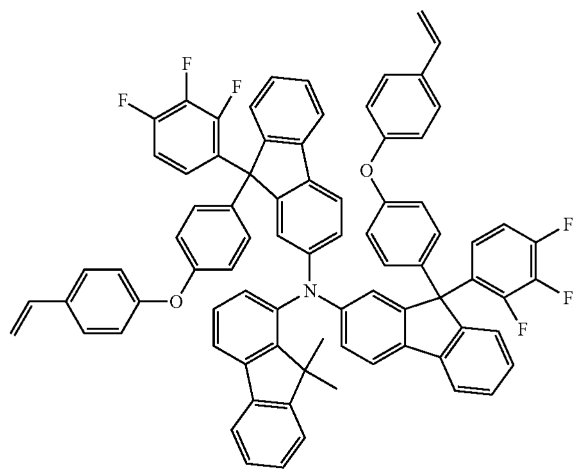
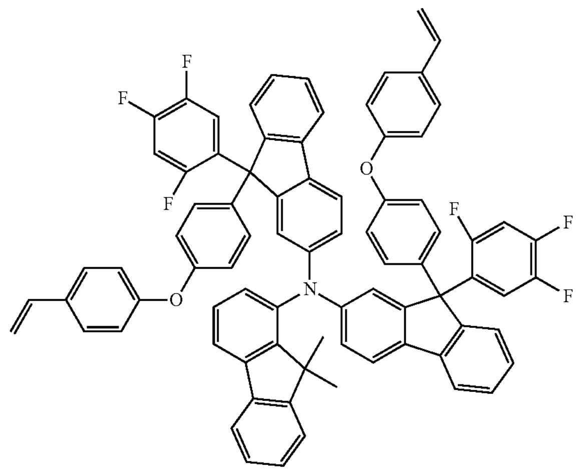

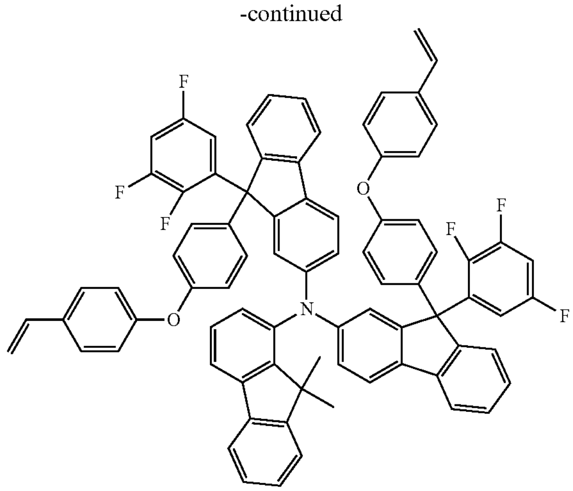
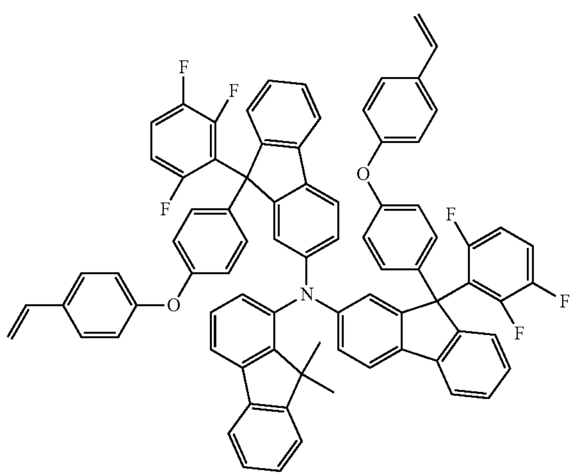
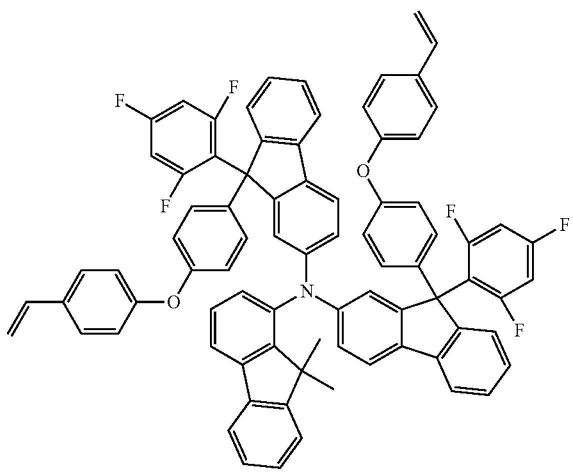
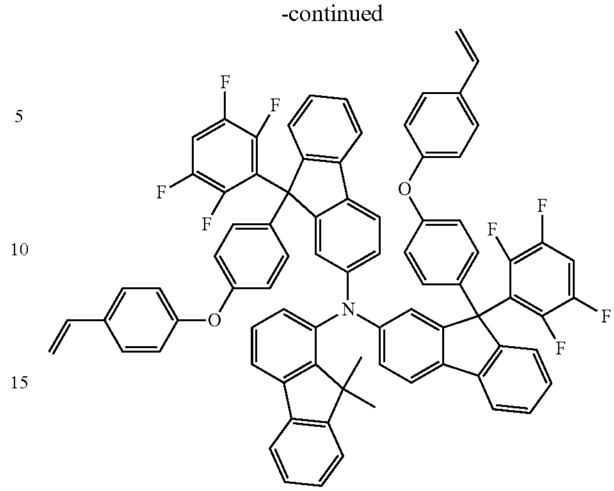
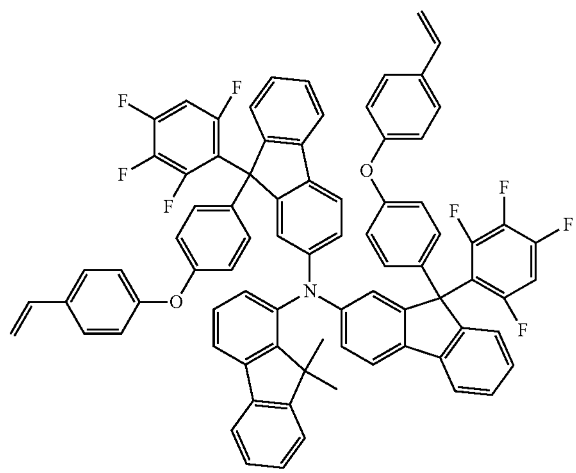
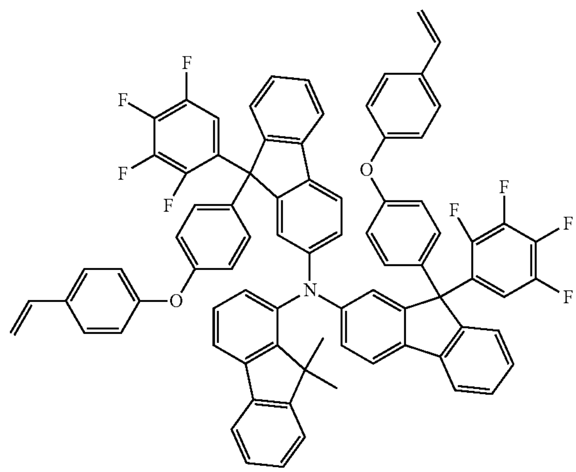

-continued
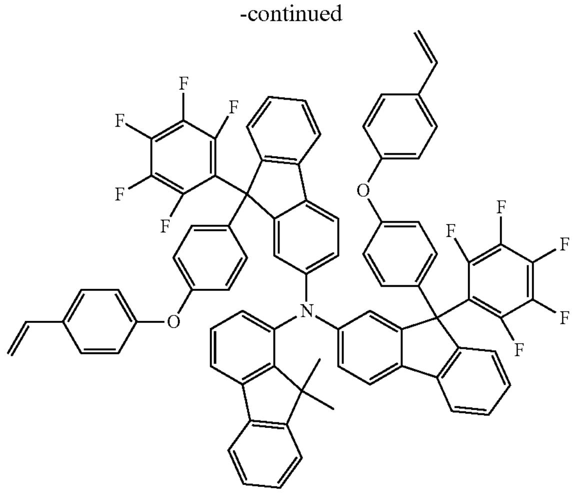
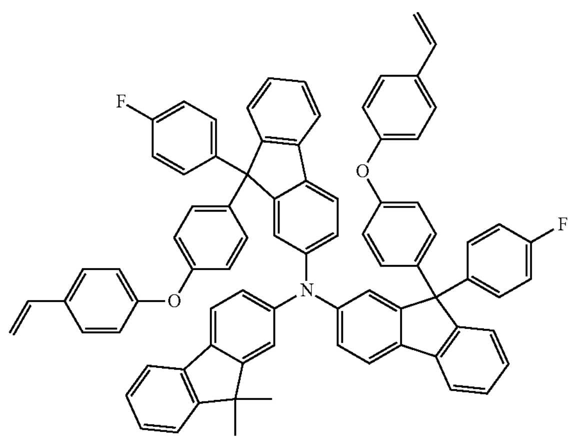
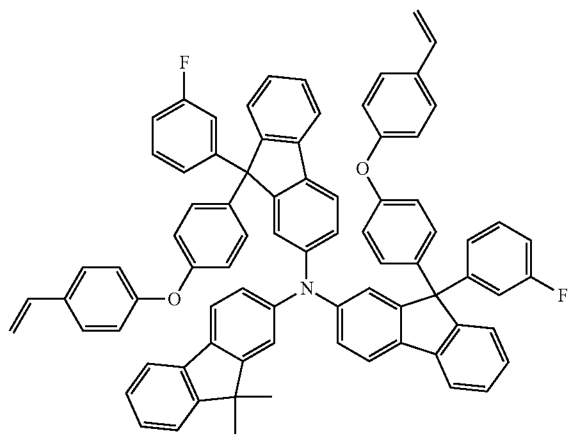
-continued
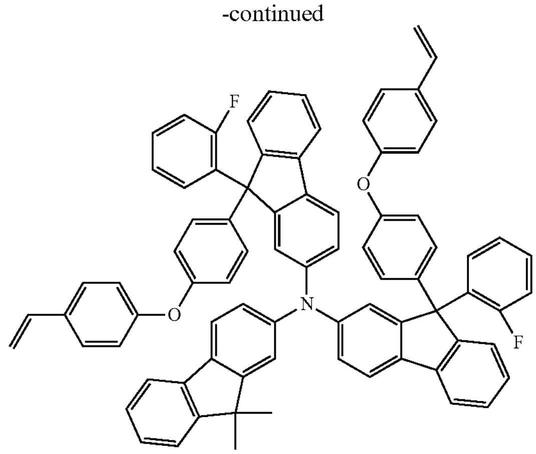
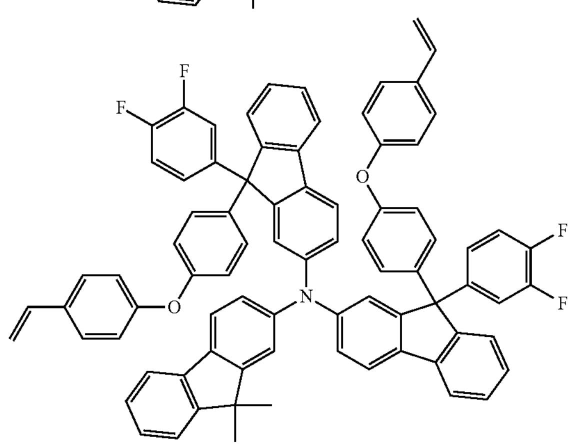
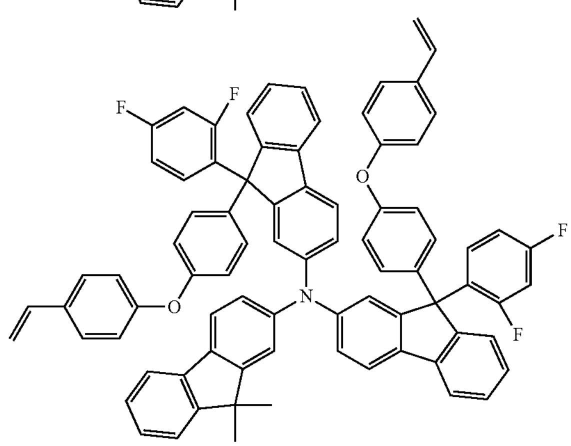
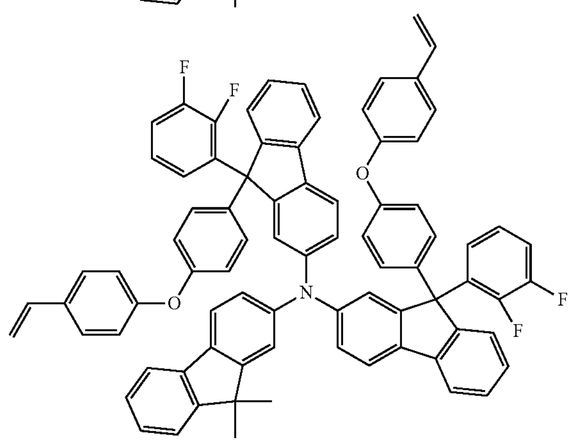

-continued
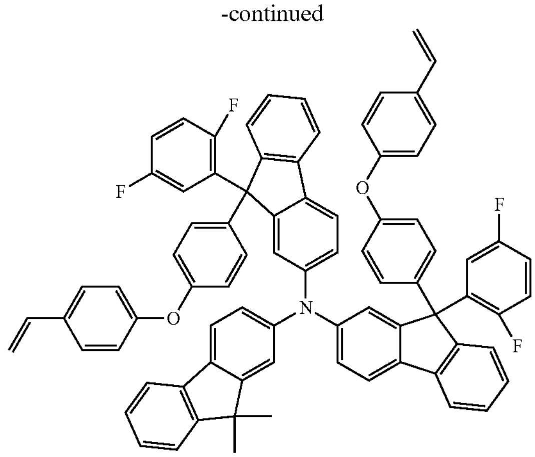
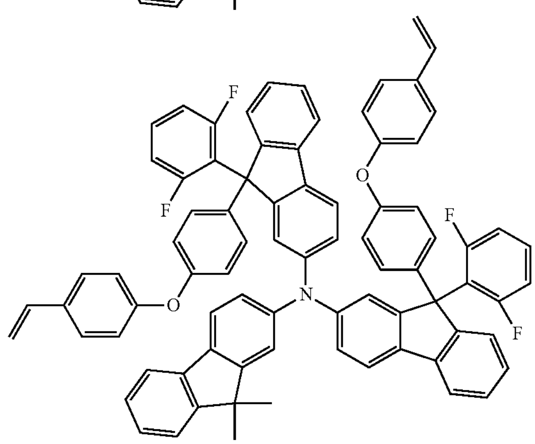
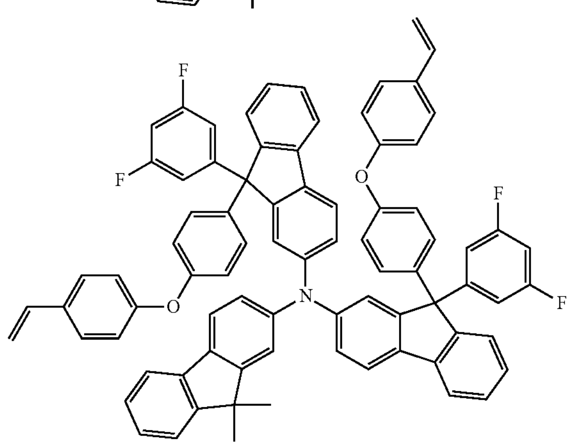
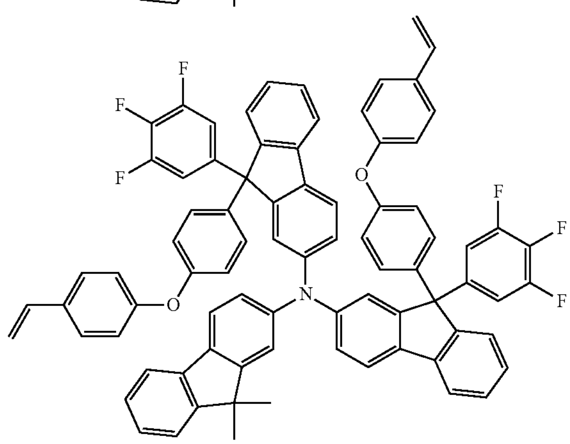
-continued
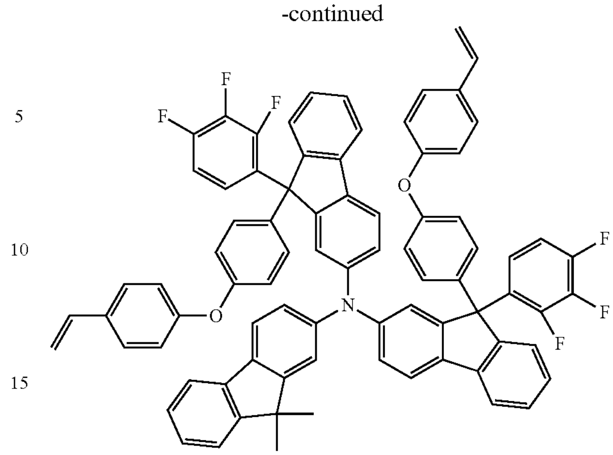
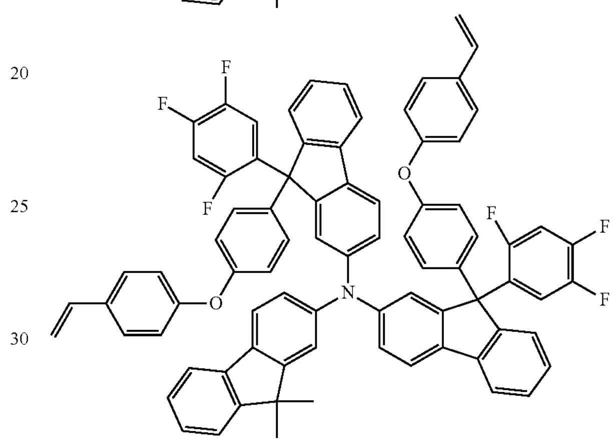
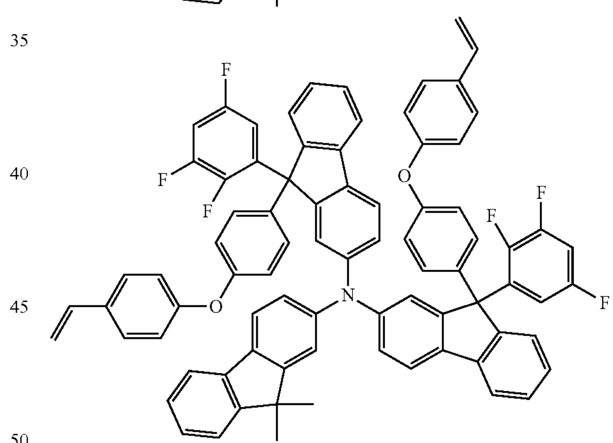
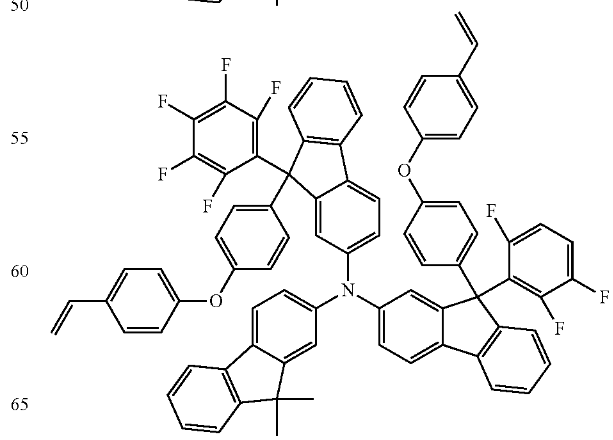

-continued
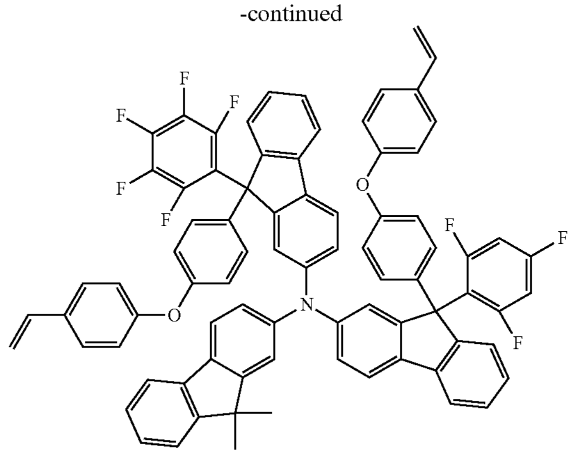
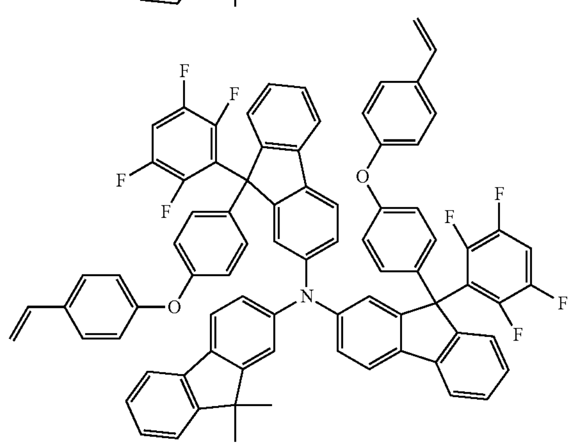
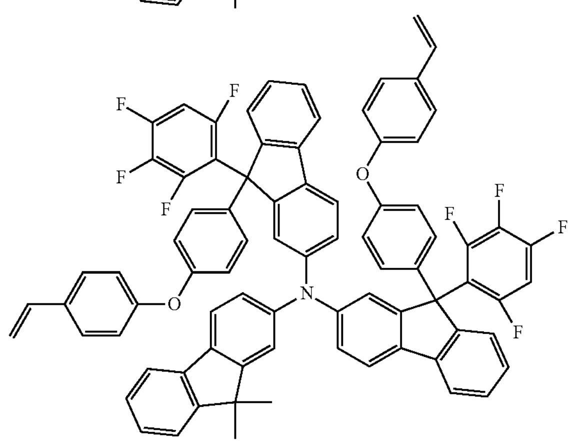
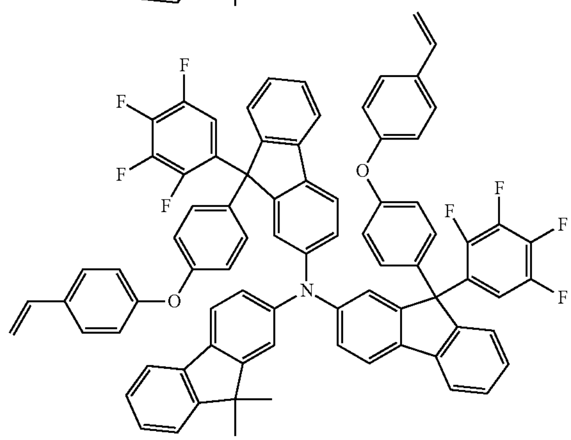
-continued
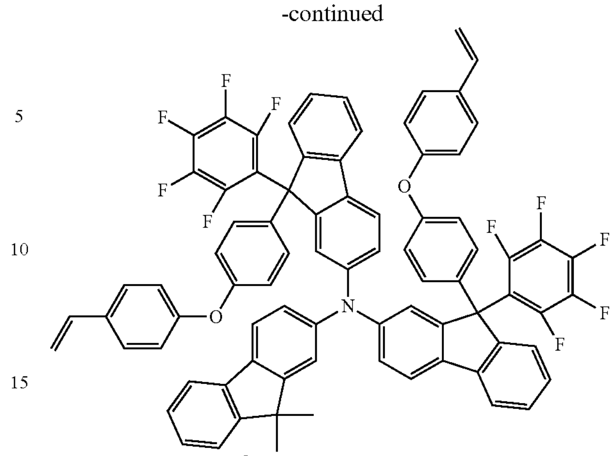
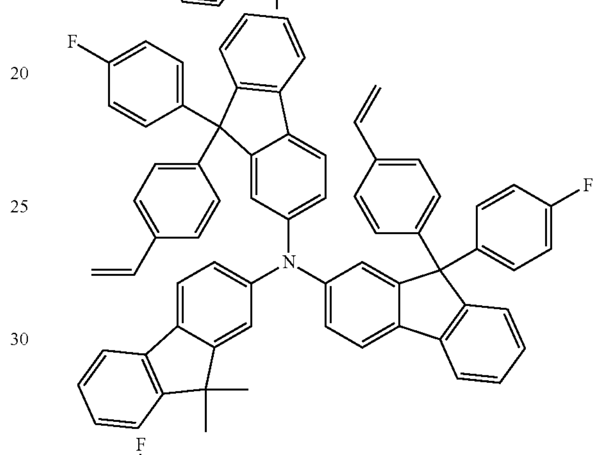
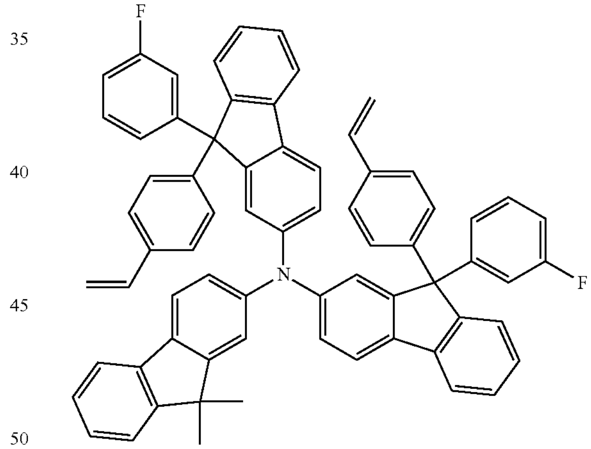
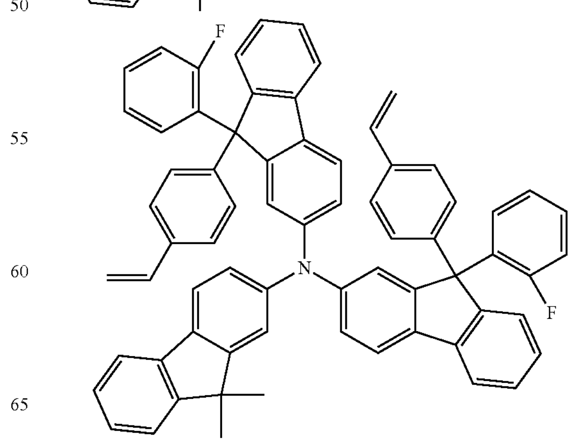

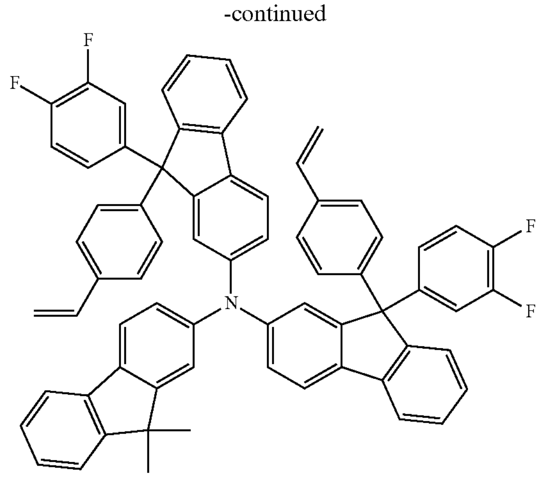
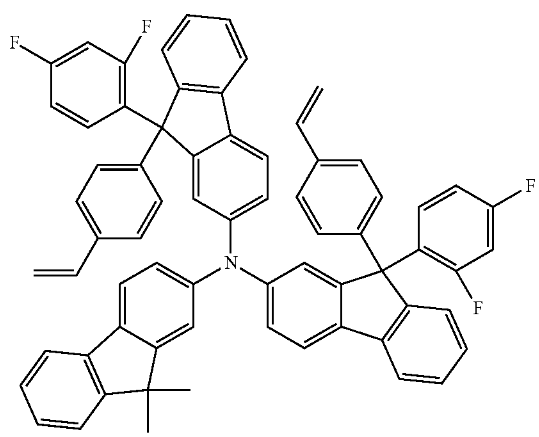
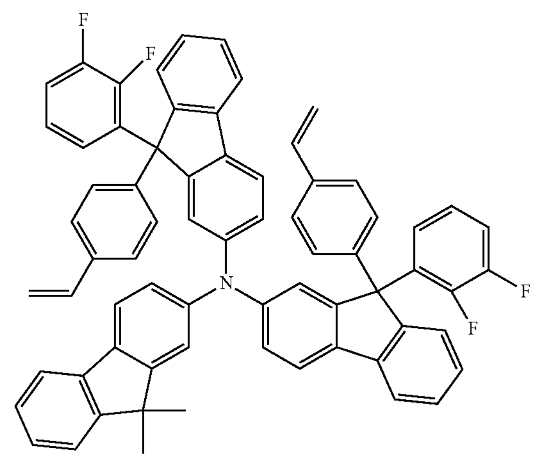
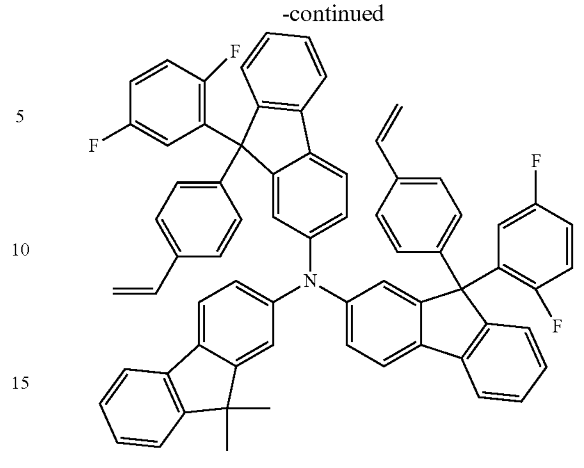
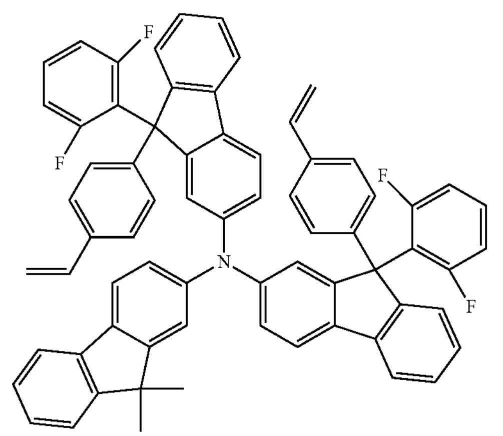
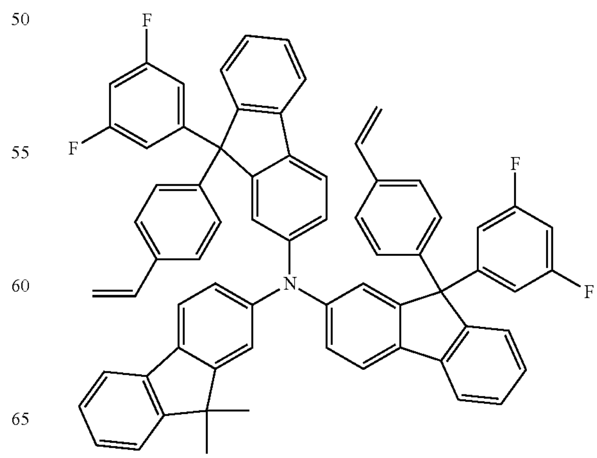

-continued
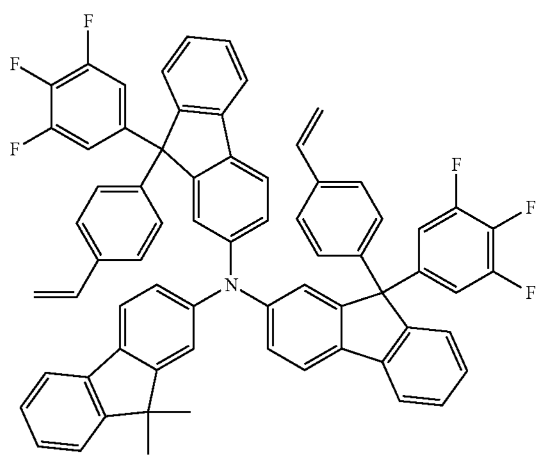
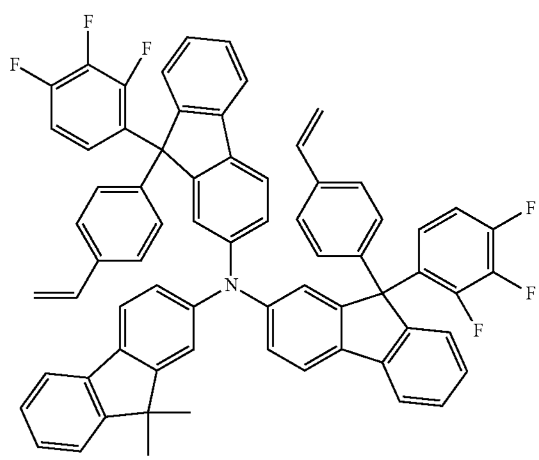
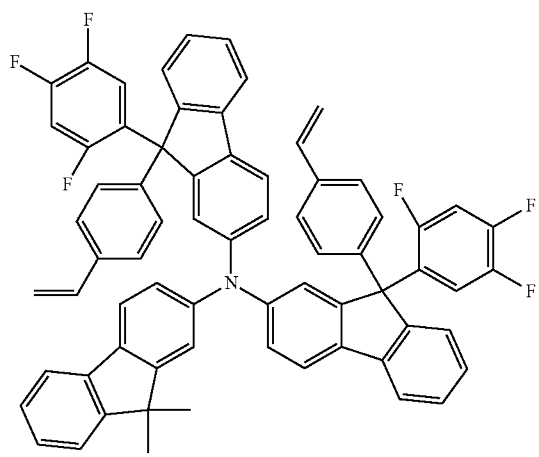
-continued
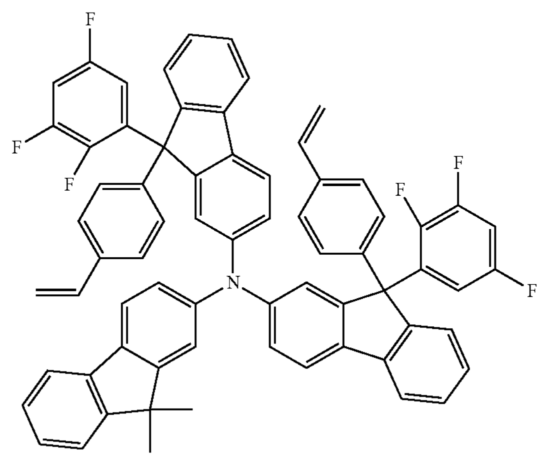
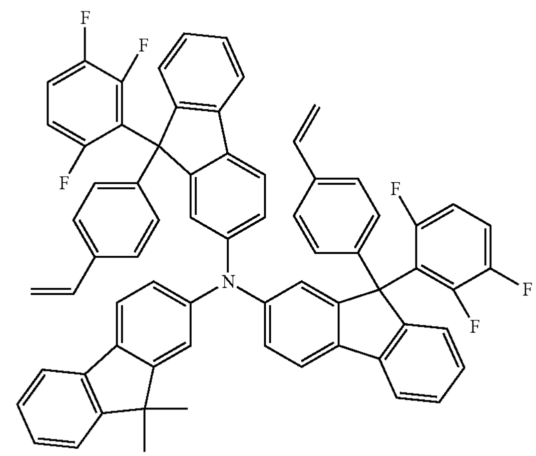
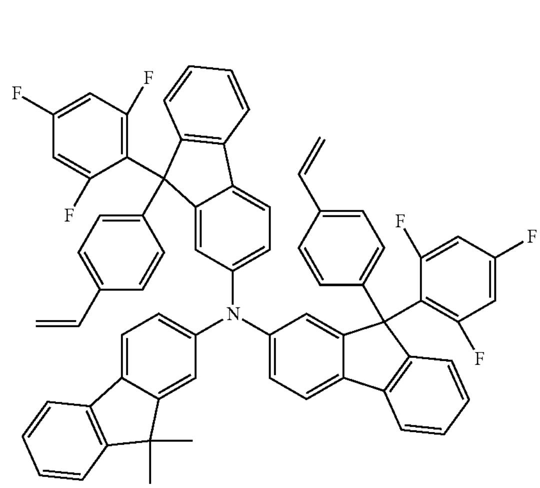

-continued
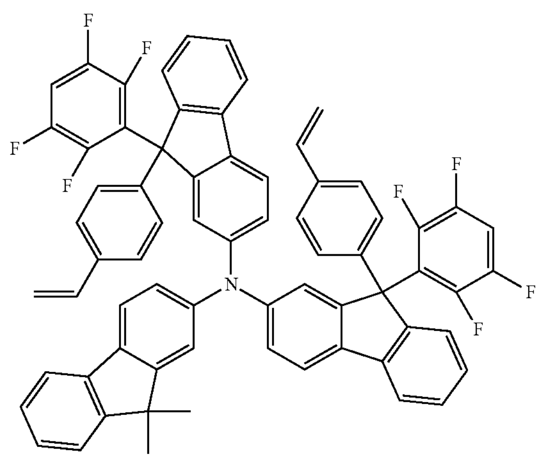
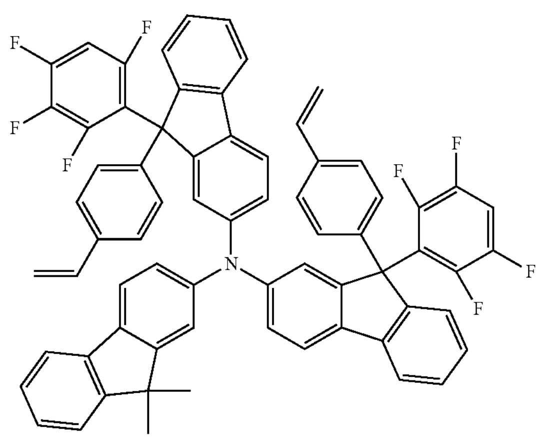
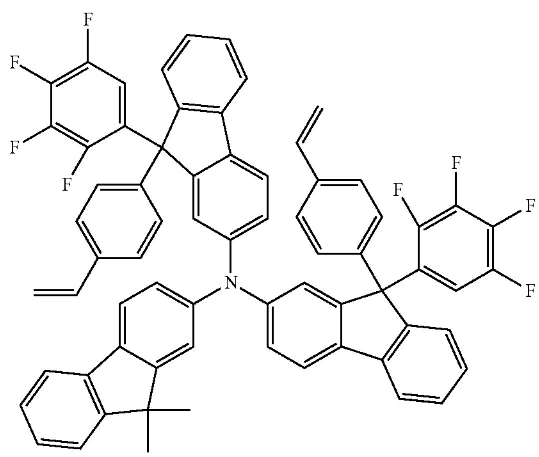
-continued
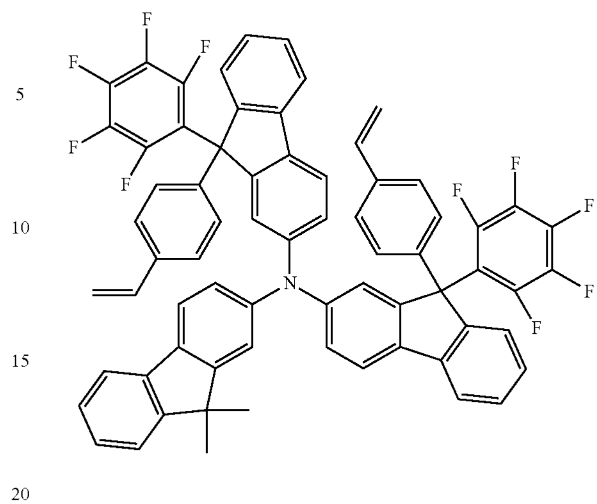
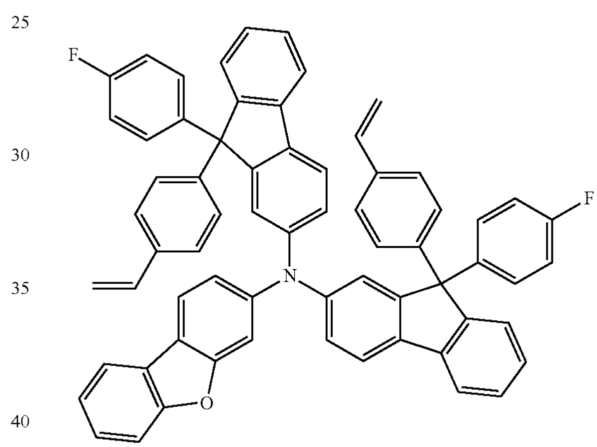
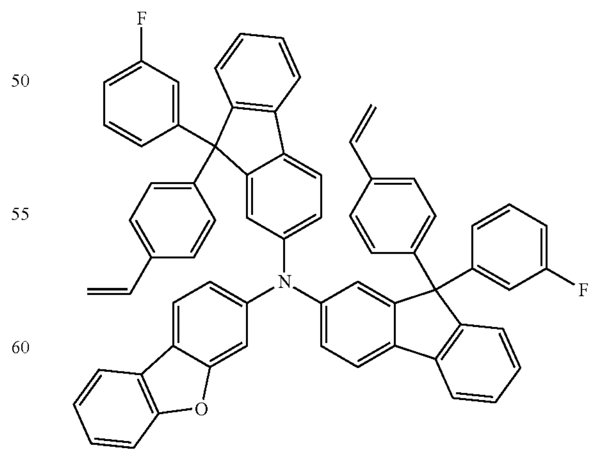

-continued
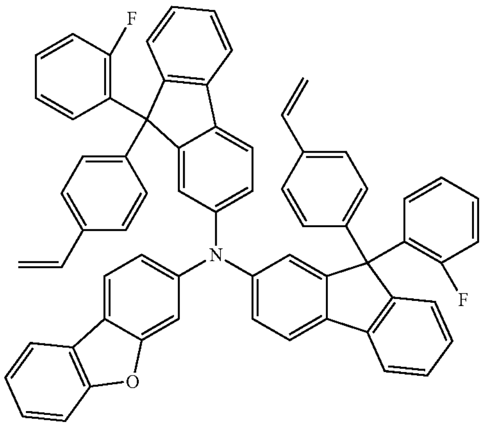
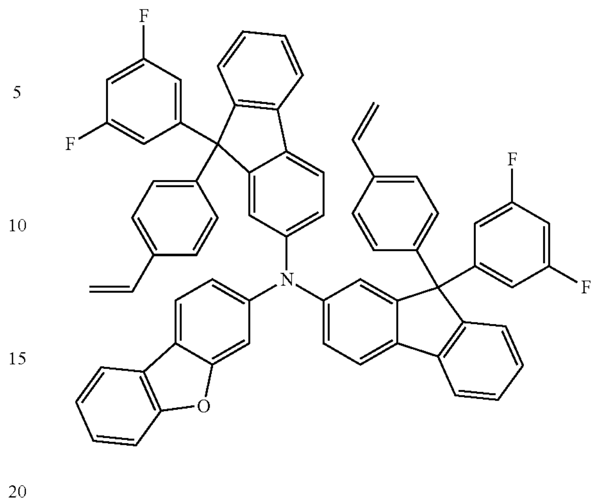
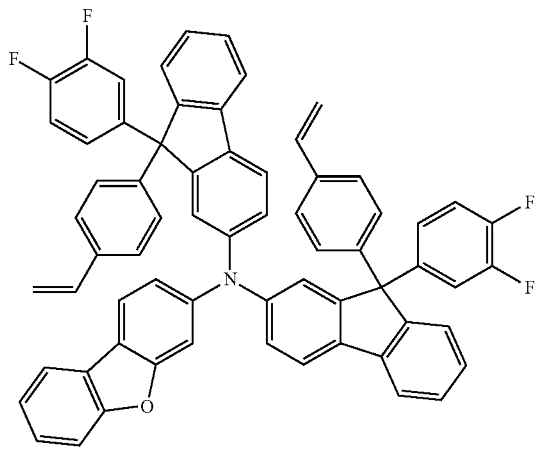
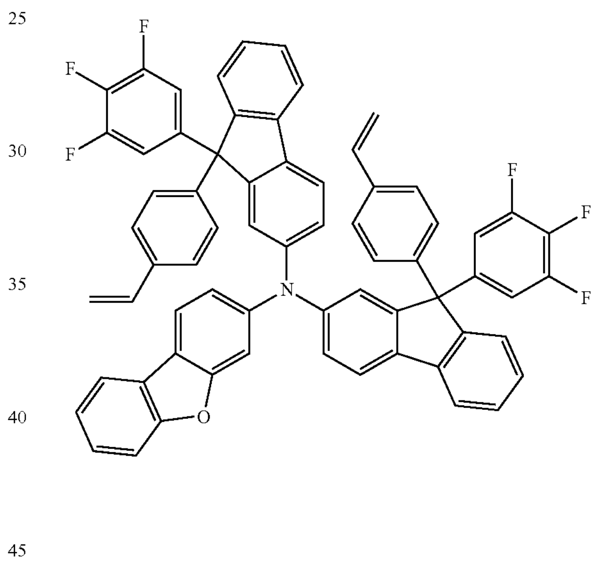
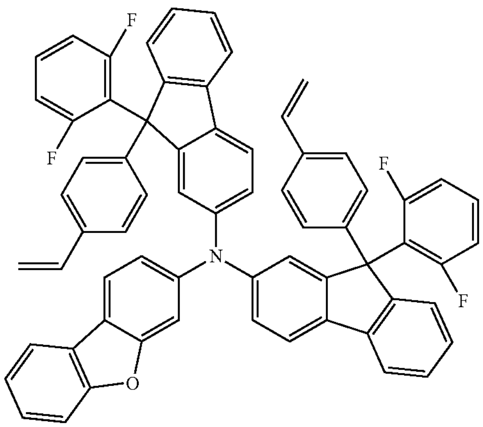
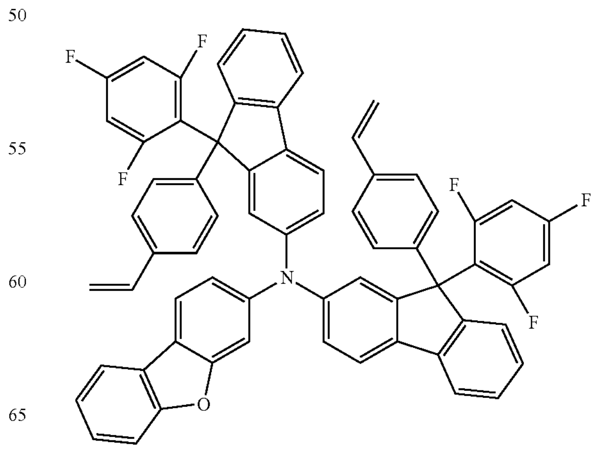

-continued
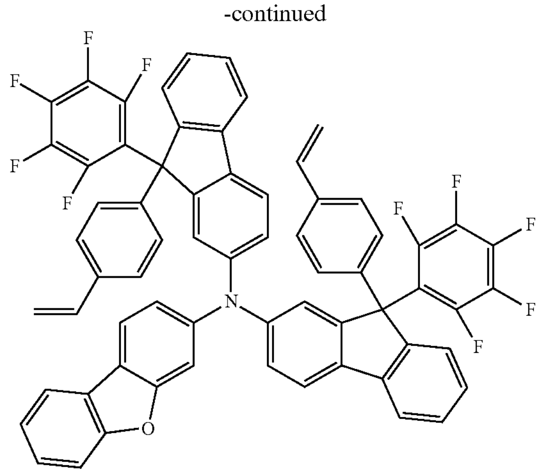
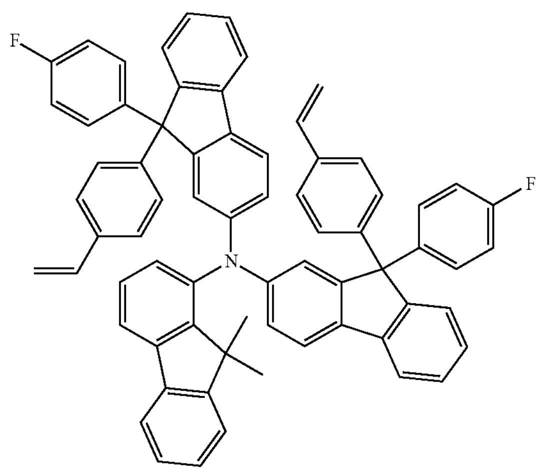
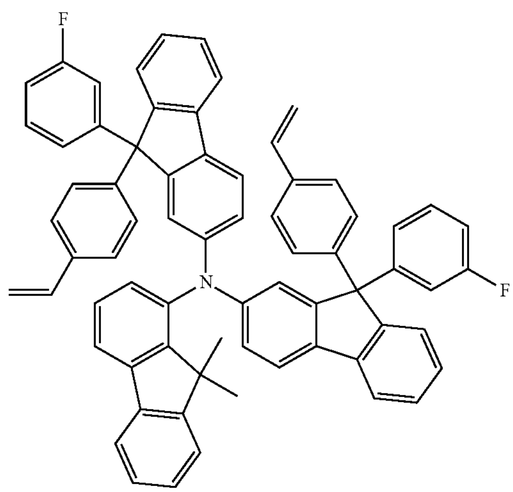
-continued
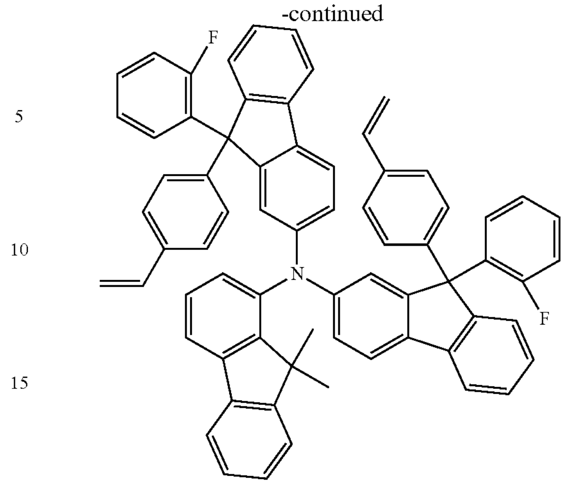
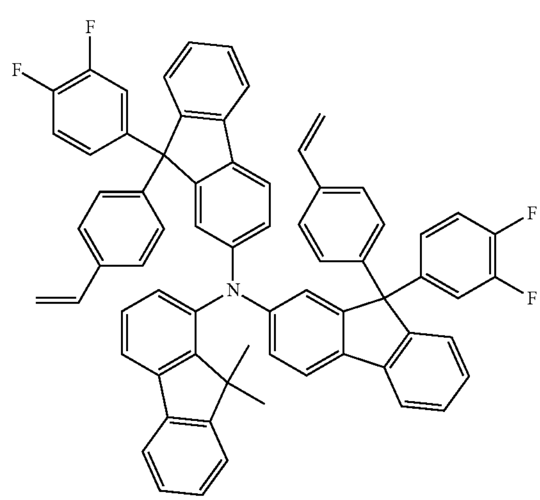
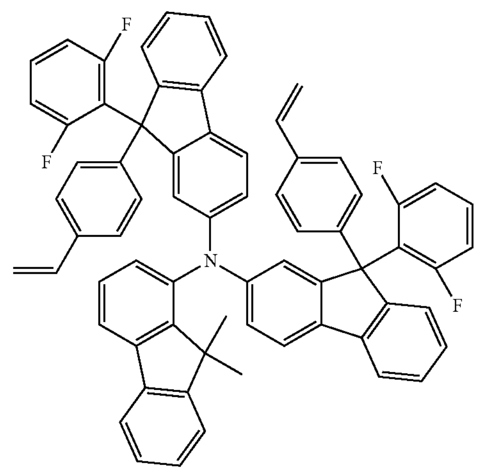

-continued
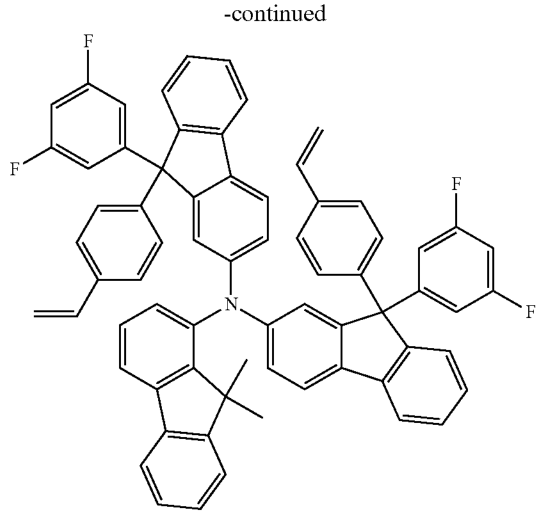
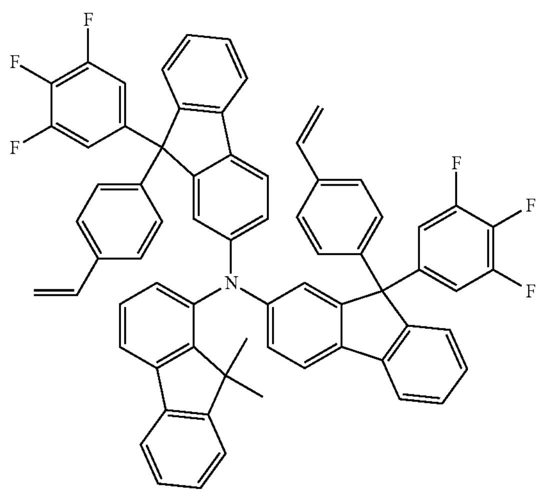
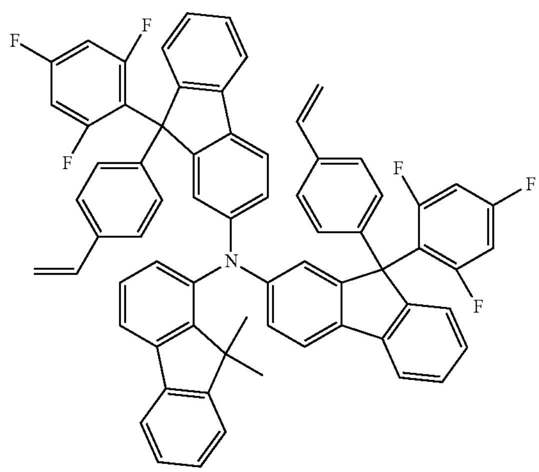
-continued
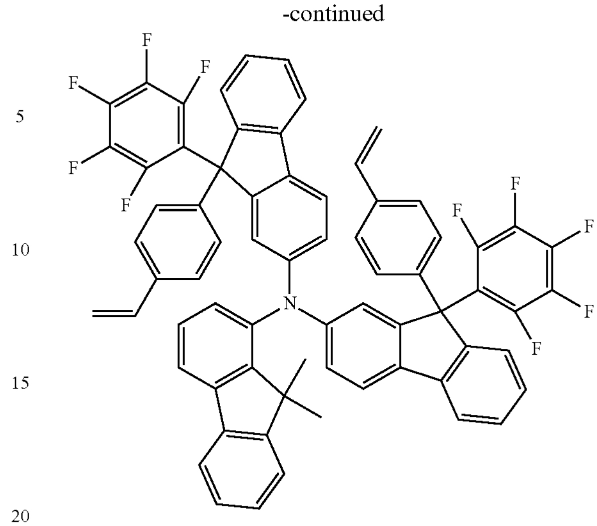
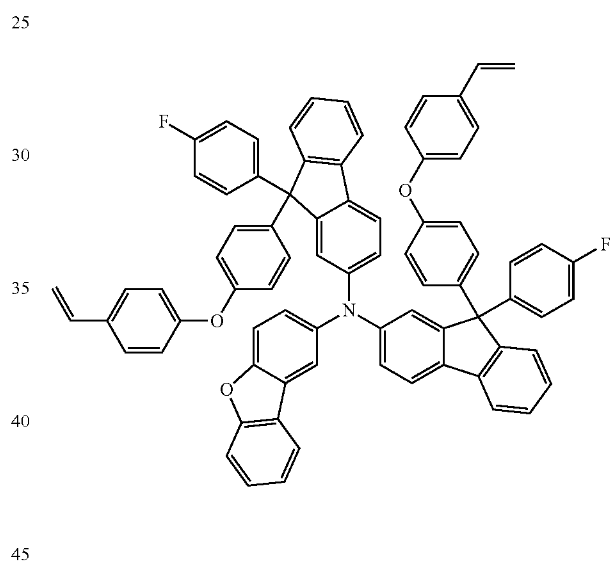
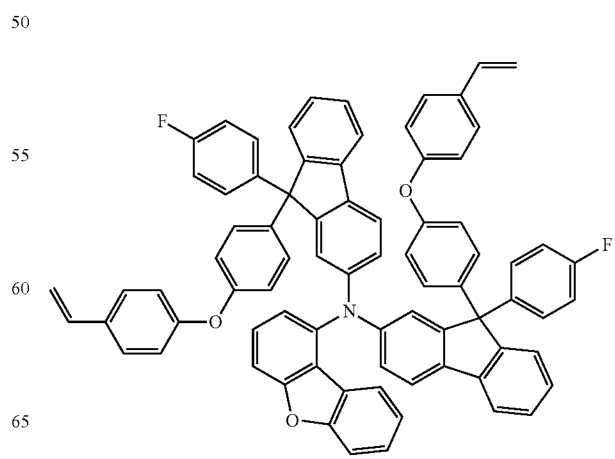

-continued
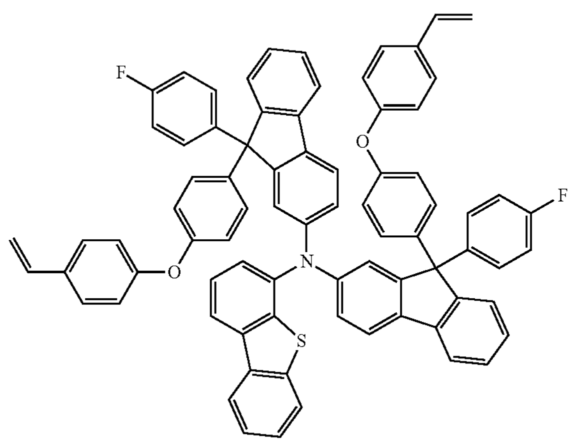
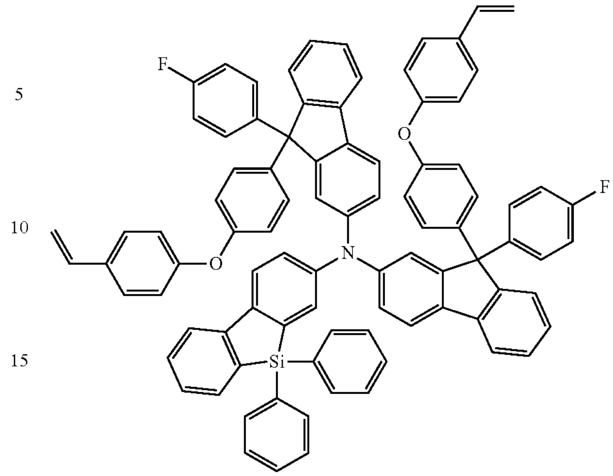
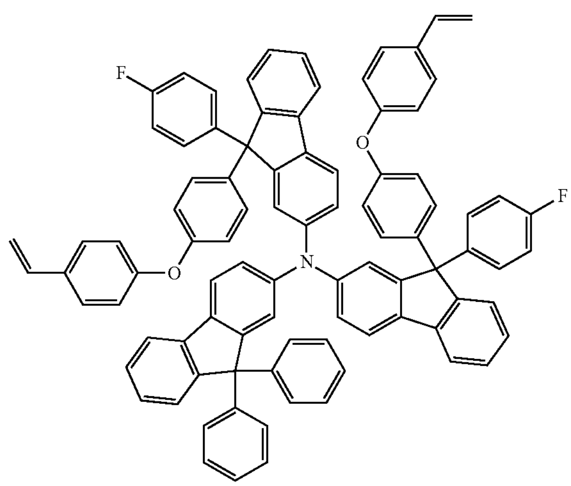
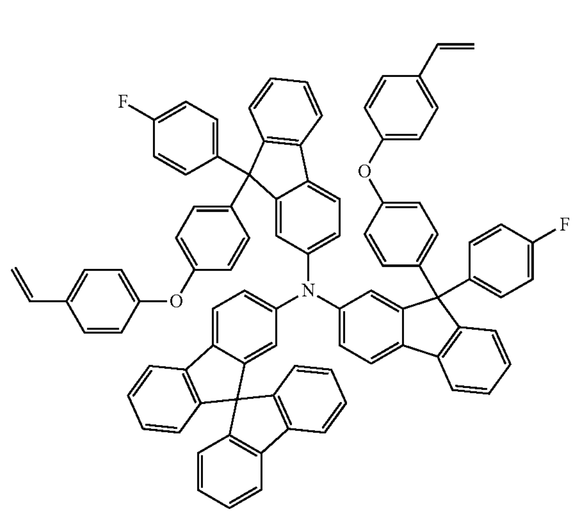
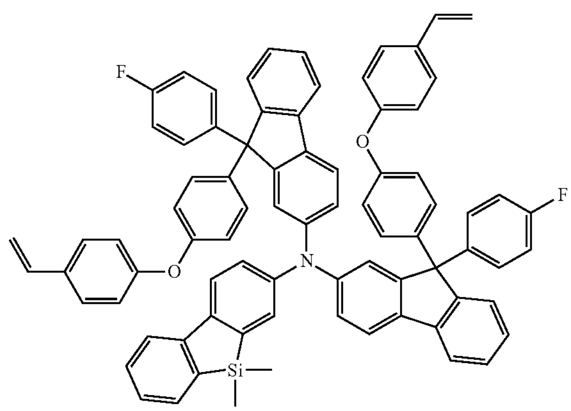
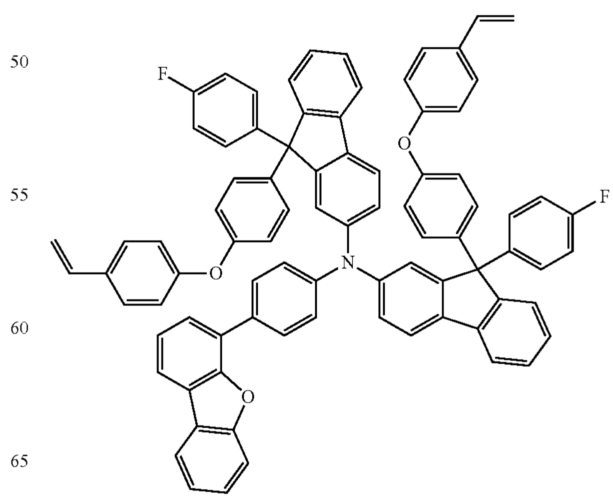

-continued
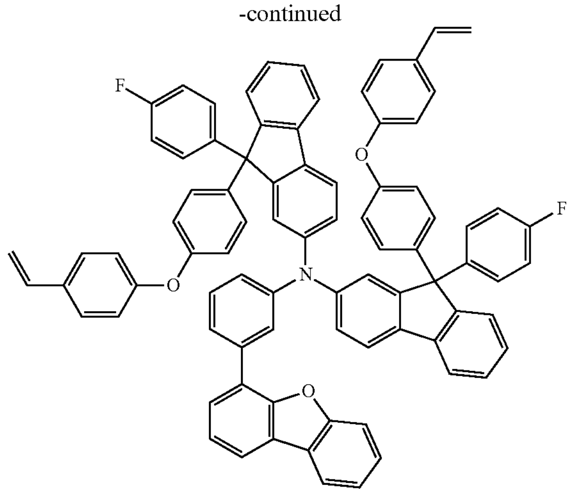
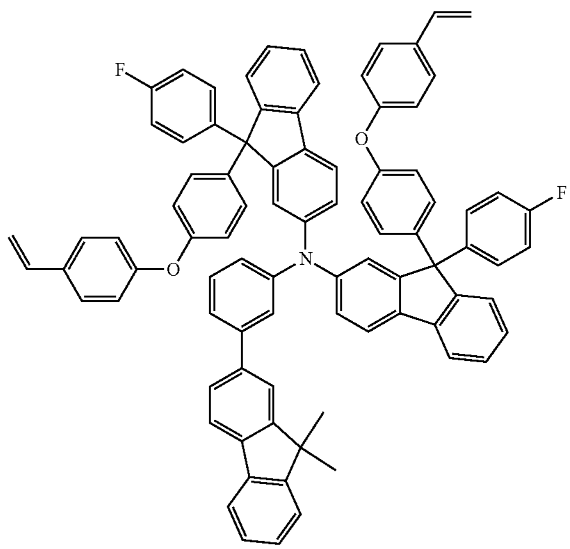
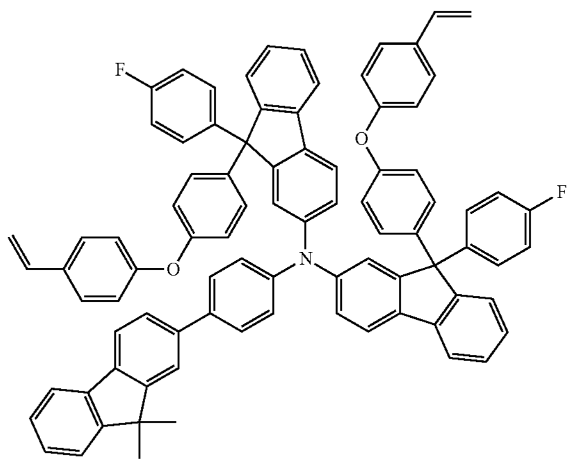
-continued
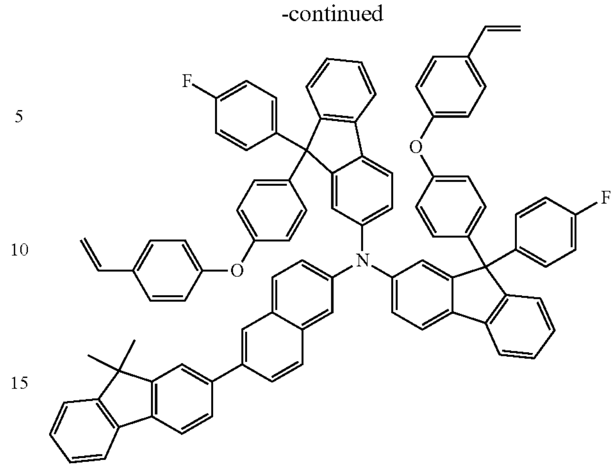
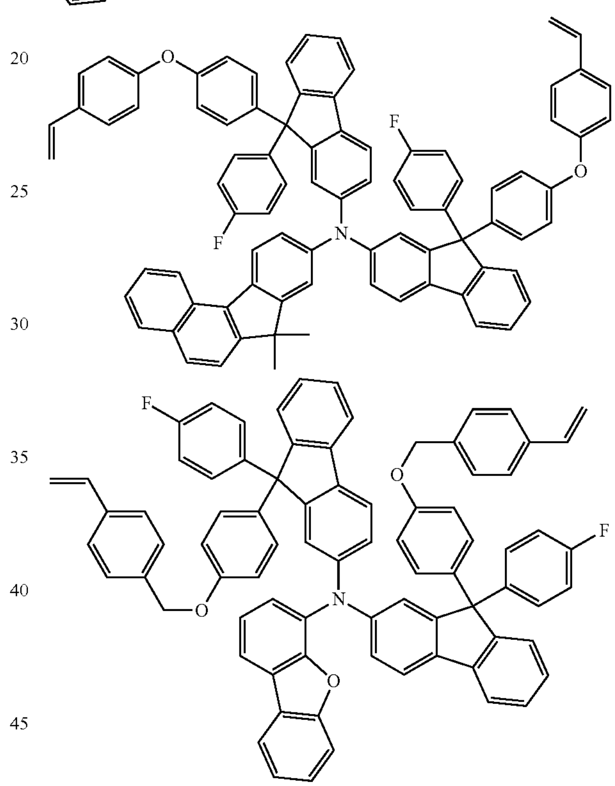
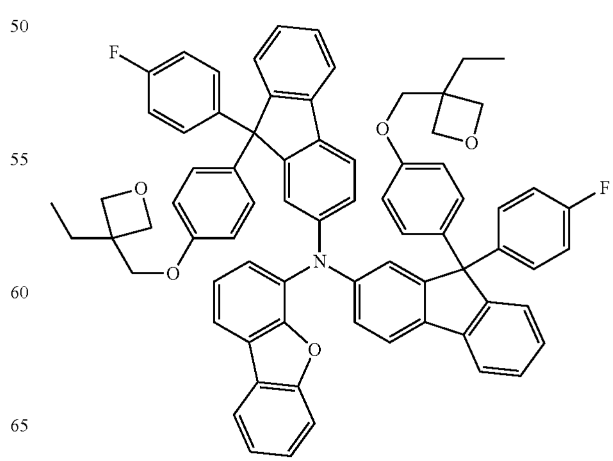

-continued
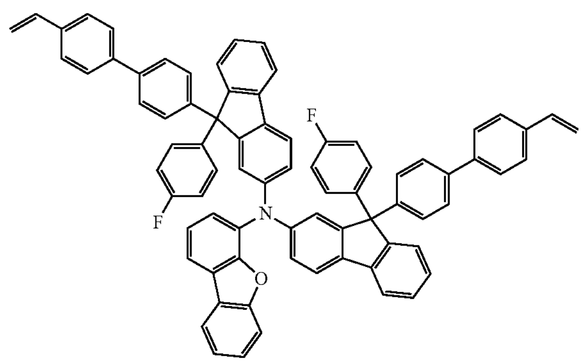
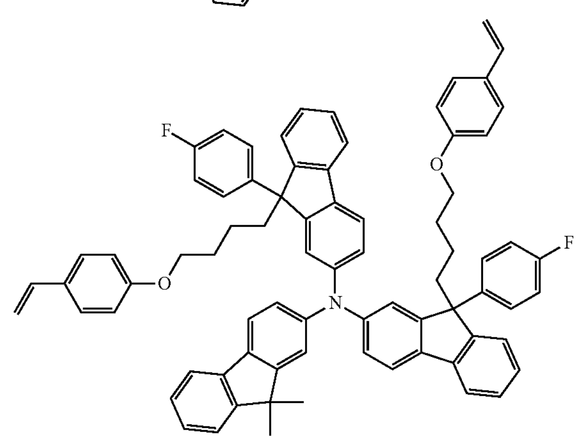
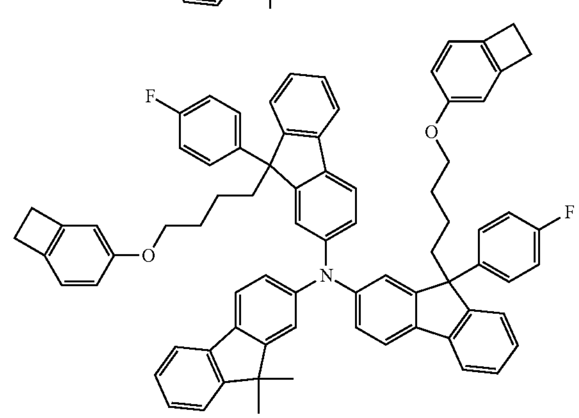
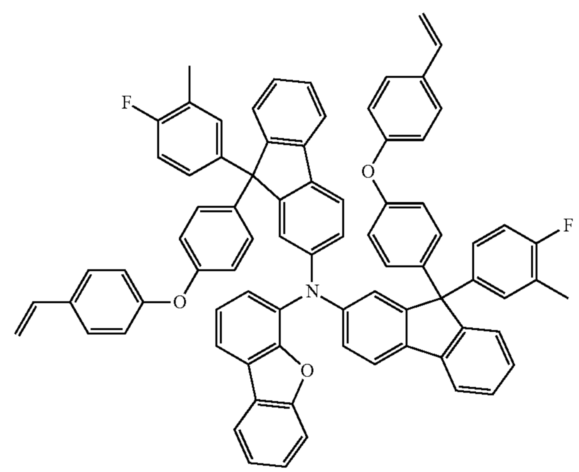
-continued
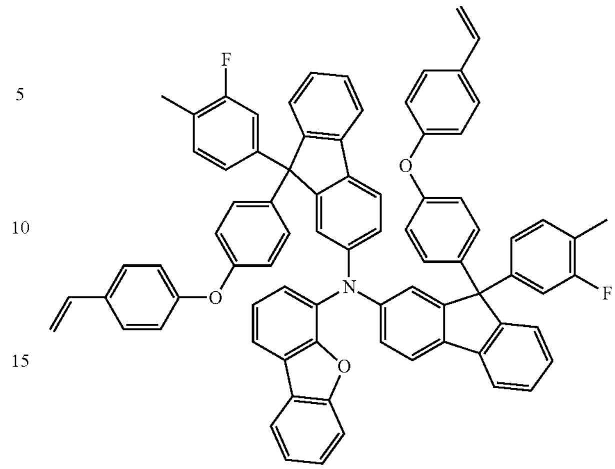
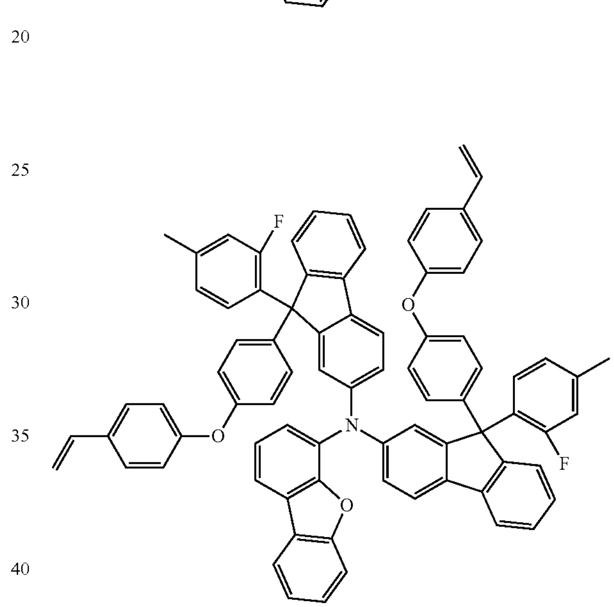
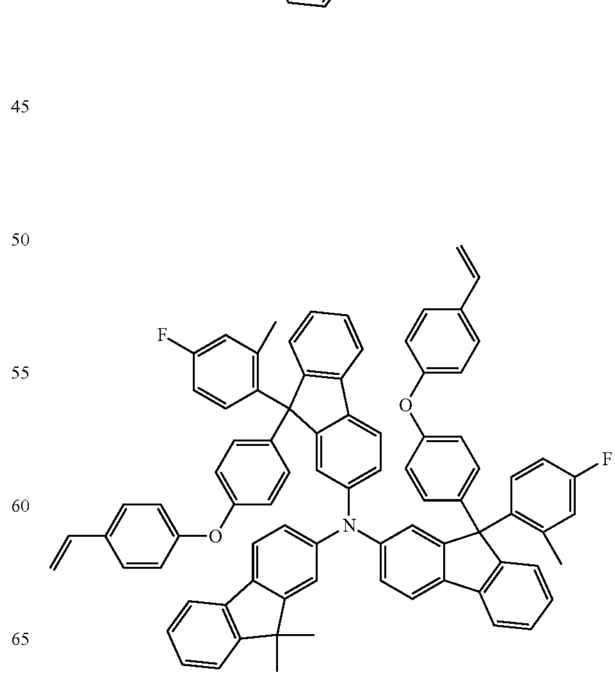

-continued
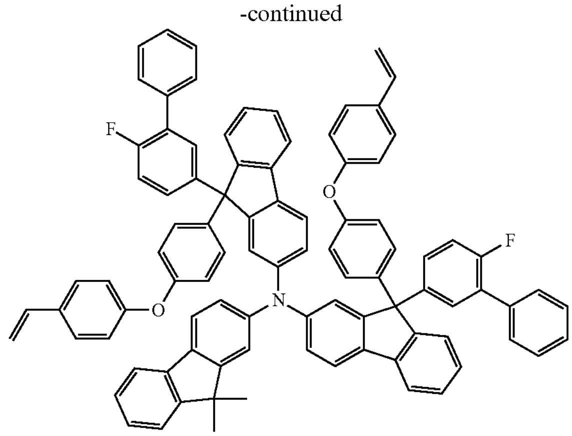
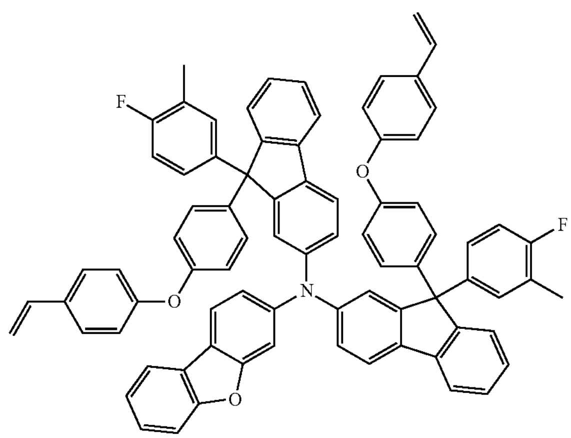
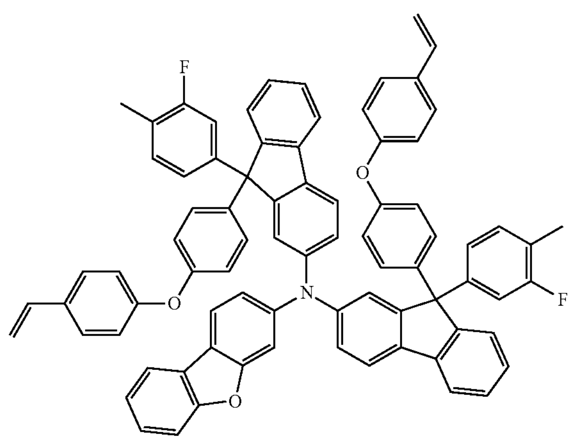
-continued
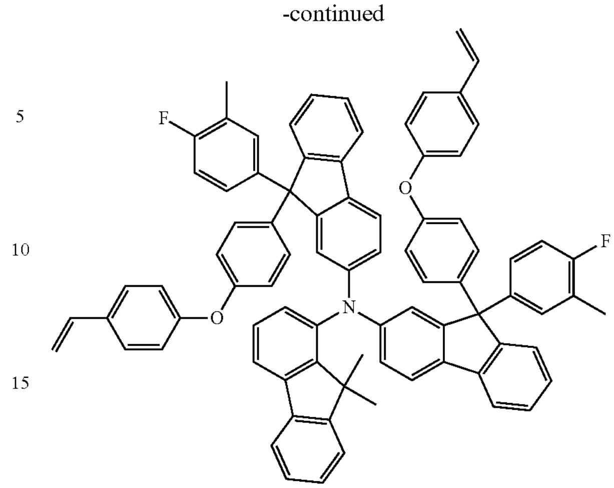
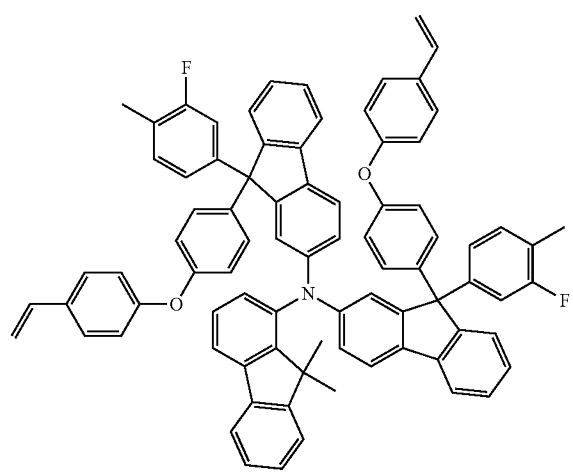
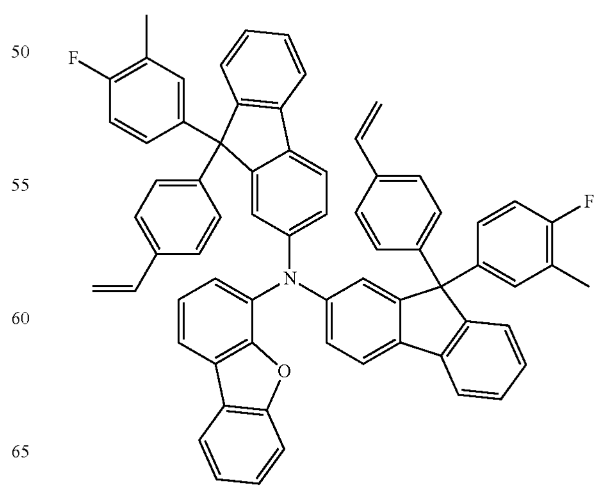

-continued
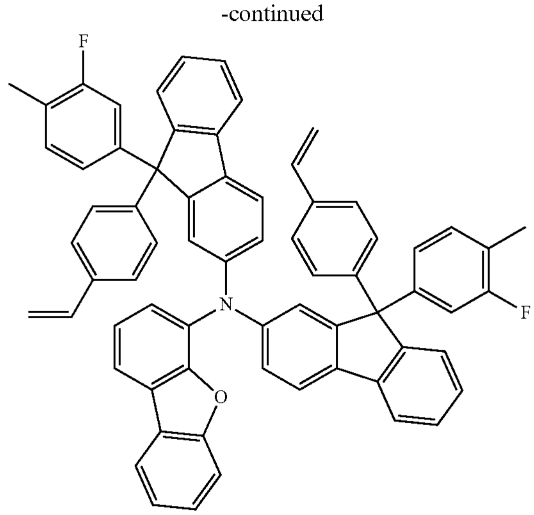
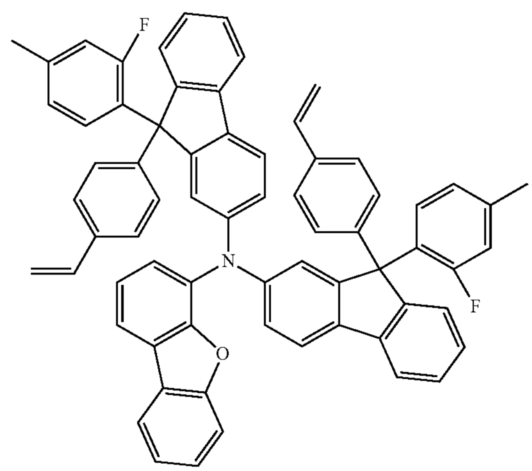
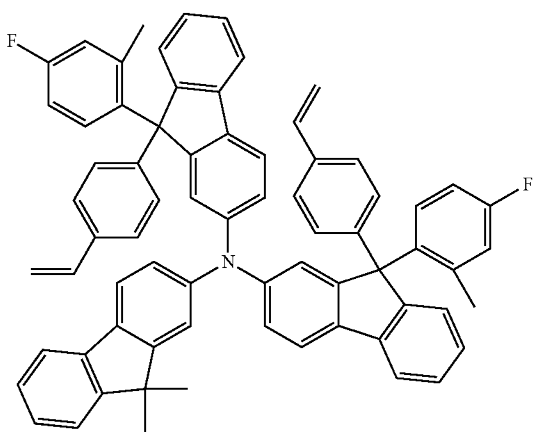
-continued
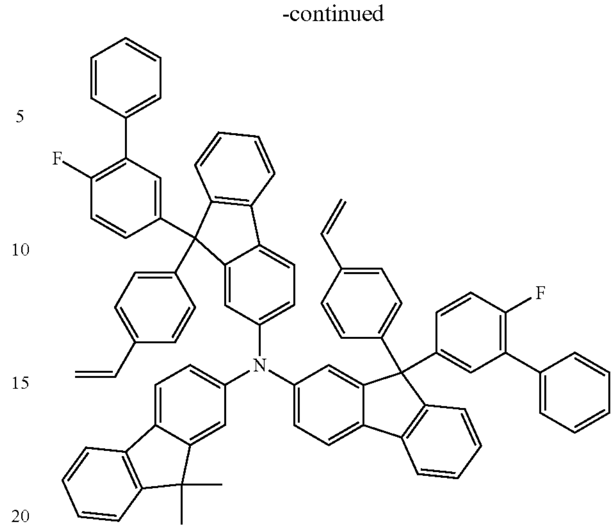
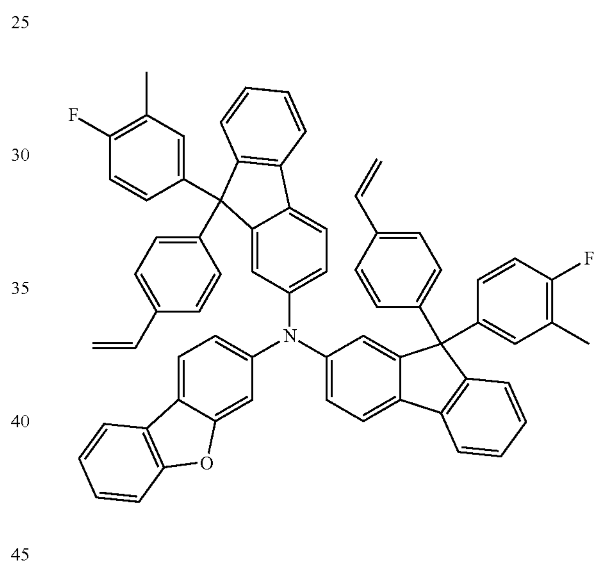
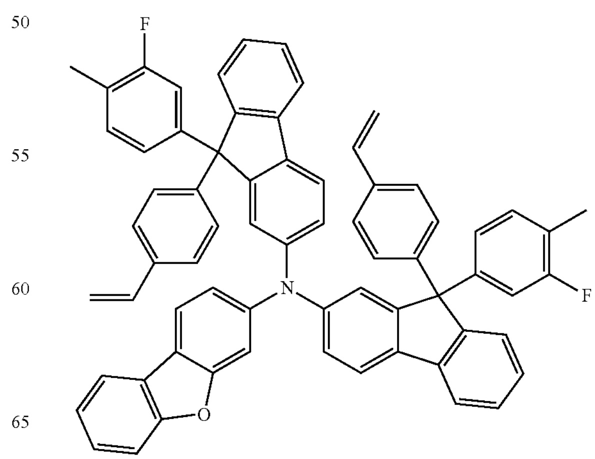

-continued
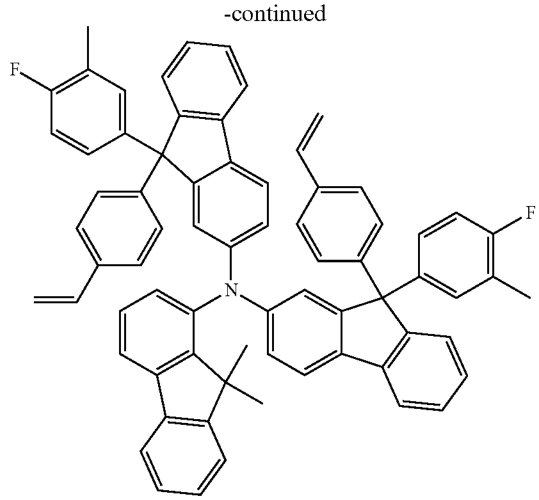
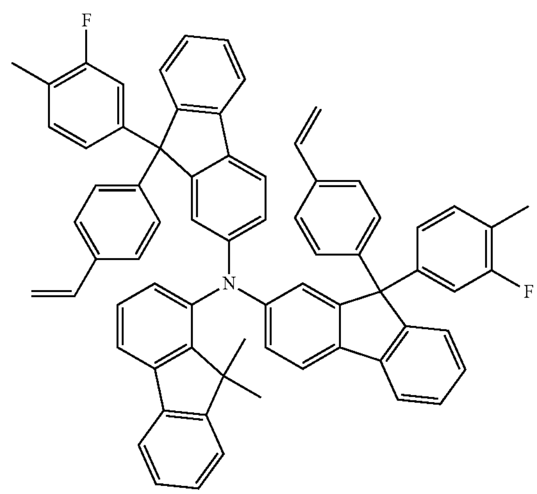
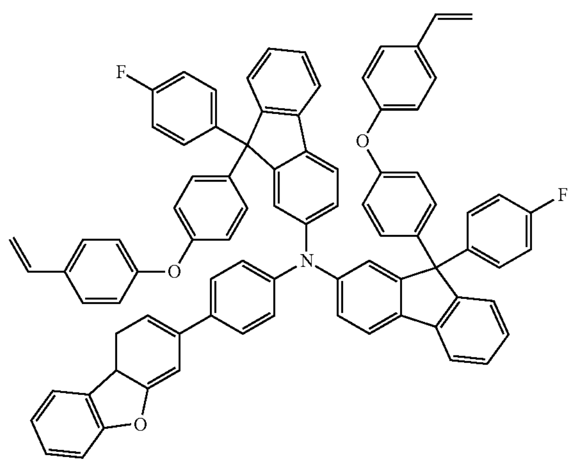
-continued
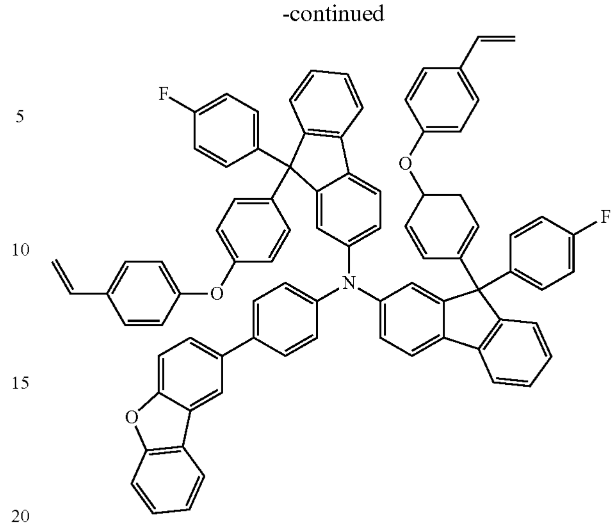
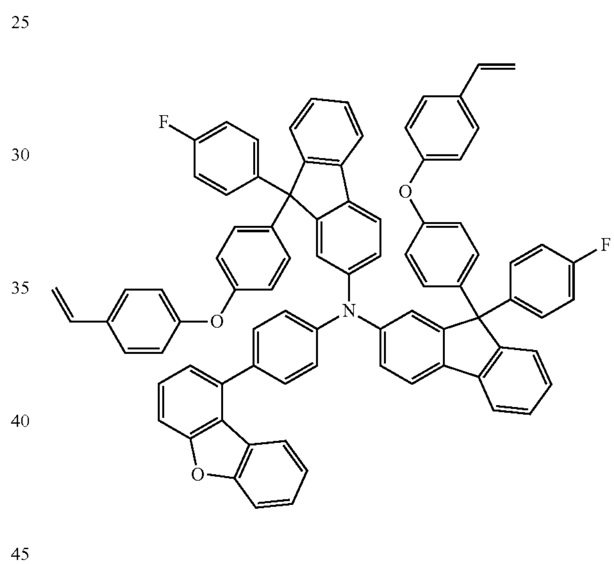
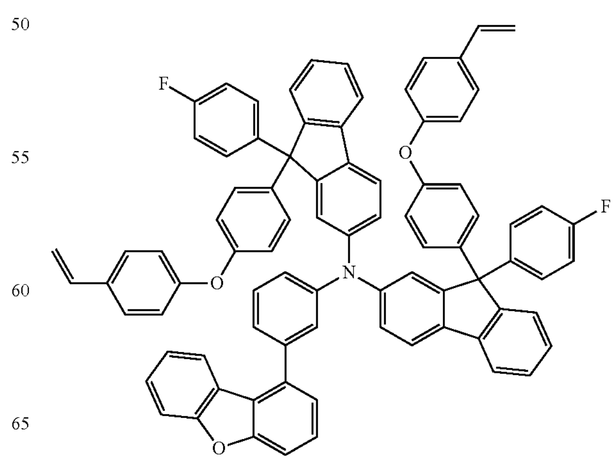

-continued
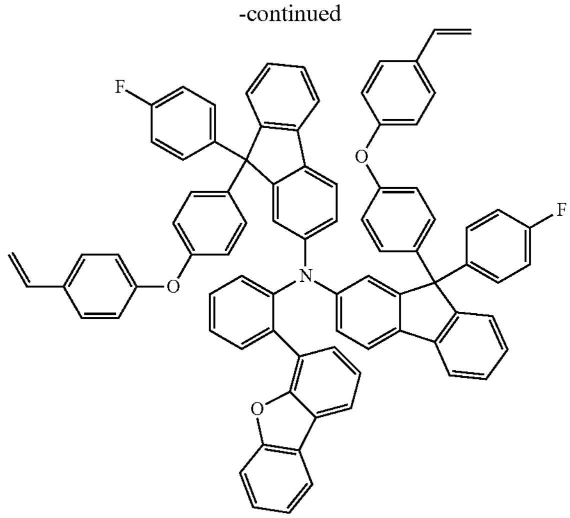
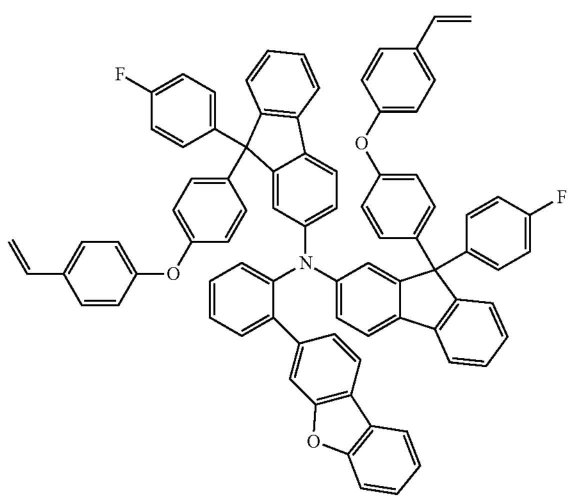
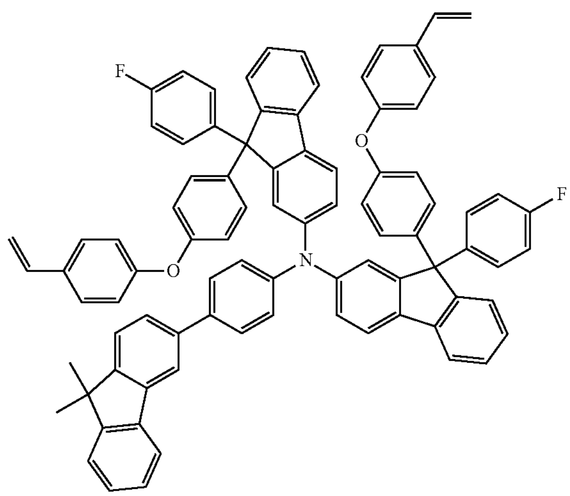
-continued
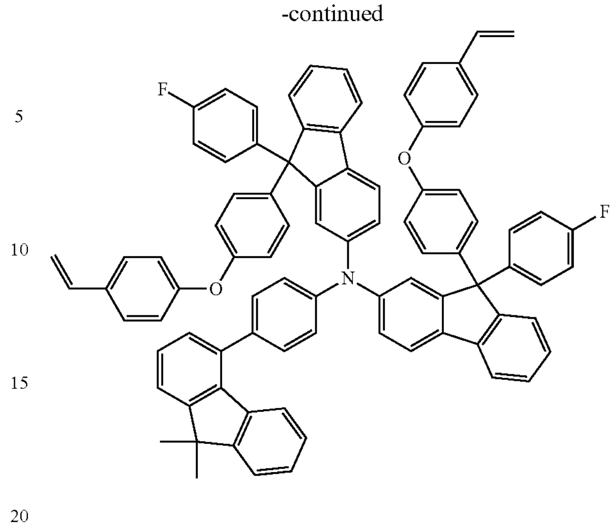
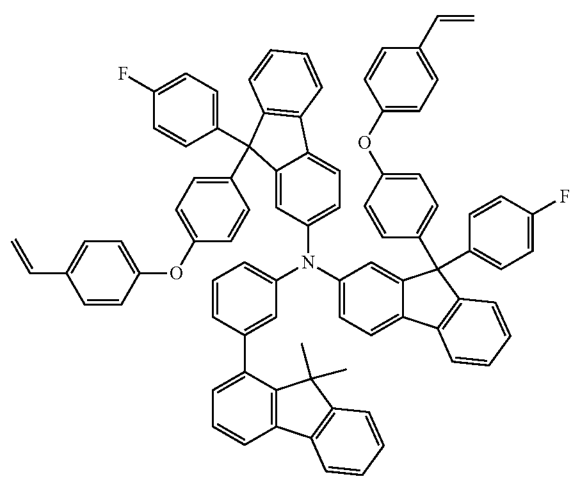
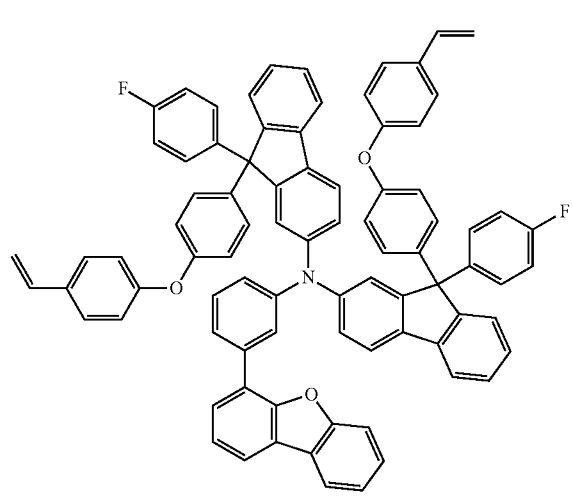

-continued
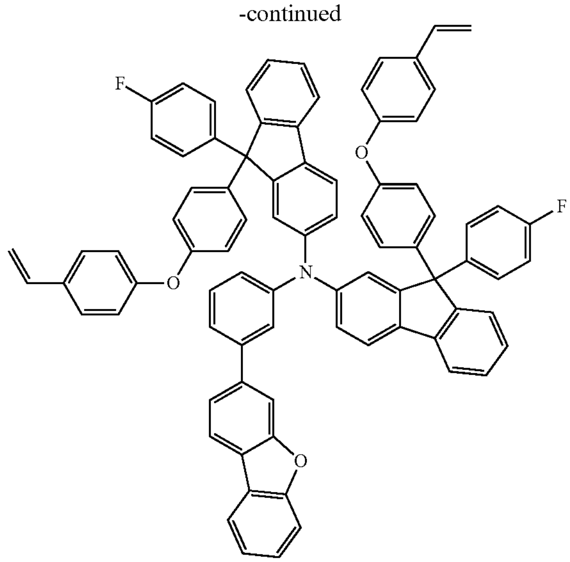
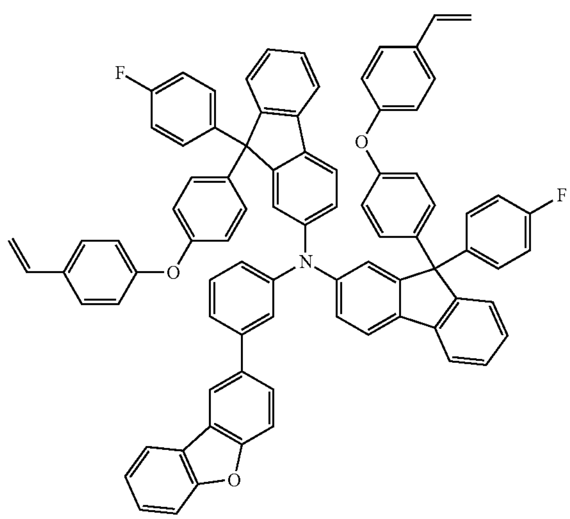
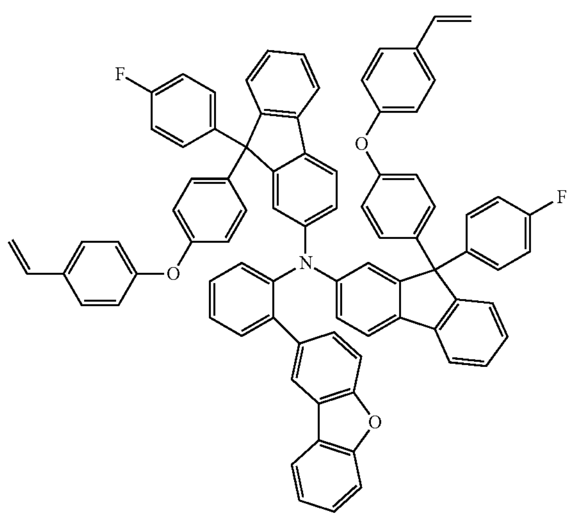
-continued
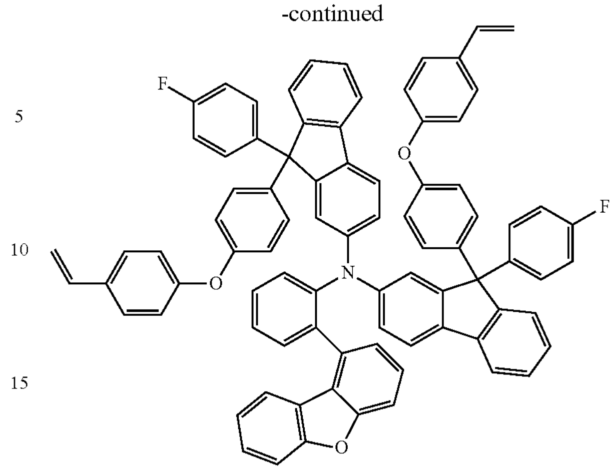
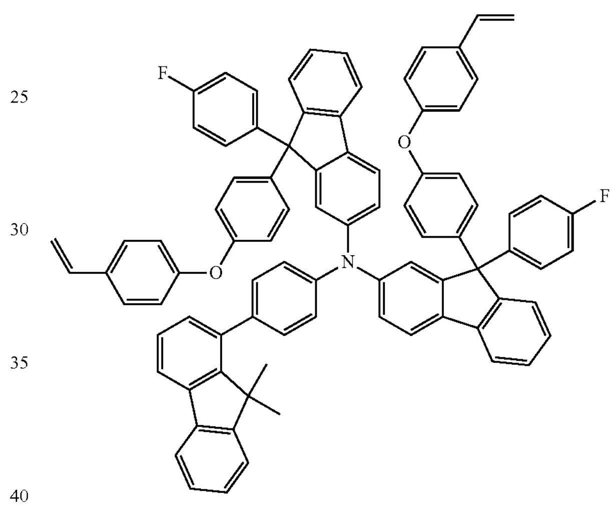
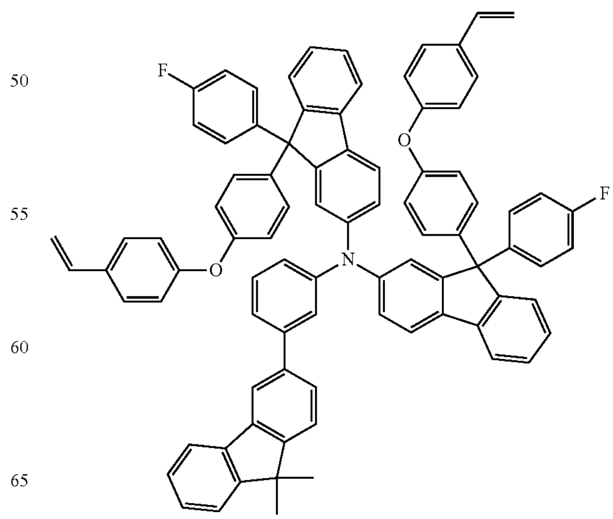

-continued
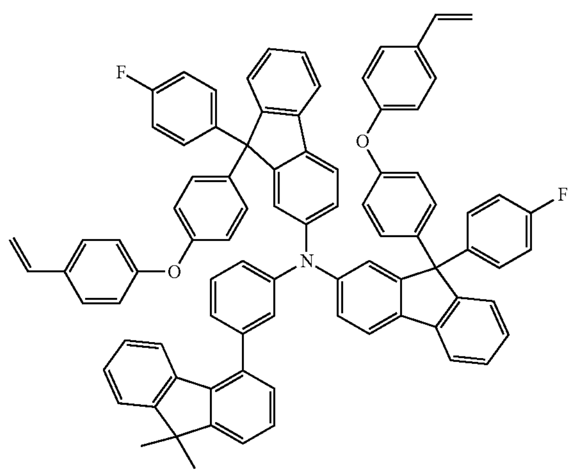
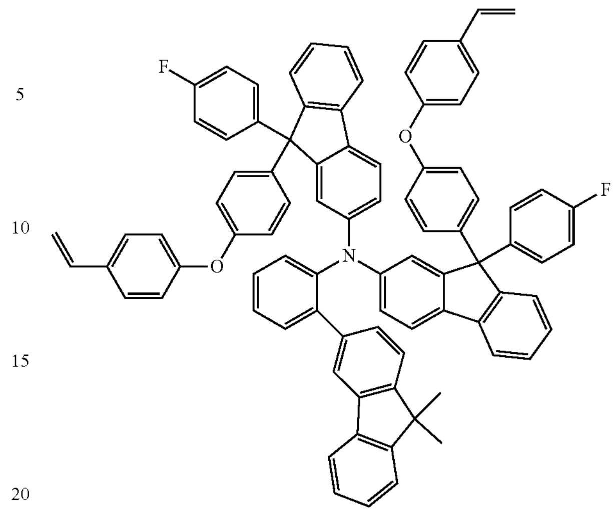
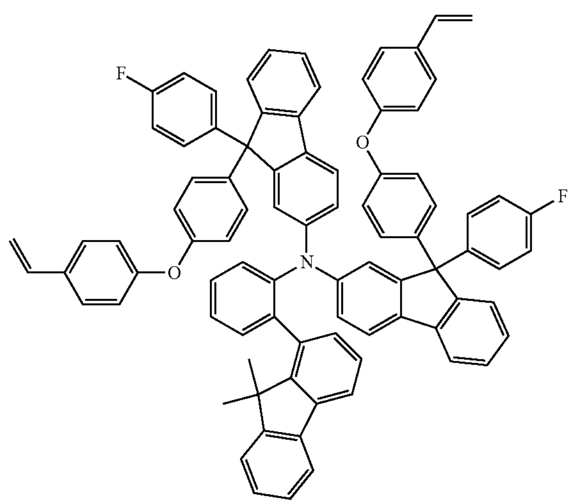
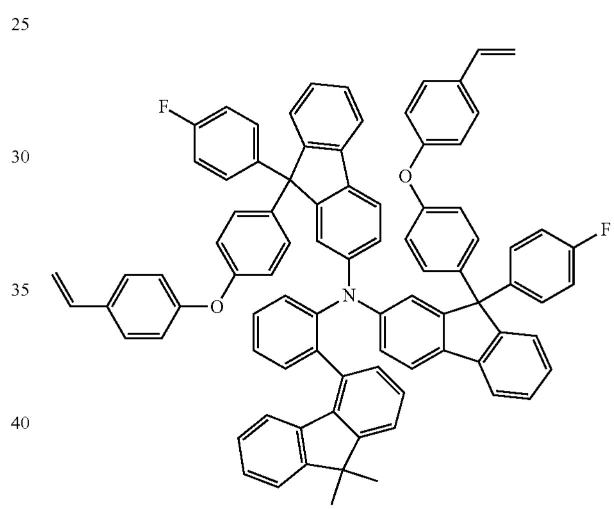
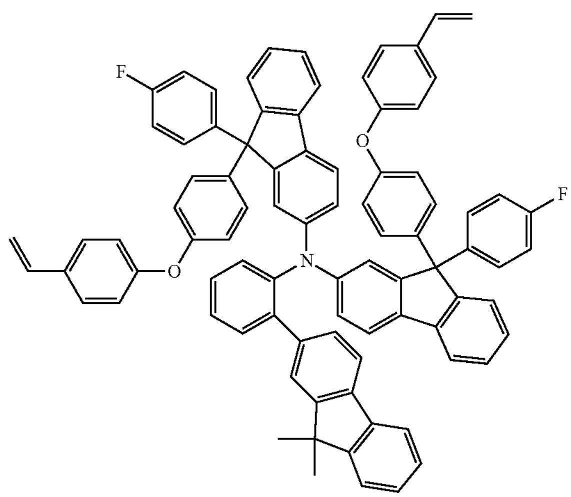
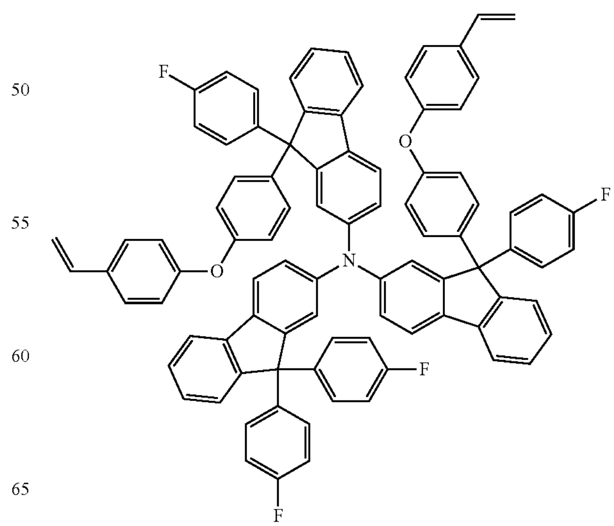
-continued -continued
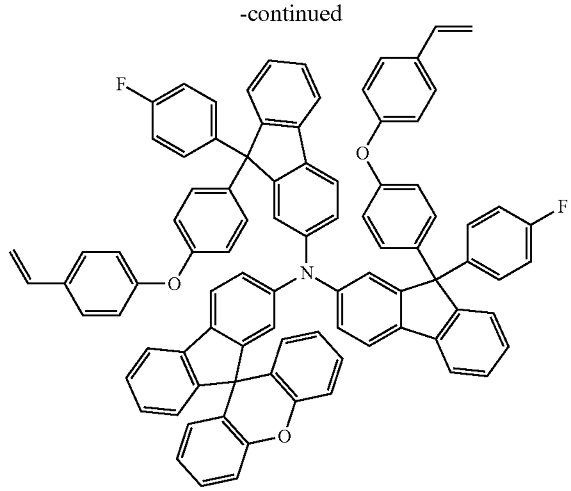
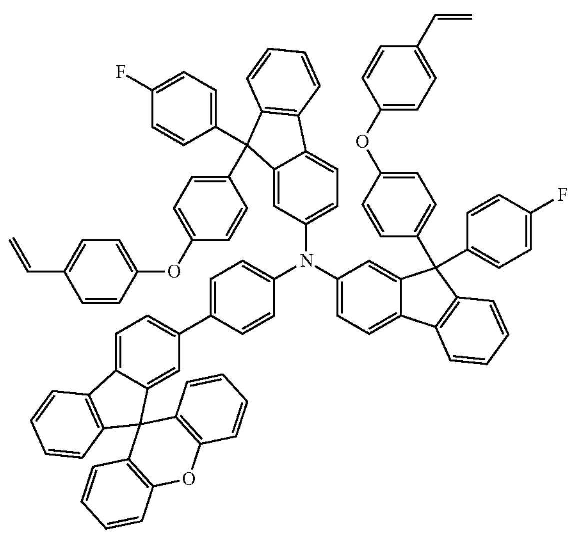
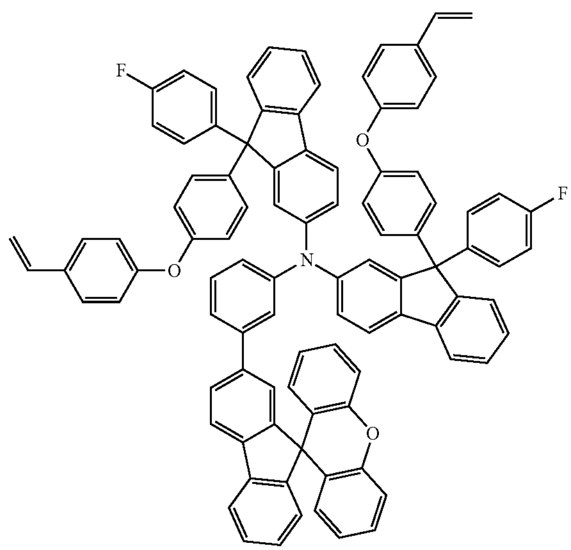
-continued
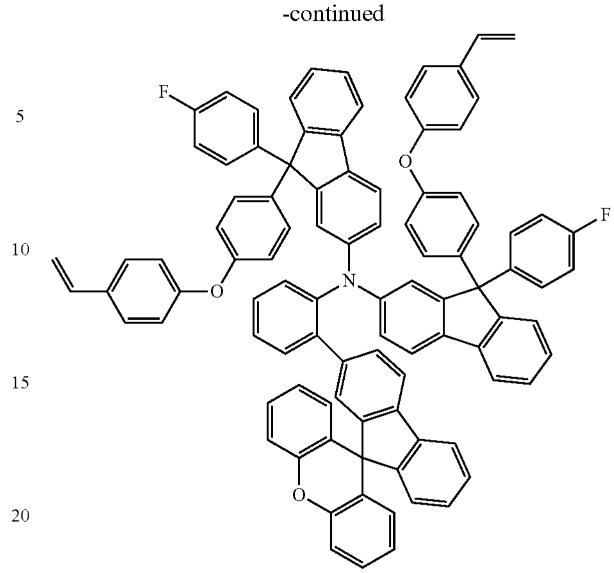
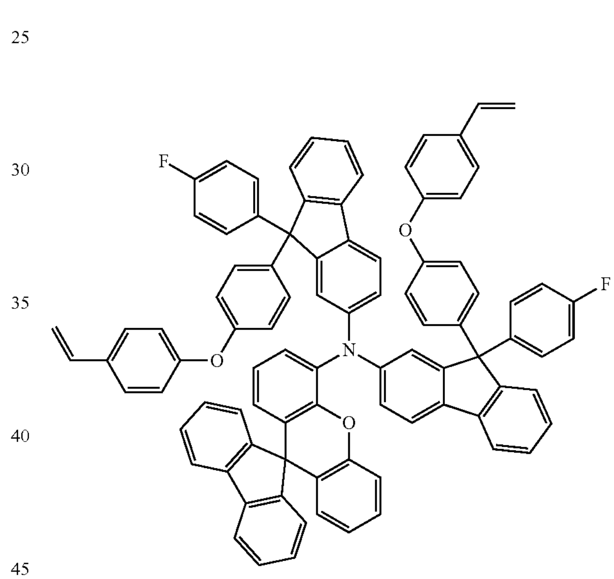
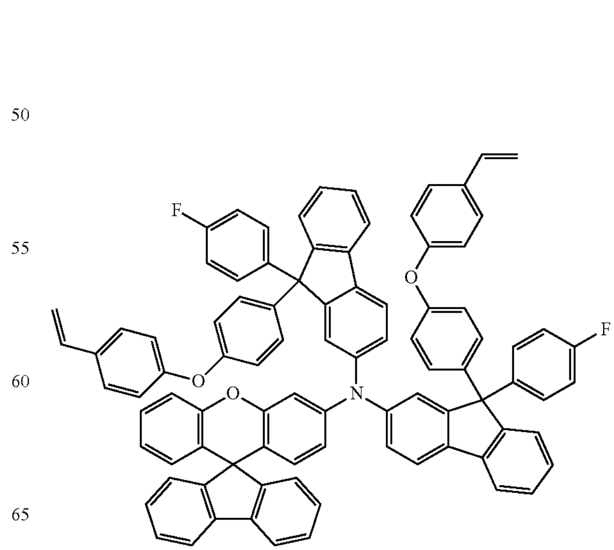

-continued
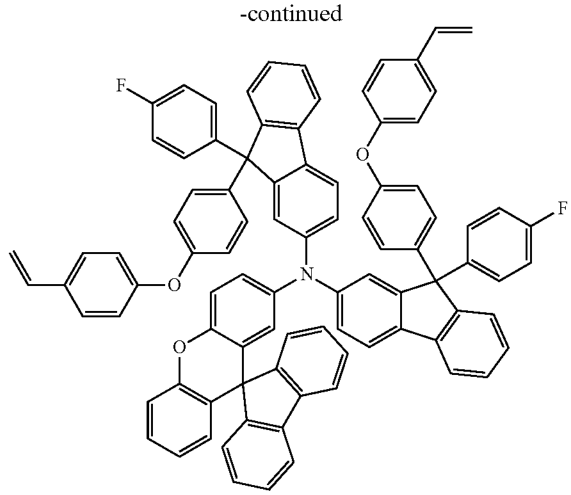
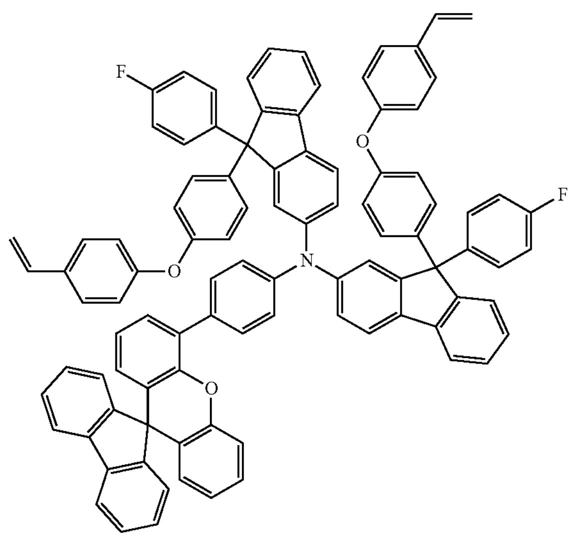
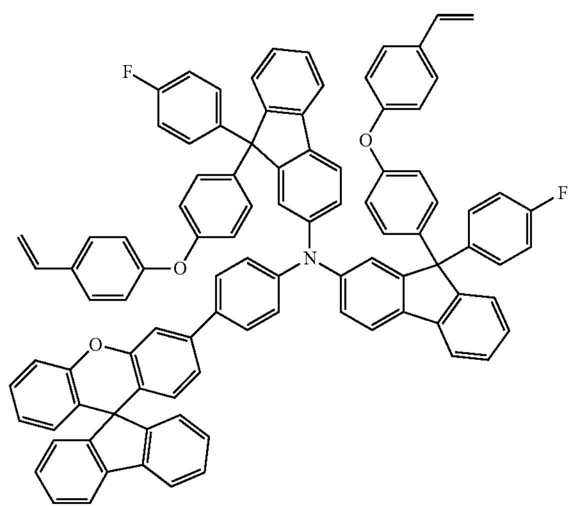
-continued
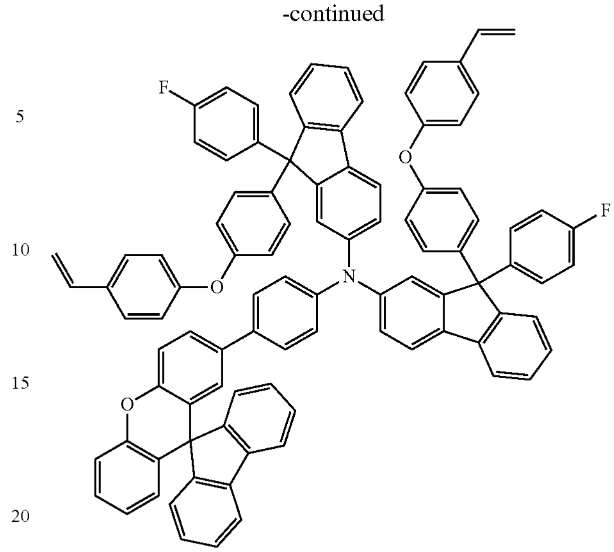
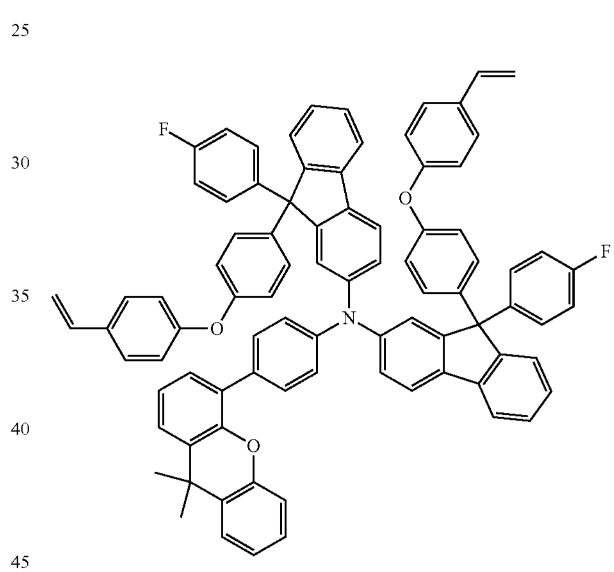
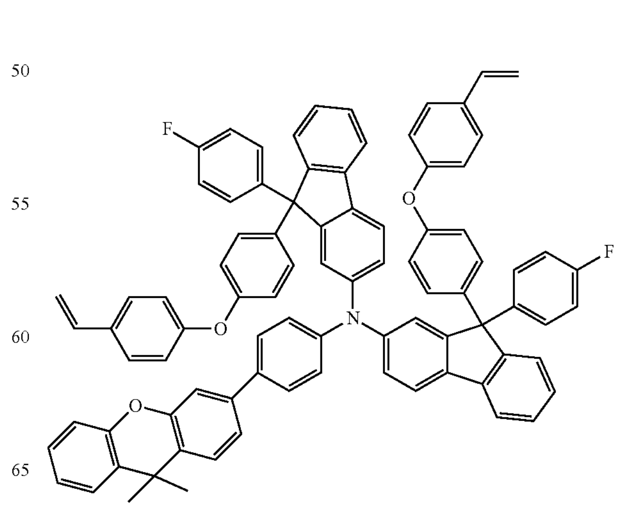

-continued
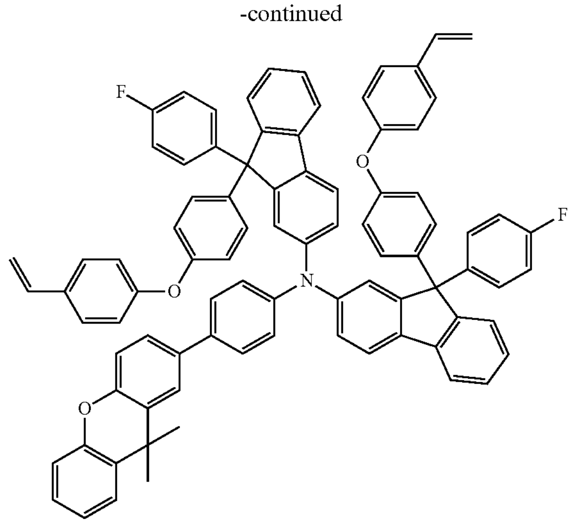
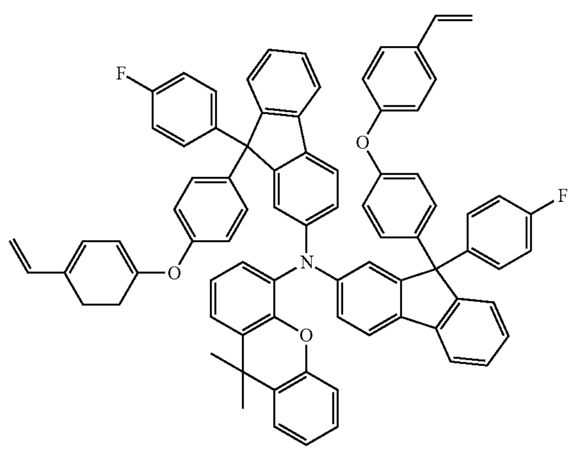
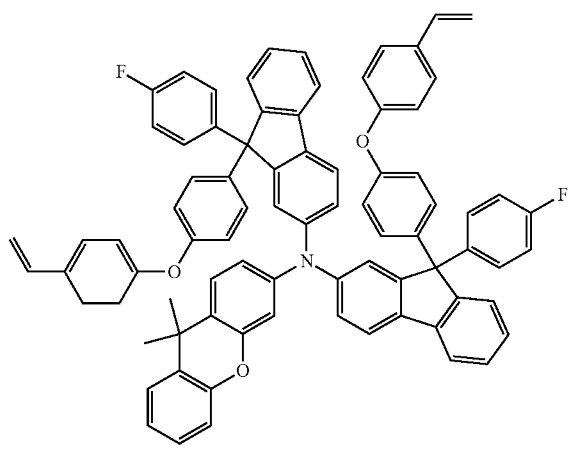
-continued
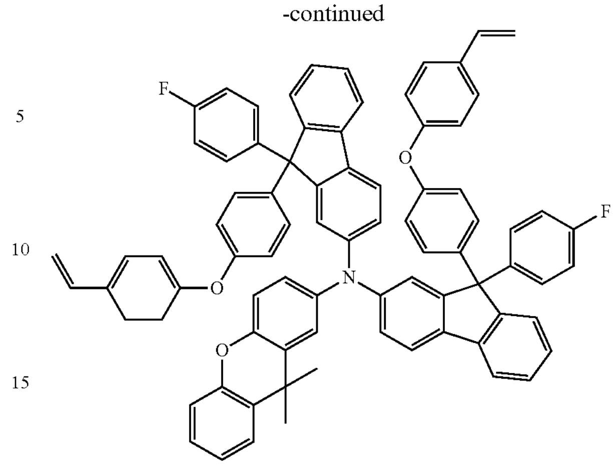
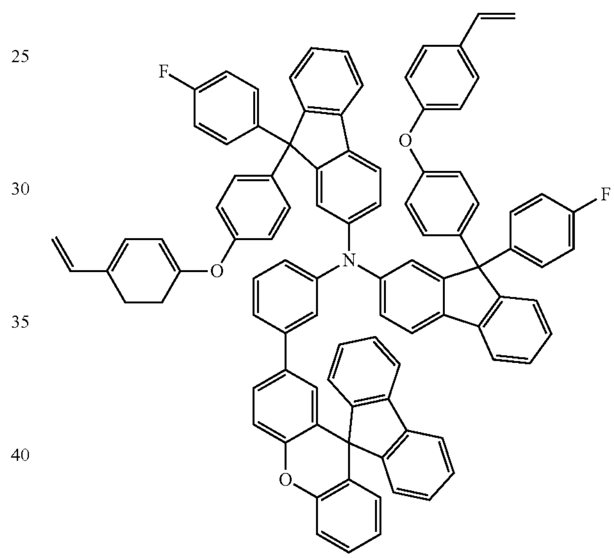
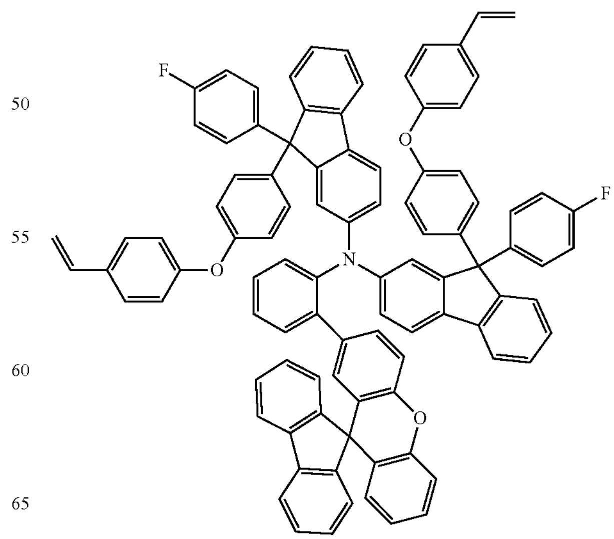

-continued

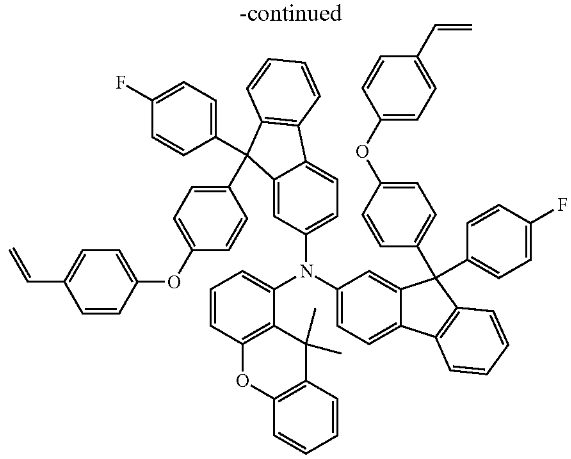

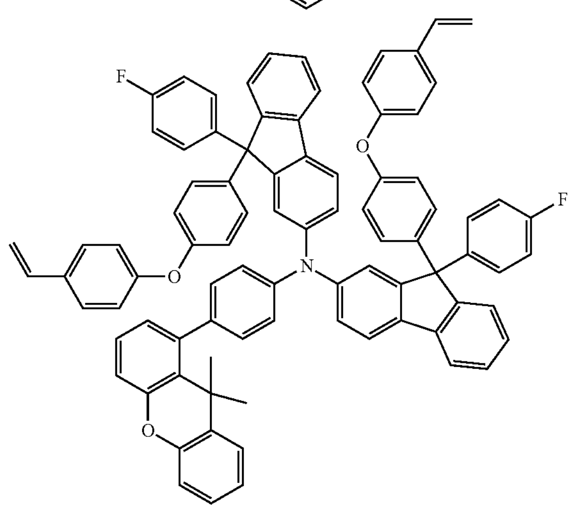

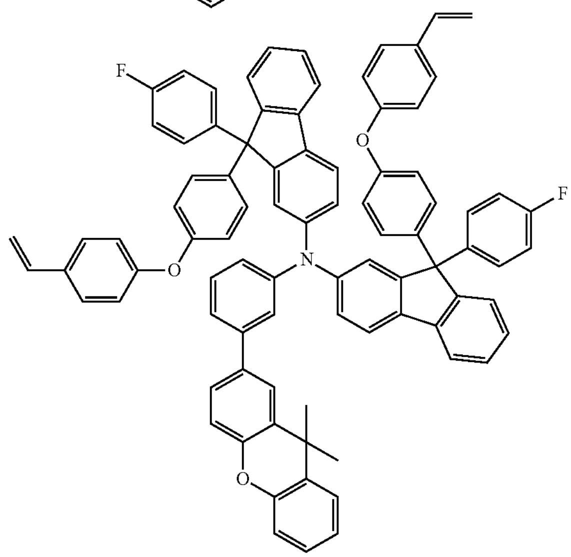

-continued

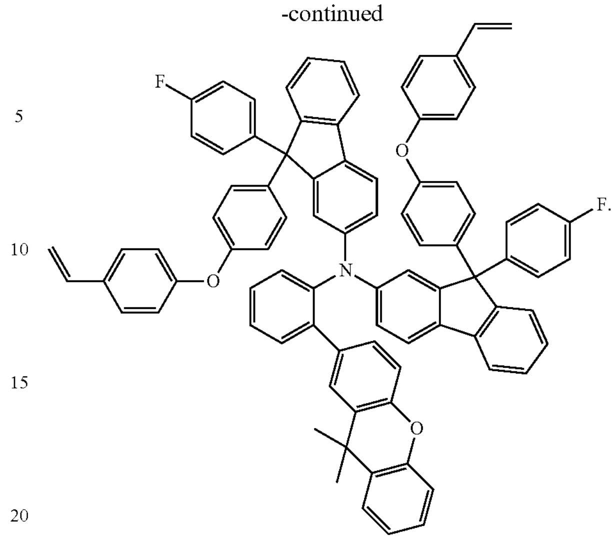

9. A coating composition comprising the compound of claim 1.

10. An organic light emitting device comprising:

a first electrode;

a second electrode; and one or more organic material layers provided between the first electrode and the second electrode, wherein the one or more organic material layers include the coating composition of claim 9 or a cured material thereof.

11. The organic light emitting device of claim 10, wherein the one or more organic material layers including the coating composition or a cured material thereof is a hole transfer layer or a hole injection layer.

12. A method for manufacturing an organic light emitting device, the method comprising:

preparing a first electrode;

forming an organic material layers on the first electrode; and forming a second electrode on the organic material layers, wherein the forming of the organic material layers includes forming one or more layers using the coating composition of claim 9.

13. The method for manufacturing an organic light emitting device of claim 12, wherein the forming of the one or more layers using the coating composition includes, coating the coating composition; and heat treating or light treating the coated coating composition.

* * * * *